(12) United States Patent
Chen et al.

(10) Patent No.: US 8,193,228 B2
(45) Date of Patent: Jun. 5, 2012

(54) SUBSTITUTED IMIDAZOLE AS BOMBESIN RECEPTOR SUBTYPE-3 MODULATORS

(75) Inventors: David Chen, Singapore (SG); Christopher L. Franklin, Keasbey, NJ (US); Peter R. Guzzo, Niskayuna, NY (US); Linus S. Lin, Westfield, NJ (US); Michael M. C. Lo, Edison, NJ (US); Ravi P. Nargund, East Brunswick, NJ (US); Iyassu K. Sebhat, Jersey City, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 412 days.

(21) Appl. No.: 12/311,487

(22) PCT Filed: Oct. 16, 2007

(86) PCT No.: PCT/US2007/022087
§ 371 (c)(1),
(2), (4) Date: Mar. 31, 2009

(87) PCT Pub. No.: WO2008/051406
PCT Pub. Date: May 2, 2008

(65) Prior Publication Data
US 2010/0022598 A1 Jan. 28, 2010

Related U.S. Application Data

(60) Provisional application No. 60/853,193, filed on Oct. 20, 2006.

(51) Int. Cl.
*A61K 31/4178* (2006.01)
*A61K 31/4164* (2006.01)
*C07D 471/04* (2006.01)
*C07D 401/10* (2006.01)
*C07D 403/10* (2006.01)
*C07D 233/64* (2006.01)

(52) U.S. Cl. ........ 514/393; 514/360; 514/385; 514/387; 514/390; 548/126; 548/300.1; 548/416; 548/578; 546/113; 546/272.7

(58) Field of Classification Search .................. 514/397, 514/393, 385, 359, 360, 387, 390; 548/311.1, 548/126, 300.1, 416, 578; 546/272.7, 113
See application file for complete search history.

(56) References Cited

U.S. PATENT DOCUMENTS

| | | | |
|---|---|---|---|
| 4,962,117 | A | 10/1990 | Young et al. |
| 6,673,941 | B2 | 1/2004 | Heerding et al. |
| 7,141,596 | B2 | 11/2006 | Combs et al. |
| 2002/0009116 | A1 | 1/2002 | Kobayashi et al. |
| 2004/0167188 | A1 | 8/2004 | Xin et al. |
| 2004/0192743 | A1 | 9/2004 | Mjalli et al. |
| 2004/0248956 | A1 | 12/2004 | Hagmann et al. |
| 2005/0130973 | A1 | 6/2005 | Xiang et al. |
| 2005/0187277 | A1 | 8/2005 | Mjalli et al. |
| 2005/0272778 | A1 | 12/2005 | Combs et al. |

FOREIGN PATENT DOCUMENTS

| | | |
|---|---|---|
| JP | 07-243068 | 9/1995 |
| JP | 11-217348 | 8/1999 |
| JP | 2003-321455 | 11/2003 |
| WO | 93/17681 | 9/1993 |
| WO | 97/40017 | 10/1997 |
| WO | 98/28269 | 7/1998 |
| WO | 99/32454 | 7/1999 |
| WO | 02/14291 | 2/2002 |
| WO | 02/098840 | 12/2002 |
| WO | 03/016291 | 2/2003 |
| WO | 03/104196 | 12/2003 |
| WO | 2004/007464 | 1/2004 |
| WO | 2004/046091 | 6/2004 |
| WO | 2004/048351 | 6/2004 |
| WO | 2004/058176 | 7/2004 |
| WO | 2004/071447 | 8/2004 |
| WO | 2004/071509 | 8/2004 |
| WO | 2004/110350 | 12/2004 |
| WO | 2005/035551 | 4/2005 |
| WO | 2005/056532 | 6/2005 |
| WO | 2005/058848 | 6/2005 |
| WO | 2005/080390 | 9/2005 |
| WO | 2005/107762 | 11/2005 |
| WO | 2008/051404 | 5/2008 |
| WO | 2008/051405 | 5/2008 |

OTHER PUBLICATIONS

Campfield, "Strategies and potential molecular targets for obesity treatment", Science (1998), 1383-1387, vol. 280.
Liu, "Molecular basis of the pharmacological difference between rat and human . . . ", Biochemistry (2002), 8954-8960, vol. 41.
Breslow, "Synthesis of some polyimidazole ligands related to zinc enzymes", J. Am. Chem. Soc. (1983), 5337-5342, vol. 105.
Porcher, "Bombesin receptor subtype-3 is expressed by the enteric nervous . . . ", Cell Tissue Res. (2005), 21-31, vol. 320.
Powers, "Effect of structural change on acute toxicity . . . ", J. Med. Chem. (1981), 604-609, vol. 24.
Tan, "Wound repair and proliferation of bronchial epithelial cells . . . ", Peptides (2006), 1852-1858, vol. 27.
Ohki-Hamazaki, "Mice lacking bombesin receptor subtype-3 . . . ", Nature (1997), 165-169, vol. 390.
Lebacq-Verheyden, "Bombesin and gastrin-releasing peptide: . . . ", Handbook of Exper. Pharmacol. (1990), 71-124, vol. 95.

*Primary Examiner* — Sreeni Padmanabhan
*Assistant Examiner* — Sahar Javanmard
(74) *Attorney, Agent, or Firm* — Baerbel R. Brown; John C. Todaro

(57) ABSTRACT

Certain novel substituted imidazoles are ligands of the human bombesin receptor and, in particular, are selective ligands of the human bombesin receptor subtype-3 (BRS-3). They are therefore useful for the treatment, control, or prevention of diseases and disorders responsive to the modulation of BRS-3, such as obesity, and diabetes.

19 Claims, No Drawings

SUBSTITUTED IMIDAZOLE AS BOMBESIN RECEPTOR SUBTYPE-3 MODULATORS

CROSS-REFERENCE TO RELATED APPLICATIONS

This application is a U.S. National Phase application under 35 U.S.C. §371 of PCT Application No. PCT/US2007/22087, filed 16 Oct. 2007, which claims priority from and the benefit of U.S. Provisional Application No. 60/853,193, filed Oct. 20, 2006.

BACKGROUND OF THE INVENTION

Obesity is a major health concern in Western societies. It is estimated that about 146 million adults in the United States are overweight or obese. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; hyperinsulinemia; glucose intolerance; dyslipidemias; hyperlipidemia; endometrial, breast, prostate and colon cancer; osteoarthritis; respiratory complications, such as obstructive sleep apnea; cholescystitis; cholelithiasis; gout; gallstones; gall bladder disease; respiratory problems; psychological disorders (such as depression, eating disorders, distorted body image and low self esteem); arteriosclerosis; heart disease; abnormal heart rhythms; angina pectoris; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death. Recent studies have found that obesity and its associated health risks also affect children and adolescents.

Obesity is now recognized as a chronic disease that requires treatment to reduce its associated health risks. Important outcomes for the treatment of obesity include weight loss, and weight management to improve cardiovascular and metabolic health and to reduce obesity-related morbidity and mortality. It has been shown that 5-10% loss of body weight can substantially improve metabolic values, such as blood glucose, blood pressure, and lipid concentrations. Hence, it is believed that a 5-10% intentional reduction in body weight may reduce morbidity and mortality.

Rodent genetics and pharmacology have implicated BRS-3 in the development of obesity, and diabetes (Ohki et al. Nature 390: 165-69 (1997)). Bombesin receptor subtype 3 is a G protein coupled receptor expressed primarily in the central nervous system, particularly the hypothalamus, a major region in the central nervous system for the regulation of food intake, metabolic rate, and body weight (Liu et al. Biochem 41: 8154-8160 (2002)). Bombesin, bombesin-like peptides, and related receptors participate in a diverse array of physiological processes. Although the natural ligand for the BRS-3 receptor has not yet been identified, bombesin-like peptides are widely distributed in the central nervous system and the gastrointestinal tract, where they bind to bombesin receptor subtype 3 (BRS-3), neuromedin B, and gastrin-releasing peptide (GRP-R) receptors, and modulate smooth muscle contraction, exocrine and endocrine processes, metabolism and behavior. BRS-3 has been implicated in the regulation of neuroendocrine function and energy metabolism (Ohki et al. Nature 390: 165-69 (1997)). One study showed that mice lacking the bombesin subtype-3 (BRS-3) receptor develop metabolic defects and obesity (Ohki et al. Nature 390: 165-69 (1997)). Specifically, mice lacking functional BRS-3 are hyperphagic and have a reduced metabolic rate, reduced core temperature which leads to the development of obesity, insulin resistance, diabetes and hypertension as they age. Additionally, bombesin-like peptides may contribute to the pathogenesis of some human carcinomas (For review' see Lebacq-Verheyden et ale in Handbook of Experime'tal Pharmacology, Sporn, M. N. and Roberts, A. B., eds., Vol. 95, pp. 71-124, Springer-Nierlag, Berlin). There is also evidence of a role for BRS-3 in cell growth and wound repair (Tan et al. Peptides 27:1852-58 (2006)) and its distribution in the rat gastrointestinal tract suggests a role in regulation of gut motility (Porcher et al., Cell Tissue Res 320:21-31 (2005)).

BRS-3 agonists to treat obesity/diabetes are disclosed in WO 2005/080390, WO 2005/056532, and WO 2003/104196. Imidazole compounds useful for the treatment of obesity and/or diabetes have been disclosed in WO 04/058176, WO 04/071447, WO 04/048351, WO 04/046091, WO 05/035551, US 2005/0187277 and US 2005/0272778. Other imidazoles are disclosed in U.S. Pat. No. 4,962,117, US 2002/009116, US 2005/0130973, WO 93/17681, WO 98/28269, WO 99/32454, WO 04/007464, WO 04/046091, WO 04/048351, JP 2003-321455, and JP 7-243068.

Weight loss drugs that are currently used in monotherapy for the treatment of obesity have limited efficacy and significant side effects. Because of the unresolved deficiencies of the various pharmacological agents used in the treatment of obesity and diabetes, there is a continuing need for a weight loss treatment with enhanced efficacy and fewer undesirable side effects. The instant invention addresses this problem by providing bombesin receptor agonists, and in particular selective agonists of the bombesin receptor subtype-3 (BRS-3), useful in the treatment and prevention of obesity, diabetes, obesity-related disorders, and diabetes related disorders.

SUMMARY OF THE INVENTION

The present invention relates to novel substituted imidazoles of formula I:

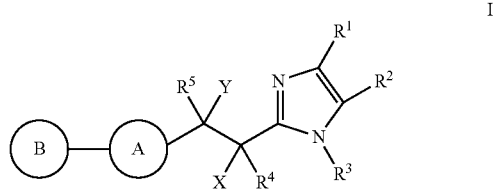

The compounds of formula I are effective as bombesin receptor subtype-3 ligands and are particularly effective as selective ligands of the bombesin receptor subtype-3. They are therefore useful for the treatment and/or prevention of disorders responsive to the modulation of the bombesin receptor subtype 3, such as obesity, diabetes, obesity-related disorders and diabetes-related disorders.

The present invention also relates to pharmaceutical compositions comprising the compounds of the present invention and a pharmaceutically acceptable carrier.

The present invention also relates to methods for the treatment or prevention of disorders, diseases, or conditions responsive to the modulation of the bombesin receptor subtype-3 in a mammal in need thereof by administering the compounds and pharmaceutical compositions of the present invention.

The present invention further relates to the use of the compounds of the present invention in the preparation of a medicament useful for the treatment or prevention of disorders, diseases, or conditions responsive to the modulation of the bombesin receptor subtype-3 in a mammal in need thereof by administering the compounds and pharmaceutical compositions of the present invention.

DETAILED DESCRIPTION OF THE INVENTION

The present invention relates to substituted imidazoles useful as bombesin receptor modulators, in particular, as selective bombesin receptor subtype-3 agonists. Compounds of the present invention are described by formula I:

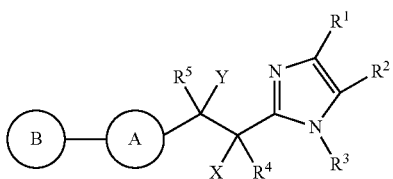

I or a pharmaceutically acceptable salt thereof; wherein
A is ring selected from the group consisting of:
(1) aryl, and
(2) heteroaryl,
wherein aryl and heteroaryl are unsubstituted or substituted with 0 to 4 substituents selected from $R^6$;
B is a mono- or bicyclic ring selected from the group consisting of:
(1) —$C_{3-8}$cycloalkyl,
(2) —$C_{3-8}$cycloalkenyl,
(3) —$C_{2-8}$heterocycloalkyl,
(4) —$C_{2-8}$heterocycloalkenyl,
(5) -aryl, and
(6) -heteroaryl,
wherein cycloalkyl, cycloalkenyl, heterocycloalkyl, heterocycloalkenyl, aryl, and heteroaryl are unsubstituted or substituted with 0 to 4 substituents selected from $R^7$;
X is independently selected from the group consisting of:
(1) hydrogen,
(2) —$C_{1-6}$alkyl,
(3) —$C_{2-8}$alkenyl,
(4) —$C_{2-8}$alkynyl,
(5) —$(CH_2)_nC_{3-7}$cycloalkyl,
(6) —$(CH_2)_nC_{2-7}$heterocycloalkyl,
(7) —$(CH_2)_n$aryl,
(8) —$(CH_2)_n$heteroaryl,
(9) —$CF_3$,
(10) halogen,
(11) —$OR^{11}$,
(12) —$OCF_3$,
(13) —$COR^9$,
(14) —$CO_2R^{11}$,
(15) —$CON(R^9)_2$,
(16) —$N(R^{11})_2$,
(17) —$N(R^9)C(O)C_{1-6}$alkyl,
(18) —$N(R^9)CO_2R^{11}$,
(19) —$N(R^9)SO_2C_{1-6}$alkyl,
(20) —$N(R^9)SO_2N(R^9)_2$,
(21) —SH,
(22) —$S(O)_{0-2}C_{1-6}$alkyl, and
(23) —$SO_2N(R^{11})_2$,
wherein alkyl, alkenyl, alkynyl, cycloalkyl, heterocycloalkyl, aryl, heteroaryl and —$(CH_2)_n$ are unsubstituted or substituted with one to five substituents selected from $R^8$, and wherein X and $R^4$ together with the atoms to which they are attached may form a 3-6 membered cycloalkyl ring containing 0-3 heteroatoms independently selected from oxygen, sulfur, and $NR^9$, and wherein the 3-6 membered cycloalkyl ring is unsubstituted or substituted with 1 to 4 substituents selected from $R^8$, provided that at least one of X, Y, $R^4$ and $R^5$ is not hydrogen;
Y is independently selected from the group consisting of:
(1) halogen,
(2) —$OR^{11}$,
(3) —$OCF_3$,
(4) —$COR^9$,
(5) —$CO_2R^9$,
(6) —$CON(R^9)_2$,
(7) —CN,
(8) —$N(R^{11})_2$,
(9) —$N(R^9)C(O)C_{1-6}$alkyl,
(10) —$N(R^9)CO_2R^{11}$,
(11) —$N(R^9)SO_2C_{1-6}$alkyl,
(12) —$N(R^9)SO_2N(R^9)_2$,
(13) —SH,
(14) —$S(O)_{0-2}C_{1-6}$alkyl, and
(15) —$SO_{0-2}N(R^{11})_2$,
wherein alkyl is unsubstituted or substituted with one to five substituents selected from $R^8$, and wherein Y and $R^6$ or Y and $R^5$ together with the atoms to which they are attached may form a 3-6 membered cycloalkyl ring containing 0-3 heteroatoms independently selected from oxygen, sulfur, and $NR^9$, and wherein the 3-6 membered cycloalkyl ring is unsubstituted or substituted with 1 to 4 substituents selected from $R^8$;
$R^1$ and $R^2$ are each independently selected from the group consisting of:
(1) hydrogen,
(2) —$(CH_2)_n$halogen,
(3) —$(CH_2)_nOR^{11}$,
(4) —$(CH_2)_nCN$,
(5) —$(CH_2)_nCF_3$,
(6) —$(CH_2)_nCHF_2$,
(7) —$(CH_2)_nCH_2F$,
(8) —$(CH_2)_nCCl_3$,
(9) —$C_{1-8}$alkyl,
(10) —$(CH_2)_nC_{2-8}$alkenyl,
(11) —$(CH_2)_nC_{2-8}$alkynyl,
(12) —$(CH_2)_nC_{3-10}$cycloalkyl,
(13) —$(CH_2)_nC_{3-10}$cycloalkenyl,
(14) —$(CH_2)_nC_{2-12}$heterocycloalkyl,
(15) —$SC_{1-8}$alkyl,
(16) —$SC_{3-8}$cycloalkyl,
(17) —$(CH_2)_n$aryl,
(18) —$(CH_2)_n$heteroaryl,
(19) —$(CH_2)_nCO_2R^9$, and
(20) —$(CH_2)_nCOC_{1-8}$alkyl,
provided that $R^1$ and $R^2$ are not both hydrogen, wherein alkyl, alkenyl, alkynyl, cycloalkyl, cycloalkenyl, heterocycloalkyl, aryl, heteroaryl, and $(CH_2)_n$ are unsubstituted or substituted with 1 to 5 substituents selected from $R^{10}$, and wherein two $R^{10}$ substituents together with the atom to which they are attached may form a 3-6 membered cycloalkyl or cycloalkenyl ring containing 0 to 3 heteroatoms independently selected from oxygen, sulfur, and $NR^9$, and wherein the 3-6 membered cycloalkyl or cycloalkenyl ring is unsubstituted or substituted with 1 to 4 substituents selected from $R^{10}$;

$R^3$ is selected from the group consisting of:
(1) hydrogen,
(2) —$C_{1-6}$alkyl, and
(3) —$COC_{1-6}$alkyl;

$R^4$ and $R^5$ are each independently selected from the group consisting of:
(1) hydrogen,
(2) halogen,
(3) —$C_{1-6}$alkyl,
(4) —$(CH_2)_nC_{3-8}$cycloalkyl,
(5) —$(CH_2)_nC_{2-8}$heterocycloalkyl,
(6) —$C_{1-6}$alkoxy,
(7) —OH,
(8) —$CH_2F$,
(9) —$CHF_2$,
(10) —$CF_3$,
(11) —CN,
(12) —$SR^{11}$,
(13) aryl, and
(14) heteroaryl,
wherein alkyl, alkoxy, cycloalkyl, heterocycloalkyl, aryl, heteroaryl, and $(CH_2)_n$ are unsubstituted or substituted with one to five substituents selected from $R^8$;

$R^6$ is selected from the group consisting of:
(1) —$C_{1-6}$alkyl,
(2) —$(CH_2)_n$halogen,
(3) —$(CH_2)_nOR^{11}$,
(4) —$(CH_2)_nCN$,
(5) —$(CH_2)_nCF_3$,
(6) —$(CH_2)_nCO_2R^9$,
(7) —$(CH_2)_nN(R^{11})_2$,
(8) —$(CH_2)_nNO_2$,
(9) —$(CH_2)_nNR^9COC_{1-6}$alkyl,
(10) —$(CH_2)_nNR^9CO_2C_{1-6}$alkyl,
(11) —$(CH_2)_nNR^9SO_2C_{1-6}$alkyl, and
(12) —$(CH_2)_nSO_{0-2}C_{1-6}$alkyl,
wherein alkyl is substituted with 1 to 3 halogens;

$R^7$ is selected from the group consisting of:
(1) —$(CH_2)_n$halogen,
(2) —$C_{1-6}$alkyl,
(3) —$C_{2-6}$alkenyl,
(4) —$(CH_2)_nC_{3-8}$cycloalkyl,
(5) —$(CH_2)_n$heterocycloalkyl,
(6) oxo,
(7) —$(CH_2)_nOR^{11}$,
(8) —$(CH_2)_nCN$,
(9) —$(CH_2)_nCOR^9$,
(10) —$(CH_2)_nCO_2R^{11}$,
(11) —$(CH_2)_nCONR^9N(R^9)_2$,
(12) —$(CH_2)_nO(CH_2)_nCO_2R^9$,
(13) —$(CH_2)_nNO_2$,
(14) —$(CH_2)_nCON(R^9)_2$,
(15) —$(CH_2)_nN(R^{11})_2$,
(16) —$(CH_2)_nNR^9(CH_2)_nCO_2R^9$,
(17) —$(CH_2)_nNR^9COC_{1-6}$alkyl,
(18) —$(CH_2)_nSO_2N(R^9)_2$,
(19) —$(CH_2)_nNR^9SO_2C_{1-6}$alkyl,
(20) —$(CH_2)_nSO_{0-2}R^{11}$,
(21) —$(CH_2)_nOP(O)_2OH$,
(22) —CH=N—OH,
(23) —$(CH_2)_n$aryl,
(24) —$(CH_2)_n$heteroaryl, and
(25) —$(CH_2)_nO(CH_2)_n$heteroaryl,
wherein alkyl, alkenyl, cycloalkyl, heterocycloalkyl, aryl, heteroaryl, and —$(CH_2)_n$ are unsubstituted or substituted with 1 to 3 halogens;

$R^8$ is selected from the group consisting of:
(1) oxo,
(2) —OH,
(3) halogen,
(4) —CN,
(5) —$CF_3$,
(6) —$CHF_2$,
(7) —$CH_2F$,
(8) —$C_{1-8}$alkyl,
(9) —$C_{1-8}$alkoxy,
(10) —$COC_{1-8}$alkyl,
(11) —$CO_2C_{1-8}$alkyl, and
(12) —$CO_2H$,
wherein each alkyl and alkoxy carbon is unsubstituted or substituted with 1 to 3 halogen substituents;

$R^9$ is selected from the group consisting of:
(1) hydrogen, and
(2) —$C_{1-6}$alkyl,
wherein alkyl is unsubstituted or substituted with 1 to 3 substituents selected from halogen and —OH;

$R^{10}$ is independently selected from the group consisting of:
(1) halogen,
(2) —OH,
(3) oxo,
(4) —CN,
(5) —$CCl_3$,
(6) —$CF_3$,
(7) —$CHF_2$,
(8) —$CH_2F$,
(9) —$SO_2C_{1-6}$alkyl,
(10) —$COC_{1-8}$alkyl,
(11) —$CO_2C_{1-8}$alkyl,
(12) —$CO_2H$,
(13) —$C_{1-8}$alkyl, and
(14) —$C_{1-8}$alkoxy,
wherein alkyl and alkoxy are unsubstituted or substituted with 1 to 4 substituents selected from —$C_{1-6}$alkyl and halogen, and wherein the —$C_{1-6}$alkyl substituent is unsubstituted or substituted with 1 to 3 halogens;

$R^{11}$ is selected from the group consisting of:
(1) hydrogen,
(2) —$C_{1-6}$alkyl,
(3) —$C_{3-8}$cycloalkyl,
(4) —$C_{2-7}$heterocycloalkyl,
(5) —$(CH_2)_m$phenyl, and
(6) —$(CH_2)_n$heteroaryl,
wherein alkyl, cycloalkyl, and heterocycloalkyl are unsubstituted or substituted with 1 to 3 halogens or —OH, and wherein phenyl and heteroaryl are unsubstituted or substituted with 1-3 halogens;
each n is independently 0, 1, 2, 3 or 4; and
each m is independently 1, 2, 3 or 4.

In a further embodiment of the compounds of the present invention, there are provided compounds of formula II:

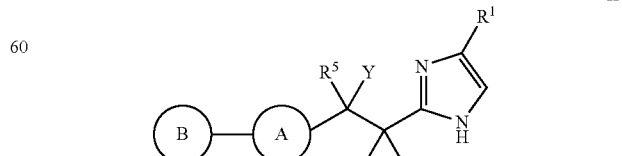

II or a pharmaceutically acceptable salt thereof.

In a further embodiment of the compounds of the present invention, there are provided compounds of formula III:

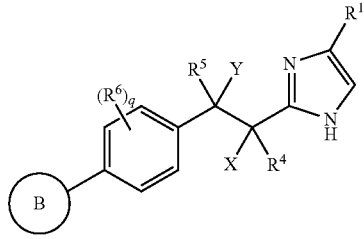

or a pharmaceutically acceptable salt thereof.

In one embodiment of the invention, A is a mono or bicyclic ring selected from the group consisting of: phenyl, pyridinyl, thienyl, triazolyl, oxazolyl, oxadiazolyl; thiazolyl, and thiadiazolyl, wherein A is unsubstituted or substituted with 0 to 4 substituents selected from $R^6$, provided that when A and B are phenyl, then A is not substituted with halogen.

In another embodiment of the invention, A is a mono or bicyclic ring selected from the group consisting of: phenyl, pyridinyl, thienyl, triazolyl, oxazolyl, oxadiazolyl, thiazolyl, and thiadiazolyl,
wherein A is unsubstituted or substituted with 0 to 4 substituents selected from $R^6$. In a class of this embodiment, A is phenyl unsubstituted or substituted with 0 to 4 substituents selected from $R^6$. In another class of this embodiment, A is pyridinyl unsubstituted or substituted with 0 to 4 substituents selected from $R^6$. In yet another class of this embodiment, A is thienyl unsubstituted or substituted with 0 to 4 substituents selected from $R^6$.

In another embodiment of the present invention, ring A and ring B are connected via a carbon-carbon bond. In another embodiment of the present invention, ring A and ring B are connected via a carbon-nitrogen bond. In another embodiment of the present invention, ring A and ring B are connected via a nitrogen-carbon bond. In another embodiment of the present invention ring A and ring B are connected via a nitrogen-nitrogen bond.

In another embodiment of the present invention, ring A and the ethylene linker carbon substituted with Y and $R^5$ are connected via a carbon-carbon bond. In another embodiment of the present invention, ring A and the ethylene linker carbon substituted with Y and $R^5$ are connected via a nitrogen-carbon bond.

In another embodiment of the invention, Ring A is selected from the group consisting of:

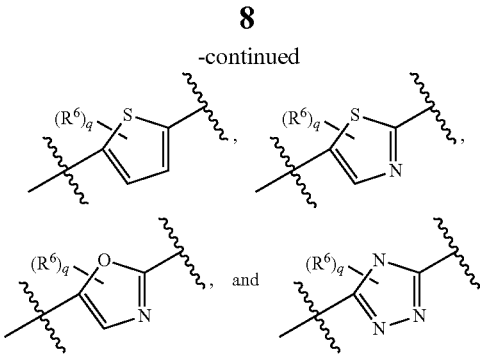

In a subclass of this embodiment, A is selected from the group consisting of:

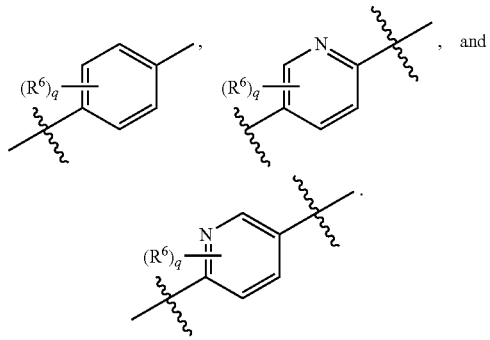

In a subclass of this embodiment, A is selected from the group consisting of:

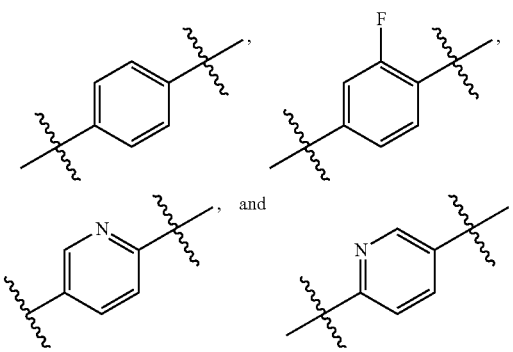

In another embodiment of the present invention, B is a mono- or bicyclic ring selected from the group consisting of: —$C_{3-8}$cycloalkyl, —$C_{3-8}$cycloalkenyl, —$C_{2-8}$heterocycloalkyl, —$C_{2-8}$heterocycloalkenyl, -aryl, and -heteroaryl, wherein cycloalkyl, cycloalkenyl, heterocycloalkyl, heterocycloalkenyl, aryl, and heteroaryl are unsubstituted or substituted with 0 to 4 substituents selected from $R^7$.

In another embodiment of the present invention, B is a mono- or bicyclic ring selected from the group consisting of: —$C_{3-8}$cycloalkyl, —$C_{2-8}$heterocycloalkyl, -aryl, and -heteroaryl, wherein cycloalkyl, heterocycloalkyl, aryl, and heteroaryl are unsubstituted or substituted with 0 to 4 substituents selected from $R^7$.

In another embodiment of this invention, B is a mono- or bicyclic ring selected from the group consisting of: —$C_{3-8}$cycloalkyl, -aryl, and -heteroaryl, wherein cycloalkyl, aryl, and heteroaryl are unsubstituted or substituted with 0 to 4 substituents selected from $R^7$.

In another embodiment of the invention, B is a ring selected from the group consisting of: cyclopentyl, oxazole, isooxazole, phenyl, pyridine, pyrazole, triazole, thiazole, isothiazole, thiophene, thiadiazole, and (1,4,5,6)tetrahydro-7H-pyrazolo-{3,4-b}-pyridine-7-yl, wherein B is unsubstituted or substituted with 0 to 4 substituents selected from $R^7$. In a class of this embodiment, B is cyclopentyl. In another class of this embodiment, B is phenyl unsubstituted or substituted with 0 to 4 substituents selected from $R^7$. In another class of this embodiment, B is pyridine unsubstituted or substituted with 0 to 4 substituents selected from $R^7$. In another class of this embodiment, B is pyrazole unsubstituted or substituted with 0 to 4 substituents selected from $R^7$. In another class of this embodiment, B is triazole unsubstituted or substituted with 0 to 4 substituents selected from $R^7$. In another class of this embodiment, B is thiazole unsubstituted or substituted with 0 to 4 substituents selected from $R^7$. In another class of this embodiment, B is isothiazole unsubstituted or substituted with 0 to 4 substituents selected from $R^7$. In another class of this embodiment, B is thiophene unsubstituted or substituted with 0 to 4 substituents selected from $R^7$. In another class of this embodiment, B is thiadiazole unsubstituted or substituted with 0 to 4 substituents selected from $R^7$. In another class of this embodiment, B is (1,4,5,6)tetrahydro-7H-pyrazolo-{3,4-b}-pyridine-7-yl unsubstituted or substituted with 0 to 4 substituents selected from $R^7$.

In another embodiment of the invention, Ring B is selected from the group consisting of:

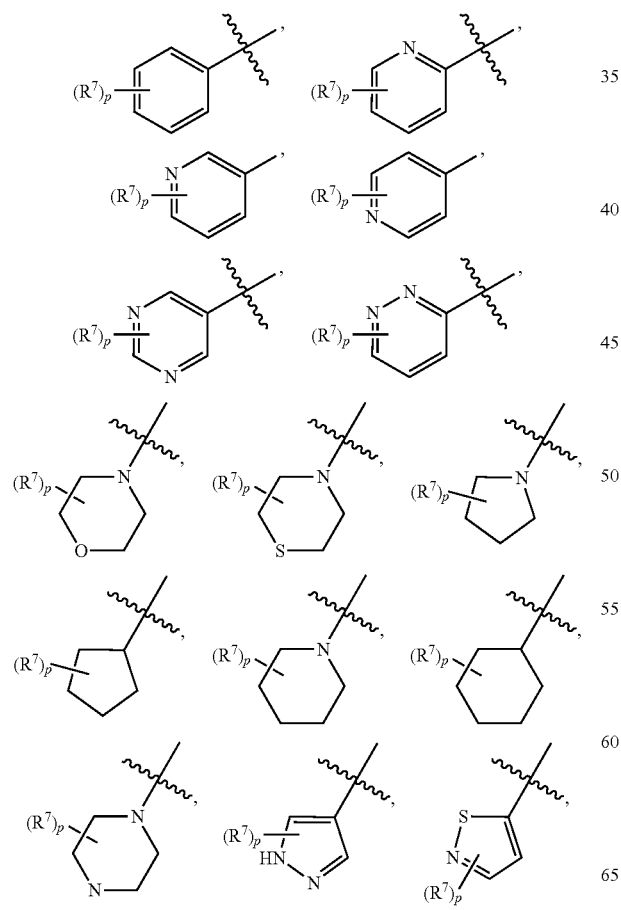

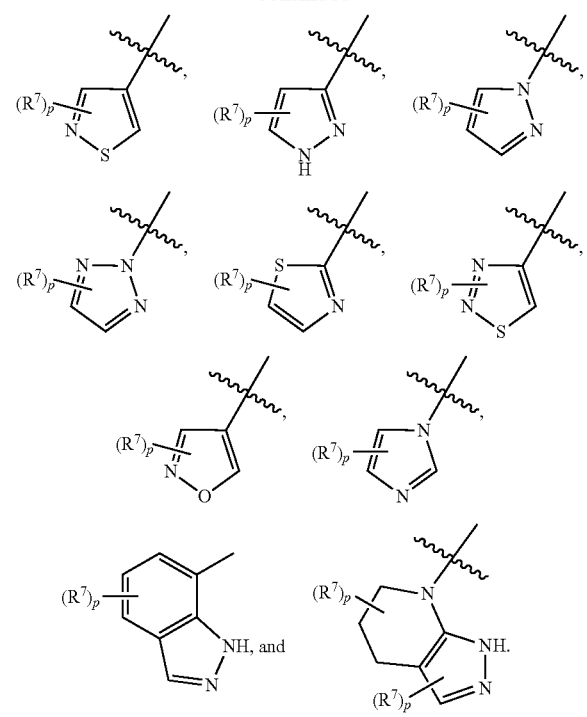

In a class of this embodiment, p is 0.

In a class of this embodiment, Ring B is selected from the group consisting of:

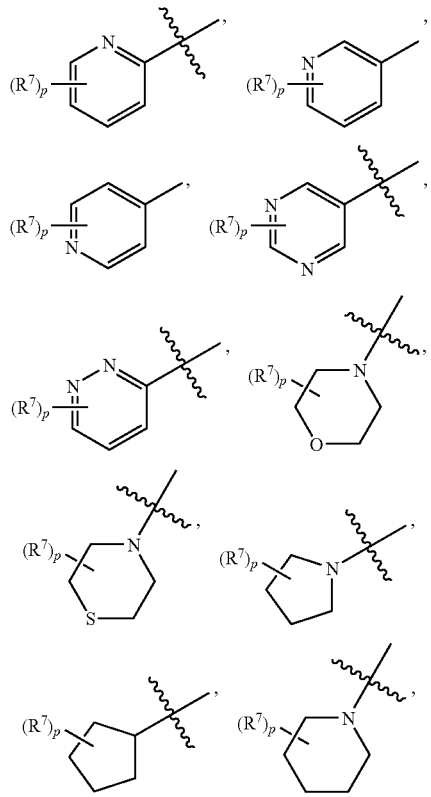

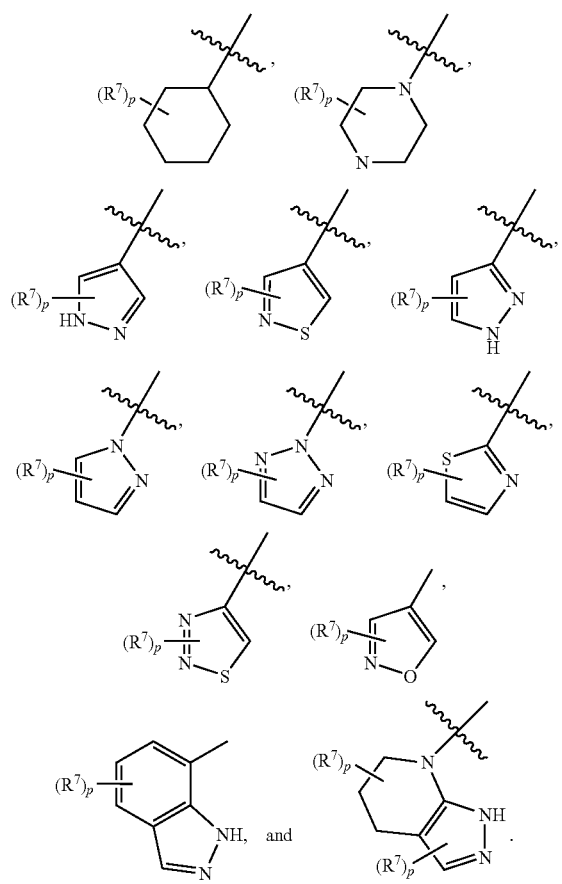
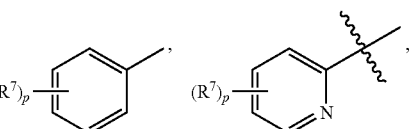
In a subclass of this class, p is 0.
In another class of this embodiment, B is selected from the group consisting of:
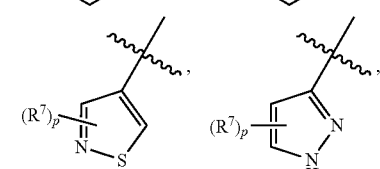
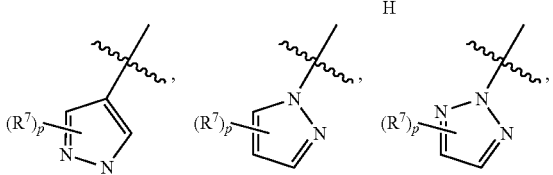
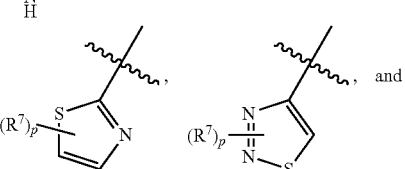
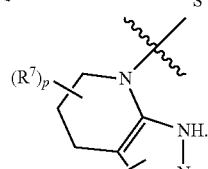
In a subclass of this class, p is 0.
In another class of this embodiment, B is selected from the group consisting of:
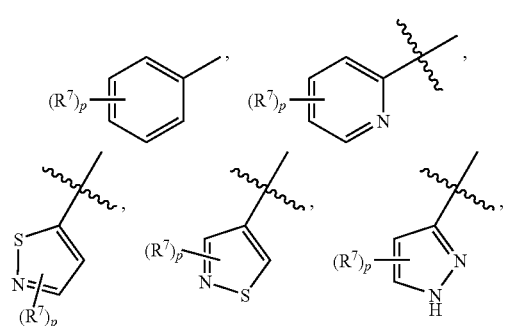
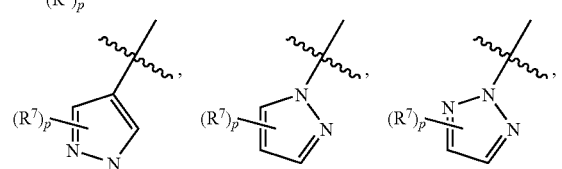
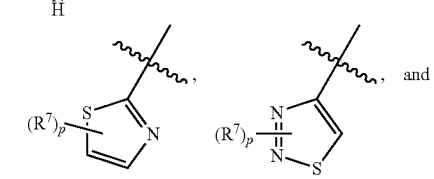
In a subclass of this class, p is 0.
In another class of this embodiment, B is selected from the group consisting of:
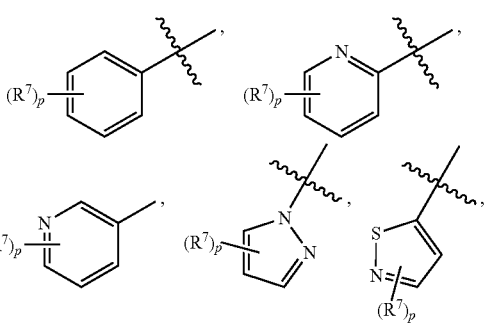

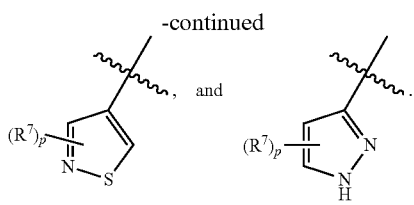

In a subclass of this class, p is 0.

In another class of this embodiment, B is selected from the group consisting of:

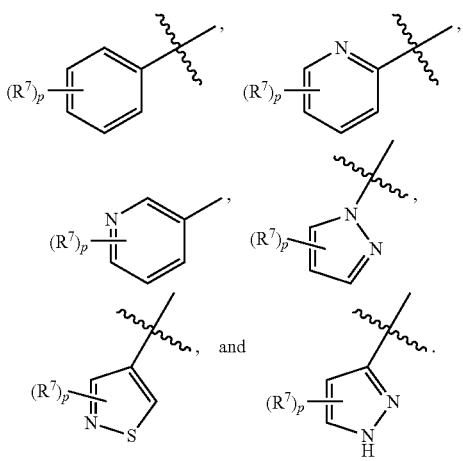

In a subclass of this class, p is 0.

In yet another class of this embodiment, B is selected from the group consisting of:

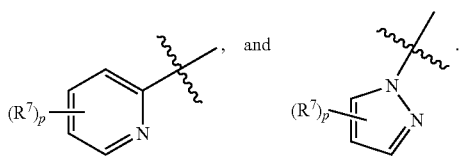

In another subclass of this class, B is

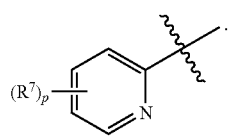

In a subclass of this subclass, p is 0.
In another subclass of this class, B is

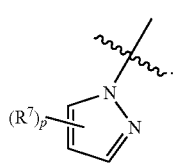

In a subclass of this subclass, p is 0.

In another embodiment of the present invention, X is independently selected from the group consisting of: hydrogen, —$C_{1-6}$alkyl, —$C_{2-8}$alkenyl, —$C_{2-8}$alkynyl, —$(CH_2)_nC_{3-7}$cycloalkyl, —$(CH_2)_nC_{2-7}$heterocycloalkyl, —$(CH_2)_n$aryl, —$(CH_2)_n$heteroaryl, —$CF_3$, halogen, —OH, —$OCF_3$, —$OC_{1-6}$alkyl, —$COR^9$, —$CO_2R^9$, —$CON(R^9)_2$, —$N(R^{11})_2$, —$N(R^9)C(O)C_{1-6}$alkyl, —$N(R^9)CO_2R^{11}$, —$N(R^9)SO_2C_{1-6}$alkyl, —$N(R^9)SO_2N(R^9)_2$, —SH, and —$S(O)_{0-2}C_{1-6}$alkyl, wherein alkyl, alkenyl, alkynyl, cycloalkyl, heterocycloalkyl, aryl and heteroaryl are unsubstituted or substituted with one to five substituents selected from $R^8$, and wherein X and $R^4$ together with the atom to which they are attached may form a 3-6 membered cycloalkyl ring containing 0-3 heteroatoms independently selected from oxygen, sulfur, and $NR^9$, wherein the 3-6 membered cycloalkyl ring is unsubstituted or substituted with 1 to 4 substituents selected from $R^8$, provided that at least one of X, Y, $R^4$ and $R^5$ is not hydrogen.

In another embodiment of the present invention, X is independently selected from the group consisting of: hydrogen, —$C_{1-6}$alkyl, —$C_{2-8}$alkenyl, —$C_{2-8}$alkynyl, —$(CH_2)_nC_{3-7}$cycloalkyl, —$(CH_2)_nC_{2-7}$heterocycloalkyl, —$(CH_2)_n$aryl, —$(CH_2)_n$heteroaryl, —$CF_3$, halogen, —OH, —$OCF_3$, —$OC_{1-6}$alkyl, —$COR^9$, —$CO_2R^9$, —$CON(R^9)_2$, —$N(R^{11})_2$, —$N(R^9)C(O)C_{1-6}$alkyl, —$N(R^9)CO_2R^{11}$, —$N(R^9)SO_2C_{1-6}$alkyl, —$N(R^9)SO_2N(R^9)_2$, —SH, and —$S(O)_{0-2}C_{1-6}$alkyl, wherein alkyl, alkenyl, alkynyl, cycloalkyl, heterocycloalkyl, aryl and heteroaryl are unsubstituted or substituted with one to five substituents selected from $R^8$, and wherein X and $R^4$ together with the atom to which they are attached may form a 3-6 membered cycloalkyl ring containing 0-3 heteroatoms independently selected from oxygen, sulfur, and $NR^9$, wherein the 3-6 membered cycloalkyl ring is unsubstituted or substituted with 1 to 4 substituents selected from $R^8$, provided that at least one of X, Y, $R^4$ and $R^5$ is not hydrogen.

In another embodiment of this invention, X is independently selected from the group consisting of: hydrogen, —$C_{1-6}$ alkyl, —$C_{2-8}$alkenyl, —$C_{2-8}$alkynyl, —$(CH_2)_nC_{3-7}$cycloalkyl, —$(CH_2)_nC_{2-7}$heterocycloalkyl, —$(CH_2)_n$aryl, —$(CH_2)_n$heteroaryl, —$CF_3$, halogen, —OH, —$OCF_3$, —$OC_{1-6}$alkyl, —$COR^9$, —$CO_2R^9$, —$CON(R^9)_2$, —$N(R^{11})_2$, —$N(R^9)C(O)C_{1-6}$alkyl, —$N(R^9)CO_2R^{11}$, —$N(R^9)SO_2C_{1-6}$alkyl, —$N(R^9)SO_2N(R^9)_2$, —SH, and —$SC_{1-6}$alkyl, wherein alkyl, alkenyl, alkynyl, cycloalkyl, heterocycloalkyl, aryl and heteroaryl are unsubstituted or substituted with one to five substituents selected from $R^8$, and wherein X and $R^4$ together with the atom to which they are attached may form a 3-6 membered cycloalkyl ring containing 0-3 heteroatoms independently selected from oxygen, sulfur, and $NR^9$, wherein the 3-6 membered cycloalkyl ring is unsubstituted or substituted with 1 to 4 substituents selected from $R^8$; provided that at least one of X, Y, $R^4$ and $R^5$ is not hydrogen.

In another embodiment of this invention, X is independently selected from the group consisting of: hydrogen, —$C_{1-6}$ alkyl, —$C_{2-8}$alkenyl, —$C_{2-8}$alkynyl, —$(CH_2)_nC_{3-7}$ cycloalkyl, —$(CH_2)_nC_{2-7}$heterocycloalkyl, —$(CH_2)_n$aryl, —$(CH_2)_n$heteroaryl, —$CF_3$, halogen, —OH, —$OCF_3$, —$OC_{1-6}$alkyl, —$COR^9$, —$CO_2R^9$, —$CON(R^9)_2$, —$N(R^{11})_2$, —$N(R^9)C(O)C_{1-6}$alkyl, —$N(R^9)CO_2R^{11}$, —$N(R^9)SO_2C_{1-6}$alkyl, —$N(R^9)SO_2N(R^9)_2$, SH, and —$SC_{1-6}$alkyl, wherein alkyl, alkenyl, alkynyl, cycloalkyl, heterocycloalkyl, aryl and heteroaryl are unsubstituted or substituted with one to five substituents selected from $R^8$; provided that at least one of X, Y, $R^4$ and $R^5$ is not hydrogen.

In another embodiment of the invention, X is independently selected from the group consisting of: hydrogen, halogen, and —OH, provided that at least one of X, Y, $R^4$ and $R^5$ is not hydrogen. In one class of this embodiment, X is hydrogen, provided that at least one of X, Y, $R^4$ and $R^5$ is not hydrogen. In another class of this embodiment, X is fluorine. In another class of this embodiment, X is —OH.

In another embodiment of the present invention, Y is independently selected from the group consisting of: halogen, —OH, —OCF$_3$, —OC$_{1-6}$alkyl, —COR$^9$, —CO$_2$R$^9$, —CON(R$^9$)$_2$, —CN —N(R$^{11}$)$_2$, —N(R$^9$)C(O)C$_{1-6}$alkyl, —N(R$^9$)CO$_2$R$^{11}$, —N(R$^9$)SO$_2$C$_{1-6}$alkyl, —N(R$^9$)SO$_2$N(R$^9$)$_2$, —SH, and —S(O)$_{0-2}$C$_{1-6}$alkyl, wherein alkyl and cycloalkyl are unsubstituted or substituted with one to five substituents selected from $R^8$, and wherein Y and $R^5$ together with the atoms to which they are attached may form a 3-6 membered cycloalkyl ring containing 0-3 heteroatoms independently selected from oxygen, sulfur, and NR$^9$, wherein the 3-6 membered cycloalkyl ring is unsubstituted or substituted with 1 to 4 substituents selected from $R^8$.

In another embodiment of the present invention, Y is independently selected from the group consisting of: halogen, —OH, —OCF$_3$, —COR$^9$, —CO$_2$R$^9$, —CON(R$^9$)$_2$, —CN —N(R$^{11}$)$_2$, —N(R$^9$)C(O)C$_{1-6}$alkyl, —N(R$^9$)CO$_2$R$^{11}$, —N(R$^9$)SO$_2$C$_{1-6}$alkyl, —N(R$^9$)SO$_2$N(R$^9$)$_2$, —SH, and —S(O)$_{0-2}$C$_{1-6}$alkyl, wherein alkyl and cycloalkyl are unsubstituted or substituted with one to five substituents selected from $R^8$, and wherein Y and $R^5$ together with the atoms to which they are attached may form a 3-6 membered cycloalkyl ring containing 0-3 heteroatoms independently selected from oxygen, sulfur, and NR$^9$, wherein the 3-6 membered cycloalkyl ring is unsubstituted or substituted with 1 to 4 substituents selected from $R^8$.

In another embodiment of the invention, Y is independently selected from the group consisting of: halogen, —OH, —OCF$_3$, —OC$_{1-6}$alkyl, —COR$^9$, —CO$_2$R$^9$, —CON(R$^9$)$_2$, —N(R$^{11}$)$_2$, —N(R$^9$)C(O)C$_{1-6}$alkyl, —N(R$^9$)CO$_2$R$^{11}$, —N(R$^9$)SO$_2$C$_{1-6}$alkyl, —N(R$^9$)SO$_2$N(R$^9$)$_2$, —SH, and —SC$_{1-6}$alkyl, wherein alkyl and cycloalkyl are unsubstituted or substituted with one to five substituents selected from $R^8$, and wherein Y and $R^5$ together with the atoms to which they are attached may form a 3-6 membered cycloalkyl ring containing 0-3 heteroatoms independently selected from oxygen, sulfur, and NR$^9$, wherein the 3-6 membered cycloalkyl ring is unsubstituted or substituted with 1 to 4 substituents selected from $R^8$.

In another embodiment of the invention, Y is independently selected from the group consisting of: halogen, —OH, —OC$_{1-6}$alkyl, —N(R$^{11}$)$_2$, —N(R$^9$)C(O)C$_{1-6}$alkyl, —N(R$^9$)CO$_2$R$^{11}$, —N(R$^9$)SO$_2$C$_{1-6}$alkyl, SH and —SC$_{1-6}$alkyl, wherein alkyl and cycloalkyl are unsubstituted or substituted with one to five substituents selected from $R^8$, and wherein Y and $R^5$ together with the atoms to which they are attached may form a 3-6 membered cycloalkyl ring containing 0-3 heteroatoms independently selected from oxygen, sulfur, and NR$^9$, wherein the 3-6 membered ring is unsubstituted or substituted with 1 to 4 substituents selected from $R^8$. In another embodiment of this invention, Y is independently selected from the group consisting of: halogen, —OH, —OC$_{1-6}$alkyl, —CO$_2$R$^9$, —CON(R$^9$)$_2$, —N(R$^{11}$)$_2$, —N(R$^9$)C(O)C$_{1-6}$alkyl, —NHCO$_2$CH$_3$, and —N(R$^9$)SO$_2$C$_{1-6}$alkyl, wherein alkyl is unsubstituted or substituted with one to five substituents selected from $R^8$, and wherein Y and $R^5$ together with the atoms to which they are attached may form a 3-6 membered cycloalkyl ring containing 0-3 heteroatoms independently selected from oxygen, sulfur, and NR$^9$, wherein the 3-6 membered ring is unsubstituted or substituted with 1 to 4 substituents selected from $R^8$. In a class of this embodiment, Y is independently selected from the group consisting of: fluorine, chlorine, —OH, —OCH$_3$, —CO$_2$H, —CO$_2$CH$_3$, —CONH$_2$, —NH$_2$, —NHCH$_3$, —NHCOCH$_3$, —NHCO$_2$CH$_3$, and —NHSO$_2$CH$_3$, wherein alkyl and cycloalkyl are unsubstituted or substituted with one to five substituents selected from $R^8$, and wherein Y and $R^5$ together with the atoms to which they are attached may form a 3-6 membered cycloalkyl ring containing 0-3 heteroatoms independently selected from oxygen, sulfur, and NR$^9$, wherein the 3-6 membered cycloalkyl ring is unsubstituted or substituted with 1 to 4 substituents selected from $R^8$. In another class of this embodiment, the ring formed by Y and $R^5$ is selected from dithiane and pyrrolidine and wherein dithiane and pyrrolidine are unsubstituted or substituted with 1 to 4 substituents selected from $R^8$.

In another embodiment, Y is —OH, and $R^5$ is selected from the group consisting of: hydrogen, CH$_3$, CH$_2$CH$_3$, cyclopropyl, CF$_3$, and CHF$_2$. In a class of this embodiment, Y is —OH and $R^5$ is hydrogen. In another class of this embodiment, Y is —OH and $R^5$ is CF$_3$. In another class of this embodiment, Y is —OH and $R^5$ is CH$_3$. In another embodiment, Y is fluorine, and $R^5$ is selected from the group consisting of: hydrogen, CH$_3$, and fluorine. In another embodiment, Y and $R^5$ form a ring selected from a pyrrolidine ring and dithiane ring. In a class of this embodiment, Y and $R^5$ form a dithiane ring.

In another embodiment of the present invention, $R^1$ and $R^2$ are each independently selected from the group consisting of: hydrogen, —(CH$_2$)$_n$halogen, —(CH$_2$)$_n$OR$^{11}$, —(CH$_2$)$_n$CN, —(CH$_2$)$_n$CF$_3$, —(CH$_2$)$_n$CHF$_2$, —(CH$_2$)$_n$CH$_2$F, —(CH$_2$)$_n$CCl$_3$, —C$_{1-8}$alkyl, —(CH$_2$)$_n$C$_{2-8}$alkenyl, —(CH$_2$)$_n$C$_{2-8}$alkynyl, —(CH$_2$)$_n$C$_{3-10}$cycloalkyl, —(CH$_2$)$_n$C$_{3-10}$cycloalkenyl, —(CH$_2$)$_n$C$_{2-12}$heterocycloalkyl, —SC$_{1-8}$alkyl, —SC$_{3-8}$cycloalkyl, —(CH$_2$)$_n$aryl, —(CH$_2$)$_n$heteroaryl, —(CH$_2$)$_n$CO$_2$R$^9$ and —(CH$_2$)$_n$COC$_{1-8}$alkyl, provided that $R^1$ and $R^2$ are not both hydrogen, wherein alkyl, alkenyl, alkynyl, cycloalkyl, cycloalkenyl, heterocycloalkyl, aryl, heteroaryl, and (CH$_2$)$_n$ are unsubstituted or substituted with 1 to 5 substituents selected from $R^{10}$, and wherein two $R^{10}$ substituents together with the atom to which they are attached may form a 3-6 membered cycloalkyl or cycloalkenyl ring containing 0 to 3 heteroatoms independently selected from oxygen, sulfur, and NR$^9$, wherein the 3-6 membered cycloalkyl or cycloalkenyl ring is unsubstituted or substituted with 1 to 4 substituents selected from $R^{10}$.

In another embodiment of the present invention, $R^1$ and $R^2$ are each independently selected from the group consisting of: hydrogen, —(CH$_2$)$_n$halogen, —(CH$_2$)$_n$OH, —(CH$_2$)$_n$CN, —(CH$_2$)$_n$CF$_3$, —(CH$_2$)$_n$CHF$_2$, —(CH$_2$)$_n$CH$_2$F, —C$_{1-8}$alkyl, —(CH$_2$)$_n$C$_{2-8}$alkenyl, —(CH$_2$)$_n$C$_{2-8}$alkynyl, —(CH$_2$)$_n$C$_{3-8}$cycloalkyl, —SC$_{1-8}$alkyl, —SC$_{1-8}$cycloalkyl, —(CH$_2$)$_n$C$_{2-8}$heterocycloalkyl, —(CH$_2$)$_n$phenyl, and —(CH$_2$)$_n$heteroaryl, provided that $R^1$ and $R^2$ are not both hydrogen, wherein alkyl, alkenyl, alkynyl, cycloalkyl, heterocycloalkyl, phenyl, heteroaryl, and (CH$_2$)$_n$ are unsubstituted or substituted with 1 to 4 substituents selected from $R^{10}$.

In another embodiment of the present invention, $R^1$ and $R^2$ are each independently selected from the group consisting of: hydrogen, halogen, —(CH$_2$)$_n$OH, —(CH$_2$)$_n$CN, —(CH$_2$)$_n$CF$_3$, —(CH$_2$)$_n$CHF$_2$, —(CH$_2$)$_n$CH$_2$F, —C$_{1-8}$alkyl, —(CH$_2$)$_n$C$_{2-8}$alkenyl, —(CH$_2$)$_n$C$_{2-8}$alkynyl, —C$_{1-6}$alkoxy, —(CH$_2$)$_n$C$_{3-8}$cycloalkyl, —N(R$^9$)C(O)C$_{1-6}$alkyl, —SC$_{1-8}$alkyl, —SC$_{1-8}$cycloalkyl, —(CH$_2$)$_n$heterocycloalkyl, —(CH$_2$)$_n$phenyl, —(CH$_2$)$_n$heteroaryl, provided that $R^1$ and $R^2$ are not both hydrogen, wherein alkyl, alkenyl, alkynyl, alkoxy, cycloalkyl, heterocycloalkyl, phenyl, heteroaryl, and (CH$_2$)$_n$ are unsubstituted or substituted with 1 to 4 substituents selected from $R^{10}$.

In another embodiment, $R^1$ and $R^2$ are each independently selected from the group consisting of: hydrogen, —(CH$_2$)$_n$OH, —(CH$_2$)$_n$CN, —(CH$_2$)$_n$CF$_3$, —(CH$_2$)$_n$CHF$_2$, —(CH$_2$)$_n$CH$_2$F, —C$_{1-8}$alkyl, —(CH$_2$)$_n$C$_{2-8}$alkenyl, —(CH$_2$)$_n$C$_{3-8}$cycloalkyl, provided that $R^1$ and $R^2$ are not both hydrogen, wherein alkyl, alkenyl, alkynyl, alkoxy, cycloalkyl, heterocycloalkyl, phenyl, heteroaryl, and $(CH_2)_n$ are unsubstituted or substituted with 1 to 4 substituents selected from $R^{10}$. In another embodiment, $R^1$ and $R^2$ are each independently selected from the group consisting of: halogen, —$(CH_2)_nOH$, —$(CH_2)_nCN$, —$(CH_2)_nCF_3$, —$(CH_2)_nCHF_2$, —$(CH_2)_nCH_2F$, —$C_{1-8}$alkyl, —$(CH_2)_nC_{2-8}$alkenyl, —$(CH_2)_nC_{3-8}$cycloalkyl, —$SC_{1-8}$cycloalkyl, and —$(CH_2)_n$phenyl, wherein alkyl, alkenyl, cycloalkyl, phenyl, and $(CH_2)_n$ are unsubstituted or substituted with 1 to 4 substituents selected from $R^{10}$. In a class of this embodiment, $R^1$ and $R^2$ are each independently selected from the group consisting of: F, Cl, Br, I, —$CH_2C(CH_3)_2CH_2OH$, —$CH_2C(CH_3)_2CH_2OH$, —$CH_2C(CH_3)_2C(CF_3)OH$, —$CH_2C(CH_3)_2CH_2CN$, —$CH_2C(CH_3)_2CF_3$, —$CH_2C(CH_3)_2CHF_2$, —$CH_2C(CH_3)_2F$, —$CH(CH_3)C(CH_3)_2F$, —$CH_3$, —$CH_2CH_3$, —$CH_2C(CH_3)_3$, —$CH_2C(CH_3)_2CH_3$, —$CH_2C(F)(CH_2CH_3)CH_3$, —$CH_2C(CH_3)_2CH_2CH_3$, —$(CH_2)_3CH_3$, —$CH_2C(CF_3)(CH_3)CH_2CH_3$, —$CH=CH_2$, —$CH_2C(CH_3)_2CH=CH_2$, —$CH_2C(CF_3)(CH_3)CH=CH_2$, —$CH_2$-cyclobutyl-$CF_3$, —$CH_2$-cyclopropyl-$CF_3$, —$CH_2$-cyclopropyl-$CH_3$, —$CH_2C(CH_3)_2$cyclopropyl, —$CH_2$cyclopentyl, —S-cyclopentyl, and phenyl.

In another embodiment of the present invention, $R^1$ is selected from the group consisting of: hydrogen, —$(CH_2)_n$halogen, —$(CH_2)_nOR^{11}$, —$(CH_2)_nCN$, —$(CH_2)_nCF_3$, —$(CH_2)_nCHF_2$, —$(CH_2)_nCH_2F$, —$(CH_2)_nCCl_3$, —$C_{1-8}$alkyl, —$(CH_2)_nC_{2-8}$alkenyl, —$(CH_2)_nC_{2-8}$alkynyl, —$(CH_2)_nC_{3-10}$cycloalkyl, —$(CH_2)_nC_{3-10}$cycloalkenyl, —$(CH_2)_nC_{2-12}$heterocycloalkyl, —$SC_{1-8}$alkyl, —$SC_{3-8}$cycloalkyl, —$(CH_2)_n$aryl, —$(CH_2)_n$heteroaryl, —$(CH_2)_nCO_2R^9$, and —$(CH_2)_nCOC_{1-8}$alkyl, provided that $R^1$ and $R^2$ are not both hydrogen, wherein alkyl, alkenyl, alkynyl, cycloalkyl, cycloalkenyl, heterocycloalkyl, aryl, heteroaryl, and $(CH_2)_n$ are unsubstituted or substituted with 1 to 5 substituents selected from $R^{10}$, and wherein two $R^{10}$ substituents together with the atom to which they are attached may form a 3-6 membered cycloalkyl or cycloalkenyl ring containing 0 to 3 heteroatoms independently selected from oxygen, sulfur, and $NR^9$, wherein the 3-6 membered cycloalkyl or cycloalkenyl ring is unsubstituted or substituted with 1 to 4 substituents selected from $R^{10}$.

In another embodiment of the present invention, $R^1$ is selected from the group consisting of: hydrogen, —$(CH_2)_n$halogen, —$(CH_2)_nOH$, —$(CH_2)_nCN$, —$(CH_2)_nCF_3$, —$(CH_2)_nCHF_2$, —$(CH_2)_nCH_2F$, —$C_{1-8}$alkyl, —$(CH_2)_nC_{2-8}$alkenyl, —$(CH_2)_nC_{2-8}$alkynyl, —$(CH_2)_nC_{3-8}$cycloalkyl, —$SC_{1-8}$alkyl, —$SC_{1-8}$cycloalkyl, —$(CH_2)_n$ $C_{2-8}$heterocycloalkyl, —$(CH_2)_n$phenyl, and —$(CH_2)_n$heteroaryl, provided that $R^1$ and $R^2$ are not both hydrogen, wherein alkyl, alkenyl, alkynyl, cycloalkyl, heterocycloalkyl, phenyl, heteroaryl, and $(CH_2)_n$ are unsubstituted or substituted with 1 to 4 substituents selected from $R^{10}$.

In another embodiment, wherein $R^1$ is independently selected from the group consisting of: —$(CH_2)_nOH$, —$(CH_2)_n$ CN, —$(CH_2)_nCF_3$, —$(CH_2)_nCHF_2$, —$(CH_2)_nCH_2F$, —$C_{1-8}$alkyl, —$(CH_2)_nC_{2-8}$alkenyl, and —$(CH_2)_nC_{3-8}$cycloalkyl, wherein alkyl, cycloalkyl, and $(CH_2)_n$ are unsubstituted or substituted with 1 to 4 substituents selected from $R^{10}$; or a pharmaceutically acceptable salt thereof.

In another embodiment of the invention, $R^1$ is independently selected from the group consisting of: hydrogen, —$(CH_2)_nOH$, —$(CH_2)_nCN$, —$(CH_2)_nCF_3$, —$(CH_2)_nCHF_2$, —$(CH_2)_nCH_2F$, —$C_{1-8}$alkyl, —$(CH_2)_nC_{2-8}$alkenyl, —$(CH_2)_nC_{3-8}$cycloalkyl, wherein alkyl, alkenyl, cycloalkyl, and $(CH_2)_n$ are unsubstituted or substituted with 1 to 4 substituents selected from $R^{10}$. In a class of this embodiment, $R^1$ is independently selected from the group consisting of: hydrogen, —$CH_2C(CH_3)_2CH_2OH$, —$CH_2C(CH_3)_2CH_2CN$, —$CH_2C(CH_3)_2CF_3$, —$CH_2C(CH_3)_2CHF_2$, —$CH_2C(CH_3)_2F$, —$CH(CH_3)C(CH_3)_2F$, —$CH_2C(CH_3)_3$, —$CH_2C(CH_3)_2CH_3$, —$CH_2C(F)(CH_2CH_3)CH_3$, —$CH_2C(CH_3)_2CH_2CH_3$, —$(CH_2)_3CH_3$, —$CH=C(CH_3)_2$, —$CH_2$-cyclobutyl-$CF_3$, —$CH_2$-cyclopropyl-$CF_3$, —$CH_2$-cyclopropyl-$CH_3$, —$CH_2$cyclopentyl, wherein alkyl, cycloalkyl, and $(CH_2)_n$ are unsubstituted or substituted with 1 to 4 substituents selected from $R^{10}$.

In another embodiment of the present invention, $R^2$ is independently selected from the group consisting of: hydrogen, halogen, —$(CH_2)_nOH$, —$C_{1-8}$alkyl, —$(CH_2)_nC_{2-8}$alkenyl, —$(CH_2)_nC_{3-8}$cycloalkyl, —$SC_{1-8}$cycloalkyl, and —$(CH_2)_n$phenyl, wherein alkyl, alkenyl, cycloalkyl, phenyl, and $(CH_2)$n are unsubstituted or substituted with 1 to 4 substituents selected from $R^{10}$. In a class of this embodiment, $R^2$ is independently selected from the group consisting of: hydrogen, F, Cl, Br, I, —$CH_2C(CH_3)_2C(CF_3)OH$, —$CH_3$, —$CH_2CH_3$, —$CH_2C(CH_3)_3$, —$CH_2C(CH_3)_2CH_2CH_3$, —$CH_2C(CF_3)(CH_3)CH_2CH_3$, —$CH=CH_2$, —$CH_2C(CH_3)_2CH=CH_2$, —$CH_2C(CF_3)(CH_3)CH=CH_2$, —$CH_2$-cyclopropyl-$CF_3$, —$CH_2C(CH_3)_2$cyclopropyl, —S-cyclopentyl, and phenyl. In another class of this embodiment, $R^2$ is hydrogen.

In another embodiment of the invention, $R^3$ is selected from the group consisting of: hydrogen, —$C_{1-6}$alkyl, and —$COC_{1-6}$alkyl. In a class of this embodiment, $R^3$ is selected from the group consisting of: hydrogen, —$CH_3$, and —$COCH_3$. In another class of this embodiment, $R^3$ is hydrogen.

In another embodiment of the present invention, $R^4$ and $R^5$ are each independently selected from the group consisting of: hydrogen, halogen, —$C_{1-6}$alkyl, —$(CH_2)_nC_{3-8}$cycloalkyl, —$(CH_2)_nC_{2-8}$heterocycloalkyl, —$C_{1-6}$alkoxy, —OH, —$CH_2F$, —$CHF_2$, —$CF_3$, —CN, —SH, —$SC_{1-6}$alkyl, aryl, and heteroaryl, wherein alkyl, alkoxy, cycloalkyl, heterocycloalkyl, aryl, heteroaryl, and $(CH_2)_n$ are unsubstituted or substituted with one to five substituents selected from $R^8$.

In another embodiment of the present invention, $R^4$ and $R^5$ are each independently selected from the group consisting of: hydrogen, halogen, —$C_{1-6}$alkyl, —$(CH_2)_nC_{3-8}$cycloalkyl, —$(CH_2)_nC_{2-8}$heterocycloalkyl, —OH, —$CH_2F$, —$CHF_2$, —$CF_3$, —CN, —SH, —$SC_{1-6}$alkyl, aryl, and heteroaryl, wherein alkyl, alkoxy, cycloalkyl, heterocycloalkyl, aryl, heteroaryl, and $(CH_2)_n$ are unsubstituted or substituted with one to five substituents selected from $R^8$.

In another embodiment of the invention, $R^4$ and $R^5$ are each independently selected from the group consisting of: hydrogen, halogen, —$C_{1-6}$alkyl, —$(CH_2)_nC_{3-8}$cycloalkyl, —OH, —$CHF_2$, and —$CF_3$, wherein alkyl, cycloalkyl, and $(CH_2)_n$ are unsubstituted or substituted with one to five substituents selected from $R^8$. In another embodiment of the invention, $R^4$ and $R^5$ are each independently selected from the group consisting of: hydrogen, F, Cl, —$CH_3$, —$CH_2CH_3$, —$(CH_2)_3CH_3$, cyclopropyl, —OH, —$CHF_2$, and —$CF_3$, wherein alkyl, cycloalkyl, and $(CH_2)_n$ are unsubstituted or substituted with one to five substituents selected from $R^8$.

In another embodiment, $R^4$ is independently selected from the group consisting of: hydrogen, halogen, and —$C_{1-6}$alkyl, wherein alkyl is unsubstituted or substituted with one to five substituents selected from $R^8$. In a class of this embodiment, $R^4$ is independently selected from the group consisting of: hydrogen, F, Cl, —$CH_3$, —$CH_2CH_3$, —$(CH_2)_3CH_3$, —OH, and —$CF_3$.

In another embodiment of the invention, $R^5$ is independently selected from the group consisting of: hydrogen, halogen, $-C_{1-6}$alkyl, $-(CH_2)C_{3-8}$cycloalkyl, $-CHF_2$, and $-CF_3$, wherein alkyl, cycloalkyl and $(CH_2)_n$ are unsubstituted or substituted with one to five substituents selected from $R^8$. In a class of this embodiment of the invention, $R^5$ is independently selected from the group consisting of: hydrogen, $-C_{1-6}$alkyl, $-(CH_2)C_{3-8}$cycloalkyl, $-CHF_2$, and $-CF_3$, wherein alkyl, cycloalkyl and $(CH_2)_n$ are unsubstituted or substituted with one to five substituents selected from $R^8$. In a subclass of this class, $R^5$ is independently selected from the group consisting of: hydrogen, $-CH_3$, $-CH_2CH_3$, $-(CH_2)_3CH_3$, cyclopropyl, $-CHF_2$ and $-CF_3$.

In another embodiment of the present invention, $R^6$ is selected from the group consisting of:
$-C_{1-6}$alkyl, $-(CH_2)_n$halogen, $-(CH_2)_nOR^{11}$, $-(CH_2)_n$CN, $-(CH_2)_nCF_3$, $-(CH_2)_nCO_2R^9$, $-(CH_2)_nN(R^{11})_2$, $-(CH_2)_nNO_2$, $-(CH_2)_nNR^9COC_{1-6}$alkyl, $-(CH_2)_nNR^9CO_2C_{1-6}$alkyl, $-(CH_2)_nNR^9SO_2C_{1-6}$alkyl, and $-(CH_2)_nSO_{0-2}C_{1-6}$alkyl, wherein alkyl is substituted with 1 to 3 halogens. In another embodiment of the present invention, $R^6$ is selected from the group consisting of: $-C_{1-6}$alkyl, halogen, $-OR^{11}$, $-CN$, $-CO_2R^9$, $-N(R^{11})_2$, $-NHCOC_{1-6}$ alkyl, $-NHCO_2C_{1-6}$alkyl, $-NHSO_2C_{1-6}$alkyl and $-SO_{0-2}C_{1-6}$alkyl. In another embodiment of the present invention, $R^6$ is selected from the group consisting of: $-C_{1-6}$alkyl, halogen, $-OR^{11}$, $-CN$, $-N(R^{11})_2$, $-NHCO_2C_{1-6}$alkyl, and $-SO_{0-2}C_{1-6}$alkyl.

In another embodiment of the present invention, $R^6$ is selected from the group consisting of: $-C_{1-6}$alkyl, halogen, $-OC_{1-6}$alkyl, $-CN$, $-CO_2H$, $-CO_2C_{1-6}$alkyl, $-OH$, $-NH_2$, $-NHCOC_{1-6}$alkyl, $-NHCO_2C_{1-6}$alkyl, and $-SOC_{1-6}$alkyl. In another embodiment of the present invention, $R^6$ is selected from the group consisting of: $-C_{1-6}$alkyl, halogen, $-OC_{1-6}$alkyl, $-CN$, $-OH$, $-NH_2$, $-NHCOC_{1-6}$alkyl, $-NHCO_2C_{1-6}$alkyl, and $-SOC_{1-6}$alkyl.

In another embodiment of the present invention, $R^6$ is selected from the group consisting of: $-C_{1-6}$alkyl, halogen, $-OC_{1-6}$alkyl, $-CN$, $-OH$, $-NH_2$, $-NHCO_2C_{1-6}$alkyl, and $-SOC_{1-6}$alkyl. In another embodiment of the invention, $R^6$ is selected from the group consisting of: $-C_{1-6}$alkyl, halogen, $-NHCO_2C_{1-6}$alkyl, and $-SOC_{1-6}$alkyl. In a class of this embodiment, $R^6$ is selected from the group consisting of: $-CH_3$ F, Cl, $-NHCO_2$t-butyl, and $-SOCH_3$. In another embodiment of this invention, $R^6$ is selected from $-C_{1-6}$alkyl, or halogen.

In another embodiment of the present invention, $R^7$ is selected from the group consisting of: $-(CH_2)_n$halogen, $-C_{1-6}$alkyl, $-C_{2-6}$alkenyl, $-(CH_2)_nC_{3-8}$cycloalkyl, $-(CH_2)_n$heterocycloalkyl, oxo, $-(CH_2)_nOR^{11}$, $-(CH_2)_n$CN, $-(CH_2)_nCOR^9$, $-(CH_2)_nCO_2R^{11}$, $-(CH_2)_n$CONR$^9$N(R$^9$)$_2$, $-(CH_2)_nO(CH_2)_nCO_2R^9$, $-(CH_2)_nNO_2$, $-(CH_2)_n$CON(R$^9$)$_2$, $-(CH_2)_nN(R^{11})_2$, $-(CH_2)_nNR^9(CH_2)_nCO_2R^9$, $-(CH_2)_nNR^9COC_{1-6}$alkyl, $-(CH_2)_nSO_2N(R^9)_2$, $-(CH_2)_nNR^9SO_2C_{1-6}$alkyl, $-(CH_2)_nSO_{0-2}R^{11}$, $-(CH_2)_n$ OP(O)$_2$OH, $-CH=N-OH$, $-(CH_2)_n$aryl, $-(CH_2)_n$heteroaryl, and $-(CH_2)_nO(CH_2)_n$heteroaryl, wherein alkyl, alkenyl, cycloalkyl, heterocycloalkyl, aryl, heteroaryl, and $-(CH_2)_n$ are unsubstituted or substituted with 1 to 3 halogens. In another embodiment of the present invention, $R^7$ is selected from the group consisting of: $-(CH_2)_n$halogen, $-C_{1-6}$alkyl, $-C_{2-6}$alkenyl, $-(CH_2)_nC_{3-8}$cycloalkyl, $-(CH_2)_n$heterocycloalkyl, $-(CH_2)_nOR^{11}$, $-(CH_2)_n$CN, $-(CH_2)_nCOR^9$, $-(CH_2)_nCO_2R^{11}$, $-(CH_2)_nCONR^9N(R^9)_2$, $-(CH_2)_nO(CH_2)_nCO_2R^9$, $-(CH_2)_nNO_2$, $-(CH_2)_nCON(R^9)_2$, $-(CH_2)_nN(R^{11})_2$, $-(CH_2)_nNR^9(CH_2)_nCO_2R^9$, $-(CH_2)_nNR^9COC_{1-6}$alkyl, $-(CH_2)_nSO_2N(R^9)_2$, $-(CH_2)_n$ NR$^9$SO$_2$C$_{1-6}$alkyl, $-(CH_2)_nSO_{0-2}R^{11}$, $-(CH_2)_nOP(O)_2$OH, $-CH=N-OH$, $-(CH_2)_n$aryl, $-(CH_2)_n$heteroaryl, and $-(CH_2)_nO(CH_2)_n$heteroaryl, wherein alkyl, alkenyl, cycloalkyl, heterocycloalkyl, aryl, heteroaryl, and $-(CH_2)_n$ are unsubstituted or substituted with 1 to 3 halogens.

In another embodiment of the present invention, $R^7$ is selected from the group consisting of: halogen, $-C_{1-6}$alkyl, $-OC_{1-6}$alkyl, $-CN$, $-OH$, oxo, $-COC_{1-6}$alkyl, $-CO_2R^{11}$, $-CON(R^9)_2$, $-CO_2N(R^9)_2$, $-N(R^{11})_2$, $-NHCO_2C_{1-6}$alkyl, $-SOC_{1-6}$alkyl, $-SO_2R^9$, and $-SO_2N(R^9)_2$, wherein alkyl is unsubstituted or substituted with 1 to 3 halogens. In another embodiment of the present invention, $R^7$ is selected from the group consisting of: halogen, $-C_{1-6}$ alkyl, $-OC_{1-6}$alkyl, $-CN$, $-OH$, $-COC_{1-6}$alkyl, $-CO_2R^{11}$, $-CON(R^9)_2$, $-CO_2N(R^9)_2$, $-N(R^{11})_2$, $-NHCO_2C_{1-6}$alkyl, $-SOC_{1-6}$alkyl, $-SO_2R^9$, and $-SO_2N(R^9)_2$, wherein alkyl is unsubstituted or substituted with 1 to 3 halogens. In another embodiment of the present invention, $R^7$ is selected from the group consisting of: halogen, $-C_{1-6}$ alkyl, $-OC_{1-6}$alkyl, $-CN$, $-OH$, $-COC_{1-6}$alkyl, $-CO_2R^{11}$, $-CON(R^9)_2$, $-CO_2N(R^9)_2$, $-N(R^{11})_2$, $-NHCO_2C_{1-6}$alkyl, $-SOC_{1-6}$alkyl, $-SO_2R^9$, and $-SO_2N(R^9)_2$, wherein alkyl is unsubstituted or substituted with 1 to 3 halogens.

In another embodiment of the present invention, $R^7$ is selected from the group consisting of: halogen, $-C_{1-6}$alkyl, $-CN$, $-OH$, $-CON(R^9)_2$, $-CO_2N(R^9)_2$, $-N(R^{11})_2$, $-NHCO_2C_{1-6}$alkyl, $-SOC_{1-6}$alkyl, $-SO_2R^9$, and $-SO_2N(R^9)_2$, wherein alkyl is unsubstituted or substituted with 1 to 3 halogens.

In another embodiment of the present invention, $R^7$ is selected from the group consisting of: halogen, $-C_{1-6}$alkyl, $-OC_{1-6}$alkyl, $-CN$, $-OH$, $-COC_{1-6}$alkyl, $-CO_2R^9$, $-CON(R^9)_2$, $-CO_2N(R^9)_2$, $-NH_2$, $-NHCO_2C_{1-6}$alkyl, $-SOC_{1-6}$alkyl; $-SO_2R^9$, and $-SO_2N(R^9)_2$, wherein alkyl is unsubstituted or substituted with 1 to 3 halogens.

In another embodiment of the invention, $R^7$ is selected from the group consisting of: halogen, $-C_{1-6}$alkyl, $-COC_{1-6}$ alkyl, $-CO_2R^9$, $-CON(R^9)_2$, $-NH_2$, $-NHCO_2C_{1-6}$alkyl, and $-SOC_{1-6}$alkyl; wherein alkyl is unsubstituted or substituted with 1 to 3 halogens. In a class of this embodiment, $R^7$ is selected from the group consisting of: F, Cl, Br, $-CH_3$, $-COCH_3$, $-CO_2H$, $-CO_2CH_3$, $-CONH_2$, $-NH_2$, $-NHCO_2$t-butyl, and $-SOCH_3$. In another embodiment of the invention, $R^7$ is selected from the group consisting of: $-C_{1-6}$alkyl, and $-NH_2$, wherein alkyl is unsubstituted or substituted with 1 to 3 halogens.

In another embodiment of the present invention, $R^8$ is selected from the group consisting of: oxo, $-OH$, halogen, $-CN$, $-CF_3$, $-CHF_2$, $-CH_2F$, and $-C_{1-8}$alkyl, wherein each alkyl carbon is unsubstituted or substituted with 1 to 3 halogen substituents. In a subclass of this class, halogen is fluorine.

In another embodiment of the present invention, $R^{10}$ is independently selected from the group consisting of: halogen, $-OH$, oxo, $-CN$, $-CCl_3$, $-CF_3$, $-CHF_2$, $-CH_2F$, $-SO_2C_{1-6}$alkyl, $-COC_{1-8}$alkyl, $-CO_2C_{1-8}$alkyl, $-CO_2H$, $-C_{1-8}$alkyl, and $-C_{1-8}$alkoxy, wherein alkyl, alkoxy, and $-(CH_2)_n$ are unsubstituted or substituted with 1 to 4 substituents selected from $-C_{1-6}$alkyl and halogen, and wherein the $-C_{1-6}$alkyl substituent is unsubstituted or substituted with 1 to 3 halogens.

In another embodiment of the present invention, $R^{10}$ is independently selected from the group consisting of: halogen, $-OH$, oxo, $-CN$, $-CF_3$, $-SO_2C_{1-6}$alkyl, $-CHF_2$, and $-C_{1-6}$alkyl.

In another embodiment of the present invention, $R^{10}$ is independently selected from the group consisting of: —OH, oxo, $SO_2CH_3$, and —$CF_3$. In another embodiment of the present invention, $R^{10}$ is independently selected from the group consisting of: —OH, oxo, and —$CF_3$.

In another embodiment of the present invention, $R^{11}$ is selected from the group consisting of: hydrogen, —$C_{1-6}$alkyl, —$C_{3-8}$cycloalkyl, —$C_{2-7}$heterocycloalkyl, —$(CH_2)_m$phenyl, and —$(CH_2)_m$heteroaryl, wherein alkyl, cycloalkyl, and heterocycloalkyl are unsubstituted or substituted with 1 to 3 halogens or —OH, and wherein phenyl and heteroaryl are unsubstituted or substituted with 1 to 3 halogens.

In another embodiment of the present invention, $R^{11}$ is selected from the group consisting of: hydrogen, —$C_{3-8}$cycloalkyl, —$C_{1-6}$alkyl, —$(CH_2)_m$phenyl, and —$(CH_2)_m$heteroaryl, wherein each alkyl and cycloalkyl carbon is unsubstituted or substituted with 1 to 3 halogens and each phenyl and heteroaryl carbon is unsubstituted or substituted with one halogen.

In another embodiment of this invention, $R^{11}$ is selected from the group consisting of: hydrogen, —$C_{1-6}$alkyl, and —$(CH_2)_m$phenyl, wherein each alkyl carbon is unsubstituted or substituted with 1 to 3 halogens and each phenyl carbon is unsubstituted or substituted with 1 to 3 halogens.

In another embodiment of the invention, $R^{11}$ is selected from the group consisting of: hydrogen, —$CH_3$, —$CH_2CH_3$, and —$CH_2$phenyl, wherein each alkyl carbon is unsubstituted or substituted with 1 to 3 halogens and each phenyl carbon is unsubstituted or substituted with 1 to 3 halogens. In another embodiment of the invention, $R^{11}$ is selected from the group consisting of: hydrogen, —$CH_3$, and —$CH_2CH_3$, wherein each alkyl carbon is unsubstituted or substituted with 1 to 3 halogens.

In another class of the embodiments, n is 0, 1, 2, 3 or 4. In a subclass of this class, n is 0, 1, 2 or 3. In another subclass of this class, n is 0. In another subclass of this class, n is 1. In another subclass of this class, n is 2. In another subclass of this class, n is 3. In another class of the embodiments, m is 1, 2, 3 or 4. In a subclass of this class, m is 1, 2 or 3. In another subclass of this class, m is 1. In another subclass of this class, m is 2. In another subclass of this class, m is 3. In another class of the embodiments, p is 0, 1, 2, 3 or 4. In a subclass of this class, p is 0, 1, 2 or 3. In a subclass of this class, p is 0. In another subclass of this class, p is 1. In another subclass of this class, p is 2. In another class of the embodiments, q is 0, 1, 2, 3 or 4. In a subclass of this class, q is 0, 1, 2 or 3. In a subclass of this class, q is 0, 1, or 2. In a subclass of this class, q is 0. In another subclass of this class, q is 1. In another subclass of this class, q is 2. In another subclass of this class, q is 3.

Illustrative but nonlimiting examples of compounds of the present invention that are useful as bombesin receptor subtype-3 agonists are the following:

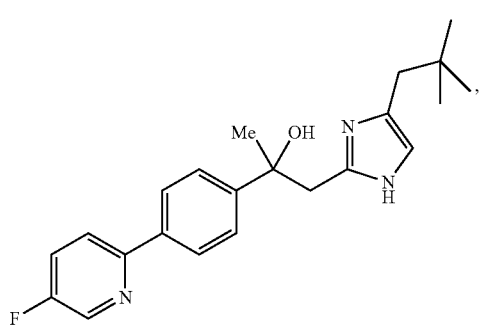

-continued

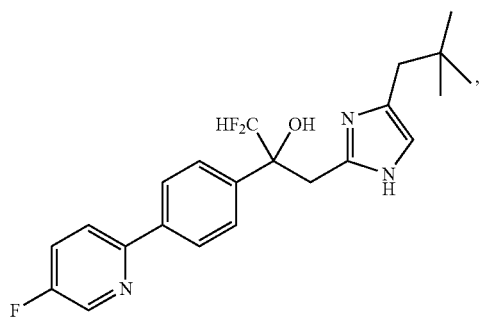

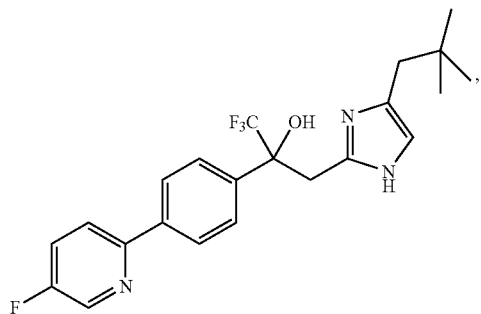

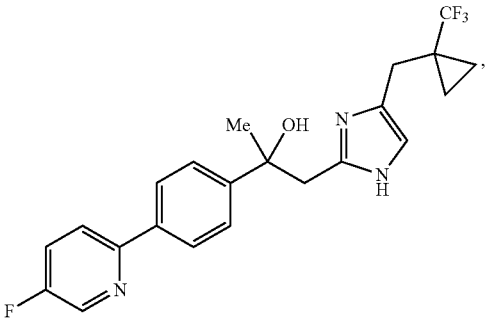

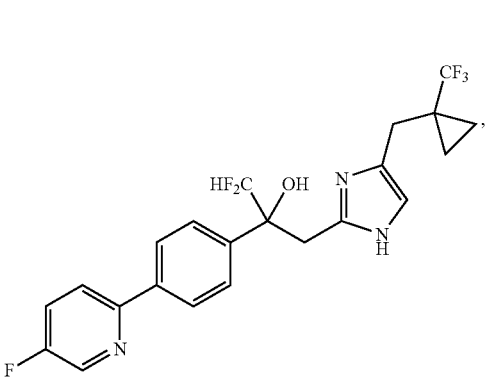

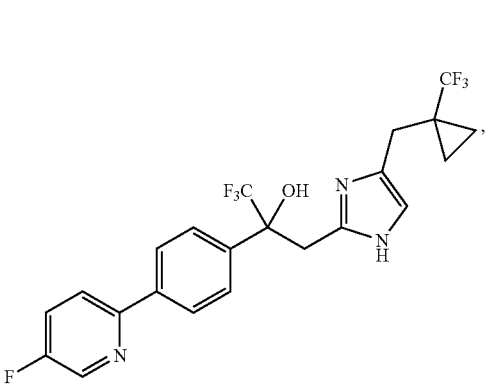

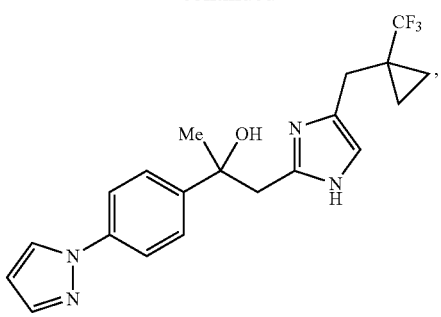

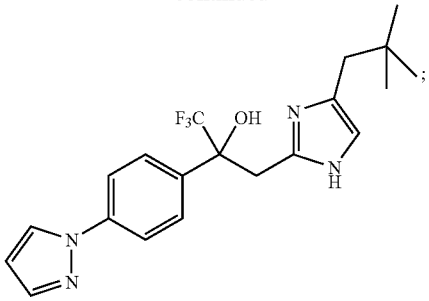

or a pharmaceutically acceptable salt thereof.

The compounds of formula I, II and III are effective as bombesin receptor ligands and are particularly effective as selective ligands of the bombesin-3 receptor. They are therefore useful for the treatment and/or prevention of disorders responsive to the modulation of the bombesin-3 receptor, such as obesity, diabetes, and obesity-related disorders. More particularly, the compounds of formula I, II and III are selective bombesin receptor subtype-3 (BRS-3) agonists useful for the treatment of disorders responsive to the activation of the bombesin-3 receptor, such as obesity, diabetes, as well as the treatment of gallstones.

One aspect of the present invention provides a method for the treatment or prevention of disorders, diseases or conditions responsive to the modulation of the bombesin receptor subtype-3 in a subject in need thereof which comprises administering to the subject a therapeutically or prophylactically effective amount of a compound of formula I, II, or III, or a pharmaceutically acceptable salt thereof.

Another aspect of the present invention provides a method for the treatment or prevention of obesity, diabetes, or an obesity related disorder in a subject in need thereof which comprises administering to said subject a therapeutically or prophylactically effective amount of a bombesin receptor subtype-3 agonist of the present invention. Another aspect of the present invention provides a method for the treatment or prevention of obesity in a subject in need thereof which comprises administering to the subject a therapeutically or prophylactically effective amount of a compound of formula I, II, or III, or a pharmaceutically acceptable salt thereof. Another aspect of the present invention provides a method for reducing food intake in a subject in need thereof which comprises administering to the subject a therapeutically or prophylactically effective amount of a compound of formula I, II, or III, or a pharmaceutically acceptable salt thereof. Another aspect of the present invention provides a method for increasing satiety in a subject in need thereof which comprises administering to the subject a therapeutically or prophylactically effective amount of a compound of formula I, II, or III, or a pharmaceutically acceptable salt thereof. Another aspect of the present invention provides a method for reducing appetite in a subject in need thereof which comprises administering to the subject a therapeutically or prophylactically effective amount of a compound of formula I, II, or III, or a pharmaceutically acceptable salt thereof. Another aspect of the present invention provides a method for reducing gastric emptying in a subject in need thereof which comprises administering to the subject a therapeutically or prophylactically effective amount of a compound of formula I, II, or III, or a pharmaceutically acceptable salt thereof. Another aspect of the present invention provides a method for the treatment or prevention of bulimia nervosa in a subject in need thereof which comprises administering to the subject a therapeutically or prophylactically effective amount of a compound of formula I, II, or III, or a pharmaceutically acceptable salt thereof.

Another aspect of the present invention provides a method for the treatment or prevention of diabetes mellitus in a subject in need thereof comprising administering to the subject a therapeutically or prophylactically effective amount of a compound of formula I, II, or III, or a pharmaceutically acceptable salt thereof. Another aspect of the present invention provides a method for the treatment or prevention of dyslipidemia in a subject in need thereof which comprises administering to the subject a therapeutically or prophylactically effective amount of a compound of formula I, II, or III, or a pharmaceutically acceptable salt thereof.

Another aspect of the present invention provides a method for the treatment or prevention of an obesity-related disorder selected from the group consisting of overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula I, II, or III, or a pharmaceutically acceptable salt thereof.

Another aspect of the present invention provides a method for the treatment or prevention of diabetes, in a subject in need thereof which comprises administering to the subject a therapeutically or prophylactically effective amount of a compound of formula I, II, or III, or a pharmaceutically acceptable salt thereof.

Another aspect of the present invention provides a method for the treatment or prevention of a diabetes related disorder in a subject in need thereof which comprises administering to the subject a therapeutically or prophylactically effective amount of a compound of formula I, II, or III, or a pharmaceutically acceptable salt thereof.

Another aspect of the present invention provides a method for the treatment or prevention of an diabetes related disorder selected from the group consisting of hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, neuropathy, Syndrome X, and ovarian hyperandrogenism (polycystic ovarian syndrome), in a subject in need thereof which comprises administering to the subject a therapeutically or prophylactically effective amount of a compound of formula I, II, or III, or a pharmaceutically acceptable salt thereof.

The present invention also relates to methods for treating or preventing obesity by administering a bombesin receptor subtype-3 agonist of the present invention in combination with a therapeutically or prophylactically effective amount of another agent known to be useful to treat or prevent the condition. The present invention also relates to methods for treating or preventing diabetes by administering the bombesin receptor subtype-3 agonist of the present invention in combination with a therapeutically or prophylactically effective amount of another agent known to be useful to treat or prevent the condition. The present invention also relates to methods for treating or preventing obesity related disorders by administering the bombesin receptor subtype-3 agonist of the present invention in combination with a therapeutically or prophylactically effective amount of another agent known to be useful to treat or prevent the condition.

Yet another aspect of the present invention relates to the use of a therapeutically effective amount of a compound of formula (I), or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or a CB1 antagonist/inverse agonist selected from: rimonabant, N-[3-(4-chlorophenyl)-2(S)-phenyl-1(S)-methylpropyl]-2-(4-trifluoromethyl-2-pyrimidyloxy)-2-methylpropanamide, N-[(1S,2S)-3-(4-chlorophenyl)-2-(3-cyanophenyl)-1-methylpropyl]-2-methyl-2-{[5-(trifluoromethyl)pyridin-2-yl]oxy}propanamide, N-[3-(4-chlorophenyl)-2-(5-chloro-3-pyridyl)-1-methylpropyl]-2-(5-trifluoromethyl-2-pyridyloxy)-2-methylpropanamide, 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol, 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)-benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[1-(3,5-difluorophenyl)-2-fluoro-2-methylpropyl]azetidin-1-yl}methyl)thiophene-3-carbonitrile, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

Another aspect of the present invention provides a pharmaceutical composition comprising a compound of formula I, II and III and a pharmaceutically acceptable carrier.

Yet another aspect of the present invention relates to the use of a compound of formula I, II and III for the manufacture of a medicament useful for the treatment or prevention, or suppression of a disease mediated by the bombesin receptor subtype-3 in a subject in need thereof.

Yet another aspect of the present invention relates to the use of a bombesin-3 agonist of the present invention for the manufacture of a medicament useful for the treatment or prevention, or suppression of a disease mediated by the bombesin-3 receptor, wherein the disease is selected from the group consisting of obesity, diabetes and an obesity-related disorder in a subject in need thereof.

Yet another aspect of the present invention relates to the use of a bombesin-3 agonist of the present invention for the manufacture of a medicament useful for the treatment or prevention of gallstones in a subject in need thereof. Yet another aspect of the present invention relates to the use of a bombesin-3 agonist of the present invention for the manufacture of a medicament useful for the treatment or prevention of dyslipidemia in a subject in need thereof. Yet another aspect of the present invention relates to the use of a bombesin-3 agonist of the present invention for the manufacture of a medicament useful for the treatment or prevention of bulimia nervosa in a subject in need thereof. Yet another aspect of the present invention relates to the use of a bombesin-3 agonist of the present invention for the manufacture of a medicament useful for the treatment or prevention of constipation in a subject in need thereof. Yet another aspect of the present invention relates to the use of a bombesin-3 agonist of the present invention for the manufacture of a medicament useful for the treatment or prevention of irritable bowel syndrome in a subject in need thereof.

Yet another aspect of the present invention relates to the use of a therapeutically effective amount of a bombesin receptor subtype-3 agonist of formula I, II or III, or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4) inhibitor, a glucagon like peptide 1 (GLP-1) agonist, a HMG-CoA reductase inhibitor, a serotonergic agent, a β-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes or an obesity-related disorder in a subject in need of such treatment. Yet another aspect of the present invention relates to the use of a therapeutically effective amount of a bombesin receptor subtype-3 agonist of formula I, II or III, and pharmaceutically acceptable salts and esters thereof, and a therapeutically effective amount of an agent selected from the group consisting of an insulin sensitizer, an insulin mimetic, a sulfonylurea, an α-glucosidase inhibitor, a dipeptydyl peptidase 4 inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist-, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament for treatment or prevention of obesity, diabetes or an obesity-related disorder which comprises an effective amount of a bombesin receptor subtype-3 agonist of formula I, II or III and an effective amount of the agent, together or separately. Yet another aspect of the present invention relates to a product containing a therapeutically effective amount of a bombesin receptor subtype-3 agonist of formula I, II or III, or a pharmaceutically acceptable salt thereof; and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype 3 agonist, a ghrelin receptor antagonist, PYY, $PYY_{3-36}$, and a NK-1 antagonist, or a pharmaceutically acceptable salt thereof, as a combined preparation for simultaneous, separate or sequential use in obesity, diabetes, or an obesity-related disorder.

The compounds of formula I, II and III can be provided in kit. Such a kit typically contains an active compound in dosage forms for administration. A dosage form contains a sufficient amount of active compound such that a beneficial effect can be obtained when administered to a patient during regular intervals, such as 1, 2, 3, 4, 5 or 6 times a day, during the course of 1 or more days. Preferably, a kit contains instructions indicating the use of the dosage form for weight reduction (e.g., to treat obesity) and the amount of dosage form to be taken over a specified time period.

Throughout the instant application, the following terms have the indicated meanings:

The term "alkyl", as well as other groups having the prefix "alk", such as alkoxy, alkanoyl, means carbon chains of the designated length which may be in a straight or branched configuration, or combinations thereof. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

The term "alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

The term "alkoxy" means alkyl chains of the designated length which contain at least one ether linkage and which may be linear or branched or combinations thereof. Examples of alkoxy include methoxy, ethoxy, 1-propoxy, 2-propoxy, 1-butoxy, 2-butoxy, methylmethoxy, methylethoxy, methyl-1-propoxy, methyl-2-propoxy, ethyl-2-methoxy, ethyl-1-methoxy and the like.

The term "halogen" includes fluorine, chlorine, bromine and iodine.

The term "aryl" includes monocyclic aromatic rings containing only carbon atoms, and bicyclic aromatic ring systems, wherein at least one ring is an aromatic ring containing only carbon atoms. Examples of aryl include phenyl, naphthyl, benzodioxole and benzocyclobutene.

The term "heteroaryl" includes monocyclic aromatic rings that contain from 1 to 4 heteroatoms selected from nitrogen, oxygen and sulfur, and bicyclic heteroaromatic ring systems containing at least one aromatic ring that contains from 1 to 4 heteroatoms selected from nitrogen, oxygen and sulfur. Examples thereof include, but are not limited to, pyridinyl, furyl, thienyl, pyrrolyl, oxazolyl, thiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like. In one embodiment of the present invention, heteroaryl is selected from the group consisting of pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl. Bicyclic heteroaromatic rings include, but are not limited to, benzothiadiazole, indole, indazole, benzothiophene, benzofuran, benzimidazole, benzisoxazole, benzothiazole, quinoline, quinazoline, benzotriazole, benzoxazole, isoquinoline, purine, furopyridine, thienopyridine, benzisodiazole, triazolopyrimidine, and 5,6,7,8-tetrahydroquinoline.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, cycloheptyl.

The term "heterocycloalkyl" is intended to include non-aromatic heterocycles containing one to four heteroatoms selected from nitrogen, oxygen and sulfur. Examples of heterocycloalkyls include, but are not limited to, azetidine, piperidine, morpholine, thiamorpholine, pyrrolidine, imidazolidine, tetrahydrofuran, piperazine, 1-thia-4-aza-cyclohexane.

Certain of the above defined terms may occur more than once in the above formula and upon such occurrence each term shall be defined independently of the other; thus for example, $NR^6R^6$ may represent $NH_2$, $NHCH_3$, $N(CH_3)CH_2CH_3$, and the like.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs. The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a bombesin subtype 3 (BRS-3) receptor "agonist" is meant an endogenous or drug substance or compound that can interact with a bombesin subtype 3 receptor and initiate a pharmacological or biochemical response characteristic of bombesin subtype 3 receptor activation. The "agonistic" properties of the compounds of the present invention were measured in the functional assay described below.

By "binding affinity" is meant the ability of a compound/drug to bind to its biological target, in the present instance, the ability of a compound of formula I, II and III, to bind to a bombesin subtype 3 receptor. Binding affinities for the compounds of the present invention were measured in the binding assay described below and are expressed as $IC_{50}$'s.

"Efficacy" describes the relative intensity of response which different agonists produce even when they occupy the same number of receptors and with the same affinity. Efficacy is the property that describes the magnitude of response. Properties of compounds can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention were measured in the functional assay described below. Compounds of formula I, II or III, may contain one or more asymmetric or chiral centers and can exist in different stereoisomeric forms, such as racemates and racemic mixtures, single enantiomers, enantiomeric mixtures, individual diastereomers and diastereomeric mixtures. All stereoisomeric forms of the intermediates and compounds of the present invention as well as mixtures thereof, including racemic and diastereomeric mixtures, which possess properties useful in the treatment of the conditions discussed herein or are intermediates useful in the preparation of compounds having such properties, form a part of the present invention.

The compounds of formula I with the substitution pattern Z correspond to racemates or racemic mixtures which include, but are not limited to, enantiomers Za and Zb; these enantiomers may be separated by chiral chromatography:

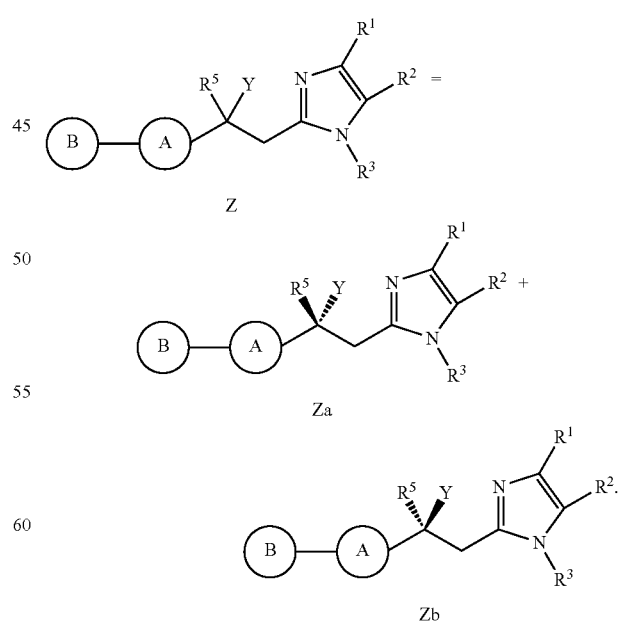

Compounds of structural formula I may be separated into their individual enantiomers and diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula I, II, and III may be obtained by stereospecific synthesis using optically pure starting materials or reagents of known absolute configuration.

It will be understood that the compounds of the present invention include hydrates, solvates, polymorphs, crystalline, hydrated crystalline and amorphous forms of the compounds of the present invention, and pharmaceutically acceptable salts thereof.

Generally, one of the enantiomers will be more active biologically than the other enantiomer. Racemic mixtures can subsequently be separated into each enantiomer using standard conditions, such as resolution or chiral chromatography. Diastereomeric mixtures may be separated into their individual diastereoisomers on the basis of their physical chemical differences by methods well known to those skilled in the art, such as by chiral chromatography using an optically active stationary phase and/or fractional crystallization from a suitable solvent. Absolute stereochemistry may be determined by X-ray crystallography of crystalline products or crystalline intermediates which are derivatized, if necessary, with a reagent containing an asymmetric center of known absolute configuration. Enantiomers may be separated by use of a chiral HPLC column and by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Alternatively, any stereoisomer of a compound of the general formula I, II, and III may be obtained by stereospecific synthesis using optically pure starting materials or reagents of known absolute configuration.

The present invention is meant to comprehend all such isomeric forms of the compounds of formula I, II and III, including the E and Z geometric isomers of double bonds and mixtures thereof. A number of the compounds of the present invention and intermediates therefor exhibit tautomerism and therefore may exist in different tautomeric forms under certain conditions. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is an imidazole moiety where the hydrogen may migrate between the ring nitrogens. Valence tautomers include interconversions by reorganization of some of the bonding electrons. All such tautomeric forms (e.g., all keto-enol and imine-enamine forms) are within the scope of the invention. The depiction of any particular tautomeric form in any of the structural formulas herein is not intended to be limiting with respect to that form, but is meant to be representative of the entire tautomeric set.

The present invention also encompasses isotopically labeled compounds which are identical to the compounds of Formula (I) or intermediates thereof but for the fact that one or more atoms are replaced by an atom having an atomic mass or mass number different from the atomic mass or mass number usually found in nature. Examples of isotopes that can be incorporated into the intermediates or compounds of the invention include isotopes of hydrogen, carbon, nitrogen, oxygen, phosphorus, sulfur, fluorine, iodine, and chlorine, such as 2H, 3H, 11C, 13C, 14C, 13N, 15N, 15O, 17O, 18O, 31P, 32P, 35S, 18F, 123I, 125I and 36Cl, respectively. Compounds of the present invention, prodrugs thereof and pharmaceutically acceptable salts, hydrates and solvates of said compounds and of said prodrugs which contain the aforementioned isotopes and/or other isotopes of other atoms are within the scope of the present invention. Certain isotopically labeled compounds of the present invention (e.g., those labeled with 3H and 14C) are useful in compound and/or substrate tissue distribution assays. Tritiated (i.e., 3H) and carbon-14 (i.e., 14C) isotopes are particularly preferred for their ease of preparation and detectability. Further, substitution with heavier isotopes such as deuterium (i.e., 2H) may afford certain therapeutic advantages resulting from greater metabolic stability (e.g., increased in vivo half-life or reduced dosage requirements) and hence may be preferred in some circumstances. Positron emitting isotopes such as 15O, 13N, 11C, and 18F are useful for positron emission tomography (PET) studies to examine substrate receptor occupancy. Isotopically labeled compounds of the present invention can generally be prepared by following procedures analogous to those disclosed in the Schemes and/or in the Examples herein by substituting an isotopically labeled reagent for a non-isotopically labeled reagent.

The compounds of the present invention and intermediates may exist in unsolvated as well as solvated forms with solvents such as water, ethanol, isopropanol and the like, and both solvated and unsolvated forms are included within the scope of the invention. Solvates for use in the methods aspect of the invention should be with pharmaceutically acceptable solvents. It will be understood that the compounds of the present invention include hydrates, solvates, polymorphs, crystalline, hydrated crystalline and amorphous forms of the compounds of the present invention, and pharmaceutically acceptable salts thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, TEA, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids. It will be understood that, as used herein, references to the compounds of formula I, II and III are meant to also include the pharmaceutically acceptable salts, such as the hydrochloride salt.

Compounds of formula I, II and III are bombesin receptor ligands and as such are useful in the treatment, control or prevention of diseases, disorders or conditions responsive to the modulation of one or more of the bombesin receptors. In particular, the compounds of formula I, II and III act as bombesin receptor subtype-3 agonists useful in the treatment, control or prevention of diseases, disorders or conditions responsive to the activation of the bombesin-3 receptor. Such diseases, disorders or conditions include, but are not limited to, obesity (by reducing food intake, reducing appetite, increasing metabolic rate, increasing satiety, reducing carbohydrate craving, reducing gastric emptying), diabetes mellitus (by enhancing glucose tolerance, decreasing insulin resistance), bulimia nervosa and related eating disorders, dyslipidemia, hypertension, hyperlipidemia, osteoarthritis, cancer, gall stones, cholelithiasis, cholecystitis, gall bladder disease, sleep apnea, depression, anxiety, compulsion, neuroses, irritable bowel syndrome, inflammatory bowel syndrome, constipation, pain, neuroprotective and cognitive and memory enhancement including the treatment of Alzheimer's disease. Such diseases, conditions and disorders also include non-obese overweight conditions and normal weight conditions where weight control or management is desired in order to prevent an obese or overweight condition from developing, or to maintain a healthy weight.

The compounds and compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, bulimia nervosa, hypertension, type 2 diabetes, elevated plasma insulin concentrations, hyperinsulinemia, insulin resistance, glucose intolerance, dyslipidemia, hyperlipidemia, endometrial cancer, breast cancer, prostate cancer, kidney cancer, colon cancer, osteoarthritis, obstructive sleep apnea, cholelithiasis, cholecystitis, gallstones, gout, gallbladder disease, abnormal heart rhythms and arrythmias, myocardial infarction, congestive heart failure, coronary heart disease, angina pectoris, sudden death, stroke, metabolic syndrome, psychological disorders (depression, eating disorders, distorted bodyweight, and low self esteem), and other pathological conditions showing reduced metabolic activity or a decrease in resting energy expenditure as a percentage of total fat-free mass, e.g, children with acute lymphoblastic leukemia. Further examples of obesity-related disorders are sexual and reproductive dysfunction, such as polycystic ovary disease, infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. Additionally, the present compounds are useful in the treatment of any condition in which it is desirable to lose weight or to reduce food intake.

Additionally, the present compounds are useful in the treatment of any condition in which it is desirable to enhance cognition and memory, such as Alzheimer's Disease. The compositions of the present invention are also useful for reducing the risk of secondary outcomes of obesity, such as reducing the risk of left ventricular hypertrophy. Therefore, the present invention provides methods of treatment or prevention of such diseases, conditions and/or disorders modulated by BRS-3 receptor agonists in an animal which comprises administering to the animal in need of such treatment a compound of formula I, II or III, in particular a therapeutically or prophylactically effective amount thereof.

Some agonists encompassed by formula I, II and III show highly selective affinity for the bombesin receptor subtype-3 (BRS-3) relative to the neuromedin B (BB1 or NMBR) receptor and the gastrin releasing peptide (BB2 or GRPR) receptor, which makes them especially useful in the prevention and treatment of obesity, diabetes, and obesity related disorders.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of $\geqq$140 mg/dl and <200 mg/dl); or insulin resistance, resulting in an increased risk of developing diabetes.

"Diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, BRS-3 agonists may also be useful to treat hypertension associated with this condition.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in type 2 diabetes.

Prevention of diabetes mellitus, in particular diabetes associated with obesity, refers to the administration of a compound or combination of the present invention to prevent or treat the onset of diabetes in a subject in need thereof. A subject in need of preventing diabetes in a prediabetic subject.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$. An overweight subject is a subject at risk of obesity.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss. Treatment of obesity also includes treatment of an overweight subject.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, hypertension, dyslipidemia, insulin resistance, hypercholesterolemia, hypertriglyceridemia, and cholelithiasis.

The terms "administration of" and or "administering" a compound should be understood to mean providing a compound of the invention or a prodrug of a compound of the invention to a subject in need of treatment. The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art. The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder. The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a subject or mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I, II and III are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of formula I, II and III are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I, II and III are useful, generally satisfactory results are obtained when the compounds of the present invention are administered at a daily dosage of from about 0.001 milligram to about 50 milligram per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating dyslipidemia, bulimia nervosa, and gallstones satisfactory results are obtained when the compounds of formula I, II and III are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I, II or III per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 600, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compounds of formula I, II and III in an acceptable intranasal formulation may be used.

For use where a composition for intravenous administration is employed, a suitable dosage range is from about 0.001 mg to about 50 mg, preferably from 0.01 mg to about 50 mg, more preferably 0.1 mg to 10 mg, of a compound of formula I, II or III per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of formula I, II and III in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Compounds of formula I, II and III may be used in combination with other drugs that are used in the treatment/prevention/suppression or amelioration of the diseases or conditions for which compounds of formula I, II and III are useful. Such other drugs may be administered, by a route and in an amount commonly used therefor, contemporaneously or sequentially with a compound of formula I, II or III. When a compound of formula I, II or III is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of formula I, II or III.

Examples of other active ingredients that may be combined with a compound of formula I, II and III for the treatment or prevention of obesity and/or diabetes, either administered separately or in the same pharmaceutical compositions, include, but are not limited to:

(a) Anti-diabetic agents, for example, (1) glitazones (e.g., ciglitazone, darglitazone, englitazone, isaglitazone (MCC-555), pioglitazone, rosiglitazone, troglitazone, tularik, BRL49653, CLX-0921, 5-BTZD), and PPAR-γ agonists such as GW-0207, LG-100641 and LY-300512; (2) biguanides such as buformin, metformin and phenformin; (3) protein tyrosine phosphatase-1B (PTP-1B) inhibitors; (4) sulfonylureas such as acetohexamide, chlorpropamide, diabinese, glibenclamide, glipizide, glyburide, glimepiride, gliclazide, glipentide, gliquidone, glisolamide, tolazamide and tolbutamide; (5) meglitinides such as repaglinide, nateglinide, and the like; (6) α-glucosidase inhibitors such as acarbose, adiposine, camiglibose, emiglitate, miglitol, voglibose, pradimicin-Q, salbostatin, CKD-711, MDL-25,637, MDL-73,945, and MOR14; (7) α-amylase inhibitors such as tendamistat, trestatin, and Al-3688; (8) insulin secretagogues such as linogliride, A-4166 and the like; (9) fatty acid oxidation inhibitors such as clomoxir, and etomoxir; (10) α-2 antagonists such as midaglizole, isaglidole, deriglidole, idazoxan, earoxan, and fluparoxan; (11) insulin and insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-$NH_2$; (12) non-thiazolidinediones such as JT-501, farglitazar (GW-2570/GI-262579), and muraglitazar; PPAR α/δagonists, such as muraglitazar, and the compounds disclosed in U.S. Pat. No. 6,414,002; (13) PPAR-α/γ dual agonists such as MK-0767/KRP-297, CLX-0940, GW-1536, GW-1929, GW-2433, L-796449, LR-90, and SB219994; (14) other insulin sensitizers; (15) VPAC2 receptor agonists; (16) glucokinase activators; (17) DPP-4 inhibitors, such as sitagliptin (Januvia™), isoleucine thiazolidide (P32/98); NVP-DPP-728; vildagliptin (LAF 237); P93/01; denagliptin (GSK 823093), SYR322, RO 0730699, TA-6666, and saxagliptin (BMS 477118); and (18) glucagon receptor antagonists;

(b) lipid lowering agents, for example, (1) bile acid sequestrants such as cholestyramine, colesevelam, colestipol, dialkylaminoalkyl derivatives of a cross-linked dextran, Colestid®, LoCholest®, and Questran®, and the like; (2) HMG-CoA reductase inhibitors such as atorvastatin, itavastatin, fluvastatin, lovastatin, pitavastatin, pravastatin, rivastatin, rosuvastatin, and simvastatin, ZD-4522, and the like; (3) HMG-CoA synthase inhibitors; (4) cholesterol absorption inhibitors such as stanol esters, β-sitosterol, sterol glycosides such as tiqueside, and azetidinones like ezetimibe; (5) acyl coenzyme A-cholesterol acyl-transferase (ACAT) inhibitors such as avasimibe, eflucimibe, KY505, and SMP797, and the like; (6) CETP inhibitors such as JTT705, torcetrapib, CP532632, BAY63-2149, SC591, and SC795, and the like; (7) squalene synthase inhibitors; (8) antioxidants such as probucol; (9) PPAR-α agonists such as beclofibrate, benzafibrate, ciprofibrate, clofibrate, etofibrate, fenofibrate, gemcabene, gemfibrozil, and other fibric acid derivatives, e.g., GW7647, BM170744, LY518674, Atromid®, Lopid®, and Tricor®, and compounds described in WO 97/36579, and the like; (10) FXR receptor modulators such as GW4064, SR103912, and the like; (11) LXR receptor ligands such as GW3965, T9013137, and XTCO179628, and the like; (12) lipoprotein synthesis inhibitors such as niacin; (13) renin/angiotensin system inhibitors; (14) PPAR-δ partial agonists; (15) bile acid reabsorption inhibitors such as BARI1453, SC435, PHA384640, S8921, AZD7706, and the like; (16) PPAR-δ agonists such as GW501516, GW590735, and compounds described in WO97/28149, and the like; (17) triglyceride synthesis inhibitors, (18) microsomal triglyceride transport (MTTP) inhibitors such as inplitapide, LAB687, and CP346086; (19) transcription modulators, (20) squalene epoxidase inhibitors; (21) low-density lipoprotein (LDL) receptor inducers; (22) platelet aggregation inhibitors; (23) 5-LO or FLAP inhibitors; and (24) niacin receptor agonists; and (c) anti-hypertensive agents, for example, (1) diuretics such as thiazides including chlorthalidone, chlorothiazide, dichlorphenamide, hydroflumethiazide, indapamide and hydrochlorothiazide; loop diuretics such as bumetanide, ethacrynic acid, furosemide, and torsemide; potassium sparing agents such as amiloride, triamterene; aldosterone antagonists such as spironolactone, and epirenone, and the like; (2) β-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, and verapamil, and the like; (4) angiotensin converting enzyme (ACE) inhibitors such as benazepril, captopril, cilazapril, delapril, enalapril, fosinopril, imidapril, lisinopril, moexipril, quinapril, quinaprilat, ramipril, perindopril, perindropril, quanipril, spirapril, tenocapril, trandolapril, and zofenopril, and the like; (5) neutral endopeptidase inhibitors such as omapatrilat, cadoxatril, ecadotril, fosidotril, sampatrilat, AVE7688, ER4030, and the like; (6) endothelin antagonists such as bosentan, tezosentan, A308165, and YM62899, and the like; (7) vasodilators such as hydralazine, clonidine, minoxidil, and nicotinyl alcohol; (8) angiotensin II receptor antagonists such as candesartan, eprosartan, irbesartan, losartan, losartan and hydrochlorothiazide, pratosartan, tasosartan, telmisartan, valsartan, EXP-3137, F16828K, and RNH6270, and the like; (9) α/β-adrenergic blockers such as nipradilol, arotinolol, and amosulalol; (10) α1 blockers such as terazosin, urapidil, prazosin, bunazosin, trimazosin, doxazosin, naftopidil, indoramin, WHIP164, and XEN010; (11) α2 agonists such as lofexidine, tiamenidine, moxonidine, rilmenidine, and guanobenz; (12) aldosterone inhibitors; and (d) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR11339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869 WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-1 agonists (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) other BRS3 (bombesin receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936,092, U.S. Pat. No. 6,046,162, U.S. Pat. No. 6,046,167, US, 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966, which are incorporated herein by reference; (51) Neuropeptide Y2 (NPY2) receptor agonists such as NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (56) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitors such as BVT 3498, BVT 2733, and those disclosed in WO 01/90091, WO 01/90090, WO 01/90092, and U.S. Pat. No. 6,730,690 and US Publication No. 2004-0133011, which are incorporated by reference herein in their entirety; and (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; (88) zonisamide, (89) neuromedin U and analogs or derivatives thereof, (90) oxyntomodulin and analogs or derivatives thereof, (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; and (92) Qnexa; and (e) smoking cessation agents, such as a nicotine agonist or a partial nicotine agonist such as varenicline, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl) benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl) (3-{(1S)-2-fluoro-1-[3-fluoro-5-(4H-1,2,4-triazol-4-yl) phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl) (3-{(1S)-2-fluoro-1-[3-fluoro-5-(1,3,4-oxadiazol-2-yl) phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl) azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H- tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl] benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl) phenyl]methyl}azetidin-3-yl)-2-fluoro-2-methylpropyl]-5-fluorobenzonitrile, 3-[(1S)-1-(1-{(S)-(4-cyanophenyl)[3-(1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl] methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl] methyl}azetidin-3-yl)-2-fluoro-2-methylpropyl]-5-fluorobenzonitrile, 3-[(1S)-1-(1-{(S)-(4-chlorophenyl)[3-(1, 2,4-oxadiazol-3-yl)phenyl]methyl}azetidin-3-yl)-2-fluoro-2-methylpropyl]-5-fluorobenzonitrile, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl] azetidin-1-yl}[3-(5-oxo-4,5-dihydro-1,3,4-oxadiazol-2-yl) phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b] pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro [cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1 (3H), 1'-cyclohexane]-4'-carboxamide, trans-N-[5-(3-fluorophenyl)-2-pyrimidinyl]-3-oxospiro[5-azaisobenzofuran-1(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro [7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-oxo-N-(2-phenyl-1,2,3-triazol-4-yl)spiro[6-azaisobenzofuran-1 (3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl) spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro [chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof.

Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl) methoxy]pyridin-2(1H)-one, 4-[(5-chloropyridin-2-yl)methoxy]-1-{4-[(1-ethylazetidin-3-yl)oxy]phenyl}pyridin-2 (1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a] pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2, 3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl] propoxy}phenyl)pyrido[2,3-d]pyrimidin-4(3H)-one 2-methyl-3-(4-{3-[(3S)-3-methylpiperidin-1-yl] propoxy}phenyl)pyrido[4,3-d]pyrimidin-4(3H)-one, 3-{4-[(1-cyclobutyl-4-piperidinyl)oxy]phenyl}-2,5-dimethyl-4 (3H)-quinazolinone, 3-{4-[(1-cyclobutyl-4-piperidinyl)oxy] phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4 (3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4, 3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy] phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]

phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof. Still further, neurokinin-1 (NK-1) receptor antagonists may be favorably employed with the BRS-3 receptor agonists of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salts thereof. Examples of other anti-obesity agents that can be employed in combination with a compound of formula I, II or III are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

The instant invention also includes administration of a single pharmaceutical dosage formulation which contains both the BRS-3 ligand or agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the BRS-3 ligand or agonist and the second active ingredient is realized by the patient at substantially the same time. Such beneficial effect is preferably achieved when the target blood level concentrations of each active ingredient are maintained at substantially the same time. It is preferred that the combination of the BRS-3 ligand or agonist and the second active ingredient be co-administered concurrently on a once-a-day dosing schedule; however, varying dosing schedules, such as the BRS-3 ligand or agonist once a day and the second active ingredient once, twice or more times per day or the BRS-3 ligand or agonist three times a day and the second active ingredient once, twice or more times per day, is also encompassed herein. A single oral dosage formulation comprised of both a BRS-3R ligand or agonist and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the bombesin receptor subtype-3 agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form. In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Another aspect of the present invention provides pharmaceutical compositions which comprise a compound of formula I, II or III, as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula I, II and III can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the typical oral dosage unit form, in which case solid pharmaceutical carriers are typically employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I, II or III may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of formula I, II and III of the present invention can be prepared according to the procedures of the following Schemes and Examples, using appropriate materials and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Reaction Scheme 1 illustrates the methods employed in the synthesis of the compounds of the present invention of formula I, II and III. All substituents are as defined above unless indicated otherwise.

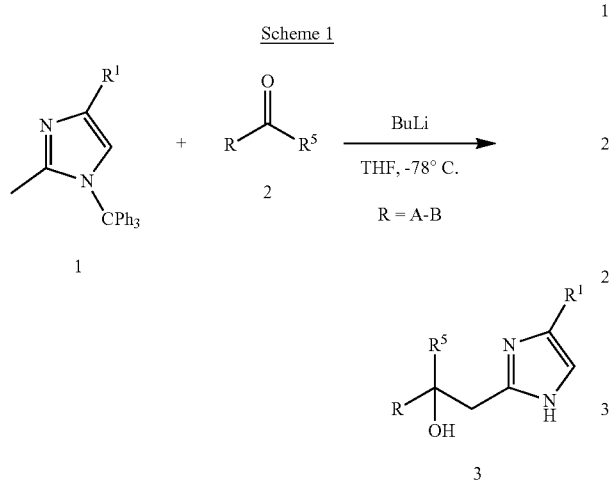

In Scheme 1, an appropriately substituted imidazole 1 is treated with butyllithium at −78° C. and subsequently reacted with a ketone 2 to afford the alcohol 3 after removal of the trityl group. Compounds of the present invention may be prepared by procedures illustrated in the accompanying scheme, intermediates and examples. In order to illustrate the invention, the following examples are included. These examples do not limit the invention. They are only meant to suggest a method of reducing the invention to practice. Those skilled in the art may find other methods of practicing the invention which are readily apparent to them. However, those methods are also deemed to be within the scope of this invention.

The LC/MS analyses were preformed using a MICROMASS ZMD mass spectrometer coupled to an AGILENT 1100 Series HPLC utilizing a YMC ODS-A 4.6×50 mm column eluting at 2.5 mL/min with a solvent gradient of 10 to 95% B over 4.5 min, followed by 0.5 min at 95% B: solvent A=0.06% TFA in water; solvent B=0.05% TFA in acetonitrile. $^1$H-NMR spectra were obtained on a 500 MHz VARIAN Spectrometer in $CDCl_3$ or $CD_3OD$ as indicated and chemical shifts are reported as δ using the solvent peak as reference and coupling constants are reported in hertz (Hz).

Abbreviations used in the following Schemes, Intermediates, and Examples are: aq. is aqueous; API-ES is atmospheric pressure ionization-electrospray (mass spectrum term); BOC (Boc) is t-butyloxycarbonyl, Bn is benzyl, Bu is butyl, calc. or calc'd is Calculated, celite is Celite™ diatomaceous earth, CBZ (Cbz) is benzyloxycarbonyl; cat. is catalytic; DCC is dicyclohexylcarbodiimide, DIEA is diisopropyl-ethylamine, DEAD is diethyl azodicarboxylate; DIBAL-H is di-isobutyl aluminum hydride; DMAP is dimethylamino pyridine; DMF is dimethylformamide; DMSO is dimethylsulfoxide; dppf is 1,1′-bis(diphenylphosphino)ferrocene; EDC is 1-ethyl-3-(3-dimethylaminopropyl)-carbodiimide hydrochloride; ES-MS and ESI-MS are electron spray ion-mass spectroscopy, Et is ethyl, EPA is ethylene polyacrylamide (a plastic); $Et_2O$ is diethyl ether; EtOAc is ethyl acetate; g is gram(s); h is hours; Hex is hexane; HOAT is 1-hydroxy-7-azabenzotriazole; HOBt is 1-hydroxybenzotriazole; HPLC is high pressure liquid chromatography; HPLC/MS is high pressure liquid chromatography/mass spectrum; in vacuo is rotoevaporation; IPAC is isopropyl acetate; KHMDS is potassium hexamethyldisilazide; L is liter; LAH is lithium aluminum hydride; LC is Liquid chromatography; LCMS or LC-MASS is liquid chromatography mass spectrum; LDA is lithium diisopropylamide, M is molar; Me is methyl; MeOH is methanol, MF is molecular formula, MW is molecular weight; min is minutes; mg is milligram(s); mL is milliliter, MeOH is methanol; min is minute(s); mmol is millimole; MS or ms is mass spectrum; MTBE is tert-butyl methyl ether, NaHMDS is sodium hexamethyl disilazide, N is normal; NaHMDS is sodium hexamethyldisilazide; NMM is N-Methylmorpholine, NMO is N-Methylmorpholine-N-oxide; NaOtBu is sodium tert-butoxide, NMR is nuclear magnetic resonance; OTf is trifluoromethanesulfonyl, PCC is pyridinium chlorochromate; PE/EA is petroleum ether/ethyl acetate; $Pd_2(dba)_3$ is tris (dibenzylideneacetone) dipalladium (0); psi is pound per square inch; PyBOP is (benzotriazol-1-yloxy)tripyrrolidinophosphonium hexafluorophosphate; $R_t$ is retention time; rt or RT is room temperature; TBAF is tetrabutyl ammonium fluoride; TEA or $Et_3N$ is triethylamine; TFA is trifluoroacetic acid; $Tf_2O$ is triflic anhydride; THF is tetrahydrofuran; TLC is thin layer chromatography; TMS is trimethyl silyl; and TosMIC or TOSMIC is tosylmethylisonitrile.

INTERMEDIATE 1

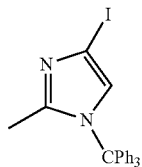

4-iodo-2-methyl-1-trityl-1H-imidazole

Step A: Sodium carbonate (25.8 g, 243.6 mmol) followed by iodine (46.4 g, 182.7 mmol) were added to an ambient temperature solution of 2-methyl-1H-imidazole (5 g, 60.9 mmol) in 1,4-dioxane/water (1:1) (500 mL). After stirring in the dark at ambient temperature overnight, the reaction mixture was concentrated to about half its original volume, diluted with ethyl acetate and washed with saturated aqueous sodium thiosulfate and brine, dried (sodium sulfate) and concentrated in vacuo to afford 4,5-diiodo-2-methyl-1H-imidazole which was used in the subsequent step without further purification.

Step B: A solution of 4,5-diiodo-2-methyl-1H-imidazole (ca. 20 g, 59.9 mmol) and sodium sulfite (22.6 g, 179 mmol) in ethanol (400 mL) and water (400 mL) was heated at 100° C. overnight. The reaction mixture was concentrated to half its original volume and partitioned between ethyl acetate and water. The organic phase was washed with brine, dried (sodium sulfate) and concentrated in vacuo to afford 4-iodo-2-methyl-1H-imidazole which was used in the subsequent step without further purification.

Step C: Triethylamine (13.4 mL, 96.2 mmol) followed by trityl chloride (20.1 g, 72.1 mmol) were added to an ambient temperature solution of 4-iodo-2-methyl-1H-imidazole (ca. 10 g, 48.1 mmol) in methylene chloride (90 mL). After stirring at ambient temperature for 2 days, the reaction mixture was diluted with methylene chloride and washed with water and brine, dried (sodium sulfate) and concentrated in vacuo. Chromatography over silica eluting with 0-15% acetone/methylene chloride afforded the title compound.

INTERMEDIATE 2

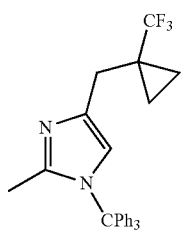

2-methyl-4-{[1-(trifluoromethyl)cyclopropyl]methyl}-1-trityl-1H-imidazole

Step A: N,O-Dimethylhydroxylamine hydrochloride (7.17 g, 73.5 mmol) was added to an ambient temperature solution of 1-trifluoromethylcyclopropane-1-carboxylic acid (10.3 g, 66.8 mmol), EDC (15.4 g, 80.2 mmol), hydroxybenzotriazole hydrate (12.28 g, 80.2 mmol) and N-methylmorpholine (36.7 mL, 33.8 mmol) in methylene chloride (50 mL) at ambient temperature. After stirring at ambient temperature overnight, the reaction mixture was poured into ethyl acetate and washed successively with 2 M hydrochloric acid, saturated aqueous sodium bicarbonate and brine, dried (sodium sulfate) and concentrated to afford N-methoxy-N-methyl-1-(trifluoromethyl)cyclopropanecarboxamide which was used in the subsequent step without further purification.

Step B: Ethylmagnesium bromide (3 M solution in diethyl ether) (633 mL, 1.9 mol) was added over 1 h to a 5° C. solution of 4-iodo-2-methyl-1-trityl-1H-imidazole (855 g, 1.9 mol) in methylene chloride (8 L). After stirring at 5° C. for 30 min, the reaction mixture was allowed to warm to ca. 12° C. and a solution of N-methoxy-N-methyl-1-(trifluoromethyl)cyclopropanecarboxamide (355 g, 1.8 mol) in methylene chloride (2 L) was added over 1 h. After stirring at ambient temperature overnight, the reaction mixture was poured into saturated aqueous ammonium chloride. The organic phase was washed with saturated aqueous sodium bicarbonate, dried (magnesium sulfate) and concentrated in vacuo. The residue was dissolved in a minimal volume of ether and crashed out with heptane. After stirring in heptane (ca. 3 L) for 1 h, solid was collected by filtration, washing with heptane to afford (2-methyl-1-trityl-1H-imidazol-4-yl)[1-(trifluoromethyl)cyclopropyl]methanone.

Step C: Hydrazine hydrate (30 mL) was added to a solution of (2-methyl-1-trityl-1H-imidazol-4-yl)[1-(trifluoromethyl)cyclopropyl]methanone (15.78 g, 34.2 mmol) and powdered potassium hydroxide (9.6 g, 171 mmol) in ethylene glycol (200 mL). After stirring at 120° C. for 20 min, the reaction mixture was heated at 180° C. for 2 h. After cooling to ambient temperature, water was added and the mixture was extracted twice with ethyl acetate. The combined organic extracts were washed with brine, dried (sodium sulfate) and concentrated in vacuo. Chromatography over silica eluting with 0-60% ethyl acetate/hexane afforded the title compound.

INTERMEDIATE 3

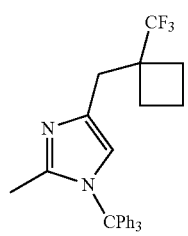

2-methyl-4-{[1-(trifluoromethyl)cyclobutyl]methyl}-1-trityl-1H-imidazole

The title compound was prepared using the procedure outlined in Intermediate 2.

INTERMEDIATE 4

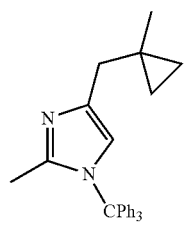

2-methyl-4-[(1-methylcyclopropyl)methyl]-1-trityl-1H-imidazole

The title compound was prepared using the procedure outlined in Intermediate 2.

INTERMEDIATE 5

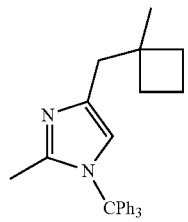

2-methyl-4-[(1-methylcyclobutyl)methyl]-1-trityl-1H-imidazole

The title compound was prepared using the procedure outlined in Intermediate 2.

INTERMEDIATE 6

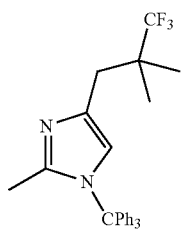

2-methyl-4-(3,3,3-trifluoro-2,2-dimethylpropyl)-1-trityl-1H-imidazole

The title compound was prepared using the procedure outlined in Intermediate 2.

INTERMEDIATE 7

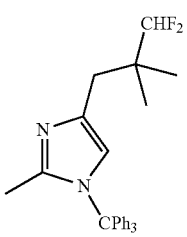

4-(3,3-difluoro-2,2-dimethylpropyl)-2-methyl-1-trityl-1H-imidazole

The title compound was prepared using the procedure outlined in Intermediate 2.

INTERMEDIATE 8

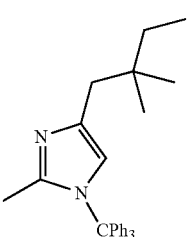

4-(2,2-dimethylbutyl)-2-methyl-1-trityl-1H-imidazole

Step A: Nitrosonium tetrafluoroborate 45 g (0.38 mol) was added in three portions to a 0° C. solution of 4,4-dimethyl-1-hexene (43 g, 0.38 mol) in acetonitrile (100 mL). After stirring at ambient temperature for 1 h, the reaction mixture was filtered and the filtrate was concentrated in vacuo. The residue was dissolved in ethyl acetate and washed with water, saturated aqueous sodium bicarbonate and brine, dried (magnesium sulfate), filtered and concentrated in vacuo to afford 4-(2,2-dimethylbutyl)-2-methyl-1H-imidazol-1-ol which was used in the subsequent step without further purification.

Step B: Triethylamine (100 mL, 0.72 mol) followed by N,N-dimethylsulfamoyl chloride (42 mL, 0.38 mol) were added to a 0° C. solution of 4-(2,2-dimethylbutyl)-2-methyl-1H-imidazol-1-ol in methylene chloride (100 mL). After stirring at ambient temperature for 2 h, the reaction mixture was washed with water and brine, dried over magnesium sulfate, filtered and concentrated in vacuo. Chromatography over silica eluting with ethyl acetate/hexane followed by methanol afforded N-({[4-(2,2-dimethylbutyl)-2-methyl-1H-imidazol-1-yl]oxy}sulfonyl)-N-methylmethanamine (ca. 50% purity by HPLC) which was dissolved in 7:1 methanol/acetic acid (400 mL), and 10% Palladium (10% on activated carbon) (6 g) was added. After stirring under 40 psi hydrogen for 2 h, the reaction mixture was filtered through celite, rinsing with methanol and concentrated in vacuo. The residue was redissolved in ethyl acetate and washed with 1 N aqueous sodium hydroxide and brine, dried (magnesium sulfate), filtered and concentrated in vacuo. Chromatography over silica eluting with 5-20% methanol/methylene chloride afforded 4-(2,2-dimethylbutyl)-2-methyl-1H-imidazole.

Step C: Triethylamine (34 mL, 0.24 mol) followed by trityl bromide (62 g, 0.19 mol) (portionwise) were added to a 0° C. solution of 4-(2,2-dimethylbutyl)-2-methyl-1H-imidazole (26.4 g, 0.16 mol) in methylene chloride (300 mL). After stirring at ambient temperature overnight, the reaction mixture was filtered and washed with water and brine, dried (magnesium sulfate), filtered and concentrated in vacuo. Chromatography over silica eluting with 10-40% ethyl acetate/hexane afforded the title compound.

INTERMEDIATE 9

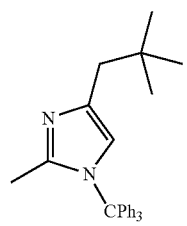

4-(2,2-dimethylpropyl)-2-methyl-1-trityl-1H-imidazole

Step A: 4,4-Dimethyl-1-pentene (59 g, 0.6 mol) was added to a 10° C. suspension of nitrosonium tetrafluoroborate (66 g, 0.56 mmol) in acetonitrile (600 mL) After stirring vigorously at ambient temperature for 30 minutes, acetonitrile was removed in vacuo to afford 4-(2,2-dimethylpropyl)-2-methyl-1H-imidazol-1-ol which was used in the subsequent step without further purification.

Step B: Titanium (III) chloride (30% weight solution in 2N HCl) (600 mL, 1.5 mol) was added to an ambient temperature solution of 4-(2,2-dimethylpropyl)-2-methyl-1H-imidazol-1-ol (ca. 0.56 mmol) in methanol (1200 mL). After stirring at ambient temperature for a few days, the reaction mixture was basified with saturated aqueous sodium bicarbonate until the black solution turned white. The reaction mixture was extracted with ether. The combined organic extracts were washed with brine, dried (magnesium sulfate), filtered and concentrated in vacuo. Chromatography over silica eluting with 10-20% ethyl acetate/hexane afforded 4-(2,2-dimethylpropyl)-2-methyl-1H-imidazole.

Step C: Triethylamine (70 mL, 0.5 mol) followed by trityl chloride (90 g, 0.32 mol) were added to an ambient temperature solution of 4-(2,2-dimethylpropyl)-2-methyl-1H-imidazole (49 g, 0.32 mmol) in methylene chloride (1 L). After stirring at ambient temperature for 30 min, the reaction mixture was washed with water and brine, dried (magnesium sulfate) and concentrated in vacuo. Chromatography over silica eluting with 10-20% ethyl acetate/hexane afforded the title compound.

INTERMEDIATE 10

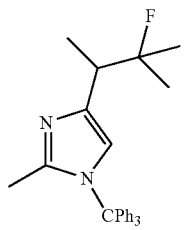

4-(2-fluoro-1,2-dimethylpropyl)-2-methyl-1-trityl-1H-imidazole

Step A: Triethylamine (5.1 mL, 36.3 mmol) followed by trityl chloride (7.6 g, 27.2 mmol) were added to an ambient temperature solution of 2-methyl-1H-imidazole-4-carboxaldehyde (2 g, 18.2 mmol) in methylene chloride (20 mL). After stirring at ambient temperature overnight, the reaction was diluted with methylene chloride and washed with water and brine, dried (sodium sulfate) and concentrated in vacuo. Chromatography over silica eluting with 30-70% ethyl acetate/hexane afforded 2-methyl-1-trityl-1H-imidazole-4-carboxaldehyde.

Step B: tert-Butyllithium (1.7 M in pentane) (1.7 mL, 2.8 mmol) was added slowly to an ambient temperature solution of 2-methyl-1-trityl-1H-imidazole-4-carboxaldehyde in tetrahydrofuran (10 mL) at 0° C. After stirring at ambient temperature for 2 h, the reaction was quenched with saturated aqueous ammonium chloride and extracted with ethyl acetate. The combined extracts were washed with brine, dried (sodium sulfate) and concentrated in vacuo. Chromatography over silica eluting with 0-60% ethyl acetate/hexane afforded 2,2-dimethyl-1-(2-methyl-1-trityl-1H-imidazol-4-yl)propan-1-ol.

Step C: 2,2-Dimethyl-1-(2-methyl-1-trityl-1H-imidazol-4-yl)propan-1-ol (200 mg, 0.49 mmol) in a minimal volume of methylene chloride was added to HF-pyridine (2 mL) at 0° C. After stirring at ambient temperature overnight, the reaction was added dropwise to TMS-ethanol and partitioned between ethyl acetate and saturated aqueous sodium bicarbonate. Organic phase was washed with brine, dried (sodium sulfate) and concentrated in vacuo. Chromatography over silica eluting with 10-70% ethyl acetate/hexane afforded the title compound.

INTERMEDIATE 11

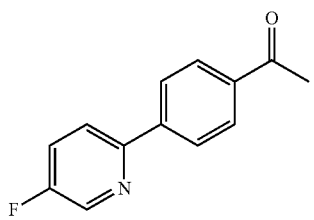

1-[4-(5-fluoropyridin-2-yl)phenyl]ethanone

Step A: Palladium tetrakis(triphenylphosphine) (1.38 g, 1.2 mmol) was added to a degassed, ambient temperature solution of 2-bromo-5-fluoropyridine (5 g, 28.4 mmol) and (4-{[methoxy(methyl)amino]carbonyl}phenyl)boronic acid (5 g, 23.9 mmol) and potassium carbonate (4.3 g, 31.1 mmol) in toluene/methanol (9.5:1) (105 mL). After stirring at 90° C. for 1.5 hr, the reaction mixture was concentrated in vacuo. The residue was partitioned between ethyl acetate and water. The organic phase was washed with brine, dried (magnesium sulfate) and concentrated in vacuo. Chromatography over silica eluting with 0-80% ethyl acetate/hexane afforded 4-(5-fluoropyridin-2-yl)-N-methoxy-N-methylbenzamide.

Step B: Methylmagnesium bromide (3 M in tetrahydrofuran) (2.1 mL, 6.2 mmol) was added to a −78° C. solution of 4-(5-fluoropyridin-2-yl)-N-methoxy-N-methylbenzamide (800 mg, 3.1 mmol) in tetrahydrofuran (20 mL). After stirring at 0° C. for 30 min, the reaction mixture was quenched with methanol and saturated aqueous ammonium chloride. The organic layer was dried (magnesium sulfate) and concentrated in vacuo. Chromatography over silica eluting with 0-15% ethyl acetate/hexane afforded the title compound.

INTERMEDIATE 12

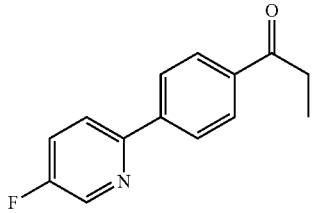

1-[4-(5-fluoropyridin-2-yl)phenyl]propan-1-one

The title compound was prepared using the procedure outlined in Intermediate 11.

INTERMEDIATE 13

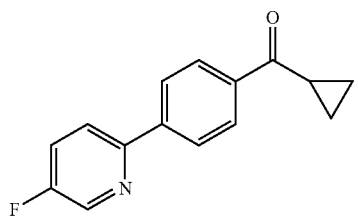

cyclopropyl[4-(5-fluoropyridin-2-yl)phenyl]methanone

The title compound was prepared using the procedure outlined in Intermediate 11.

INTERMEDIATE 14

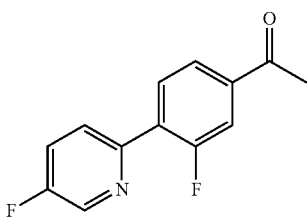

1-[3-fluoro-4-(5-fluoropyridin-2-yl)phenyl]ethanone

Step A: N,O-Dimethylhydroxylamine (2.45 g, 25.1 mmol) was added to an ambient temperature solution of 4-bromo-3-fluorobenzoic acid (5 g, 22.8 mmol), EDC (5.25 g, 27.4 mmol), HOBt (4.2 g, 27.4 mmol) and NMM (12.55 mL, 114.2 mmol) in methylene chloride (50 mL). After stirring at ambient temperature overnight, the reaction mixture was poured into ethyl acetate and washed successively with saturated aqueous sodium bicarbonate and brine, dried (sodium sulfate) and concentrated in vacuo. Chromatography over silica eluting with 40-80% ethyl acetate/hexane afforded 4-bromo-3-fluoro-N-methoxy-N-methylbenzamide.

Step B: Methylmagnesium chloride (3 M in toluene/tetrahydrofuran) (2.54 mL, 7.6 mmol) was added to a 0° C. solution of 4-bromo-3-fluoro-N-methoxy-N-methylbenzamide (500 mg, 1.9 mmol) in tetrahydrofuran (10 mL). After stirring at 0° C. for 30 min, the reaction mixture was cooled to −78° C. and n-butyllithium (2.6 mL, 4.2 mmol) was added. After stirring at −78° C. for 2 h, triisopropylborate (1.5 mL, 6.7 mmol) was added and the reaction allowed to warm slowly to ambient temperature over 3 h. 1 M hydrochloric acid (5 mL) was added and the reaction stirred for 10 min. The reaction mixture was concentrated in vacuo to remove tetrahydrofuran, saturated with sodium chloride and extracted with diethyl ether. Combined ethereal extracts were extracted with 0.5 N aqueous sodium hydroxide (6×5 mL). Combined extracts were acidified, saturated with sodium chloride and reextracted with ethyl acetate. The combined extracts were washed with brine, dried (sodium sulfate) and concentrated in vacuo to afford (4-acetyl-2-fluorophenyl)boronic acid which was used in the subsequent step without further purification.

Step C: Palladium tetrakis(triphenylphosphine) (98 mg, 0.09 mmol) was added to a degassed, ambient temperature solution of 2-bromopyridine (360 mg, 2.04 mmol), potassium carbonate (306 mg, 2.2 mmol) and (4-acetyl-2-fluorophenyl)boronic acid (310 mg, 1.7 mmol) in degassed toluene/methanol (10:1) (22 mL). After stirring at 90° C. for 2 h, the reaction mixture was washed with water and brine, dried (sodium sulfate) and concentrated. Chromatography over silica eluting with 0-20% ethyl acetate/hexane afforded the title compound.

INTERMEDIATE 15

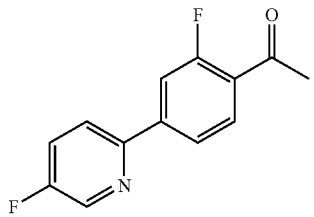

1-[2-fluoro-4-(5-fluoropyridin-2-yl)phenyl]ethanone

The title compound was prepared using the procedure outlined in Intermediate 14.

INTERMEDIATE 16

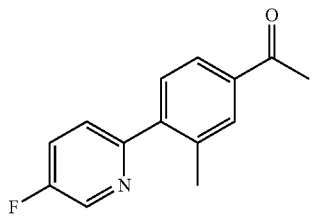

1-[4-(5-fluoropyridin-2-yl)-3-methylphenyl]ethanone

The title compound was prepared using the procedure outlined in Intermediate 14.

INTERMEDIATE 17

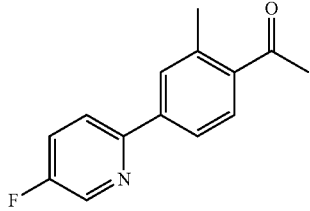

1-[4-(5-fluoropyridin-2-yl)-2-methylphenyl]ethanone

The title compound was prepared using the procedure outlined in Intermediate 14.

INTERMEDIATE 18

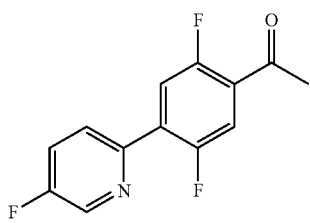

1-[2,5-difluoro-4-(5-fluoropyridin-2-yl)phenyl]ethanone

Step A: $Pd_2 dba_3$ (2.2 g, 2.4 mmol) was added to a degassed, ambient temperature solution of 4-chloro-2,5-difluoroacetophenone (9.05 g, 48 mmol), bis(pinacolato)diboron (19 g, 75 mmol) and potassium acetate (11.67 g, 119 mmol) in 1,4-dioxane (100 mL). After heating at 100° C. for 18 hours, the reaction mixture was poured into saturated aqueous sodium bicarbonate and extracted with ethyl acetate. The organic phase was dried (magnesium sulfate) and concentrated in vacuo. Chromatography over silica eluting with 0-100% ethyl acetate/hexane afforded 1-[2,5-difluoro-4-(4,4,5,5-tetramethyl-1,3,2-dioxaborolan-2-yl)phenyl]ethanone.

Step B: $Pd(dppf)Cl_2$ (579 mg, 0.7 mmol) was added to a degassed, ambient temperature solution of 1-[2,5-difluoro-4-(4,4,5,5-tetramethyl-1,3,2-dioxaborolan-2-yl)phenyl]ethanone (2 g, 7.1 mmol), 2-bromo-5-fluoropyridine (2.5 g, 14 mmol) and sodium carbonate (2.26 g, 21 mmol) in N,N-dimethylformamide (20 mL) and water (10 mL). After heating at 80° C. overnight, the reaction mixture was poured into water and extracted with diethyl ether. The combined organic phases were dried (magnesium sulfate), filtered and concentrated in vacuo. Chromatography over silica eluting with 0-50% ethyl acetate/hexane afforded the title compound.

INTERMEDIATE 19

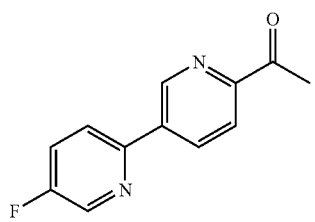

1-(5-fluoro-2,3'-bipyridin-6'-yl)ethanone

Palladium tetrakis(triphenylphosphine) (289 mg, 0.25 mmol) was added to a degassed, ambient temperature solution of 2-bromopyridine (660 mg, 3.75 mmol), 1-(5-bromopyridin-2-yl)-ethanone (500 mg, 2.5 mmol) and hexamethylditin (1.2 g, 3.75 mmol) in degassed 1,4-dioxane (8 mL). After stirring at 110° C. overnight, the reaction mixture was cooled and KF/celite (1:1) was added. After stirring vigorously for 1 hr, reaction mixture was filtered and concentrated. Chromatography over silica eluting with 0-50% ethyl acetate/hexane afforded the title compound.

INTERMEDIATE 20

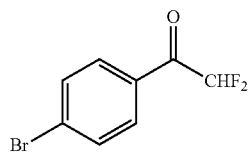

1-(4-bromophenyl)-2,2-difluoroethanone n-Butyllithium (1.6 M in hexane) (165 mL, 0.264 mmol) was added dropwise to a −78° C. solution of 1,4-dibromobenzene (60.1 g) in diethyl ether (500 mL). After stirring at −78° C. for 2 h, ethyl trifluoroacetate (40 g) was added dropwise and the mixture was allowed to warm to ambient temperature overnight. The reaction mixture was cooled to −20° C., quenched with saturated aqueous ammonium chloride and extracted with ether. The combined organic phases were washed with saturated aqueous sodium bicarbonate, dried (sodium sulfate) and concentrated in vacuo. Chromatography over silica eluting with petroleum ether/ethyl acetate (20:1) afforded the title compound.

INTERMEDIATE 21

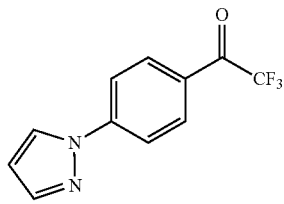

2,2,2-trifluoro-1-[4-(1H-pyrazol-1-yl)phenyl]ethanone

4-Bromo-2,2,2-trifluoroacetophenone (17.4 g, 68.8 mmol) was added to a stirred, room temperature mixture of pyrazole (4.45 g, 65.3 mmol), potassium carbonate (19.96 g, 144 mmol), rac-trans-N,N'-dimethylcyclohexane-1,2-diamine (1.956 g, 13.75 mmol) and copper (I) iodide (17.19 mL, 3.44 mmol) in toluene and the mixture was stirred at reflux overnight. The reaction mixture was cooled, filtered and concentrated in vacuo. Chromatography over silica eluting with 0-40% ethyl acetate/hexane afforded the title compound.

INTERMEDIATE 22

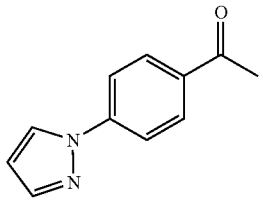

1-[4-(1H-pyrazol-1-yl)phenyl]ethanone

The title compound was prepared using the procedure outlined in Intermediate 21.

INTERMEDIATE 23

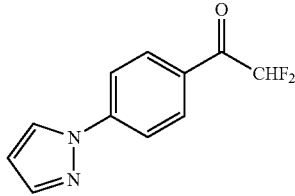

2,2-difluoro-1-[4-(1H-pyrazol-1-yl)phenyl]ethanone

The title compound was prepared using the procedure outlined in Intermediate 21.

INTERMEDIATE 24

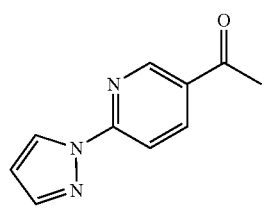

1-[6-(1H-pyrazol-1-yl)pyridin-3-yl]ethanone

Step A: N,O-Dimethylhydroxylamine (1.03 g, 10.6 mmol) was added to an ambient temperature solution of 6-(1H-pyrazol-1-yl)nicotinic acid (2 g, 10.6 mmol), EDC (2.4 g, 12.7 mmol), HOBt (1.94 g, 12.7 mmol) and NMM (5.2 mL, 47.6 mmol) in methylene chloride (100 mL). After stirring at ambient temperature overnight, the reaction mixture was diluted with methylene chloride and washed successively with saturated aqueous sodium bicarbonate and brine, dried (sodium sulfate) and concentrated in vacuo. Chromatography over silica eluting with 0-100% ethyl acetate/hexane afforded N-methoxy-N-methyl-6-(1H-pyrazol-1-yl)nicotinamide.

Step B: Methylmagnesium bromide (3 M in tetrahydrofuran) (3.16 mL, 9.5 mmol) was added to a −78° C. solution of N-methoxy-N-methyl-6-(1H-pyrazol-1-yl)nicotinamide (2.0 g, 8.6 mmol) in tetrahydrofuran (10 mL). After stirring at ambient temperature overnight, the reaction mixture was quenched with brine and extracted with ethyl acetate. The combined organic extracts were dried (magnesium sulfate) and concentrated in vacuo to afford the title compound.

INTERMEDIATE 25

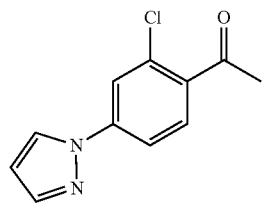

1-[2-chloro-4-(1H-pyrazol-1-yl)phenyl]ethanone

The title compound was prepared using the procedure outlined in Intermediate 24.

INTERMEDIATE 26

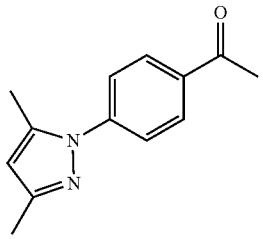

1-[4-(3,5-dimethyl-1H-pyrazol-1-yl)phenyl]ethanone

The title compound was prepared using the procedure outlined in Intermediate 24.

INTERMEDIATE 27

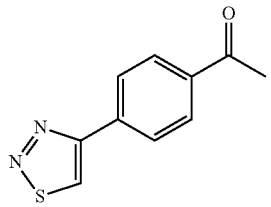

1-[4-(1,2,3-thiadiazol-4-yl)phenyl]ethanone

Step A: Methylmagnesium chloride (3 M in tetrahydrofuran) (0.83 mL, 2.5 mmol) was added to a −78° C. solution of 4-(1,2,3-thiadiazol-4-yl)benzaldehyde (473 mg, 2.5 mmol) in tetrahydrofuran (10 mL). After stirring at −78° C. for 2 h, the reaction mixture was quenched with saturated aqueous ammonium chloride and extracted with ethyl acetate. The combined organic extracts were washed with brine, dried (magnesium sulfate) and concentrated in vacuo. Chromatography over silica eluting with 0-100% ethyl acetate/hexane afforded 1-[4-(1,2,3-thiadiazol-4-yl)phenyl]ethanol.

Step B: Dess-Martin periodinane (2.1 g, 5.0 mmol) was added to an ambient temperature solution of 1-[4-(1,2,3-thiadiazol-4-yl)phenyl]ethanol (513 mg, 2.5 mmol) in methylene chloride (20 mL). After stirring at ambient temperature for 1 h, a solution of saturated aqueous sodium bicarbonate/saturated aqueous sodium thiosulfate (1:1) was added and the solution stirred until clear. The reaction mixture was extracted with methylene chloride. The combined organic extracts were dried (magnesium sulfate) and concentrated in vacuo to afford the title compound which was used in subsequent steps without further purification.

INTERMEDIATE 28

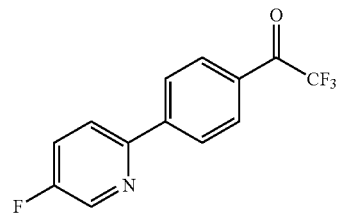

2,2,2-trifluoro-1-[4-(5-fluoropyridin-2-yl)phenyl]ethanone

Step A: Pd(dppf)Cl$_2$ (2.92 g, 4 mol) was added to a degassed, ambient temperature solution of 4'-bromo-2,2,2-trifluoroacetophenone (20 g, 0.08 mol), bis(pinacolato)diboron (21 g, 0.08 mol) and potassium acetate (19.6 g, 0.2 mol) in N,N-dimethylformamide (360 mL). After heating at 90° C. for 24 hours, the reaction mixture was cooled and concentrated in vacuo, the residue was dissolved in methylene chloride (600 mL), filtered and concentrated in vacuo. Chromatography over silica eluting with petroleum ether/ethyl acetate (20:1) afforded 2,2,2-trifluoro-1-[4-(4,4,5,5-tetramethyl-1,3,2-dioxaborolan-2-yl)phenyl]ethanone.

Step B: Pd(dppf)Cl$_2$ (2.5 g, 3.3 mmol) was added to a degassed, ambient temperature solution of 2,2,2-trifluoro-1-[4-(4,4,5,5-tetramethyl-1,3,2-dioxaborolan-2-yl)phenyl] ethanone (20 g, 67 mmol), 2-bromo-5-fluoropyridine (11.6 g, 67 mmol) and sodium carbonate (12.7 g, 134 mmol) in N,N-dimethylformamide (4400 mL) and water (90 mL). After heating at 90° C. overnight, the reaction mixture was poured into ice (400 g) and extracted with diethyl ether. The combined organic extracts were dried (magnesium sulfate), filtered and concentrated in vacuo. Chromatography over silica eluting with petroleum ether/ethyl acetate (20:1) afforded the title compound.

INTERMEDIATE 29

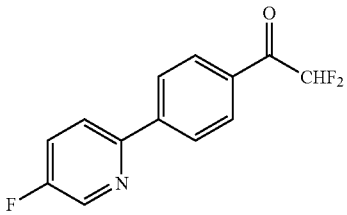

2,2-difluoro-1-[4-(5-fluoropyridin-2-yl)phenyl]ethanone

Step A: Pd(dppf)Cl$_2$ (0.73 g, 1 mol) was added to a degassed, ambient temperature suspension of 1-(4-bromophenyl)-2,2-difluoroethanone (9.4 g, 0.04 mol), bis(pinacolato)diboron (17.7 g, 0.05 mol) and potassium acetate (8.83 g, 0.09 mol) in N,N-dimethylformamide (190 mL). After heating at 90° C. for 48 h, the reaction mixture was cooled and the solvents removed in vacuo. The residue was dissolved in methylene chloride (150 mL), filtered and concentrated in vacuo. Chromatography over silica eluting with petroleum ether/ethyl acetate (20:1) afforded 2,2-difluoro-1-[4-(4,4,5,5-tetramethyl-1,3,2-dioxaborolan-2-yl)phenyl]ethanone.

Step B: Pd(dppf)Cl$_2$ (3.06 g, 4.2 mmol) was added to a degassed, ambient temperature solution of 2,2-difluoro-1-[4-(4,4,5,5-tetramethyl-1,3,2-dioxaborolan-2-yl)phenyl]ethanone (30 g, 84 mmol), 2-bromo-5-fluoropyridine (15 g, 84 mmol) and sodium carbonate (20 g, 189 mmol) in N,N-dimethylformamide (400 mL) and H$_2$O (100 mL). After stirring at 90° C. overnight, the reaction mixture was poured into ice and extracted with diethyl ether. The combined organic extracts were dried (magnesium sulfate), filtered and concentrated in vacuo. Chromatography over silica eluting with petroleum ether/ethyl acetate (20:1) afforded the title compound.

INTERMEDIATE 30

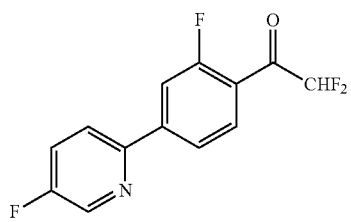

2,2-difluoro-1-[2-fluoro-4-(5-fluoropyridin-2-yl)phenyl]ethanone

Step A: To 1-bromo-2-fluoro-4-hydroxybenzene (100 g, 0.52 mol) and K$_2$CO$_3$ (179.4 g, 1.3 mol) in 1300 mL acetone was added dimethyl sulfate (98.38 g, 0.78 mol). After refluxing overnight, the reaction mixture was cooled, filtered and dried over Na$_2$SO$_4$, and the filtrate was concentrated to afford 1-bromo-2-fluoro-4-methoxybenzene as a brown oil.

Step B: To 1-bromo-2-fluoro-4-methoxybenzene (123 g, 0.6 mol) in 1300 mL Et$_2$O at −78° C. was added n-BuLi (276 mL, 2.5 M) dropwise. After stirring at −78° C. for 2 hours, ethyl difluoroacetate (82.6 g, 0.67 mol) was added dropwise at −78° C. The reaction was stirred overnight at 25° C., and was quenched with saturated ammonium chloride solution at −20° C., followed by 1N HCl (final pH=4). The organic layer was separated and aqueous layer was extracted with Et$_2$O. The combined extracts were dried over MgSO$_4$, filtered and concentrated, and the residue was purified by column chromatography (PE/EA 20:1) to afford 2,2-difluoro-1-(2-fluoro-4-methoxyphenyl)ethanone as an oil.

Step C: To 2,2-difluoro-1-(2-fluoro-4-methoxyphenyl)ethanone (45.0 g, 0.22 mol) in 400 mL of CH$_2$Cl$_2$ at −78° C. was added BBr$_3$ (165.67 g, 0.66 mol) in 100 mL of CH$_2$Cl$_2$ dropwise. The resulting solution was stirred overnight at 25° C., and was quenched by dropwise addition of CH$_3$OH (900 mL) at −30° C. and after stirring for 2 hours at −30° C. and for 1 hour at 25° C., the solvents were evaporated and the residue was purified by column chromatography (PE/EA 6:1) to afford 2,2-difluoro-1-(2-fluoro-4-hydroxyphenyl)ethanone as a solid.

Step D: To 2,2-difluoro-1-(2-fluoro-4-hydroxyphenyl)ethanone (39.0 g, 0.2 mol) and Et$_3$N (20.7 g, 0.2 mol) in CH$_2$Cl$_2$ at 0° C. was added Tf$_2$O (58 g, 0.2 mol) dropwise while keeping the temperature at 0° C. The ice-salt bath was removed, and when the temperature rose to 25° C., a solution of saturated NaHCO$_3$ was added. The aqueous phase was extracted with CH$_2$Cl$_2$ and the combined extracts were dried over MgSO$_4$, and concentrated, and the residue was purified by column chromatography (PE/EA 10:1) to afford 4-(difluoroacetyl)-3-fluorophenyl trifluoromethanesulfonate as an brown oil.

Step E: A mixture 4-(difluoroacetyl)-3-fluorophenyl trifluoromethanesulfonate (15.46 g, 48 mmol), bis(pinacolato)diboron (14.63 g, 57.6 mmol), KOAc (9.42 g, 96 mmol) and DMF (200 mL) degassed and was filled with nitrogen. Pd(dppf)Cl$_2$ (1.76 g, 2.4 mmol) was added and the mixture was again degassed and filled with nitrogen. After stirring overnight at 90° C., the mixture was cooled and volatiles were removed under reduced pressure. The residue was taken up by CH$_2$Cl$_2$ and the mixture was filtered. The filtrate was evaporated and the residue was purified by column chromatography (PE/EA 20:1) to give 2,2-difluoro-1-[2-fluoro-4-(4,4,5,5-tetramethyl-1,3,2-dioxaborolan-2-yl)phenyl]ethanone.

Step F: A mixture of 2,2-difluoro-1-[2-fluoro-4-(4,4,5,5-tetramethyl-1,3,2-dioxaborolan-2-yl)phenyl]ethanone (21 g, 70 mmol), 2-bromo-5-fluoropyridine (12.32 g, 70 mmol), Na$_2$CO$_3$ (14.84 g, 140 mmol) in DMF (300 mL) and H$_2$O (80 mL) was degassed and filled with nitrogen. Then Pd(dppf)Cl$_2$ (2.56 g, 3.5 mmol) was added and the mixture was again degassed and filled with nitrogen. After stirring overnight at 90° C., the reaction mixture was poured into ice (80 g) and extracted with Et$_2$O (500 mL×3). The combined extracts were dried (MgSO$_4$), filtered and concentrated, and the residue was purified by column chromatography (PE/EA 20:1) to give the title compound.

INTERMEDIATE 31

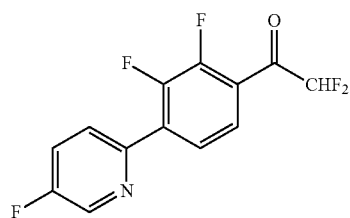

1-[2,3-difluoro-4-(5-fluoropyridin-2-yl)phenyl]-2,2-difluoroethanone

Step A: Pd(PPh$_3$)$_4$ (3.85 g, 3.3 mmol) was added to a degassed solution of 2-bromo-5-fluoropyridine (12.9 g, 73 mmol) and 2,3-difluoro-4-formylboronic acid (12.4 g, 66.7 mmol) and potassium carbonate (10.1 g, 73.4 mmol) in toluene/methanol (10:1) (350 mL) at ambient temperature. After stirring at 90° C. for 2 hr, the reaction mixture was partitioned between ethyl acetate and water. Organic phase was washed with brine, dried (sodium sulfate) and concentrated to afford 2,3-difluoro-4-(5-fluoropyridin-2-yl)benzaldehyde as an off-white solid which was used without further purification.

Step B: A solution of ethyl bromodifluoromethylphosphonate (3.2 g, 12.1 mmol) in tetrahydrofuran (20 mL) was added dropwise to a solution of isopropylmagnesium chloride (2 M in tetrahydrofuran) (6.1 mL, 12.1 mmol) in tetrahydrofuran (20 mL) at −78° C. After stirring at −78° C. for 5 min, a solution of 2,3-difluoro-4-(5-fluoropyridin-2-yl)benzaldehyde (1.92 g, 8.1 mmol) in tetrahydrofuran (20 mL) was added dropwise. After stirring for a further 5 min at −78° C. then a further 1 h between −78 and 0 then a further 1 h between 0 and ambient temperature. The reaction mixture was poured into saturated ammonium chloride and extracted with methylene chloride. Combined extracts were washed with saturated aqueous sodium bicarbonate, dried (sodium sulfate) and concentrated in vacuo to afford a slightly yellow oil. Chromatography over silica eluting with 0-40% acetone/methylene chloride afforded diethyl {2-[2,3-difluoro-4-(5-fluoropyridin-2-yl)phenyl]-1,1-difluoro-2-hydroxyethyl}phosphonate as an off-white solid.

Step C: Dess-Martin reagent (1.75 g, 4.1 mmol) was added to a solution of diethyl{2-[2,3-difluoro-4-(5-fluoropyridin-2-yl)phenyl]-1,1-difluoro-2-hydroxyethyl}phosphonate (876 mg, 2.1 mmol) in methylene chloride (30 mL) at room temp—solution darkens to deep red over 1 hr. After stirring at rt for 1 hr, a solution of saturated aqueous sodium bicarbonate and saturated aqueous sodium thiosulfate (1:1) (ca. 20 mL) was added and the solution stirred until clear. The reaction mixture was extracted with dichloromethane, dried (sodium sulfate) and concentrated to afford diethyl {2-[2,3-difluoro-4-(5-fluoropyridin-2-yl)phenyl]-1,1-difluoro-2-oxoethyl}phosphonate as an off white solid which was used without further purification.

Step D: 1 M Aqueous sodium hydroxide (1 mL, 1 mmol) was added to a solution of diethyl {2-[2,3-difluoro-4-(5-fluoropyridin-2-yl)phenyl]-1,1-difluoro-2-oxoethyl}phosphonate (872 mg, 2 mmol) in methanol (8 mL) at room temp. After stirring at rt for 30 min, the reaction was quenched with 1 N hydrochloric acid. The reaction mixture was extracted with ethyl acetate washed with saturated aqueous sodium bicarbonate and brine, dried (sodium sulfate) and concentrated. Chromatography over silica eluting with 0-60% ethyl acetate/hexane afforded the title compound as a white solid.

INTERMEDIATE 32

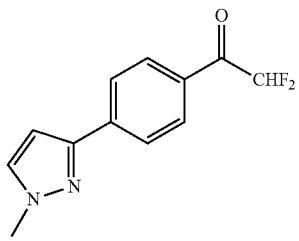

2,2-difluoro-1-[4-(1-methyl-1H-pyrazol-3-yl)phenyl]ethanone

The title compound was prepared using the procedure outlined in Intermediate 31.

INTERMEDIATE 33

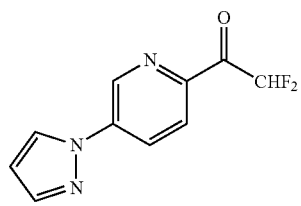

2,2-difluoro-1-[5-(1H-pyrazol-1-yl)pyridin-2-yl]ethanone

Step A: To a solution of 2,5-dibromopyridine (15.21 g, 64 mmol) in anhydrous toluene (150 mL) at −78° C. under nitrogen was added dropwise with n-BuLi (2.5 M in hexane, 25 mL, 62 mmol). Stirring was continued at −78° C. for 2 h, then ethyl difluoroacetate (11 g, 80 mmol) was added dropwise at −78° C. The mixture was stirred overnight while the temperature rose to room temperature. The mixture was partitioned between EtOAc and brine, the water layer was extracted with EtOAc, the combined organic extracts were dried and concentrated, flash chromatography on silica gel afforded 8.53 g of 1-(5-bromopyridin-2-yl)-2,2-difluoroethanone as white solid.

Step B: A mixture of 1-(5-bromopyridin-2-yl)-2,2-difluoroethanone (7.064 g, 30 mmol), pyrazole (1.85 g, 27 mmol), CuI (0.273 g, 1.4 mmol), racemic trans-N,N'-dimethylcyclohexane-1,2-diamine (0.714 g, 5 mmol), K₂CO₃ (7.894 g, 57 mmol) was added to a sealed tube and dissolved in toluene (12 mL). The mixture was stirred vigorously overnight at 110° C. The mixture was cooled and filtered through Celite, washing with EtOAc. The combined filtrate and washings were concentrated, flash chromatography on silica gel afforded the title compound as a white solid.

INTERMEDIATE 34

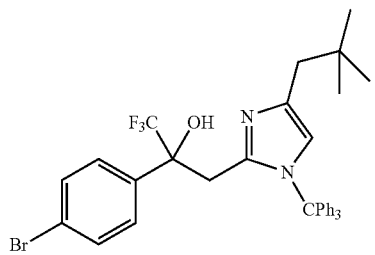

2-(4-bromophenyl)-3-[4-(2,2-dimethylpropyl)-1-trityl-1H-imidazol-2-yl]-1,1,1-trifluoropropan-2-ol n-Butyllithium (2.5 M in hexanes) (7.9 mL, 19.8 mmol) was added to a solution of 4-(2,2-dimethylpropyl)-2-methyl- 1-trityl-1H-imidazole (5.2 g, 13.2 mmol) in tetrahydrofuran (50 mL) at −78° C. over 30 min. After stirring at −78° C. for 30 min, 4-bromoacetophenone (5 g, 19.8 mmol) in tetrahydrofuran (25 mL) was added dropwise over 30 min. After stirring at −78° C. for 1 hr, the reaction mixture was allowed to warm to ambient temperature over 1 h and quenched with saturated aqueous ammonium chloride. The reaction mixture was extracted with ether (2×10 mL). Combined extracts were washed with water (50 mL), dried (sodium sulfate) and concentrated in vacuo to afford a slightly yellow oil. Chromatography over silica eluting with 0-20% ethyl acetate/hexane afforded the title compound as an off-white solid.

INTERMEDIATE 35

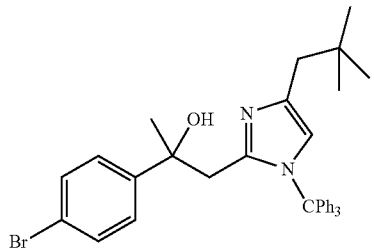

2-(4-bromophenyl)-1-[4-(2,2-dimethylpropyl)-1-trityl-1H-imidazol-2-yl]propan-2-ol The title compound was prepared using the procedure outlined in Intermediate 34.

INTERMEDIATE 36

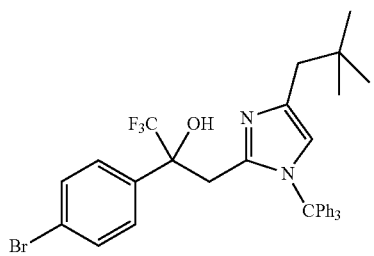

2-(4-bromophenyl)-3-[4-(2,2-dimethylpropyl)-1-trityl-1H-imidazol-2-yl]-1,1-difluoropropan-2-ol The title compound was prepared using the procedure outlined in Intermediate 34.

INTERMEDIATE 37

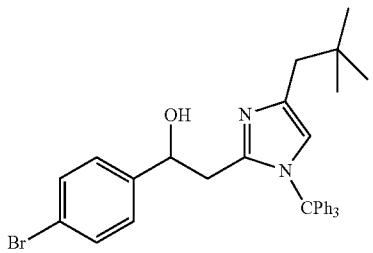

1-(4-bromophenyl)-2-[4-(2,2-dimethylpropyl)-1-trityl-1H-imidazol-2-yl]ethanol

The title compound was prepared using the procedure outlined in Intermediate 34.

INTERMEDIATE 38

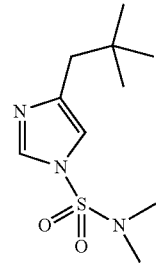

4-(2,2-dimethylpropyl)-N,N-dimethyl-1H-imidazole-1-sulfonamide

Step A: To a cooled (0° C.) solution of 3,3-dimethylbutyraldehyde (32.7 g, 0.33 mol) in THF (500 mL) was added TosMIC (51.2 g) followed by t-BuOK (1.5 g) and the reaction was warmed to r.t. and stirred for additional 2 hours. The mixture was concentrated in vacuo, redissolved in $NH_3$/MeOH (500 mL) and heated in a steal tube at 100° C. for 16 hrs. The crude reaction mixture was concentrated in vacuo, and the residue was purified by silica gel chromatography using acetone as eluent to give 5-(2,2-dimethylpropyl)-1H-imidazole as a dark oil which was used directly to the next step.

Step B: A solution of 5-(2,2-dimethylpropyl)-1H-imidazole, dimethylsulfamoyl chloride (25 mL), $Et_3N$ (45 mL) in $CH_2Cl_2$ (300 mL) was added DMAP (0.8 g). The reaction mixture was refluxed overnight. The solvent was evaporated and the residue was purified by silica gel chromatography to give the title compound as a white solid.

INTERMEDIATE 39

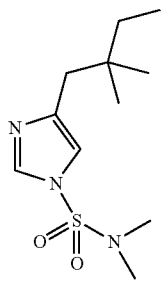

4-(2,2-dimethylbutyl)-N,N-dimethyl-1H-imidazole-1-sulfonamide

Step A: 2-Methyl-2-butanol (480 mL, 4.4 mol) and vinylidene chloride (508 mL, 5.2 mol) were added to sulfuric acid (2 L) at 10° C. Methanol (1750 mL) was added slowly, and the reaction mixture reached 60 C for 15 minutes due to exotherm. After 30 min, the reaction mixture was cooled and poured into a stirred mixture of ether and ice water. The ethereal layer was washed with 1 N aqueous sodium hydroxide and brine, dried (magnesium sulfate), filtered, and concentrated in vacuo to afford methyl 3,3-dimethylpentanoate which was used in the subsequent step without further purification.

Step B: DIBAL-H (1 M in methylene chloride) (2.4 1 L, 2.4 mol) was added to a −50° C. solution of methyl 3,3-dimethylpentanoate (172 g, 1.2 mol) in methylene chloride (1 L). After stirring at 0° C. for 30 minutes the reaction mixture was poured into saturated aqueous sodium potassium tartrate (3 L) and extracted with methylene chloride. The combined organic extracts were washed with brine, dried (magnesium sulfate), filtered and concentrated in vacuo to afford 3,3-dimethylpentan-1-ol which was used in the subsequent step without further purification.

Step C: Celite (200 g) followed by pyridinium chlorochromate (500 g, 2.3 mol) were added to a solution of 3,3-dimethylpentan-1-ol (ca. 1.2 mol) in methylene chloride (1.2 L). After stirring at 30° C. for 1 h, the reaction mixture was filtered through a plug of silica gel eluting with methylene chloride. The filtrate was washed with water, saturated aqueous sodium bicarbonate, and brine, dried (magnesium sulfate), filtered and concentrated in vacuo to afford 3,3-dimethylpentanal which was used in the subsequent step without further purification.

Step D: TosMIC (154 g, 0.9 mol) was added to an ambient temperature, saturated solution of ammonia in methanol (7 L). After stirring at ambient temperature for 1 h, 3,3-dimethylpentanal (ca. 0.6 mol) was added over 20 min. After stirring at reflux for 3 h, the reaction mixture was poured into cold 1 N hydrochloric acid and washed with hexane. The aqueous layer was basified with 10 N aqueous sodium hydroxide and extracted with ether. The combined organic extracts were washed with brine, dried (magnesium sulfate), filtered and concentrated in vacuo. Chromatography over silica eluting with 5-10% methanol/methylene chloride afforded 4-(2,2-dimethylbutyl)-1H-imidazole.

Step E: N-methylmorpholine (54 mL, 0.48 mol) was added to a solution of 4-(2,2-dimethylbutyl)-1H-imidazole (36 g, 0.24 mol) in dimethoxyethane (360 mL). After warming to 40° C., N,N-dimethylsulfamoyl chloride (38 mL, 0.36 mol) was added over 15 min. After stirring at 40° C. for 2 h, N-methylmorpholine (11 mL) and N,N-dimethylsulfamoyl chloride (8 mL) were added. After stirring for an additional 2 h, and the reaction mixture was cooled and filtered rinsing with ether. The filtrate was extracted with ether. The combined organic extracts were washed with brine, dried (magnesium sulfate), filtered, concentrated in vacuo. Chromatography over silica afforded the title compound.

INTERMEDIATE 40

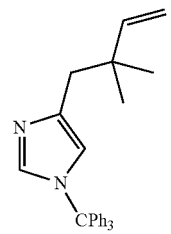

4-(2,2-dimethylbut-3-en-1-yl)-1-trityl-1H-imidazole

Step A: DIBAL-H (1 M in methylene chloride) (1.6 L, 1.6 mol) was added over 1 h to a −55° C. solution of methyl-3,3-dimethyl-4-pentenoate (114 g, 0.8 mol) in methylene chloride (600 mL). After stirring at 0° C. for 1 h, the reaction mixture was poured slowly into 1 L of ice cold 2N hydrochloric acid and extracted with methylene chloride. The combined organic extracts were washed with brine, dried (magnesium sulfate), filtered and concentrated in vacuo to afford 3,3-dimethylpent-4-en-1-ol which was used in the subsequent step without further purification.

Step B: Celite (200 g) followed by pyridinium chlorochromate (346 g, 1.6 mol) (portionwise) were added to a vigorously stirred 0° C. solution of 3,3-dimethylpent-4-en-1-ol (ca. 0.8 mol) in methylene chloride (1 L). After stirring at ambient temperature for 1.5 h, the reaction mixture was filtered through silica gel eluting with methylene chloride. The filtrate was washed with brine, dried (magnesium sulfate), filtered, and concentrated in vacuo to afford 3,3-dimethylpent-4-enal which was used in the subsequent step without further purification.

Step C: At 30° C., 3,3-dimethylpent-4-enal (126 g, 0.34 mol) was added over 20 minutes to an ambient temperature, saturated solution of ammonia in methanol (2.7 L). After stirring at 40° C. for 30 minutes, TosMIC (67 g, 0.4 mol) was added. After stirring at reflux overnight, the reaction mixture was concentrated, dissolved in ether and poured into 2N ammonium hydroxide (1500 mL) and stirred. The aqueous phase was extracted with ether. The combined organic extracts were washed with brine, dried (magnesium sulfate), filtered, and concentrated in vacuo to afford 4-(2,2-dimethylbut-3-en-1-yl)-1H-imidazole which was used in the subsequent step without further purification.

Step D: Triethylamine (1.5 mL, 53 mmol) followed by of trityl chloride (9 g, 32 mmol) were added to a 0° C. solution of 4-(2,2-dimethylbut-3-en-1-yl)-1H-imidazole (4 g, 27 mmol) in methylene chloride (40 mL). After stirring at ambient temperature for 3 h, the reaction mixture was poured into saturated aqueous ammonium chloride and extracted with methylene chloride. The combined organic extracts were washed with brine, dried (magnesium sulfate), filtered and concentrated in vacuo. Chromatography over silica eluting with 10-40% ethyl acetate/hexane afforded the title compound.

INTERMEDIATE 41

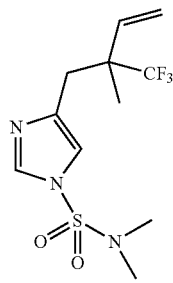

N,N-dimethyl-4-[2-methyl-2-(trifluoromethyl)but-3-en-1-yl]-1H-imidazole-1-sulfonamide Step A: 1,1,1-Trifluoroacetone (680 mg, 6.1 mmol) was added to an ambient temperature solution of benzyl (triphenylphosphoranylidene)acetate (2.5 g, 6.1 mmol) in methylene chloride (10 mL). After stirring in a sealed tube for 72 h, the reaction mixture was concentrated in vacuo. Chromatography over silica eluting with 0-20% ethyl acetate/hexane afforded benzyl 4,4,4-trifluoro-3-methylbut-2-enoate.

Step B: Benzyl 4,4,4-trifluoro-3-methylbut-2-enoate (1.87 g, 7.67 mmol) in diethyl ether (5 mL) was added dropwise to a suspension of LAH (291 mg, 1.67 mmol) in diethyl ether (10 mL). After stirring at −78° C. for 10 min and at 0° C. for a further 30 min, the reaction mixture was filtered through cotton, quenched with sodium potassium tartrate and stirred vigorously until layers separated. The aqueous phase was extracted with diethyl ether. The combined ethereal layers were dried (magnesium sulfate) and concentrated in vacuo to afford 4,4,4-trifluoro-3-methylbut-2-en-1-ol which was used in the subsequent step without further purification.

Step C: Triethyl orthoformate (6.51 mL, 35.7 mmol) was added to an ambient temperature mixture of 4,4,4-trifluoro-3-methylbut-2-en-1-ol (ca. 500 mg, 3.57 mmol) and propionic acid (13 μL, 0.18 mmol). After heating in a sealed tube at 200° C. for 30 h, the reaction mixture was cooled, diluted with diethyl ether and washed with saturated aqueous sodium bicarbonate. The organic phase was dried (magnesium sulfate) and concentrated in vacuo. Chromatography over silica eluting with 0-20% ethyl acetate/hexane afforded ethyl 3-methyl-3-(trifluoromethyl)pent-4-enoate.

Step D: Ethyl 3-methyl-3-(trifluoromethyl)pent-4-enoate (5 g, 23.8 mmol) in diethyl ether (20 mL) was added dropwise to a suspension of LAH (291 mg, 1.67 mmol) in diethyl ether (80 mL). After stirring at −78° C. for 30 min and at 0° C. for a further 30 min, the reaction mixture was quenched with sodium potassium tartrate and stirred vigorously until layers separated. The aqueous phase was extracted with diethyl ether. The combined ethereal layers were dried (magnesium sulfate) and concentrated in vacuo to afford 3-methyl-3-(trifluoromethyl)pent-4-en-1-ol which was used in the subsequent step without further purification.

Step E: PCC (15.4 g, 71.4 mmol) was added to an ambient temperature solution of 3-methyl-3-(trifluoromethyl)pent-4-en-1-ol (4.0 g, 23.8 mmol) in methylene chloride (100 mL). After stirring at ambient temperature for 1.5 h, celite was added and the reaction stirred vigorously for 10 min. The reaction mixture was filtered through celite and concentrated in vacuo. TosMIC (9.3 g, 47.6 mmol) followed by potassium tert-butoxide (cat.) were added to a solution of crude residue in tetrahydrofuran (50 mL). After stirring at ambient temperature for 2 h, the reaction mixture was concentrated in vacuo. Ammonia (7 N in methanol) (50 mL) was added to the crude residue. After stirring at 100° C. overnight, the reaction mixture was cooled and concentrated in vacuo. The residue was partitioned between 10% aqueous sodium hydroxide and methylene chloride. The aqueous phase was extracted with methylene chloride. The combined organic extracts were dried (magnesium sulfate) and concentrated in vacuo. Chromatography over silica eluting with 0-100% acetone/methylene chloride afforded 4-[2-methyl-2-(trifluoromethyl)but-3-en-1-yl]-1H-imidazole.

Step F: Triethylamine (3 mL, 14.02 mmol) followed by dimethylsulfamoyl chloride (1.5 mL, 14.02 mmol) were added to an ambient temperature solution of 4-[2-methyl-2-(trifluoromethyl)but-3-en-1-yl]-1H-imidazole (1.43 g, 7.01 mmol) in methylene chloride (20 mL). After stirring at ambient temperature overnight, the reaction mixture was diluted with water and extracted with ethyl acetate and methylene chloride. The combined organic extracts were dried (magnesium sulfate) and concentrated in vacuo. Chromatography over silica eluting with 0-100% ethyl aceate/hexane afforded the title compound.

INTERMEDIATE 42

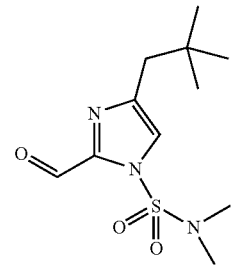

4-(2,2-dimethylpropyl)-2-formyl-N,N-dimethyl-1H-imidazole-1-sulfonamide n-Butyllithium (2.5 M in hexane) (0.83 mL, 2.2 mmol) was added to a −78° C. solution of 4-(2,2-dimethylpropyl)-N,N-dimethyl-1H-imidazole-1-sulfonamide (54 mg, 2.2 mmol) in tetrahydrofuran (5 mL). After stirring at −78° C. for 10 min, N,N-dimethylformamide (0.17 mL, 2.2 mmol) was added and the reaction allowed to warm to ambient temperature. After stirring at ambient temperature for a further 5 min, the reaction mixture was quenched with water and extracted with methylene chloride. The combined aqueous phases were dried (magnesium sulfate) and concentrated. Chromatography over silica eluting with 0-80% ethyl acetate/hexane afforded the title compound.

INTERMEDIATE 43

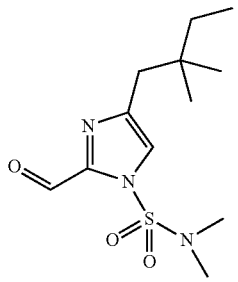

4-(2,2-dimethylbutyl)-2-formyl-N,N-dimethyl-1H-imidazole-1-sulfonamide

The title compound was prepared using the procedure outlined in Intermediate 42.

INTERMEDIATE 44

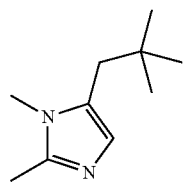

5-(2,2-dimethylpropyl)-1,2-dimethyl-1H-imidazole

Methyltriflate (0.17 mL, 1.52 mmol) was added to intermediate 9 (500 mg, 1.27 mmol) in methylene chloride (5 mL). After stirring at ambient temperature overnight, volatiles were removed. The residue was dissolved in TFA (0.5 mL). After stirring at 60° C. for 2 h, volatiles were removed and the residue partitioned between 2 N hydrochloric acid and diethyl ether. The aqueous phase was basified with 5 N sodium hydroxide and extracted with ethyl acetate. The organic extracts were washed with brine, dried and concentrated to afford the title compound which was used without further purification.

INTERMEDIATE 45

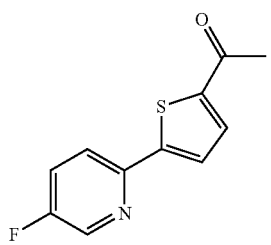

1-[5-(5-fluoropyridin-2-yl)-2-thienyl]ethanone

The title compound was prepared using the procedure outlined in Intermediate 19.

INTERMEDIATE 46

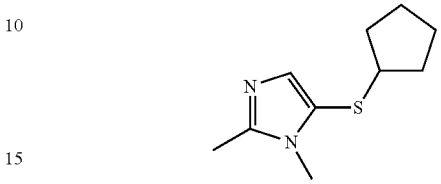

5-(cyclopentylthio)-1,2-dimethyl-1H-imidazole

A solution of tin (II) chloride (5.80 g, 25.7 mmol) in concentrated hydrochloric acid (minimal volume) was added to a solution of 1,2-dimethylimidazole-5-sulfonyl chloride (1 g, 5.14 mmol) in acetic acid (30 mL). After stirring at 70° C. for 45 min, the reaction mixture was concentrated in vacuo. The residue was dissolved in 20% aqueous sodium hydroxide until basic. Cyclopentyl iodide was added. After stirring at room temperature for 1 h, The solution was extracted with chloroform. The organic phase was dried (magnesium sulfate) and concentrated in vacuo to furnish the title compound which was used without further purification.

EXAMPLE 1

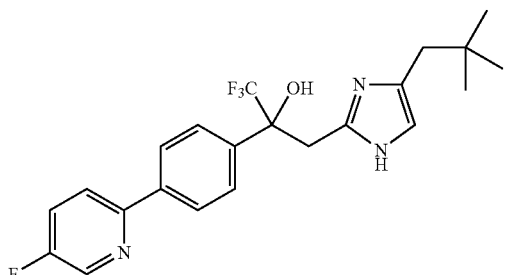

3-[4-(2,2-dimethylpropyl)-1H-imidazol-2-yl]-1,1,1-trifluoro-2-[4-(5-fluoropyridin-2-yl)phenyl]propan-2-ol Step A: 1,1'-Bis(diphenylphosphino)ferrocene-palladium (II)dichloride dichloromethane complex (590 mg, 0.72 mmol) was added to a degassed, ambient temperature solution of 2-(4-bromophenyl)-3-[4-(2,2-dimethylpropyl)-1-trityl-1H-imidazol-2-yl]-1,1,1-trifluoropropan-2-ol (9.4 g, 14.4 mmol) and bis(pinacolato)diboron (4.0 g, 15.9 mmol) in dimethylsulfoxide (75 mL). After stirring at 90° C. for 90 min, the reaction mixture was poured into water and extracted with diethyl ether containing a small amount of ethyl acetate. The combined organic extracts were washed with brine, dried (sodium sulfate) and concentrated in vacuo. Chromatography over silica eluting with 0-20% ethyl acetate/hexane afforded 3-[4-(2,2-dimethylpropyl)-1-trityl-1H-imidazol-2-yl]-1,1,1-trifluoro-2-[4-(4,4,5,5-tetramethyl-1,3,2-dioxaborolan-2-yl)phenyl]propan-2-ol.

Step B: 1,1'-bis(diphenylphosphino)ferrocene-palladium (II)dichloride dichloromethane complex (458 mg, 0.56 mmol) was added to a degassed, ambient temperature solution of 3-[4-(2,2-dimethylpropyl)-1-trityl-1H-imidazol-2-yl]-1,1,1-trifluoro-2-[4-(4,4,5,5-tetramethyl-1,3,2-dioxaborolan-2-yl)phenyl]propan-2-ol, sodium carbonate (2.4 g, 22.5 mmol) and 2-bromo-5-fluoropyridine (3.0 g, 16.8 mmol) in N,N-dimethylformamide/water (4:1) (150 mL). After stirring at 90° C. for 2 h, the reaction mixture was poured into water and extracted with ethyl acetate. The combined organic extracts were washed with brine, dried (sodium sulfate) and concentrated in vacuo. Chromatography over silica eluting with 0-40% ethyl acetate/hexane afforded 3-[4-(2,2-dimethylpropyl)-1-trityl-1H-imidazol-2-yl]-1,1,1-trifluoro-2-[4-(5-fluoropyridin-2-yl)phenyl]propan-2-ol.

Step C: Hydrogen chloride (4 M in 1,4-dioxane) (108 mL, 433 mmol) was added to an ambient temperature solution of 3-[4-(2,2-dimethylpropyl)-1-trityl-1H-imidazol-2-yl]-1,1,1-trifluoro-2-[4-(5-fluoropyridin-2-yl)phenyl]propan-2-ol (5.75 g, 8.7 mmol) in methanol (30 mL). After stirring at 70° C. for 1 h, volatiles were removed. The residue was partitioned between diethyl ether and 1N hydrochloric acid. The aqueous phase was washed with diethyl ether, basified with 2.5 N aqueous sodium hydroxide and extracted with ethyl acetate. The combined organic extracts were washed with brine, dried (sodium sulfate) and concentrated in vacuo to afford the title compound. LCMS: 422 (M+H). High pressure liquid chromatography (Chiralcel AD-H column) eluting with 15% isopropanol/heptane afforded the two individual enantiomers (E1 and E2). $^1$H NMR (500 MHz, CDCl$_3$) δ 8.52 (s, 1H), 7.87 (d, J=7.3 Hz, 2H), 7.67-7.65 (m, 3H), 7.48-7.45 (m, 2H), 6.56 (s, 1H), 3.46 (dd, J=15.1, 51.1), 2.33 (s, 2H), 0.80 (s, 9H).

The compounds in Table 1 were prepared using the appropriate starting materials and reagents following procedures similar to those described above for Example 1:

TABLE 1

| Example | Name | Structure | Enantiomer | HPLC-mass spectrum m/e |
|---|---|---|---|---|
| 2 | | 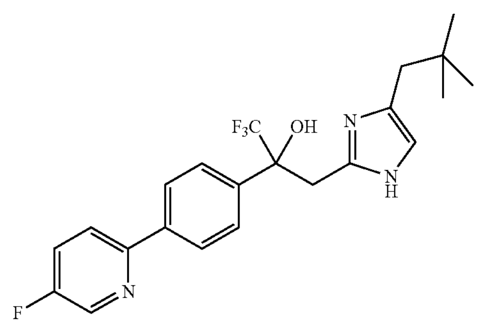 | E1 | 422 (M + H) |
| 3 | | 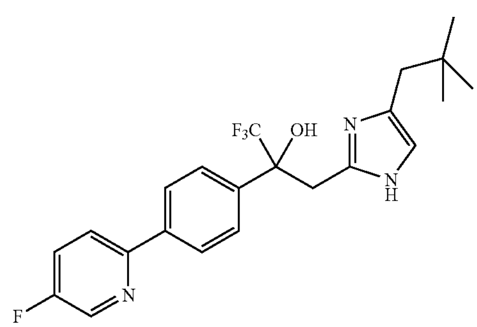 | E2 | 422 (M + H) |
| 4 | 1-[4-(2,2-dimethylpropyl)-1H-imidazol-2-yl]-2-[4-(5-fluoropyridin-2-yl)phenyl]propan-2-ol | 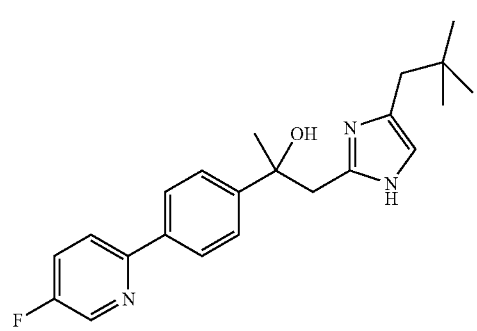 | E1 + E2 | 368 (M + H) |

TABLE 1-continued
| Example | Name | Structure | Enantiomer | HPLC-mass spectrum m/e |
|---|---|---|---|---|
| 5 | | 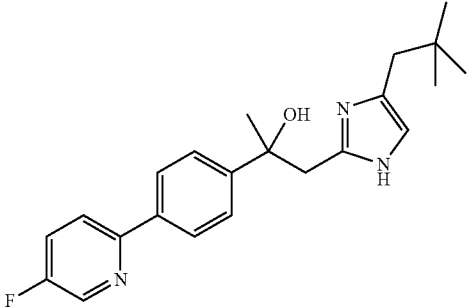 | E1 | 368 (M + H) |
| 6 | | 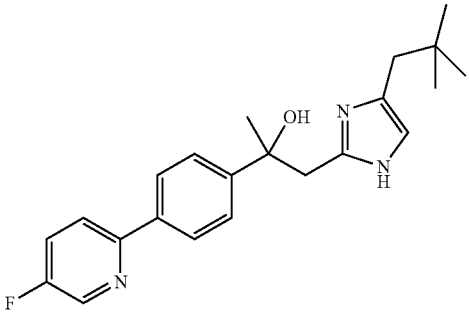 | E2 | 368 (M + H) |
| 7 | 1,1,1-trifluoro-2-(4-isothiazol-4-ylphenyl)-3-(4-{[1-(trifluoromethyl)cyclopropyl]methyl}-1H-imidazol-2-yl)propan-2-ol | 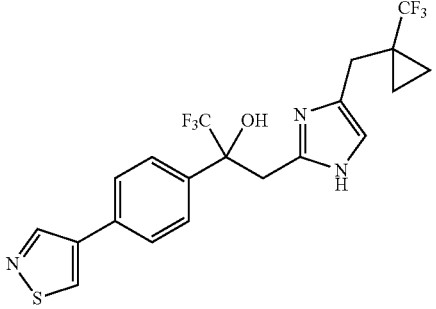 | E1 + E2 | 462 (M + H) |
| 8 | | 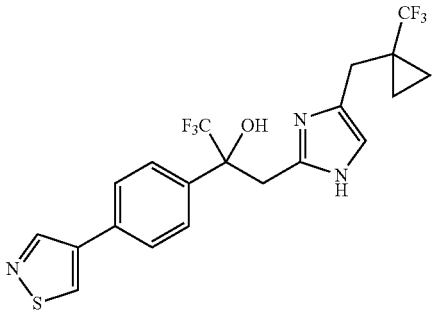 | E1 | 462 (M + H) |

TABLE 1-continued

| Example | Name | Structure | Enantiomer | HPLC-mass spectrum m/e |
|---|---|---|---|---|
| 9 | | 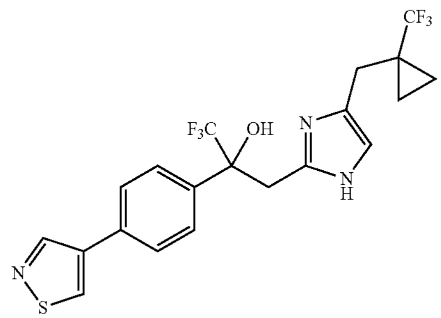 | E2 | 462 (M + H) |
| 10 | 1,1,1-trifluoro-2-(4-isothiazol-5-ylphenyl)-3-(4-{[1-(trifluoromethyl)cyclopropyl]-methyl}-1H-imidazol-2-yl)propan-2-ol | 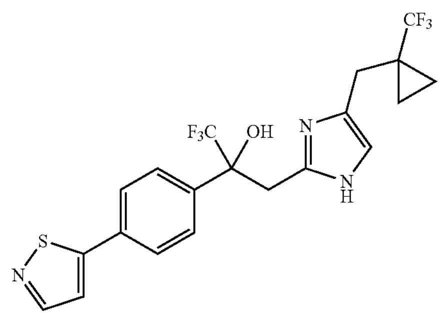 | E1 + E2 | 462 (M + H) |
| 11 | | 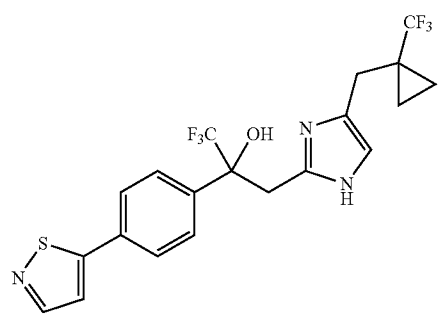 | E1 | 462 (M + H) |
| 12 | | 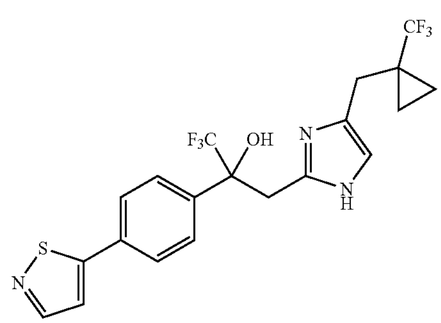 | E2 | 462 (M + H) |

TABLE 1-continued

| Example | Name | Structure | Enantiomer | HPLC-mass spectrum m/e |
|---|---|---|---|---|
| 13 | 2-[4-(2-aminopyridin-3-yl)phenyl]-1,1,1-trifluoro-3-(4-{[1-(trifluoromethyl)cyclopropyl]methyl}-1H-imidazol-2-yl)propan-2-ol | 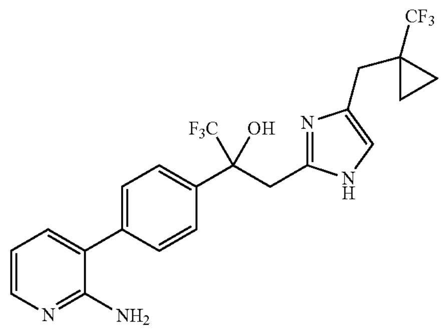 | E1 + E2 | 471 (M + H) |
| 14 | | 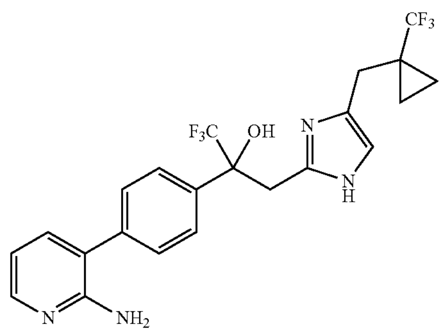 | E1 | 471 (M + H) |
| 15 | | 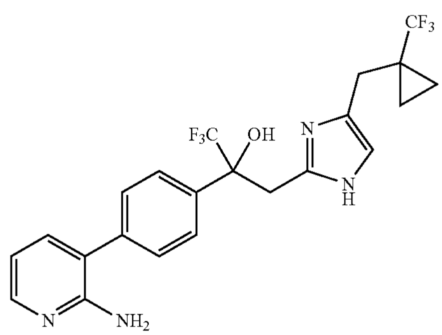 | E2 | 471 (M + H) |
| 16 | 1,1,1-trifluoro-2-[4-(1,3-thiazol-2-yl)phenyl]-3-(4-{[1-(trifluoromethyl)cyclopropyl]methyl}-1H-imidazol-2-yl)propan-2-ol | 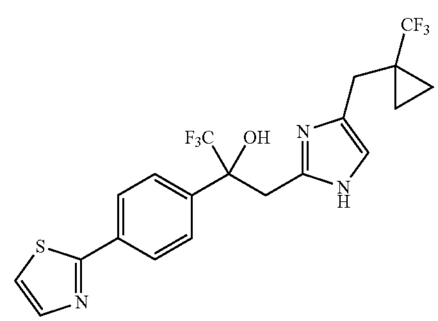 | E1 + E2 | 462 (M + H) |

*E1 is the faster eluting enantiomer by HPLC on a chiralpak AD or AD-H column eluting with IPA/heptane and E2 is the slower eluting enantiomer by HPLC on a chiralpak AD or AD-H column eluting with IPA/heptane.

EXAMPLE 17

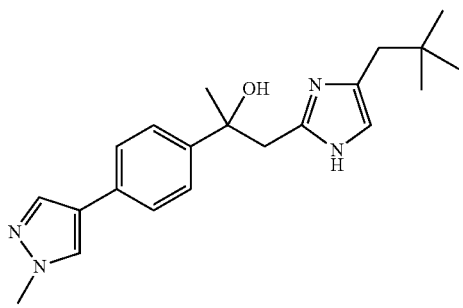

1-[4-(2,2-dimethylpropyl)-1H-imidazol-2-yl]-2-[4-(1-methyl-1H-pyrazol-4-yl)phenyl]propan-2-ol Step A: Palladium tetrakis(triphenylphosphine) (50 mg, 0.04 mmol) was added to a degassed, ambient temperature solution of 2-(4-bromophenyl)-1-[4-(2,2-dimethylpropyl)-1-trityl-1H-imidazol-2-yl]propan-2-ol (500 mg, 0.84 mmol), potassium carbonate (151 mg, 1.1 mmol) and 1-methyl-4-(4,4,5,5-tetramethyl-1,3,2-dioxaborolan-2-yl)-1H-pyrazole (193 mg, 0.9 mmol) in toluene/methanol (10:1) (4.4 mL). After stirring at 90° C. for 2 hr, the reaction mixture was washed with water and brine, dried (sodium sulfate) and concentrated in vacuo. Chromatography over silica eluting with 20-100% ethyl acetate/hexane afforded 1-[4-(2,2-dimethylpropyl)-1-trityl-1H-imidazol-2-yl]-2-[4-(1-methyl-1H-pyrazol-4-yl)phenyl]propan-2-ol.

Step B: Hydrogen chloride (4 M in 1,4-dioxane) (5.25 mL, 21 mmol) was added to an ambient temperature solution of 1-[4-(2,2-dimethylpropyl)-1-trityl-1H-imidazol-2-yl]-2-[4-(1-methyl-1H-pyrazol-4-yl)phenyl]propan-2-ol (250 mg, 0.42 mmol) in methanol (10 mL). After stirring at 70° C. for 1 h, volatiles were removed. The residue was partitioned between diethyl ether and 1 N hydrochloric acid. The aqueous phase was washed with diethyl ether, basified with 2.5 N aqueous sodium hydroxide and extracted with ethyl acetate. The combined organic extracts were washed with brine, dried (sodium sulfate) and concentrated in vacuo to afford the title compound. (M+H) found 339.

The compounds in Table 2 were prepared using the appropriate starting materials and reagents following procedures similar to those described above for Example 17:

TABLE 2

| Example | Name | Structure | Enantiomer | HPLC-mass spectrum m/e |
|---|---|---|---|---|
| 18 | 2-[4-(2,2-dimethylpropyl)-1H-imidazol-2-yl]-1-[4-(1-methyl-1H-pyrazol-4-yl)phenyl]ethanol | 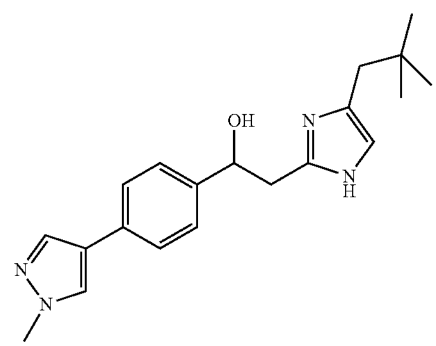 | E1 + E2 | 339 (M + H) |
| 19 | 3-[4-(2,2-dimethylpropyl)-1H-imidazol-2-yl]-1,1,1-trifluoro-2-[4-(1H-pyrazol-3-yl)phenyl]propan-2-ol | 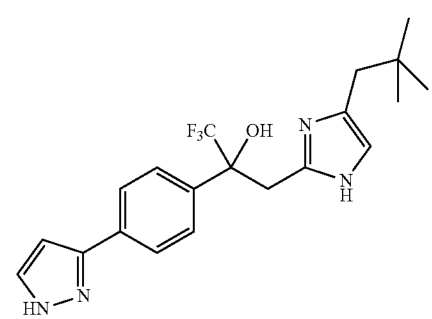 | E1 + E2 | 393 (M + H) |

TABLE 2-continued

| Example | Name | Structure | Enantiomer | HPLC-mass spectrum m/e |
|---|---|---|---|---|
| 20 | 2-[4-(3-amino-1-methyl-1H-pyrazol-4-yl)phenyl]-1-[4-(2,2-dimethylpropyl)-1H-imidazol-2-yl]propan-2-ol | 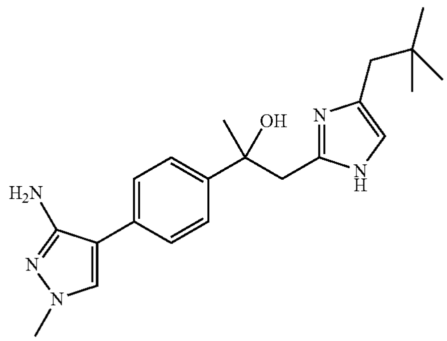 | E1 + E2 | 368 (M + H) |
| 21 | 3-[4-(2,2-dimethylpropyl)-1H-imidazol-2-yl]-1,1,1-trifluoro-2-[4-(1-methyl-1H-pyrazol-4-yl)phenyl]propan-2-ol | 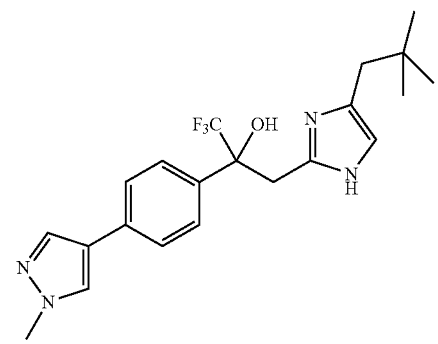 | E1 + E2 | 407 (M + H) |

*E1 is the faster eluting enantiomer by HPLC on a chiralpak AD or AD-H column eluting with IPA/heptane and E2 is the slower eluting enantiomer by HPLC on a chiralpak AD or AD-H column eluting with IPA/heptane.

EXAMPLE 22

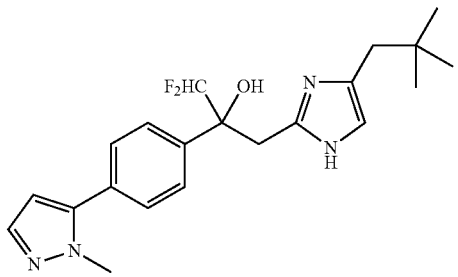

3-[4-(2,2-dimethylpropyl)-1H-imidazol-2-yl]-1,1-difluoro-2-[4-(1-methyl-1H-pyrazol-5-yl)phenyl]propan-2-ol Step A: Lithium diisopropylamide (1.5 M in cyclohexane) (9.7 mL, 14.6 mmol) was added to a −78° C. solution of 1-methylpyrazole (1 g, 12.2 mmol) in tetrahydrofuran (15 mL). After stirring at −78° C. for 15 min, chloro-tri-n-butylstannane (3.9 mL, 14.6 mmol) was added dropwise. The reaction mixture was allowed to warm to ambient temperature overnight. The reaction mixture was quenched with saturated aqueous ammonium chloride, diluted with water and extracted with ethyl acetate. The combined organic extracts were dried (magnesium sulfate), filtered and concentrated in vacuo. Chromatography over silica eluting with 0-100 ethyl acetate/hexane afforded 1-methyl-5-(tributylstannyl)-1H-pyrazole.

Step B: Bis(triphenylphosphine) palladium (II) chloride (49 mg, 0.07 mmol) was added to a degassed, ambient temperature solution of 1-methyl-5-(tributylstannyl)-1H-pyrazole (259 mg, 0.70 mmol) and 2-(4-bromophenyl)-3-[4-(2,2-dimethylpropyl)-1-trityl-1H-imidazol-2-yl]-1,1-difluoropropan-2-ol (483 mg, 0.77 mmol) in tetrahydrofuran (15 mL). After stirring at 75° C. overnight, the reaction mixture was cooled and cesium fluoride (50% on celite) was added. After stirring vigorously at ambient temperature for 1 h, the reaction mixture was filtered, rinsing with ethyl acetate. The filtrate was washed with water, dried (magnesium sulfate), filtered and concentrated in vacuo. Chromatography over silica eluting with 0-100% ethyl acetate/hexane afforded 3-[4-(2,2-dimethylpropyl)-1-trityl-1H-imidazol-2-yl]-1,1-difluoro-2-[4-(1-methyl-1H-pyrazol-5-yl)phenyl]propan-2-ol.

Step C: Hydrogen chloride (4 M in 1,4-dioxane) (1 mL, 0.25 mmol) was added to an ambient temperature solution of 3-[4-(2,2-dimethylpropyl)-1-trityl-1H-imidazol-2-yl]-1,1-difluoro-2-[4-(1-methyl-1H-pyrazol-5-yl)phenyl]propan-2-ol (30 mg, 0.05 mmol) in methanol (1 mL). After stirring at 70° C. for 1 h, volatiles were removed in vacuo. The residue was partitioned between diethyl ether and 1 N hydrochloric acid. The aqueous phase was washed with diethyl ether, basified with 2.5 N aqueous sodium hydroxide and extracted with ethyl acetate. Combined extracts were washed with brine, dried (sodium sulfate) and concentrated in vacuo to afford the title compound. $^1$H NMR (500 MHz, CD$_3$OD) δ

7.58 (d, J=8.0 Hz, 2H), 7.46 (d, J=1.5 Hz, 1H), 7.39 (d, J=8.0 Hz, 2H), 6.51 (s, 1H), 6.30 (d, J=1.5 Hz, 1H), 5.98 (t, J=55.7 Hz, 1H), 3.81 (s, 3H), 3.42-3.28 (m, 2H), 2.31 (s, 2H), 0.76 (s, 9H).

EXAMPLE 23

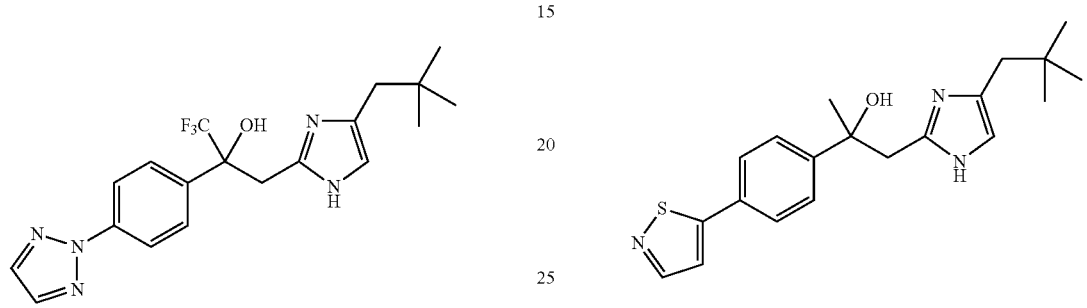

3-[4-(2,2-dimethylpropyl)-1H-imidazol-2-yl]-1,1,1-trifluoro-2-[4-(2H-1,2,3-triazol-2-yl)phenyl]propan-2-ol Step A: A mixture of copper (I) iodide (1 mg, 0.01 mmol), 2-(4-bromophenyl)-3-[4-(2,2-dimethylpropyl)-1-trityl-1H-imidazol-2-yl]-1,1,1-trifluoropropan-2-ol (50 mg, 0.08 mmol), 1,2,3-triazole (11 mg, 0.15 mmol) and potassium carbonate (21 mg, 0.15 mmol) in N-methylpyrrolidinone (1 mL) were irradiated in a microwave reactor at 195° C. for 1 h. The reaction mixture was diluted with water and extracted with ethyl acetate. The combined organic phases were dried (magnesium sulfate), filtered and concentrated in vacuo. High pressure liquid chromatography (KR100-5C18 100× 21.2 mm column) eluting with 10-100% acetonitrile/water containing 0.1% trifluoroacetic acid afforded 3-[4-(2,2-dimethylpropyl)-1-trityl-1H-imidazol-2-yl]-1,1,1-trifluoro-2-[4-(2H-1,2,3-triazol-2-yl)phenyl]propan-2-ol.

Step B: Hydrogen chloride (4 M in 1,4-dioxane) (1 mL, 0.25 mmol) was added to an ambient temperature solution of 3-[4-(2,2-dimethylpropyl)-1-trityl-1H-imidazol-2-yl]-1,1,1-trifluoro-2-[4-(2H-1,2,3-triazol-2-yl)phenyl]propan-2-ol (250 mg, 0.42 mmol) in methanol (1 mL). After stirring at 70° C. for 1 h, volatiles were removed in vacuo. The residue was partitioned between diethyl ether and 1 N hydrochloric acid. The aqueous phase was washed with diethyl ether, basified with 2.5 N aqueous sodium hydroxide and extracted with ethyl acetate. The combined organic extracts were washed with brine, dried (sodium sulfate) and concentrated in vacuo to afford the title compound. (M+H) found 394

EXAMPLE 24

1-[4-(2,2-dimethylpropyl)-1H-imidazol-2-yl]-2-(4-isothiazol-5-ylphenyl)propan-2-ol Step A: Palladium tetrakis(triphenylphosphine) (39 mg, 0.03 mmol) was added to a degassed, ambient temperature solution of 5-bromoisothiazole (55 mg, 0.34 mmol), 2-(4-bromophenyl)-1-[4-(2,2-dimethylpropyl)-1-trityl-1H-imidazol-2-yl]propan-2-ol (200 mg, 0.34 mmol) and hexamethylditin (110 mg, 0.34 mmol) in 1,4-dioxane (15 mL). After stirring at 90° C. for 16 h, the reaction mixture was diluted with water and extracted with ethyl acetate and methylene chloride. The combined organic extracts were concentrated in vacuo. Chromatography over silica eluting with 0-50% ethyl acetate/hexane afforded 1-[4-(2,2-dimethylpropyl)-1-trityl-1H-imidazol-2-yl]-2-(4-isothiazol-5-ylphenyl)propan-2-ol.

Step B: Hydrogen chloride (4 M in 1,4-dioxane) (2 mL, 0.5 mmol) was added to an ambient temperature solution of 1-[4-(2,2-dimethylpropyl)-1-trityl-1H-imidazol-2-yl]-2-(4-isothiazol-5-ylphenyl)propan-2-ol (103 mg, 0.17 mmol) in methanol (4 mL). After stirring at 70° C. for 1 h, volatiles were removed in vacuo. The residue was basified with 10% aqueous sodium hydroxide and extracted with ethyl acetate. Combined extracts were dried (magnesium sulfate) and concentrated in vacuo. Chromatography over silica eluting with 0-100% acetone/methylene chloride afforded the title compound. LCMS: 356 (M+H). Individual enantiomer (E1 or E2) was obtained by HPLC separation on a chrial column.

The compounds in Table 3 were prepared using the appropriate starting materials and reagents following procedures similar to those described above for Example 24:

TABLE 3

| Example | Name | Structure | Enantiomer | HPLC-mass spectrum m/e |
|---|---|---|---|---|
| 25 | | (structure) | E1 | 356 (M + H) |
| 26 | | (structure) | E2 | 356 (M + H) |
| 27 | 3-[4-(2,2-dimethylpropyl)-1H-imidazol-2-yl]-1,1,1-trifluoro-2-(4-isothiazol-5-ylphenyl)propan-2-ol | | E1 + E2 | 410 (M + H) |
| 28 | | (structure) | E1 | 410 (M + H) |
| 29 | | (structure) | E2 | 410 (M + H) |

*E1 is the faster eluting enantiomer by HPLC on a chiralpak AD or AD-H column eluting with IPA/heptane and E2 is the slower eluting enantiomer by HPLC on a chiralpak AD or AD-H column eluting with IPA/heptane.

EXAMPLE 30

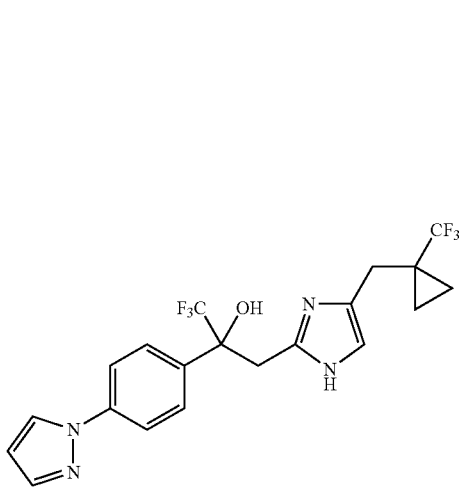

1,1,1-trifluoro-2-[4-(1H-pyrazol-1-yl)phenyl]-3-(4-{[1-(trifluoromethyl)cyclopropyl]methyl}-1H-imidazol-2-yl)propan-2-ol BuLi (1.6 M in hexanes) (21.00 ml, 33.6 mmol) was added dropwise to a stirred, degassed, −78° C. mixture of intermediate 2 (10 g, 22.40 mmol) in tetrahydrofuran (150 mL) and the mixture was stirred at −78° C. for 15 minutes. The mixture was added dropwise (via cannula) over 40 minutes to intermediate 21 (8.07 g, 33.6 mmol) in degassed tetrahydrofuran (100 mL) and the resulting reaction mixture was stirred at −78° C. for 2 hours. The reaction was then quenched with saturated aqueous ammonium chloride and extracted with ethyl acetate. The organic phase was separated, washed with saturated brine, dried (sodium sulfate), filtered and concentrated in vacuo to give a crude residue. HCl (101 ml, 403 mmol) (4 M in dioxane) was added to a stirred, room temperature mixture of the crude residue in methanol (100 mL) and the mixture was stirred at 70° C. for 45 minutes. The volatiles were removed, and the resulting residue was partitioned between 2M aqueous sodium hydroxide and ethyl acetate. The organic phase was separated, washed with saturated brine, dried (sodium sulfate), filtered and concentrated in vacuo to give the crude product. Chromatography of the crude product over silica eluting with 20-80% EtOAc/hexane afforded the title compound as an off-white solid. $^1$H NMR (500 MHz, CD$_3$OD) δ 8.24 (d, J=2.6 Hz, 1H), 7.87 (d, J=7.3 Hz, 2H), 7.79 (d, J=8.9 Hz, 2H), 7.73 (d, J=1.8 Hz, 1H), 7.64 (d, J=8.7 Hz, 2H), 7.20 (s, 1H), 6.53 (dd, J=2.2 Hz, 1H) 3.73 (d, J=2 Hz, 2H), 3.0 (d, J=16.3 Hz, 1H), 2.92 (d, J=16 Hz, 1H), 0.93 (m, 2H), 0.67 (d, J=9.8 Hz, 1H), 0.62 (d, J=9.9 Hz, 1H).

EXAMPLE 31

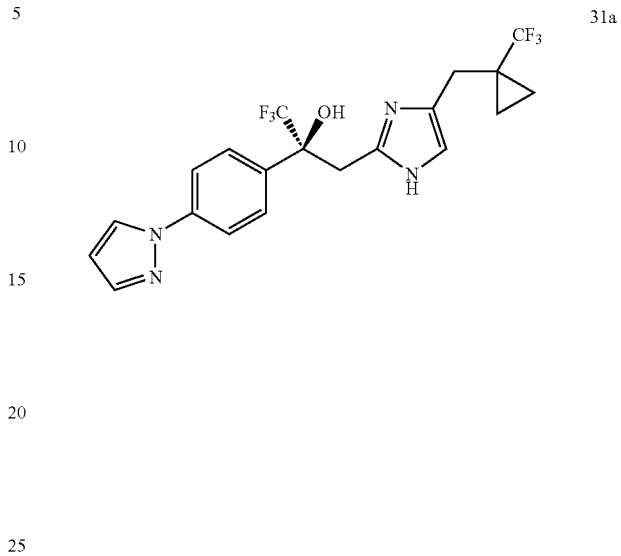

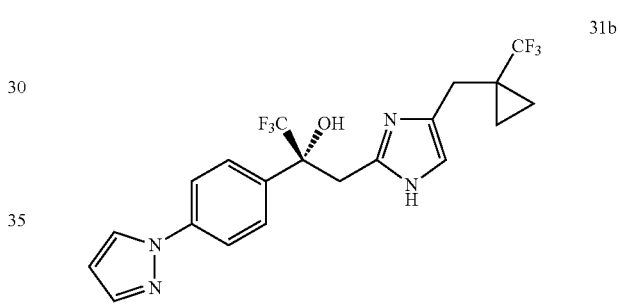

(2S)-1,1,1-trifluoro-2-[4-(1H-pyrazol-1-yl)phenyl]-3-(4-{[1-(trifluoromethyl)cyclopropyl]methyl}-1H-imidazol-2-yl)propan-2-ol and (2R)-1,1,1-trifluoro-2-[4-(1H-pyrazol-1-yl)phenyl]-3-(4-{[1-(trifluoromethyl)cyclopropyl]methyl}-1H-imidazol-2-yl)propan-2-ol Individual enantiomers (E1 and E2) were obtained by HPLC separation of 1,1,1-trifluoro-2-[4-(1H-pyrazol-1-yl)phenyl]-3-(4-{[1-(trifluoromethyl)cyclopropyl]methyl}-1H-imidazol-2-yl)propan-2-ol (as prepared in Example 30) on a chiral column (ChiralCel AD-H) eluting with IPA/heptane to afford the title compounds. $^1$H NMR (500 MHz, CD$_3$OD) δ 8.24 (d, J=2.5 Hz, 1H), 7.79 (d, J=8.9 Hz, 2H), 7.73 (s, 1H), 7.64 (d, J=8.7 Hz, 2H), 6.53 (s, 1H), 3.73 (s, 2H), 3.00 (d, J=16 Hz, 1H), 2.92 (d, J=16, 1H), 0.93 (s, 2H), 0.69-0.61 (m, 2H). (M+H) found 445.

The compounds in Table 4 were prepared using the appropriate starting materials and reagents following procedures similar to those described above for Example 30:

TABLE 4

| Example | Name | Structure | Enantiomer | HPLC-mass spectrum m/e |
|---|---|---|---|---|
| 32 | 1-[4-(2,2-dimethylpropyl)-1H-imidazol-2-yl]-2-[3-fluoro-4-(5-fluoropyridin-2-yl)phenyl]propan-2-ol | 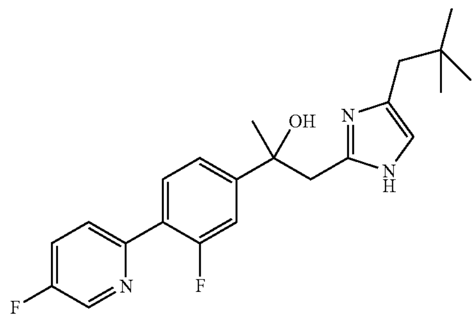 | E1 + E2 | 386 (M + H) |
| 33 | | 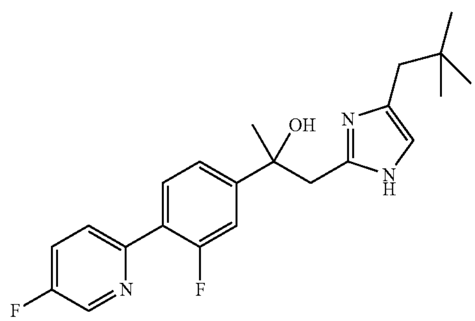 | E1 | 386 (M + H) |
| 34 | | 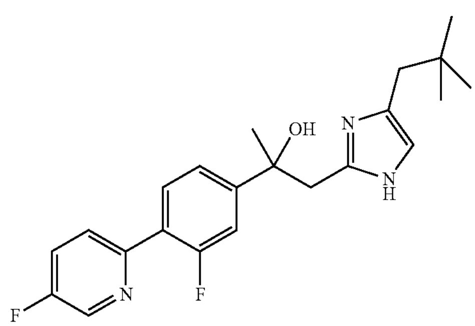 | E2 | 386 (M + H) |
| 35 | 1-[4-(2,2-dimethylpropyl)-1H-imidazol-2-yl]-2-[4-(5-fluoropyridin-2-yl)-3-methylphenyl]propan-2-ol | 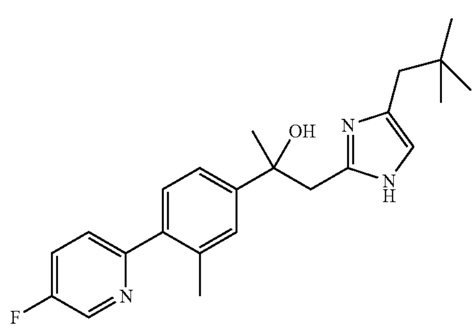 | E1 + E2 | 382 (M + H) |

TABLE 4-continued

| Example | Name | Structure | Enantiomer | HPLC-mass spectrum m/e |
|---|---|---|---|---|
| 36 | 1-[4-(2,2-dimethylpropyl)-1H-imidazol-2-yl]-2-[4-(5-fluoropyridin-2-yl)-2-methylphenyl]propan-2-ol | 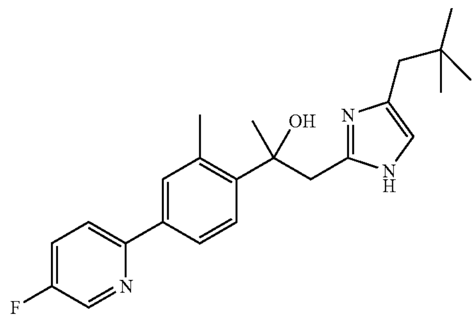 | E1 + E2 | 382 (M + H) |
| 37 | | 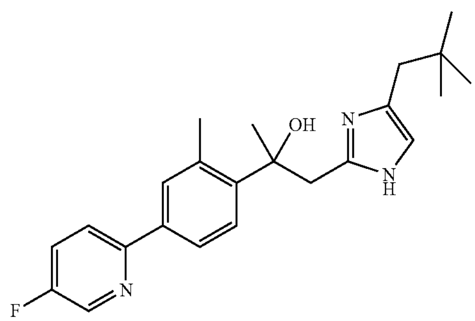 | E1 | 382 (M + H) |
| 38 | | 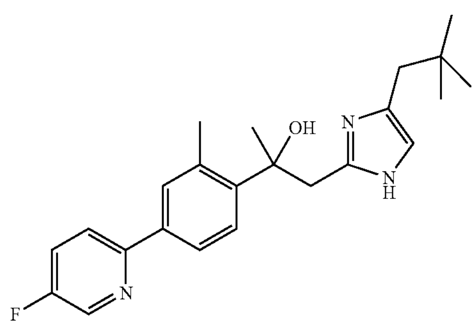 | E2 | 382 (M + H) |
| 39 | 1-[4-(2,2-dimethylpropyl)-1H-imidazol-2-yl]-2-(5-fluoro-2,3'-bipyridin-6'-yl)propan-2-ol | 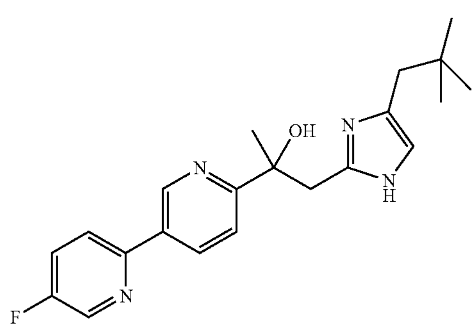 | | 369 (M + H) |

TABLE 4-continued

| Example | Name | Structure | Enantiomer | HPLC-mass spectrum m/e |
|---|---|---|---|---|
| 40 | 3-[4-(2,2-dimethylpropyl)-1H-imidazol-2-yl]-1,1-difluoro-2-[4-(5-fluoropyridin-2-yl)phenyl]propan-2-ol | 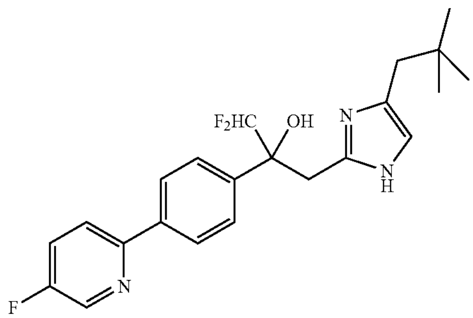 | E1 + E2 | 404 (M + H) |
| 41 | | 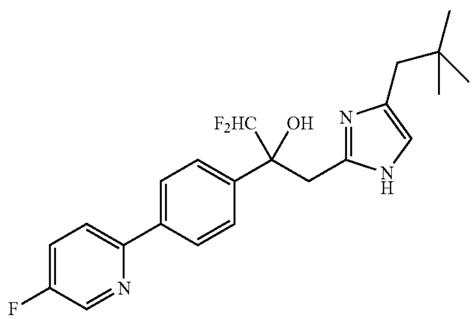 | E1 | 404 (M + H) |
| 42 | | 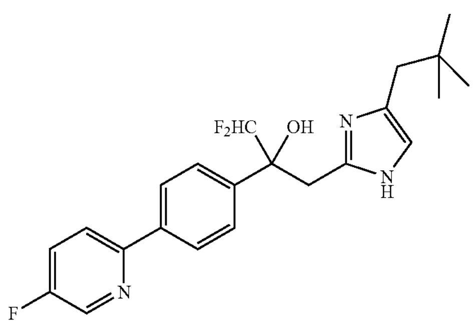 | E2 | 404 (M + H) |
| 43 | 3-[4-(2,2-dimethylpropyl)-1H-imidazol-2-yl]-1,1-difluoro-2-[2-fluoro-4-(5-fluoropyridin-2-yl)phenyl]propan-2-ol | 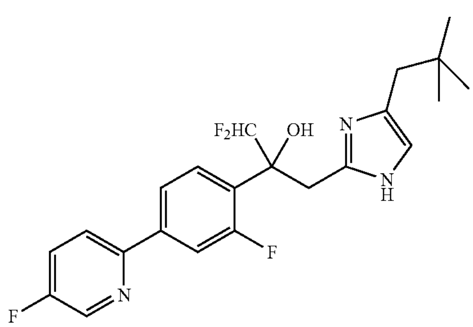 | E1 + E2 | 422 (M + H) |

TABLE 4-continued

| Example | Name | Structure | Enantiomer | HPLC-mass spectrum m/e |
|---|---|---|---|---|
| 44 | 2-[2,3-difluoro-4-(5-fluoropyridin-2-yl)phenyl]-3-[4-(2,2-dimethylpropyl)-1H-imidazol-2-yl]-1,1-difluoropropan-2-ol | 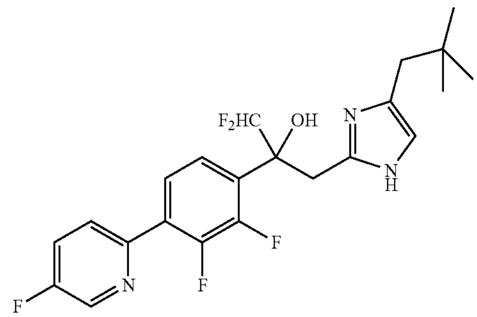 | E1 + E2 | 440 (M + H) |
| 45 | 1,1-difluoro-2-[4-(5-fluoropyridin-2-yl)phenyl]-3-(4-{[1-(trifluoromethyl)cyclopropyl]methyl}-1H-imidazol-2-yl)propan-2-ol | 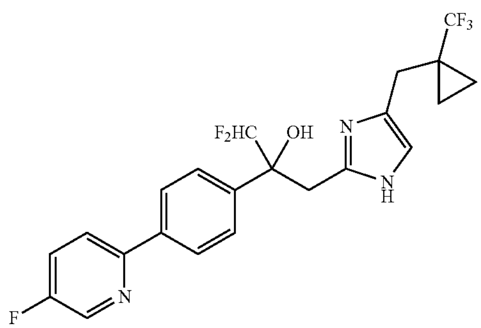 | E1 + E2 | 456 (M + H) |
| 46 | | 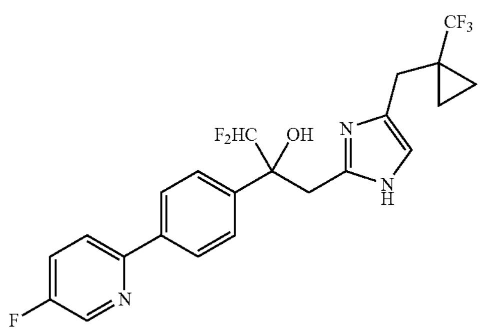 | E1 | 456 (M + H) |
| 47 | | 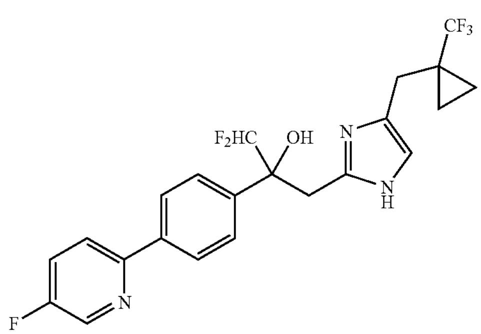 | E2 | 456 (M + H) |

TABLE 4-continued

| Example | Name | Structure | Enantiomer | HPLC-mass spectrum m/e |
|---|---|---|---|---|
| 48 | 2-[4-(5-fluoropyridin-2-yl)phenyl]-1-(4-{[1-(trifluoromethyl)cyclobutyl]methyl}-1H-imidazol-2-yl)propan-2-ol | 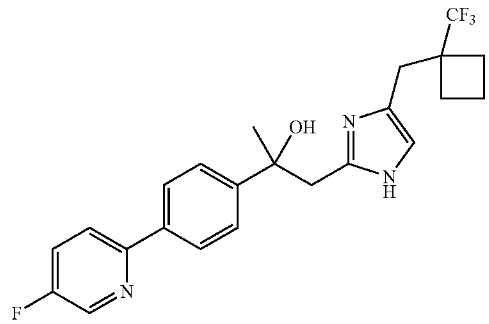 | E1 + E2 | 434 (M + H) |
| 49 | 2-[4-(5-fluoropyridin-2-yl)phenyl]-1-(4-{[1-(trifluoromethyl)cyclopropyl]methyl}-1H-imidazol-2-yl)propan-2-ol | 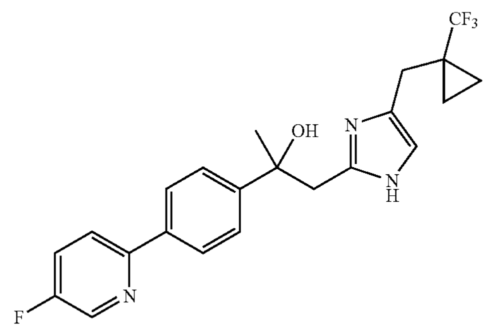 | E1 + E2 | 420 (M + H) |
| 50 | | 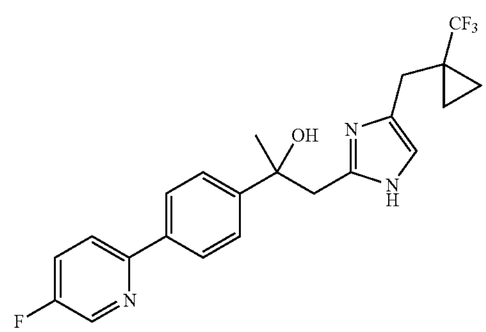 | E1 | 420 (M + H) |
| 51 | | 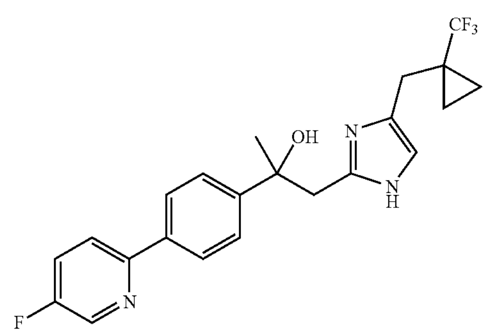 | E2 | 420 (M + H) |

TABLE 4-continued

| Example | Name | Structure | Enantiomer | HPLC-mass spectrum m/e |
|---|---|---|---|---|
| 52 | 2-[4-(1H-pyrazol-1-yl)phenyl]-1-(4-{[1-(trifluoromethyl)cyclopropyl]methyl}-1H-imidazol-2-yl)propan-2-ol | 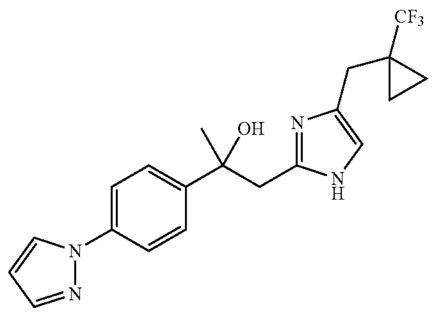 | E1 + E2 | 391 (M + H) |
| 53 | | 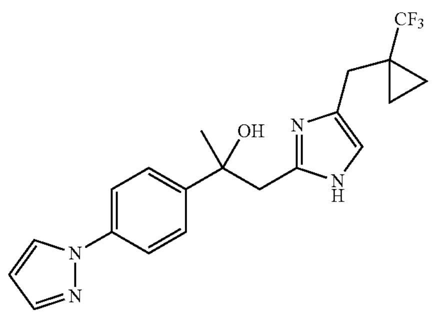 | E1 | 391 (M + H) |
| 54 | | 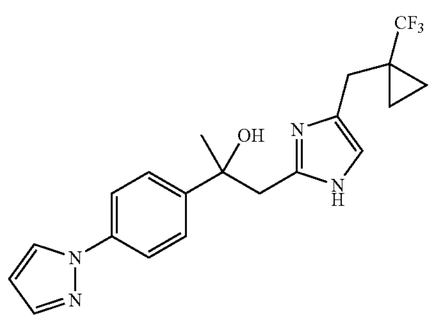 | E2 | 391 (M + H) |
| 55 | 1,1,1-trifluoro-2-[4-(5-fluoropyridin-2-yl)phenyl]-3-(4-{[1-(trifluoromethyl)cyclopropyl]methyl}-1H-imidazol-2-yl)propan-2-ol | 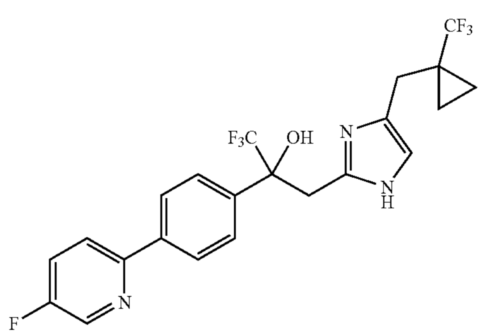 | E1 | 474 (M + H) |

TABLE 4-continued

| Example | Name | Structure | Enantiomer | HPLC-mass spectrum m/e |
|---|---|---|---|---|
| 56 | | 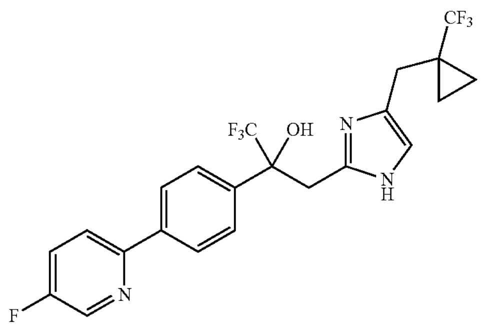 | E2 | 474 (M + H) |
| 57 | 1-[4-(2,2-dimethylpropyl)-1H-imidazol-2-yl]-2-[2-fluoro-4-(5-fluoropyridin-2-yl)phenyl]propan-2-ol. | 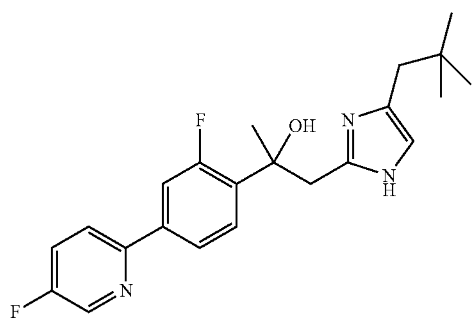 | E1 + E2 | 386 (M + H) |
| 58 | 2-[4-(2,2-dimethylpropyl)-1H-imidazol-2-yl]-1-[4-(5-fluoropyridin-2-yl)-phenyl]ethanol | 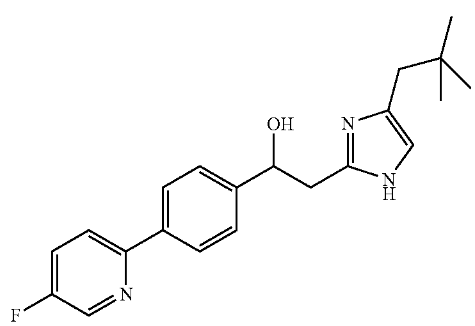 | E1 + E2 | 354 (M + H) |
| 59 | 2-[4-(2,2-dimethylpropyl)-1H-imidazol-2-yl]-1-[2-fluoro-4-(5-fluoropyridin-2-yl)phenyl]ethanol | 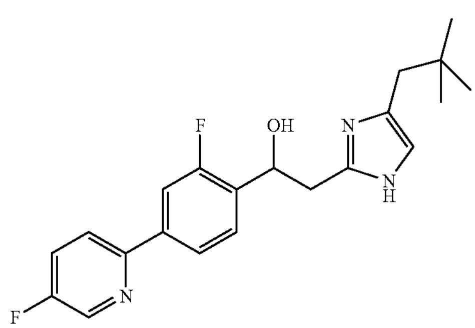 | E1 + E2 | 372 (M + H) |

TABLE 4-continued

| Example | Name | Structure | Enantiomer | HPLC-mass spectrum m/e |
|---|---|---|---|---|
| 60 | 1-[4-(2,2-dimethylpropyl)-1H-imidazol-2-yl]-2-[4-(1H-pyrazol-1-yl)phenyl]propan-2-ol | 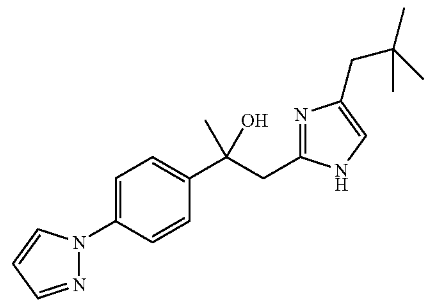 | E1 + E2 | 339 (M + H) |
| 61 | | 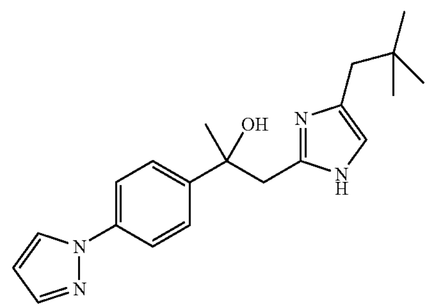 | E1 | 339 (M + H) |
| 62 | | 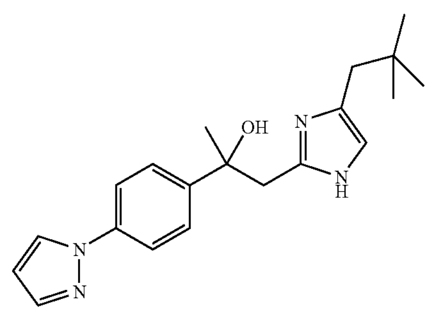 | E2 | 339 (M + H) |
| 63 | 2-[4-(1H-pyrazol-1-yl)phenyl]-1-(4-{[1-(trifluoromethyl)cyclobutyl]methyl}-1H-imidazol-2-yl)propan-2-ol | 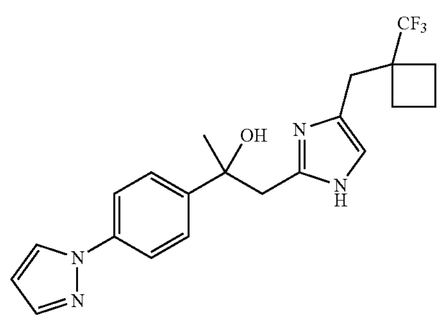 | E1 + E2 | 405 (M + H) |
| 64 | 2-[2,5-difluoro-4-(1H-pyrazol-1-yl)phenyl]-1-[4-(2,2-dimethylpropyl)-1H-imidazol-2-yl]propan-2-ol | 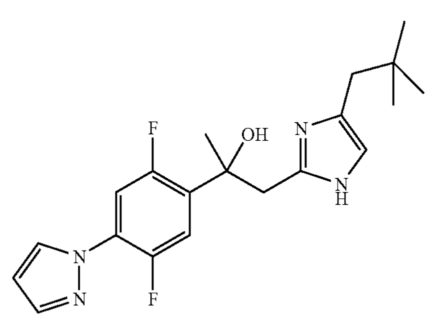 | E1 + E2 | 375 (M + H) |

TABLE 4-continued

| Example | Name | Structure | Enantiomer | HPLC-mass spectrum m/e |
|---|---|---|---|---|
| 65 | | 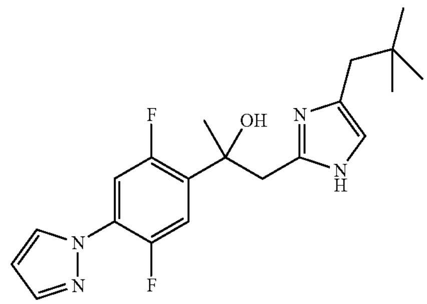 | E1 | 375 (M + H) |
| 66 | | 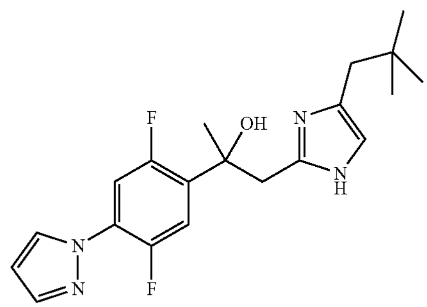 | E2 | 375 (M + H) |
| 67 | 3-[4-(2,2-dimethylpropyl)-1H-imidazol-2-yl]-1,1-difluoro-2-[4-(1-methyl-1H-pyrazol-3-yl)phenyl]propan-2-ol | 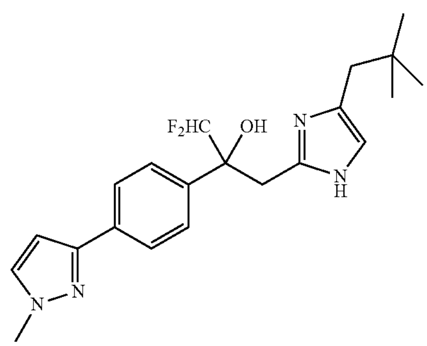 | E1 + E2 | 389 (M + H) |
| 68 | | 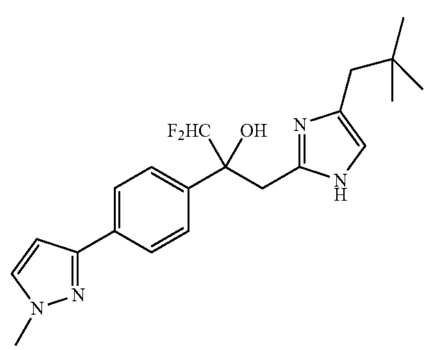 | E1 | 389 (M + H) |

TABLE 4-continued

| Example | Name | Structure | Enantiomer | HPLC-mass spectrum m/e |
|---------|------|-----------|------------|------------------------|
| 69 | | 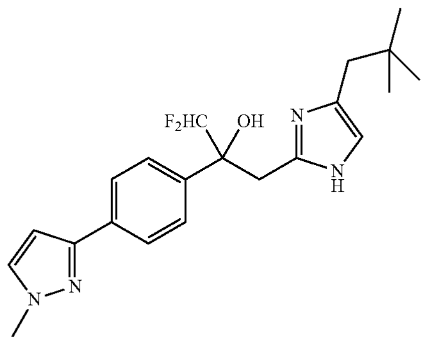 | E2 | 389 (M + H) |
| 70 | 1-[4-(2,2-dimethylpropyl)-1H-imidazol-2-yl]-2-[6-(1H-pyrazol-1-yl)pyridin-3-yl]propan-2-ol | 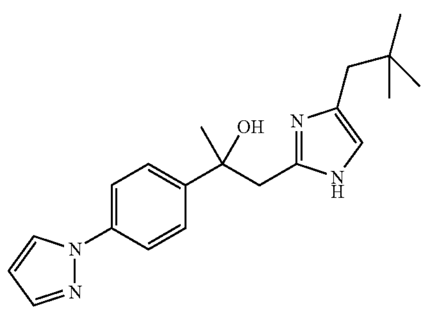 | E1 | 340 (M + H) |
| 71 | | 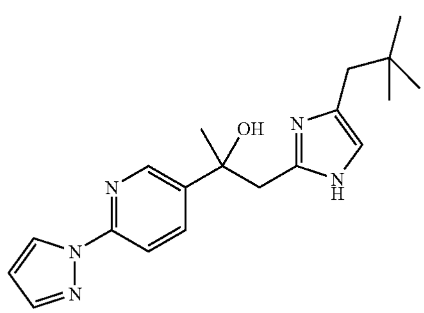 | E2 | 340 (M + H) |
| 72 | 1,1-difluoro-2-[4-(1H-pyrazol-1-yl)phenyl]-3-(4-{[1-(trifluoromethyl)cyclopropyl]methyl}-1H-imidazol-2-yl)propan-2-ol | 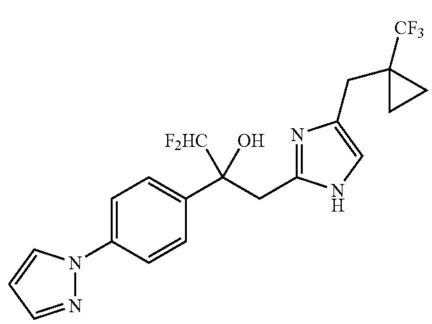 | E1 | 427 (M + H) |

TABLE 4-continued

| Example | Name | Structure | Enantiomer | HPLC-mass spectrum m/e |
|---------|------|-----------|------------|------------------------|
| 73 | | 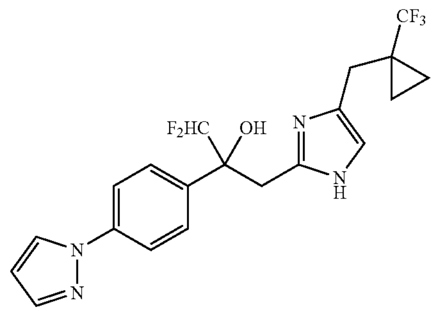 | E2 | 427 (M + H) |
| 74 | 2-[2-chloro-4-(1H-pyrazol-1-yl)phenyl]-1-[4-(2,2-dimethylpropyl)-1H-imidazol-2-yl]propan-2-ol | 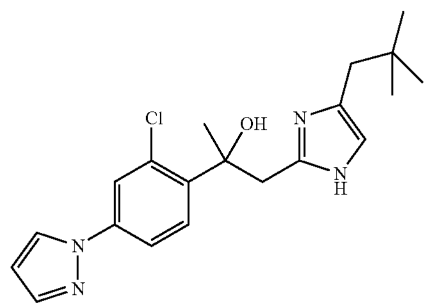 | E1 + E2 | 373 (M + H) |
| 75 | 3-[4-(2,2-dimethylpropyl)-1H-imidazol-2-yl]-1,1-difluoro-2-[4-(1H-pyrazol-1-yl)phenyl]propan-2-ol | 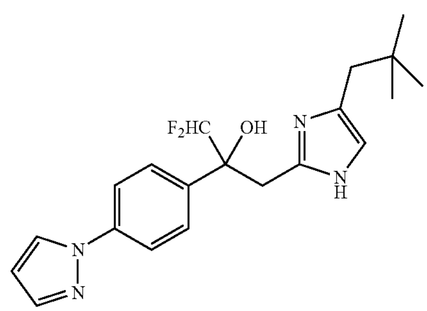 | E1 + E2 | 375 (M + H) |
| 76 | | 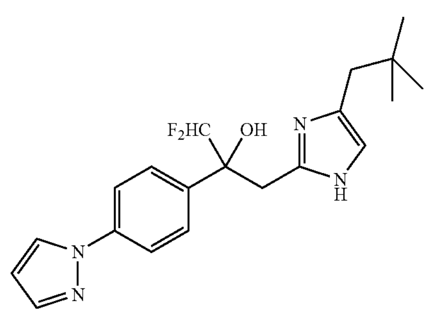 | E1 | 375 (M + H) |
| 77 | | 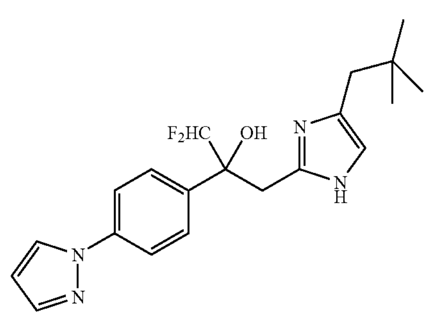 | E2 | 375 (M + H) |

TABLE 4-continued

| Example | Name | Structure | Enantiomer | HPLC-mass spectrum m/e |
|---|---|---|---|---|
| 78 | 3-[4-(2,2-dimethylpropyl)-1H-imidazol-2-yl]-1,1,1-trifluoro-2-[4-(1H-pyrazol-1-yl)phenyl]propan-2-ol | 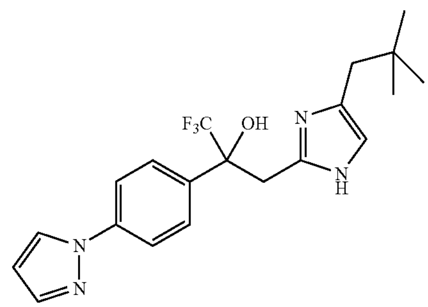 | E1 + E2 | 395 (M + H) |
| 79 | | 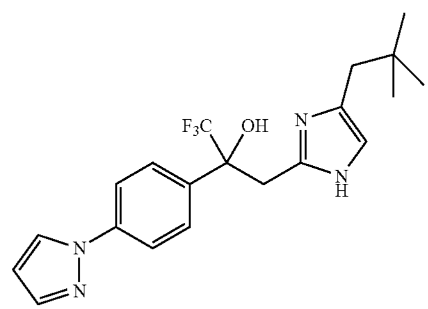 | E1 | 395 (M + H) |
| 80 | | 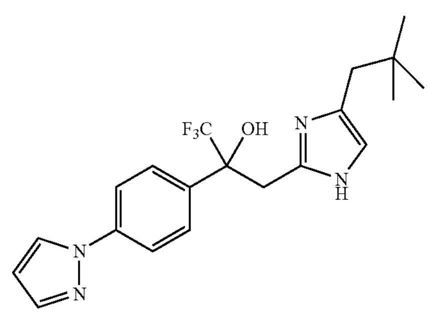 | E2 | 395 (M + H) |
| 81 | 1-[4-(2,2-dimethylpropyl)-1H-imidazol-2-yl]-2-[4-(1,2,3-thiadiazol-4-yl)phenyl]propan-2-ol | 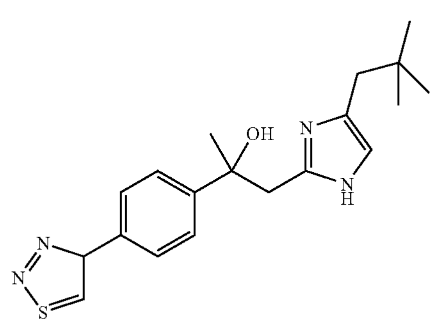 | E1 + E2 | 357 (M + H) |

TABLE 4-continued

| Example | Name | Structure | Enantiomer | HPLC-mass spectrum m/e |
|---|---|---|---|---|
| 82 | 1-[4-(2,2-dimethylpropyl)-1H-imidazol-2-yl]-2-[4-(3,5-dimethyl-1H-pyrazol-1-yl)phenyl]propan-2-ol | 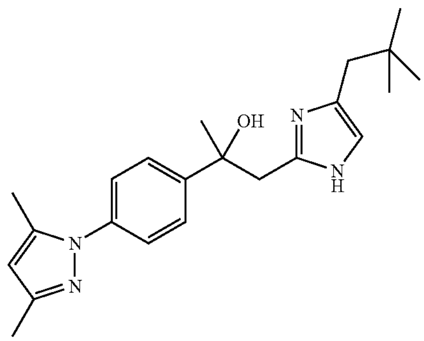 | E1 + E2 | 368 (M + H) |
| 83 | 1-[4-(2-cyclopropyl-2-methylpropyl)-1H-imidazol-2-yl]-2-[2-fluoro-4-(5-fluoropyridin-2-yl)phenyl]propan-2-ol | 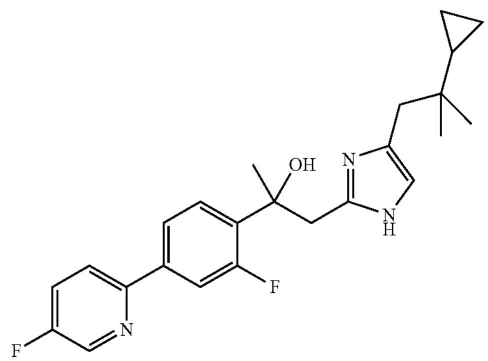 | E1 + E2 | 412 (M + H) |
| 84 | 2-[2,5-difluoro-4-(5-fluoropyridin-2-yl)phenyl]-1-[4-(2,2-dimethylpropyl)-1H-imidazol-2-yl]propan-2-ol | 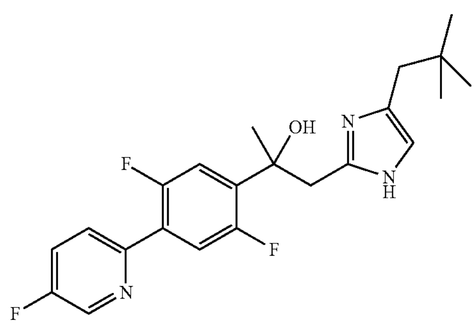 | E1 + E2 | 404 (M + H) |
| 85 | | 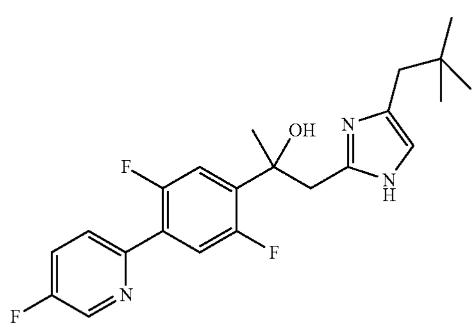 | E1 | 404 (M + H) |

TABLE 4-continued

| Example | Name | Structure | Enantiomer | HPLC-mass spectrum m/e |
|---|---|---|---|---|
| 86 | | 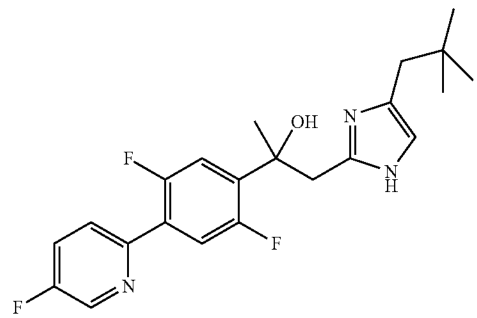 | E2 | 404 (M + H) |
| 87 | 3-[4-(2,2-dimethylbut-3-en-1-yl)-1H-imidazol-2-yl]-1,1-difluoro-2-[4-(5-fluoropyridin-2-yl)phenyl]propan-2-ol | 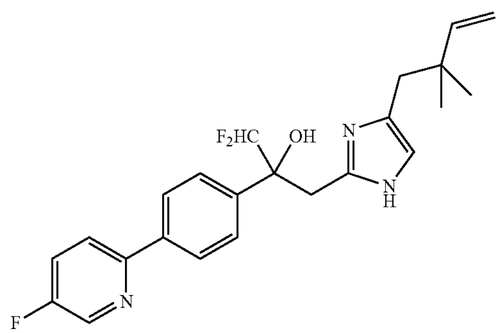 | E1 + E2 | 416 (M + H) |
| 88 | | 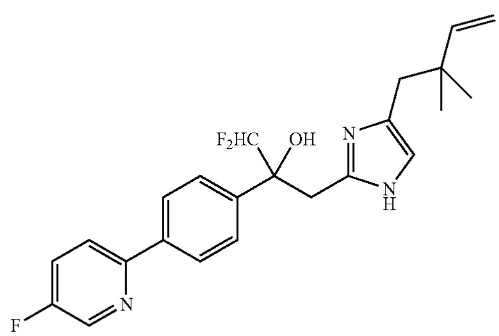 | E1 | 416 (M + H) |
| 89 | | 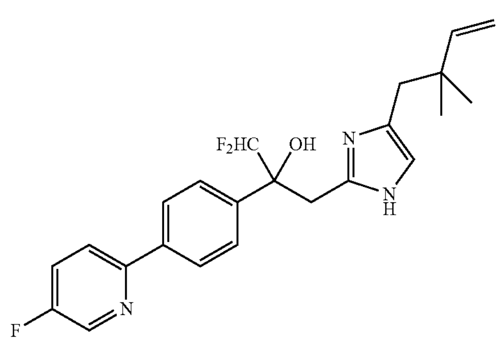 | E2 | 416 (M + H) |

TABLE 4-continued

| Example | Name | Structure | Enantiomer | HPLC-mass spectrum m/e |
|---|---|---|---|---|
| 90 | 1-[4-(2-fluoro-2-methylpropyl)-1H-imidazol-2-yl]-2-[4-(5-fluoropyridin-2-yl)phenyl]propan-2-ol | 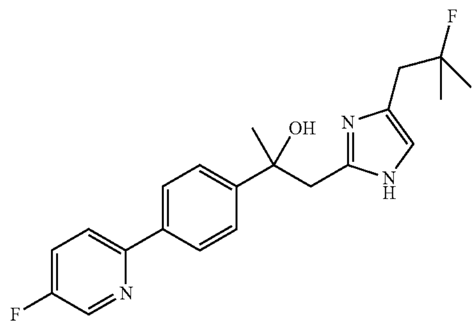 | E1 + E2 | 372 (M + H) |
| 91 | | 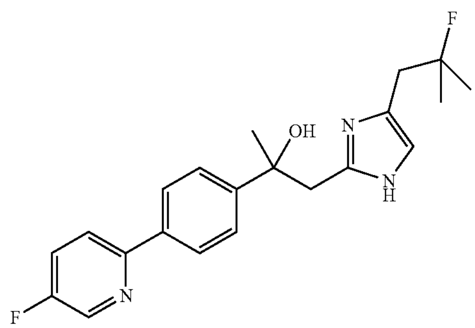 | E1 | 372 (M + H) |
| 92 | | 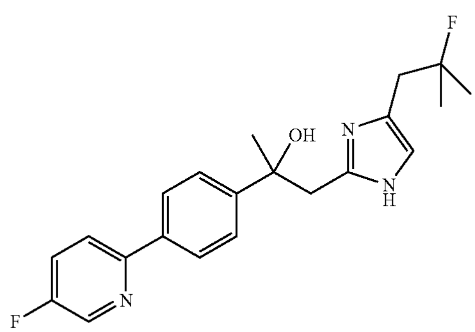 | E2 | 372 (M + H) |
| 93 | 3-[4-(2-ethyl-2-fluorobutyl)-1H-imidazol-2-yl]-1,1-difluoro-2-[4-(5-fluoropyridin-2-yl)phenyl]propan-2-ol | 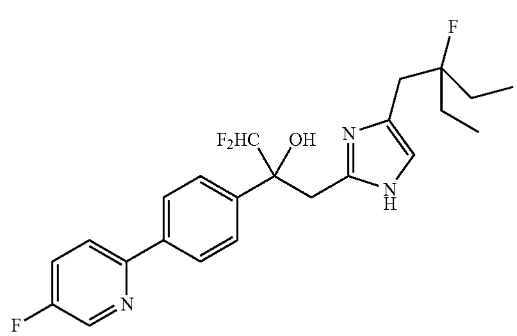 | E1 + E2 | 436 (M + H) |

TABLE 4-continued

| Example | Name | Structure | Enantiomer | HPLC-mass spectrum m/e |
|---|---|---|---|---|
| 94 | | 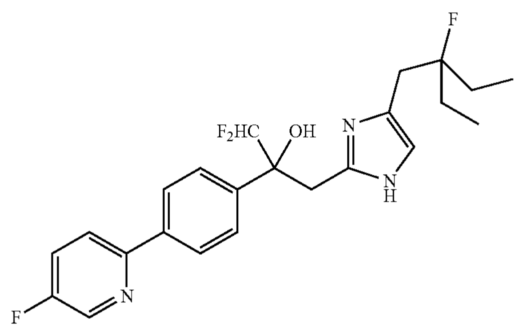 | E1 | 436 (M + H) |
| 95 | | 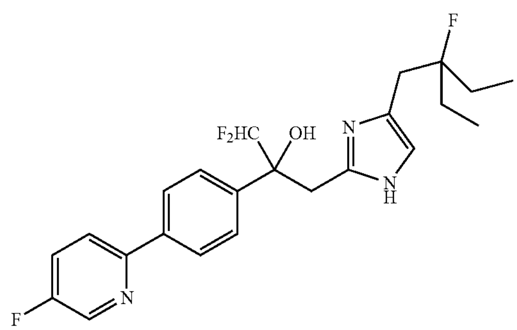 | E2 | 436 (M + H) |
| 96 | 3-[4-(3,3-difluoro-2,2-dimethylpropyl)-1H-imidazol-2-yl]-1,1-difluoro-2-[4-(5-fluoropyridin-2-yl)phenyl]propan-2-ol | 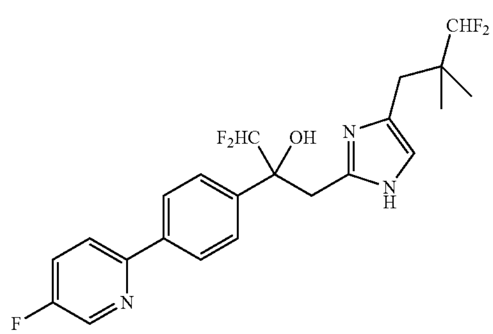 | E1 + E2 | 440 (M + H) |
| 97 | | 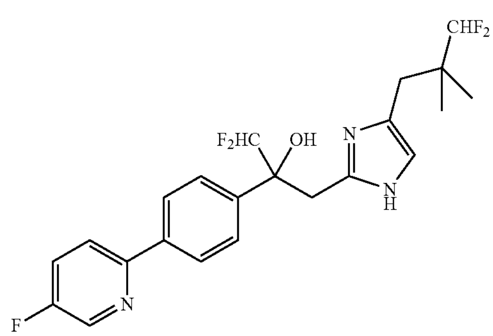 | E1 | 440 (M + H) |

TABLE 4-continued

| Example | Name | Structure | Enantiomer | HPLC-mass spectrum m/e |
|---|---|---|---|---|
| 98 | | 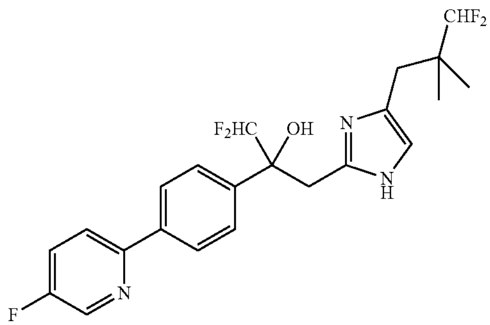 | E2 | 440 (M + H) |
| 99 | 3-[4-(3,3-difluoro-2,2-dimethylpropyl)-1H-imidazol-2-yl]-1,1,1-trifluoro-2-[4-(5-fluoropyridin-2-yl)phenyl]propan-2-ol | 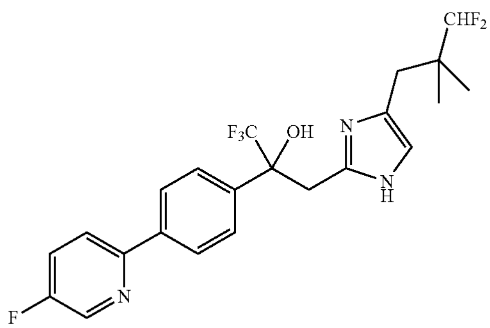 | E1 + E2 | 458 (M + H) |
| 100 | | 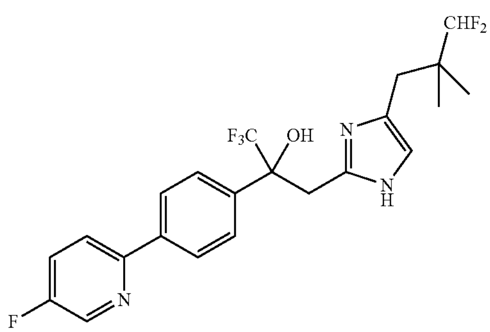 | E1 | 458 (M + H) |
| 101 | | 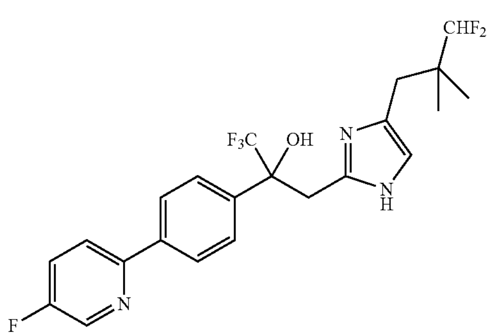 | E2 | 458 (M + H) |

TABLE 4-continued

| Example | Name | Structure | Enantiomer | HPLC-mass spectrum m/e |
|---|---|---|---|---|
| 102 | 3-[4-(3,3-difluoro-2,2-dimethylpropyl)-1H-imidazol-2-yl]-1,1-difluoro-2-[4-(1H-pyrazol-1-yl)phenyl]-propan-2-ol | 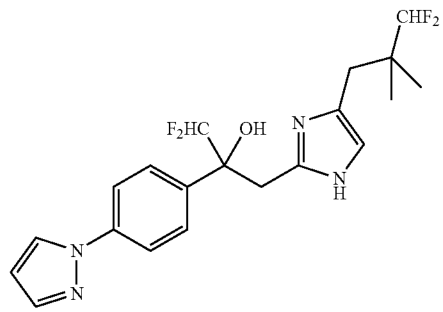 | E1 + E2 | 411 (M + H) |
| 103 | | 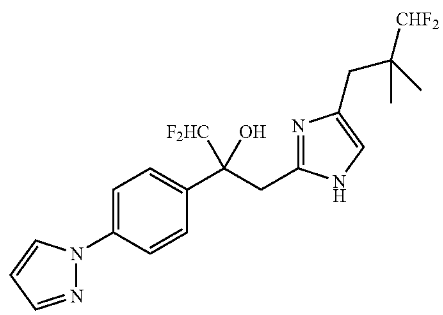 | E1 | 411 (M + H) |
| 104 | | 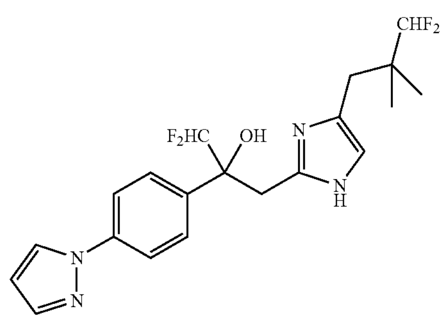 | E2 | 411 (M + H) |
| 105 | 3-[4-(3,3-difluoro-2,2-dimethylpropyl)-1H-imidazol-2-yl]-1,1,1-trifluoro-2-[4-(1H-pyrazol-1-yl)phenyl]-propan-2-ol | 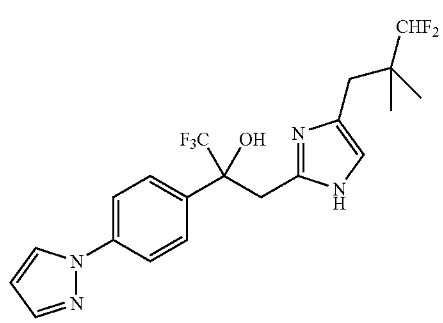 | E1 + E2 | 429 (M + H) |

TABLE 4-continued

| Example | Name | Structure | Enantiomer | HPLC-mass spectrum m/e |
|---|---|---|---|---|
| 106 | | 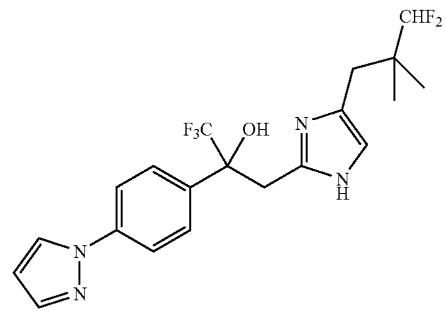 | E1 | 429 (M + H) |
| 107 | | 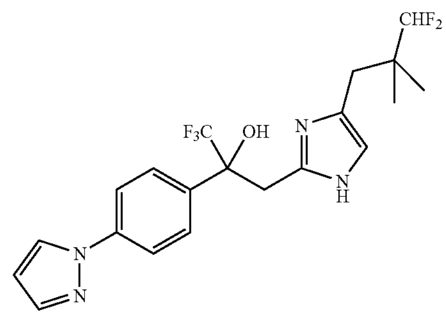 | E2 | 429 (M + H) |
| 108 | 1,1-difluoro-2-[4-(5-fluoropyridin-2-yl)phenyl]-3-[4-(3,3,3-trifluoro-2,2-dimethyl-propyl)-1H-imidazol-2-yl]propan-2-ol | 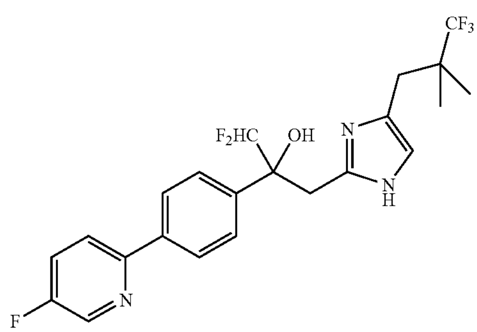 | E1 + E2 | 458 (M + H) |
| 109 | | 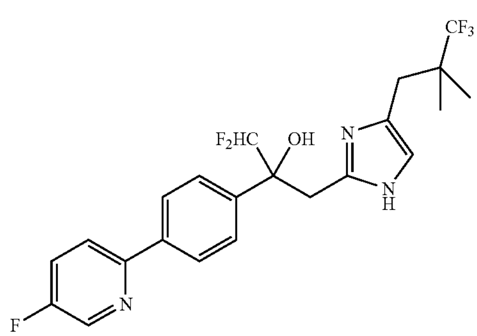 | E1 | 458 (M + H) |

TABLE 4-continued

| Example | Name | Structure | Enantiomer | HPLC-mass spectrum m/e |
|---|---|---|---|---|
| 110 | | 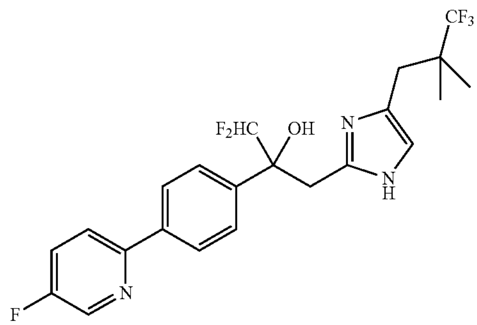 | E2 | 458 (M + H) |
| 111 | 1,1,1-trifluoro-2-[4-(1H-pyrazol-1-yl)phenyl]-3-[4-(3,3,3-trifluoro-2,2-dimethylpropyl)-1H-imidazol-2-yl]propan-2-ol | 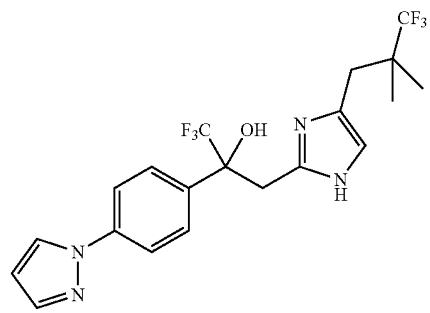 | E1 + E2 | 447 (M + H) |
| 112 | | 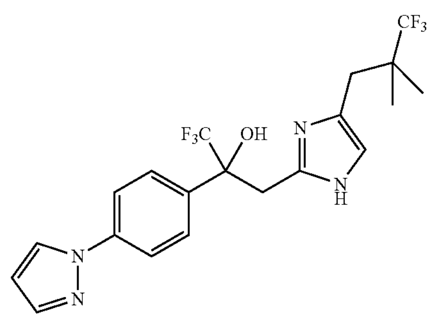 | E1 | 447 (M + H) |
| 113 | | 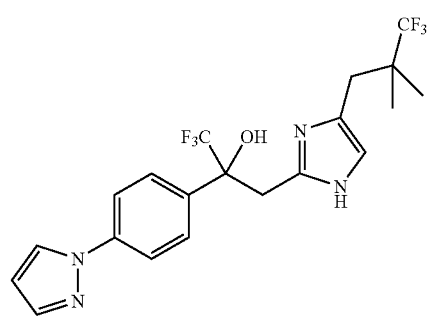 | E2 | 447 (M + H) |

TABLE 4-continued

| Example | Name | Structure | Enantiomer | HPLC-mass spectrum m/e |
|---|---|---|---|---|
| 114 | 1,1-difluoro-2-[2-fluoro-4-(1H-pyrazol-1-yl)phenyl]-3-(4-{[1-(trifluoromethyl)cyclopropyl]methyl}-1H-imidazol-2-yl)propan-2-ol | 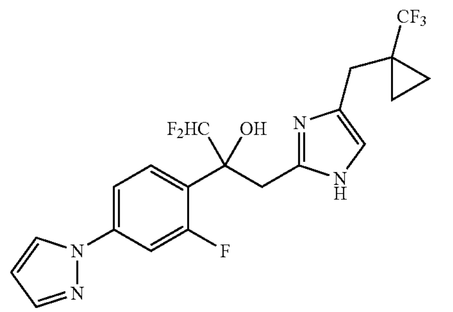 | E1 + E2 | 445 (M + H) |
| 115 | 1,1-difluoro-2-[5-(1H-pyrazol-1-yl)pyridin-2-yl]-3-(4-{[1-(trifluoromethyl)cyclopropyl]methyl}-1H-imidazol-2-yl)propan-2-ol | 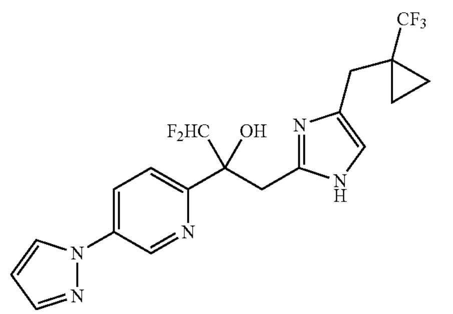 | E1 + E2 | 428 (M + H) |
| 116 | 1,1-difluoro-2-[4-(1H-pyrazol-1-yl)phenyl]-3-[4-(3,3,3-trifluoro-2,2-dimethylpropyl)-1H-imidazol-2-yl]propan-2-ol | 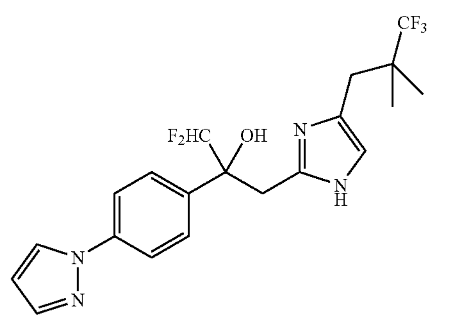 | E1 + E2 | 429 (M + H) |
| 117 | 1-[4-(3,3-difluoro-2,2-dimethylpropyl)-1H-imidazol-2-yl]-2-[4-(5-fluoropyridin-2-yl)phenyl]propan-2-ol | 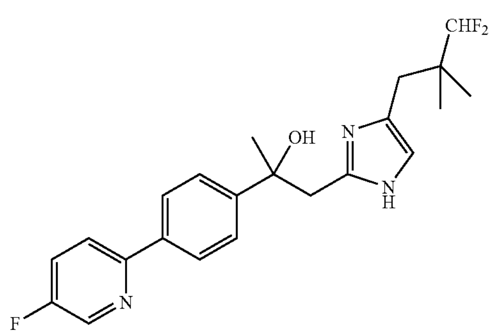 | E1 + E2 | 404 (M + H) |

TABLE 4-continued

| Example | Name | Structure | Enantiomer | HPLC-mass spectrum m/e |
|---|---|---|---|---|
| 118 | 1-{4-[(1-methylcyclopropyl)methyl]-1H-imidazol-2-yl}-2-[4-(1H-pyrazol-1-yl)phenyl]propan-2-ol | 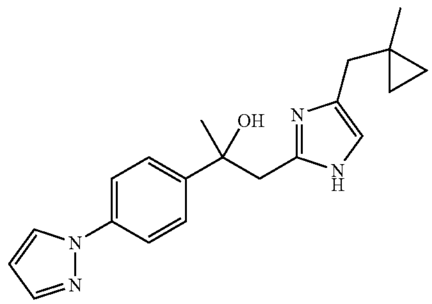 | E1 + E2 | 337 (M + H) |
| 119 | | 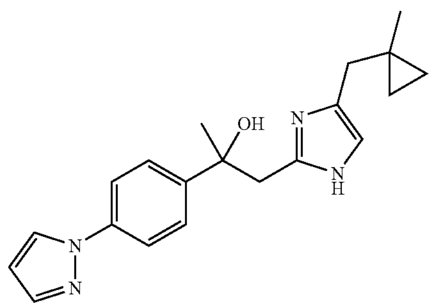 | E1 | 337 (M + H) |
| 120 | | 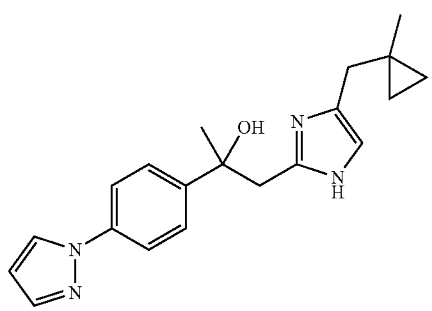 | E2 | 337 (M + H) |
| 121 | 1,1-difluoro-3-{4-[(1-methylcyclopropyl)methyl]-1H-imidazol-2-yl}-2-[4-(1H-pyrazol-1-yl)phenyl]propan-2-ol | 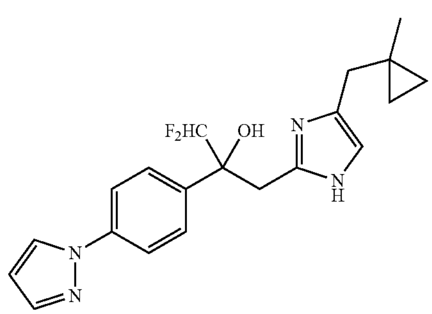 | E1 + E2 | 373 (M + H) |
| 122 | | 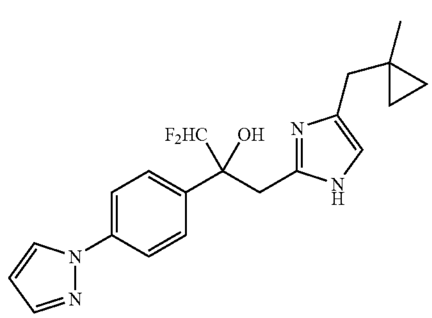 | E1 | 373 (M + H) |

TABLE 4-continued

| Example | Name | Structure | Enantiomer | HPLC-mass spectrum m/e |
|---|---|---|---|---|
| 123 | | 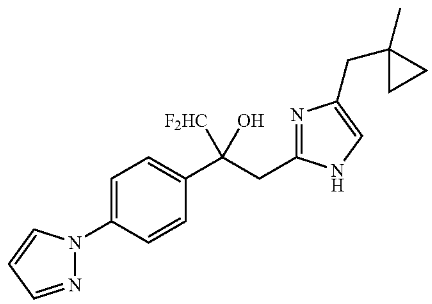 | E2 | 373 (M + H) |
| 124 | 1,1-difluoro-3-[4-(2-fluoro-1,2-dimethyl-propyl)-1H-imidazol-2-yl]-2-[4-(5-fluoropyridin-2-yl)-phenyl]propan-2-ol | 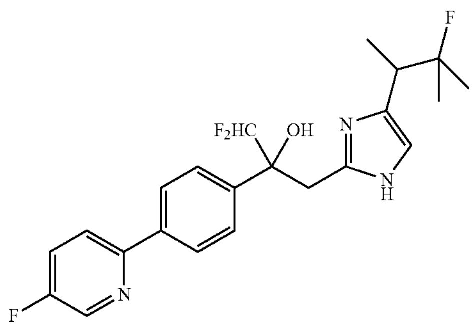 | E1 + E2 | 422 (M + H) |
| 125 | 2-[4-(2,2-dimethylbutyl)-1H-imidazol-2-yl]-1-(4-pyridin-2-ylphenyl)ethanol | 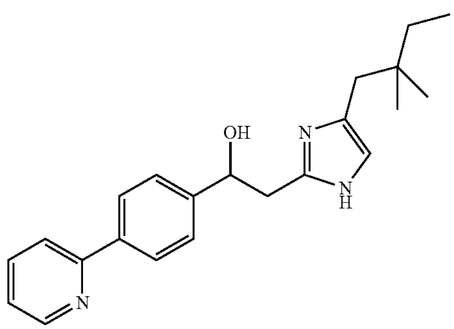 | E1 + E2 | 350 (M + H) |
| 126 | | 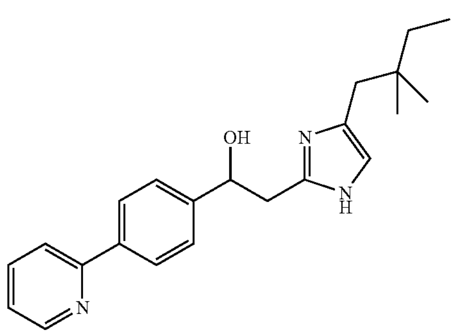 | E1 | 350 (M + H) |

TABLE 4-continued

| Example | Name | Structure | Enantiomer | HPLC-mass spectrum m/e |
|---|---|---|---|---|
| 127 | | 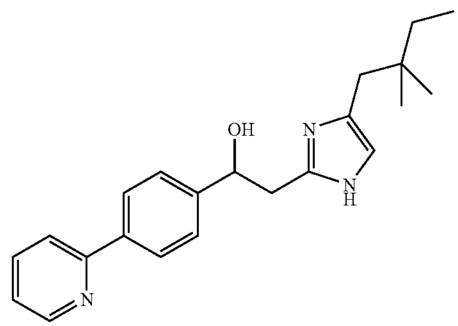 | E2 | 350 (M + H) |
| 128 | 1-[4-(2,2-dimethylbutyl)-1H-imidazol-2-yl]-2-[4-(5-fluoropyridin-2-yl)phenyl]propan-2-ol | 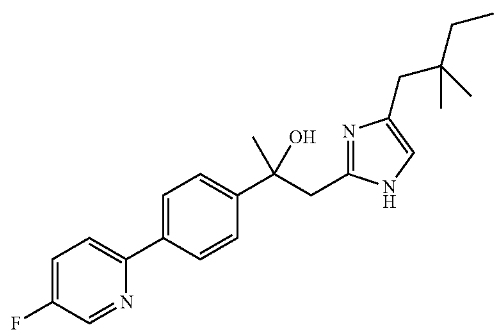 | E1 + E2 | 382 (M + H) |
| 129 | | 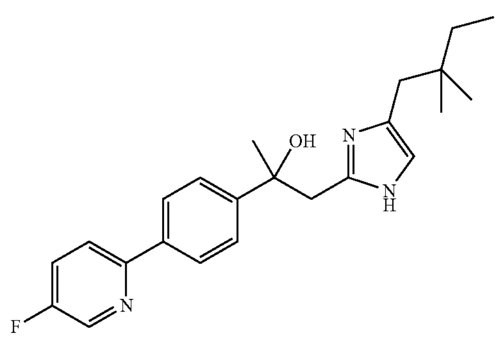 | E1 | 382 (M + H) |
| 130 | | 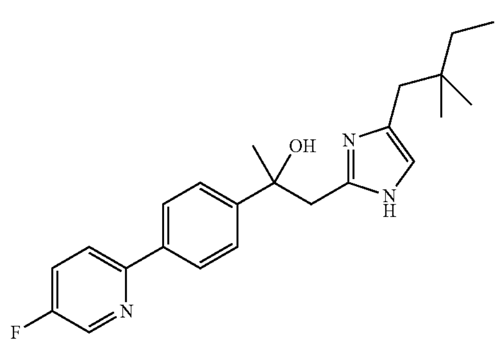 | E2 | 382 (M + H) |

TABLE 4-continued

| Example | Name | Structure | Enantiomer | HPLC-mass spectrum m/e |
|---|---|---|---|---|
| 131 | 1-[4-(2,2-dimethylbutyl)-1H-imidazol-2-yl]-2-[4-(5-fluoropyridin-2-yl)phenyl]butan-2-ol | 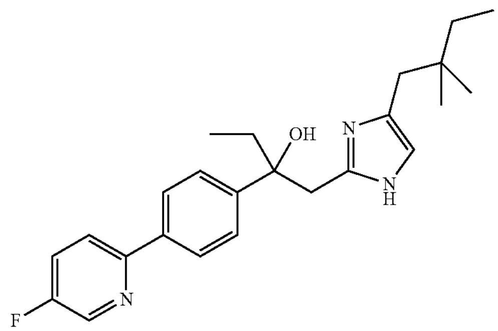 | E1 + E2 | 396 (M + H) |
| 132 | | 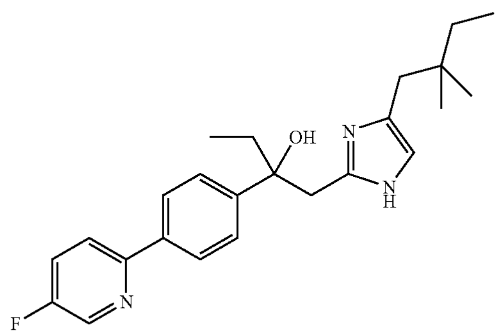 | E1 | 396 (M + H) |
| 133 | | 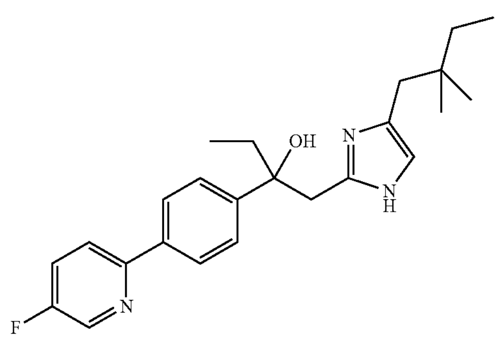 | E2 | 396 (M + H) |
| 134 | 1-cyclopropyl-2-[4-(2,2-dimethylbutyl)-1H-imidazol-2-yl]-1-[4-(5-fluoropyridin-2-yl)phenyl]ethanol | 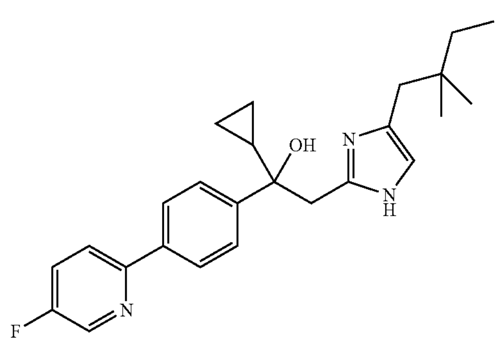 | E1 + E2 | 408 (M + H) |

TABLE 4-continued

| Example | Name | Structure | Enantiomer | HPLC-mass spectrum m/e |
|---|---|---|---|---|
| 135 | | 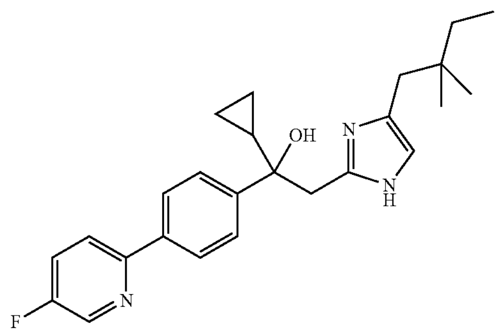 | E1 | 408 (M + H) |
| 136 | | 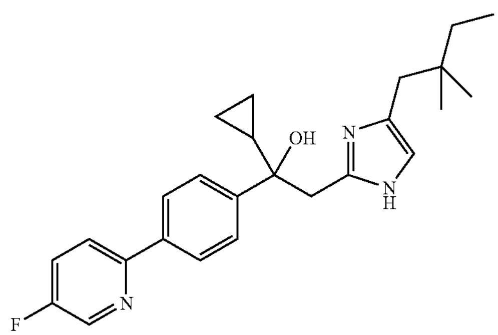 | E2 | 408 (M + H) |
| 137 | 1,1-difluoro-3-[4-(2-fluoro-2-methylpropyl)-1H-imidazol-2-yl]-2-[4-(5-fluoropyridin-2-yl)phenyl]propan-2-ol | 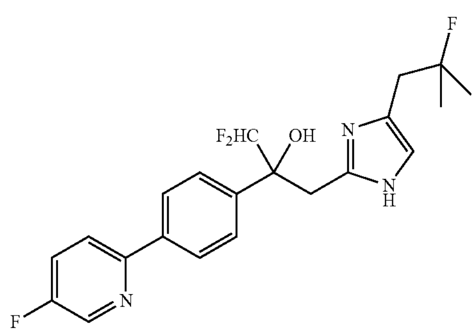 | E1 + E2 | 408 (M + H) |
| 138 | | 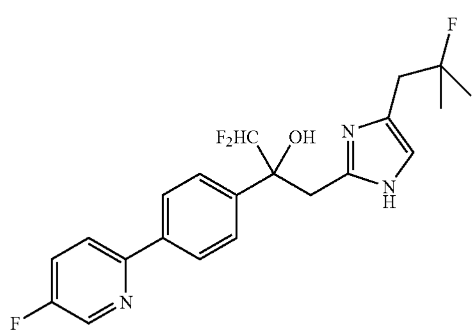 | E1 | 408 (M + H) |

TABLE 4-continued

| Example | Name | Structure | Enantiomer | HPLC-mass spectrum m/e |
|---|---|---|---|---|
| 139 | | 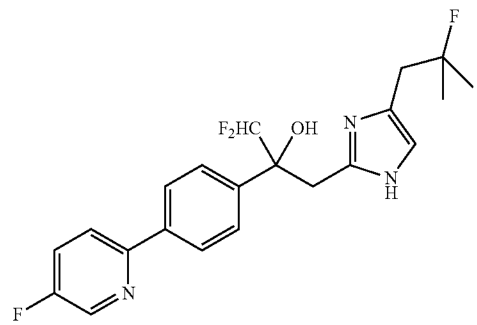 | E2 | 408 (M + H) |
| 140 | 1,1,1-trifluoro-3-{4-[(1-methylcyclopropyl)methyl]-1H-imidazol-2-yl}-2-[4-(1H-pyrazol-1-yl)phenyl]propan-2-ol | 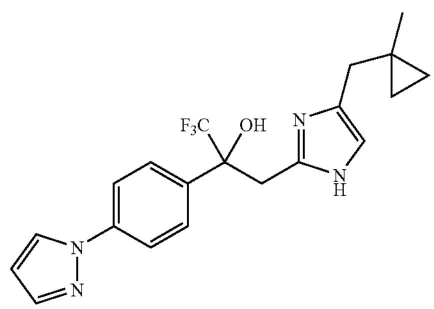 | E1 | 391 (M + H) |
| 141 | | 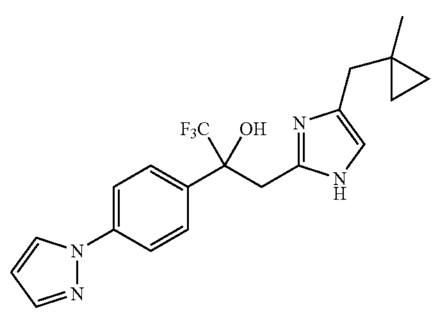 | E2 | 391 (M + H) |
| 142 | 2-[4-(4-bromo-1H-pyrazol-1-yl)phenyl]-1,1,1-trifluoro-3-{4-[(1-methylcyclopropyl)methyl]-1H-imidazol-2-yl}propan-2-ol | 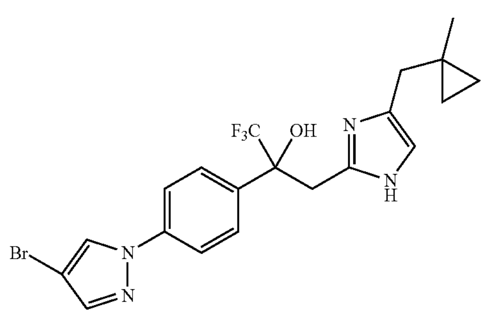 | E1 | 471 (M + H) |

TABLE 4-continued

| Example | Name | Structure | Enantiomer | HPLC-mass spectrum m/e |
|---|---|---|---|---|
| 143 | | 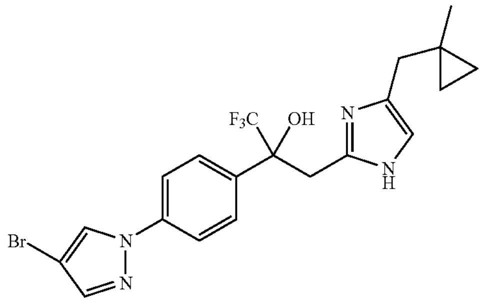 | E2 | 471 (M + H) |
| 144 | 1,1,1-trifluoro-3-{4-[(1-methylcyclo-butyl)methyl]-1H-imidazol-2-yl}-2-[4-(1H-pyrazol-1-yl)phenyl]propan-2-ol | 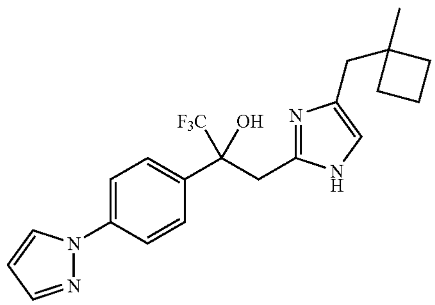 | E1 | 405 (M + H) |
| 145 | | 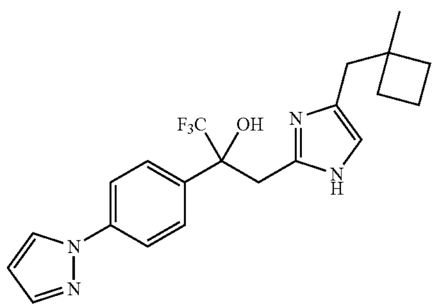 | E2 | 405 (M + H) |
| 146 | 1-{4-[(1-methylcyclo-butyl)methyl]-1H-imidazol-2-yl}-2-[4-(1H-pyrazol-1-yl)phenyl]propan-2-ol | 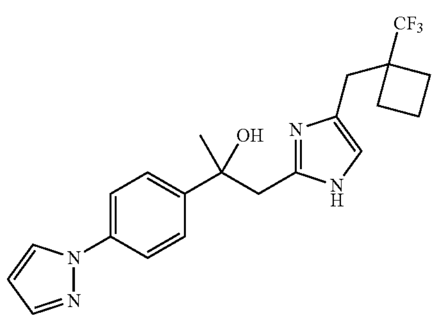 | E1 | 351 (M + H) |
| 147 | | 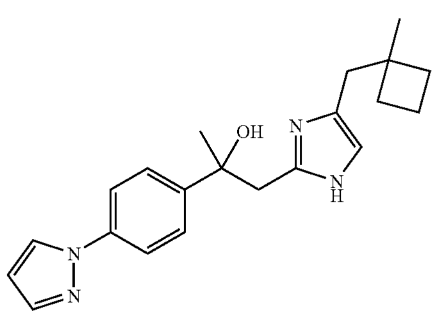 | E2 | 351 (M + H) |

TABLE 4-continued

| Example | Name | Structure | Enantiomer | HPLC-mass spectrum m/e |
|---|---|---|---|---|
| 148 | 1,1,1-trifluoro-2-[4-(1H-pyrazol-1-yl)phenyl]-3-(4-{[1-(trifluoromethyl)cyclobutyl]methyl}-1H-imidazol-2-yl)propan-2-ol | 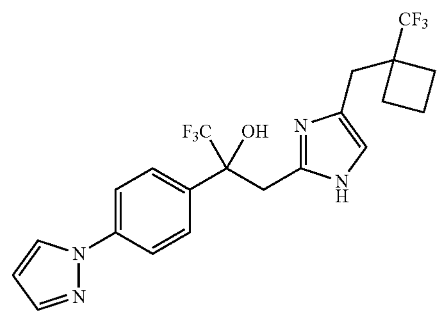 | E1 | 459 (M + H) |
| 149 | | 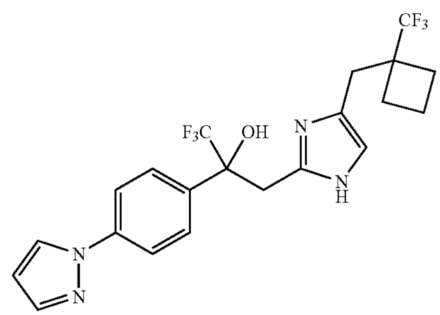 | E2 | 459 (M + H) |
| 150 | 2-[4-(1H-pyrazol-1-yl)phenyl]-1-(4-{[1-(trifluoromethyl)cyclobutyl]methyl}-1H-imidazol-2-yl)propan-2-ol | 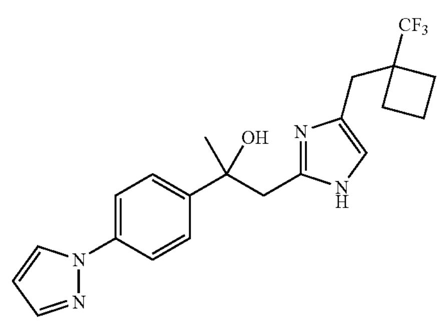 | E1 | 405 (M + H) |
| 151 | | 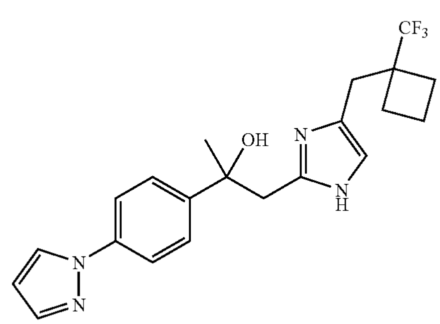 | E2 | 405 (M + H) |

TABLE 4-continued

| Example | Name | Structure | Enantiomer | HPLC-mass spectrum m/e |
|---------|------|-----------|------------|------------------------|
| 152 | 3-[4-(cyclopentylmethyl)-1H-imidazol-2-yl]-1,1-difluoro-2-[4-(5-fluoropyridin-2-yl)phenyl]propan-2-ol | 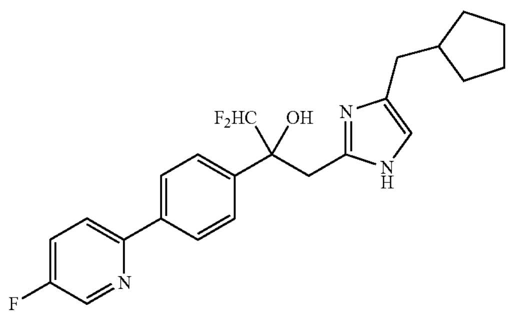 | E1 + E2 | 416 (M + H) |
| 153 | 3-[5-(2,2-dimethylpropyl)-1-methyl-1H-imidazol-2-yl]-1,1-difluoro-2-[4-(5-fluoropyridin-2-yl)phenyl]propan-2-ol | 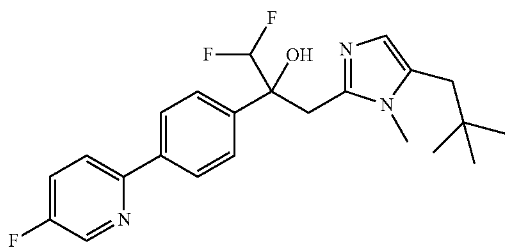 | E1 + E2 | 418 (M + H) |
| 154 | 1-[4-(2,2-dimethylpropyl)-1H-imidazol-2-yl]-2-[5-(5-fluoropyridin-2-yl)-2-thienyl]propan-2-ol | 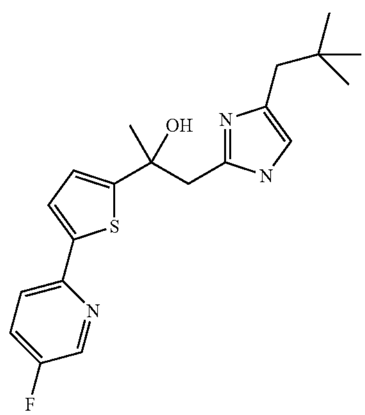 | E1 + E2 | 374 (M + H) |

*E1 is the faster eluting enantiomer by HPLC on a chiralpak AD or AD-H column eluting with IPA/heptane and E2 is the slower eluting enantiomer by HPLC on a chiralpak AD or AD-H column eluting with IPA/heptane.

EXAMPLE 155

2-(4-{2-[4-(2,2-dimethylpropyl)-1H-imidazol-2-yl]-1-fluoro-1-methylethyl}phenyl)-5-fluoropyridine

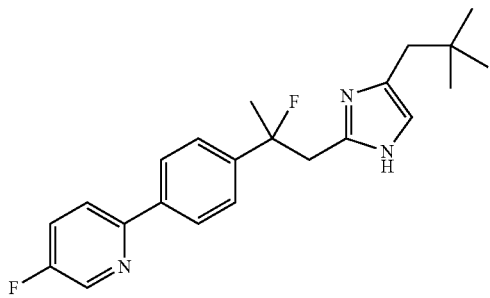

1-[4-(2,2-dimethylpropyl)-1H-imidazol-2-yl]-2-[4-(5-fluoropyridin-2-yl)phenyl]propan-2-ol (250 mg, 0.68 mmol) in a minimal volume of methylene chloride was added to HF-pyridine (0.5 mL). After stirring at ambient temperature for 1 h, the reaction was added dropwise to trimethylsilylethanol at 0° C. and concentrated in vacuo azeotroping with toluene. The residue was partitioned between ethyl acetate and 1 M aqueous sodium hydroxide. The organic phase was washed with brine, dried (sodium sulfate) and concentrated in vacuo. High pressure liquid chromatography (Chiralcel AD column) eluting with 20% isopropanol/heptane afforded the separate enantiomers. $^1$H NMR (500 MHz, CDCl$_3$) δ 8.52 (d, J=2.7 Hz, 1H), 7.90 (d, J=8.2 Hz, 2H), 7.69 (dd, J=4.3, 8.7 Hz, 1 h), 7.48-7.42 (m, 3h), 6.62 (s, 1H), 3.39 (d, J=25.4 Hz, 1H), 2.39 (s, 2H), 1.68 (d, J=22.8, 3H), 0.86 (s, 9H).

The compounds in Table 5 were prepared using the appropriate starting materials and reagents following procedures similar to those described above for Example 155:

TABLE 5

| Example | Name | Structure | Enantiomer | HPLC-mass spectrum m/e |
|---|---|---|---|---|
| 156 | 1-(4-{2-[4-(2,2-dimethylpropyl)-1H-imidazol-2-yl]-1-fluoro-1-methylethyl}phenyl)-1H-pyrazole | 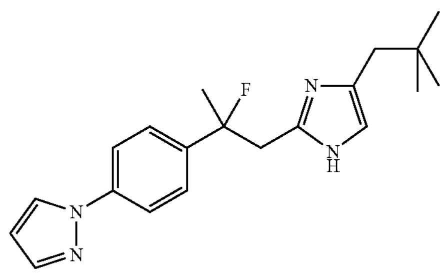 | E1 + E2 | 341 (M + H) |
| 157 | | 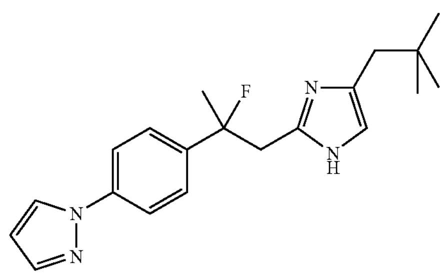 | E1 | 341 (M + H) |
| 158 | | 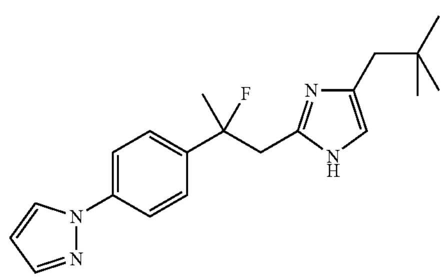 | E2 | 341 (M + H) |
| 159 | 1-{4-[1-fluoro-1-methyl-2-(4-{[1-(trifluoromethyl)cyclopropyl]methyl}-1H-imidazol-2-yl)ethyl]phenyl}-1H-pyrazole | 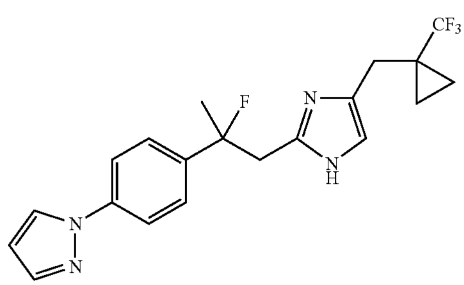 | E1 | 393 (M + H) |
| 160 | | 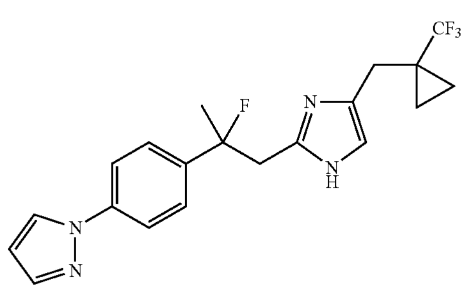 | E2 | 393 (M + H) |

*E1 is the faster eluting enantiomer by chromatography on a chiralpak AD or AD-H column eluting with IPA/heptane and E2 is the slower eluting enantiomer by chromatography on a chiralpak AD or AD-H column eluting with IPA/heptane.

EXAMPLE 161

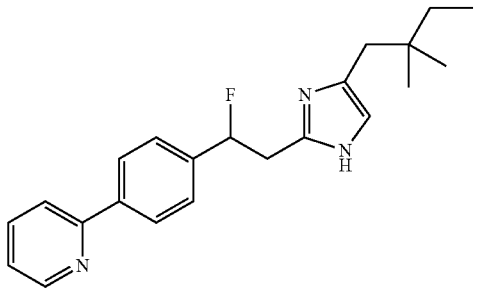

2-(4-{2-[4-(2,2-dimethylbutyl)-1H-imidazol-2-yl]-1-fluoroethyl}phenyl)pyridine

Step A: Diethylaminosulfur trifluoride (0.1 mL, 0.78 mmol) was added to a 0° C. solution of 2-[4-(2,2-dimethylbutyl)-1-trityl-1H-imidazol-2-yl]-1-(4-pyridin-2-ylphenyl)ethanol (385 mg, 0.65 mmol) in methylene chloride (10 mL). After stirring at 0° C. for 30 min then warming to ambient temperature then letting sit at −20° C. overnight, triethylamine (1 mL) was added. After stirring for a further 5 min, the reaction mixture was concentrated in vacuo. Chromatography over silica eluting with 0-40% ethyl acetate/hexane afforded 2-(4-{2-[4-(2,2-dimethylbutyl)-1-trityl-1H-imidazol-2-yl]-1-fluoroethyl}phenyl)pyridine.

Step B: Hydrogen chloride (4 M in 1,4-dioxane) (4 mL, 1 mmol) was added to an ambient temperature solution of 2-(4-{2-[4-(2,2-dimethylbutyl)-1-trityl-1H-imidazol-2-yl]-1-fluoroethyl}phenyl)pyridine (240 mg, 0.4 mmol) in methanol (20 mL). After stirring at ambient temperature for 3 h, volatiles were removed in vacuo. The residue was partitioned between 1 N hydrochloric acid and diethyl ether. The aqueous phase was washed with diethyl ether, basified with saturated aqueous sodium carbonate and extracted with diethyl ether and ethyl acetate. The combined extracts were dried (magnesium sulfate) and concentrated in vacuo to afford the title compound. High pressure liquid chromatography (Chiralcel OJ column) eluting with 15% ethanol/hexane afforded the separate enantiomers. (M+H) found 352.

EXAMPLE 162

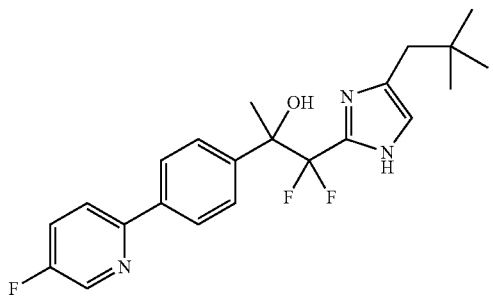

1-[4-(2,2-dimethylpropyl)-1H-imidazol-2-yl]-1,1-difluoro-2-[4-(5-fluoropyridin-2-yl)phenyl]propan-2-ol Step A: A solution of ethyl bromo(difluoro)acetate (0.53 mL, 4.1 mmol) and 1-[4-(5-fluoropyridin-2-yl)phenyl]ethanone (800 mg, 3.7 mmol) in tetrahydrofuran (40 mL) was added to a 0.1 M solution of samarium diiodide in tetrahydrofuran (82 mL, 8.2 mmol) at ambient temperature. After stirring at ambient temperature for 3 min, the reaction was cooled and quenched with 1N aqueous hydrochloric acid. Volatiles were removed in vacuo and the residue was partitioned between ethyl acetate and 1 N hydrochloric acid. The organic phase was washed with saturated aqueous sodium bicarbonate and brine, dried (sodium sulfate) and concentrated in vacuo. Chromatography over silica eluting with 0-40% ethyl acetate/hexane afforded ethyl 2,2-difluoro-3-[4-(5-fluoropyridin-2-yl)phenyl]-3-hydroxybutanoate.

Step B: Trimethylaluminum (2 M in toluene) (5.9 mL, 11.8 mmol) was added dropwise to ammonium chloride (631 mg, 11.8 mmol) at 0° C. After stirring at ambient temperature for 1 h until no further gas evolution, a solution of ethyl 2,2-difluoro-3-[4-(5-fluoropyridin-2-yl)phenyl]-3-hydroxybutanoate (400 mg, 1.2 mmol) in toluene (2 mL) was added. After stirring at 80° C. for a further 20 h, the reaction mixture was cooled to 0° C. and quenched with methanol (1 mL). After stirring at ambient temperature for a further 1 h, the reaction mixture was filtered rinsing with methanol. The filtrate was concentrated in vacuo to afford 2,2-difluoro-3-[4-(5-fluoropyridin-2-yl)phenyl]-3-hydroxybutanimidamide which was used in the subsequent step without further purification.

Step C: 1-bromo-4,4-dimethylpentan-2-one (500 mg, 2.6 mmol) was added to an ambient temperature solution of 2,2-difluoro-3-[4-(5-fluoropyridin-2-yl)phenyl]-3-hydroxybutanimidamide (365 mg, 1.2 mmol) and sodium acetate (290 mg, 3.5 mmol) in 1,4-dioxane (20 mL). After stirring at reflux for 1 h, volatiles were removed in vacuo. The residue was partitioned between ethyl acetate and 1 N aqueous sodium hydroxide. The organic phase was washed with brine, dried (sodium sulfate) and concentrated in vacuo. Chromatography over silica eluting with 0-30% ethyl acetate/hexane afforded the title compound. $^1$H NMR (500 MHz, CDCl$_3$) δ 8.50 (d, J=3.0 Hz, 1H), 7.83 (d, J=8.4 Hz, 2H), 7.67 (dd, J=4.3, 8.8 Hz, 1H), 7.58 (d, J=8.5 Hz, 2H), 7.45 (dt, J=2.8, 8.4, 1H) 6.69 (s, 1H), 2.39 (s, 2H), 1.77 (s, 3H), 0.84 (s, 9H).

The compounds in Table 6 were prepared using the appropriate starting materials and reagents following procedures similar to those described above for Example 162:

TABLE 6

| Example | Name | Structure | Enantiomer | HPLC-mass spectrum m/e |
|---|---|---|---|---|
| 163 | 1-[4-(2,2-dimethylpropyl)-1H-imidazol-2-yl]-1,1-difluoro-2-[4-(1H-pyrazol-1-yl)phenyl]propan-2-ol | 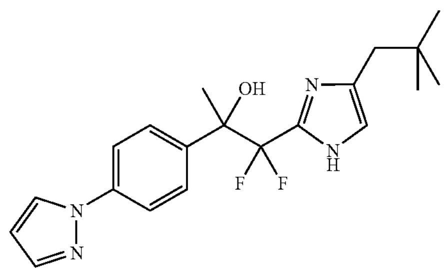 | E1 + E2 | 375 (M + H) |
| 164 | | 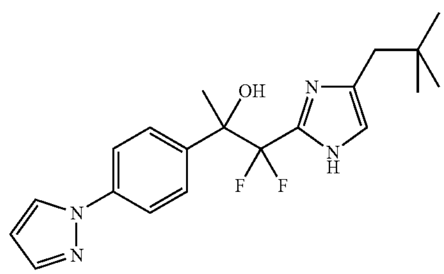 | E1 | 375 (M + H) |
| 165 | | 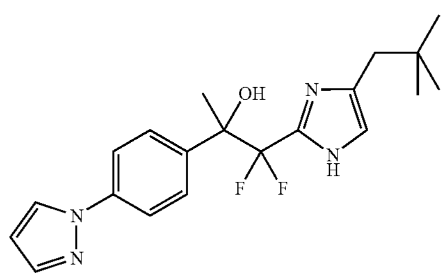 | E2 | 375 (M + H) |

*E1 is the faster eluting enantiomer by HPLC on a chiralpak AD or AD-H column eluting with IPA/heptane and E2 is the slower eluting enantiomer by HPLC on a chiralpak AD or AD-H column eluting with IPA/heptane.

EXAMPLE 166

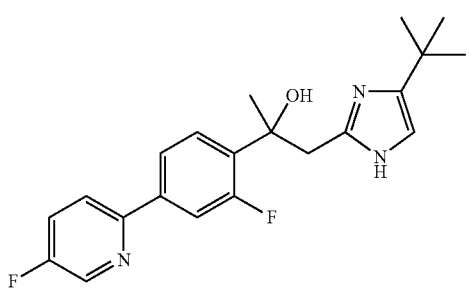

1-(4-tert-butyl-1H-imidazol-2-yl)-2-[2-fluoro-4-(5-fluoropyridin-2-yl)phenyl]propan-2-ol Step A: A mixture of 1-[2-fluoro-4-(5-fluoropyridin-2-yl)phenyl]ethanone (3.6 g, 15.3 mmol) and ethyl bromoacetate (12.8 g, 76.5 mmol) in tetrahydrofuran (35 mL) was added dropwise to a refluxing suspension of zinc (Reike, activated) (5 g) in tetrahydrofuran (100 mL). After stirring at reflux for a further 15 min, the reaction was cooled, poured into ice water and extracted with ethyl acetate. The combined organic extracts were washed with brine, dried (sodium sulfate) and concentrated in vacuo. Chromatography over silica eluting with 10-50% ethyl acetate/hexane over 48 fractions afforded ethyl 3-[2-fluoro-4-(5-fluoropyridin-2-yl)phenyl]-3-hydroxybutanoate.

Step B: Trimethylaluminum (2 M in toluene) (47 mL, 93.3 mmol) was added to suspension of ammonium chloride (5.5 g, 102.7 mmol) in toluene (45 mL) at 0° C. dropwise. After stirring at ambient temperature for 1 h until no further gas evolution (2 h), a solution of ethyl 3-[2-fluoro-4-(5-fluoropyridin-2-yl)phenyl]-3-hydroxybutanoate (2.7 g, 8.2 mmol) in toluene (15 mL) was added. After stirring at 80° C. for a further 20 h, the reaction mixture was carefully poured into a slurry of silica (35 g) in chloroform (130 mL) and stirred for 5 min. The silica was filtered, rinsing with methanol. The filtrate was concentrated in vacuo to ca. 5 mL and refiltered. The resulting filtrate was concentrated in vacuo. High pressure liquid chromatography (KR100-5C18 100×21.2 mm column) eluting with 10-100% acetonitrile/water containing 0.1% trifluoroacetic acid afforded the di(trifluoroacetate) salt of (±)-3-[2-fluoro-4-(5-fluoropyridin-2-yl)phenyl]-3-hydroxybutanimidamide.

Step C: A solution of the di(trifluoroacetate) salt of (±)-3-[2-fluoro-4-(5-fluoropyridin-2-yl)phenyl]-3-hydroxybutanimidamide (50 mg, 0.10 mmol), potassium bicarbonate (19 mg, 0.19 mmol) and 1-bromo-3,3-dimethylbutan-2-one (52 mg, 0.29 mmol) in tetrahydrofuran (1 mL) and water (0.25 mL) were stirred at ambient temperature overnight. Volatiles were removed in vacuo and the residue was purified by HPLC (Gilson; KR100-5C18 100×21.2 mm column; 10-100% MeCN/H$_2$O) over 12 min to afford the title compound as a white solid. $^1$H NMR (500 MHz, CD$_3$OD) δ 8.51 (d, J=2.8 Hz, 1H), 7.90 (dd, J=4.3, 8.8 Hz, 1H), 7.76-7.58 (m, 4H), 6.99 (s, 1H), 3.45 (AB, J=14.9 Hz, 2H), 3.30 (bs, 1H), 1.732 (s, 3H), 1.23 (s, 9H).

EXAMPLE 167

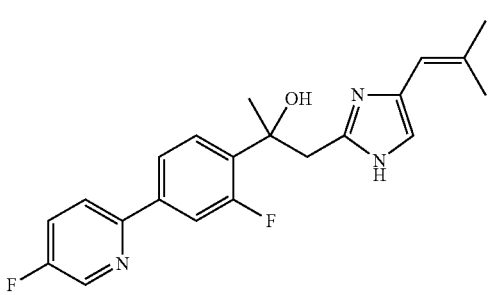

2-[2-fluoro-4-(5-fluoropyridin-2-yl)phenyl]-1-[4-(2-methylprop-1-en-1-yl)-1H-imidazol-2-yl]propan-2-ol Step A: To a 100-mL round-bottom flask containing 4-methyl-4-(methylthio)pentan-2-one (1.19 g, 8.10 mmol) was added acetic acid (50 mL) and a 50 wt % aqueous solution of hydrogen peroxide (6.6 mL, 96 mmol). After 12 hours, the reaction mixture was quenched by sodium bisulfite solution and extracted with diethyl ether. The combined organic extracts were washed with brine, dried (magnesium sulfate), and concentrated in vacuo. Chromatography over silica eluting with 45% ethyl acetate/hexane afforded 4-methyl-4-(methylsulfonyl)pentan-2-one as a white solid.

Step B: 1-Bromo-4-methyl-4-(methylsulfonyl)pentan-2-one was prepared according to the procedure described in Powers, L. J.; Fogt, S. W.; Ariyan, Z. S.; Rippin, D. J.; Heilman, R. D.; Matthews, R. J. *J. Med. Chem.* 1981, 24, 604-609.

Step C In a quartz tube, 1-bromo-4-methyl-4-(methylsulfonyl)pentan-2-one (26 mg, 0.10 mmol), the di(trifluoroacetate) salt of (±)-3-[2-fluoro-4-(5-fluoropyridin-2-yl)phenyl]-3-hydroxybutanimidamide (105 mg, 0.202 mmol), and sodium hydrogen carbonate (53 mg, 0.63 mmol) were suspended in a mixture of tetrahydrofuran (1.5 mL) and water (0.5 mL). After being irradiated by microwave (120° C., 10 min), the reaction mixture was purified by reversed-phase high performance liquid chromatography to afford the di(trifluoroacetate) salt of the title compound. (M+H) found 370.

EXAMPLE 168

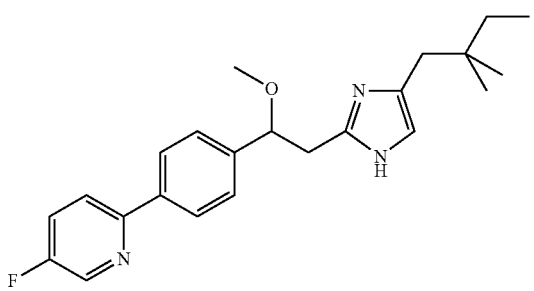

2-(4-{2-[4-(2,2-dimethylbutyl)-1H-imidazol-2-yl]-1-methoxyethyl}phenyl)-5-fluoropyridine Step A: Potassium tert-butoxide (21 mg, 0.19 mmol) was added to a solution of 2-[4-(2,2-dimethylbutyl)-1-trityl-1H-imidazol-2-yl]-1-[4-(5-fluoropyridin-2-yl)phenyl]ethanol (104 gm, 0.17 mmol) and methyl iodide (19 μL, 0.31 mmol) in tert-butanol (17 mL) at ambient temperature. After stirring overnight, the reaction mixture was washed with brine (100 mL), dried (magnesium sulfate) and concentrated in vacuo. Chromatography over silica eluting with 0-50% ethyl acetate/hexane afforded 2-(4-{2-[4-(2,2-dimethylbutyl)-1-trityl-1H-imidazol-2-yl]-1-methoxyethyl}phenyl)-5-fluoropyridine as an off-white solid.

Step B: Hydrochloric acid (2N, 4 mL) was added to a solution of 2-(4-{2-[4-(2,2-dimethylbutyl)-1-trityl-1H-imidazol-2-yl]-1-methoxyethyl}phenyl)-5-fluoropyridine in methanol (4 mL) at ambient temperature. The solution was stirred at 70° C. for 2 hr. Concentration of the solution afforded the title compound as a white solid. $^1$H NMR (500 MHz, CD$_3$OD) δ 8.66-8.60 (m, 1H), 8.05-7.83 (m, 5H), 7.45-7.37 (m, 2H), 7.16 (s, 1H), 4.72-4.68 (m, 1H), 3.28 (s, 3H), 2.51 (s, 2H), 1.28-1.20 (m, 2H), 0.86 (t, J=7.0 Hz, 3H), 0.83 (s, 6H).

EXAMPLE 169

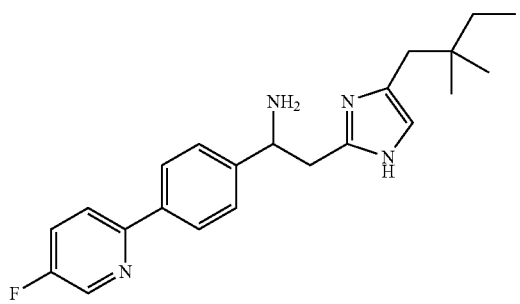

2-[4-(2,2-dimethylbutyl)-1H-imidazol-2-yl]-1-[4-(5-fluoropyridin-2-yl)phenyl]ethanamine Step A: DEAD (72 μL, 0.46 mmol) was added to an ambient temperature solution of 2-[4-(2,2-dimethylbutyl)-1-trityl- 1H-imidazol-2-yl]-1-[4-(5-fluoropyridin-2-yl)phenyl]ethanol (140 mg, 0.23 mmol), diphenylphosphoryl azide (0.1 mL, 0.46 mmol) and triphenylphosphine (150 mg, 0.57 mmol) in tetrahydrofuran (5 mL). After stirring at ambient temperature overnight, the reaction mixture was concentrated. Chromatography over silica eluting with 0-60% ethyl acetate/hexane afforded 2-(4-{1-azido-2-[4-(2,2-dimethylbutyl)-1-trityl-1H-imidazol-2-yl]ethyl}phenyl)-5-fluoropyridine.

Step B: Pd (10 wt % on activated carbon) (10 mg, cat.) was added to a degassed solution of 2-(4-{1-azido-2-[4-(2,2-dimethylbutyl)-1-trityl-1H-imidazol-2-yl]ethyl}phenyl)-5-fluoropyridine (110 mg, 0.17 mmol) in methanol (6 mL). After stirring under an atmosphere of hydrogen overnight, the reaction mixture was filtered through celite rinsing with methanol. The filtrate was concentrated to afford 2-[4-(2,2-dimethylbutyl)-1-trityl-1H-imidazol-2-yl]-1-[4-(5-fluoropyridin-2-yl)phenyl]ethanamine which was used in the next step without further purification.

Step C: Hydrogen chloride (4 M in dioxane) (2 mL, 0.5 mmol) was added to a solution of 2-[4-(2,2-dimethylbutyl)-1-trityl-1H-imidazol-2-yl]-1-[4-(5-fluoropyridin-2-yl)phenyl]ethanamine (20 mg, 0.03 mmol) in methanol (6 mL). After stirring at 60° C. for 1 h, volatiles were removed. The residue was purified by preparative HPLC eluting with 10-50% acetonitrile/water and lyophilized to afford the title compound. (M+H) found 367.

EXAMPLE 170

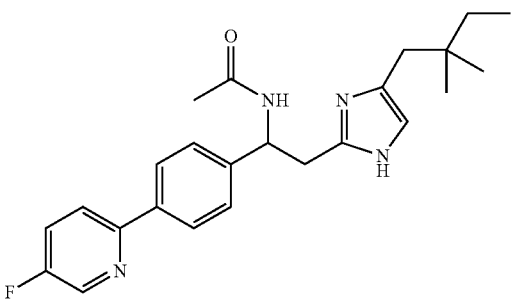

N-{2-[4-(2,2-dimethylbutyl)-1H-imidazol-2-yl]-1-[4-(5-fluoropyridin-2-yl)phenyl]ethyl}acetamide Step A: Acetic anhydride (16 μL, 0.17 mmol) was added to a solution of 2-[4-(2,2-dimethylbutyl)-1-trityl-1H-imidazol-2-yl]-1-[4-(5-fluoropyridin-2-yl)phenyl]ethanamine (51 mg, 0.08 mmol) in dichloromethane (4 mL) at ambient temperature. After stirring for 2 hr, the reaction mixture concentrated in vacuo to afford N-{2-[4-(2,2-dimethylbutyl)-1-trityl-1H-imidazol-2-yl]-1-[4-(5-fluoropyridin-2-yl)phenyl]ethyl}acetamide which was used without further purification.

Step B: Hydrogen chloride (4N, 2 mL) in dioxane was added to a solution of N-{2-[4-(2,2-dimethylbutyl)-1-trityl-1H-imidazol-2-yl]-1-[4-(5-fluoropyridin-2-yl)phenyl]ethyl}acetamide in methanol (4 mL) at ambient temperature. The solution was stirred at 50° C. for 2 hr. Concentration of the solution afforded the title compound as a white solid. $^1$H NMR (500 MHz, CD$_3$OD) δ 8.95-8.92 (m, 1H), 8.45-8.39 (m, 1H), 8.33 (dd, J=4.5, 9.0 Hz, 1H), 7.97 (d, J=8.5 Hz, 2H), 7.67 (d, J=8.0 Hz, 2H), 7.18 (s, 1H), 5.49 (t, J=8.0 Hz, 1H), 3.56-3.48 (m, 3H), 2.52 (s, 2H), 1.96 (s, 3H), 1.25 (q, J=7.5, 15.0 Hz, 2H), 0.87 (t, J=7.5 Hz, 3H), 0.84 (s, 3H), 0.83 (s, 3H).

EXAMPLE 171

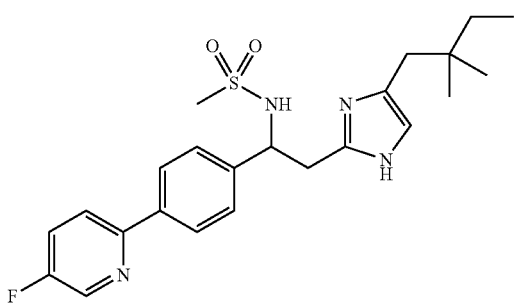

N-{2-[4-(2,2-dimethylbutyl)-1H-imidazol-2-yl]-1-[4-(5-fluoropyridin-2-yl)phenyl]ethyl}-methanesulfonamide Step A: Methanesulfonyl chloride (12 μL, 0.16 mmol) was added to a solution of 2-[4-(2,2-dimethylbutyl)-1-trityl-1H-imidazol-2-yl]-1-[4-(5-fluoropyridin-2-yl)phenyl]ethanamine (49 mg, 0.08 mmol) and triethylamine (24 μL, 0.17 mmol) in dichloromethane (4 mL) at ambient temperature. After stirring for 2 hr, the reaction mixture concentrated in vacuo to afford N-{2-[4-(2,2-dimethylbutyl)-1-trityl-1H-imidazol-2-yl]-1-[4-(5-fluoropyridin-2-yl)phenyl]ethyl}methanesulfonamide which was used without further purification.

Step B: Hydrogen chloride (4N, 2 mL) in dioxane was added to a solution of N-{2-[4-(2,2-dimethylbutyl)-1-trityl-1H-imidazol-2-yl]-1-[4-(5-fluoropyridin-2-yl)phenyl]ethyl}methanesulfonamide in methanol (4 mL) at ambient temperature. The solution was stirred at 50° C. for 2 hr. Concentration of the solution afforded the title compound as a white solid. $^1$H NMR (500 MHz, CD$_3$OD) δ 8.51 (d, J=2.5 Hz, 1H), 8.00 (d, J=8.0 Hz, 2H), 7.91 (dd, J=4.2, 8.7 Hz, 1H), 7.67 (td, J=3.0, 8.5 Hz, 1H), 7.52 (d, J=8.0 Hz, 2H), 7.13 (s, 1H), 4.95 (t, J=8.1 Hz, 1H), 3.59 (dd, J=8.1, 14.8 Hz, 1H), 3.41 (dd, J=8.1, 14.8 Hz, 1H), 2.66 (s, 3H), 2.48 (dd, J=14.7, 19.7 Hz, 2H), 1.96 (s, 3H), 1.20 (q, J=7.2, 14.7 Hz, 2H), 0.83 (t, J=7.2 Hz, 3H), 0.79 (s, 3H), 0.79 (s, 3H).

EXAMPLE 172

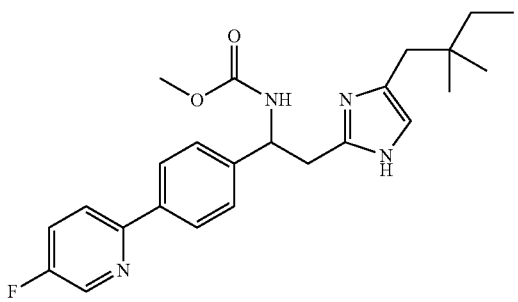

Methyl {2-[4-(2,2-dimethylbutyl)-1H-imidazol-2-yl]-1-[4-(5-fluoropyridin-2-yl)phenyl]ethyl}carbamate Step A: Methylchoroformate (16 μL, 0.21 mmol) was added to a solution of 2-[4-(2,2-dimethylbutyl)-1-trityl-1H-imidazol-2-yl]-1-[4-(5-fluoropyridin-2-yl)phenyl]ethanamine (64 mg, 0.11 μmol) and triethylamine (31 μL, 0.22 mmol) in dichloromethane (5 mL) at ambient temperature. After stirring for 2 hr, the reaction mixture concentrated in vacuo to afford methyl {2-[4-(2,2-dimethylbutyl)-1-trityl-1H-imidazol-2-yl]-1-[4-(5-fluoropyridin-2-yl)phenyl]ethyl}carbamate which was used without further purification.

Step B: Hydrogen chloride (4N, 2 mL) in dioxane was added to a solution of methyl {2-[4-(2,2-dimethylbutyl)-1-trityl-1H-imidazol-2-yl]-1-[4-(5-fluoropyridin-2-yl)phenyl]ethyl}carbamate in methanol (4 mL) at ambient temperature. The solution was stirred at 50° C. for 2 hr. Concentration of the solution afforded the title compound as a white solid. $^1$H NMR (500 MHz, CD$_3$OD) δ 8.51 (d, J=3.0 Hz, 1H), 7.95 (d, J=8.5 Hz, 2H), 7.88 (dd, J=4.0, 9.0 Hz, 1H), 7.66 (td, J=3.0, 8.5 Hz, 1H), 7.44 (d, J=8.0 Hz, 2H), 7.13 (s, 1H), 5.15 (t, J=7.7 Hz, 1H), 3.59 (s, 3H), 3.51 (dd, J=8.5, 15.0 Hz, 1H), 3.41 (dd, J=7.0, 14.5 Hz, 1H), 2.49 (dd, J=14.7, 18.7 Hz, 2H), 1.20 (q, J=7.5, 15.2 Hz, 2H), 0.84 (t, J=7.5 Hz, 3H), 0.80 (s, 3H), 0.79 (s, 3H).

EXAMPLE 173

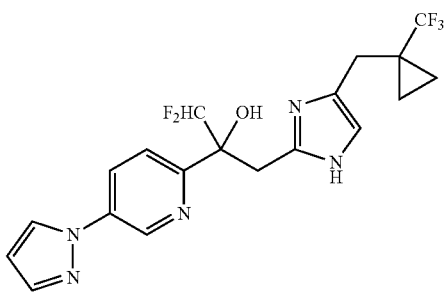

1,1-difluoro-2-[5-(1H-pyrazol-1-yl)pyridin-2-yl]-3-(4-{[1-(trifluoromethyl)cyclopropyl]methyl}-1H-imidazol-2-yl)propan-2-ol Step A: (+)-Menthyl chloroformate (20 μL, 0.09 mmol) was added to a solution of racemic 1,1-difluoro-2-[5-(1H-pyrazol-1-yl)pyridin-2-yl]-3-(4-{[1-(trifluoromethyl)cyclopropyl]methyl}-1H-imidazol-2-yl)propan-2-ol in pyridine (1 mL). After stirring at ambient temperature for 1 h, the reaction mixture was partitioned between ethyl acetate and 1 N hydrochloric acid. The organic phase was concentrated in vacuo. Purification by HPLC (Gilson; Chiralcel AS column; 2.5% ethanol/hexane) to afford two diastereomers of (1S,2R,5S)-2-isopropyl-5-methylcyclohexyl2-{3,3-difluoro-2-hydroxy-2-[5-(1H-pyrazol-1-yl)pyridin-2-yl]propyl}-4-{[1-(trifluoromethyl)cyclo-propyl]methyl}-1H-imidazole-1-carboxylate as a white solid.

Step B: Each diastereomer was separately treated with 1 N aqueous sodium hydroxide (a few drops) in methanol (minimal volume). After stirring at ambient temperature for 5 min, brine and ethyl acetate were added. The organic phase was dried (magnesium sulfate) and concentrated in vacuo. The residue was purified by preparative HPLC (Gilson; KR100-5C18 100×21.2 mm column), eluting with 10-100% acetonitrile/water+0.1% TFA over 12 min. The combined fractions were stirred with potassium carbonate until basic and extracted with methylene chloride. The combined organic extracts were dried (magnesium sulfate) and concentrated in vacuo to afford the two enantiomers as white solids. LCMS: 428 (M+H).

EXAMPLE 174

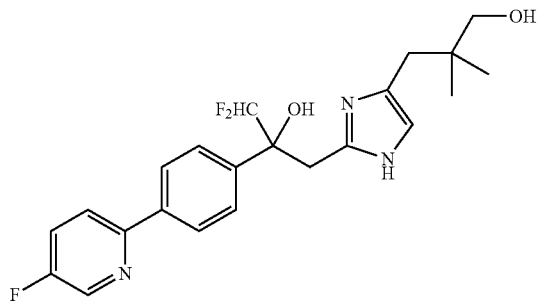

3-(2-{3,3-difluoro-2-[4-(5-fluoropyridin-2-yl)phenyl]-2-hydroxypropyl}-1H-imidazol-4-yl)-2,2-dimethylpropan-1-ol Step A: NMO (214 mg, 1.8 mmol) followed by osmium tetroxide (2.5 wt % in n-butanol) (cat.) were added to a solution of 3-[4-(2,2-dimethylbut-3-en-1-yl)-1-trityl-1H-imidazol-2-yl]-1,1-difluoro-2-[4-(5-fluoropyridin-2-yl)phenyl]propan-2-ol (600 mg, 0.91 mmol) in acetone/water (2:1) (12 mL). After stirring at ambient temperature overnight, the reaction mixture was quenched with saturated aqueous sodium thiosulfate and extracted with ethyl acetate. The combined organic extracts were dried (magnesium sulfate) and concentrated in vacuo. Chromatography over silica eluting with 0-100% ethyl acetate/hexane afforded 4-(2-{3,3-difluoro-2-[4-(5-fluoropyridin-2-yl)phenyl]-2-hydroxypropyl}-1-trityl-1H-imidazol-4-yl)-3,3-dimethylbutane-1,2-diol.

Step B: Sodium periodate was added to a solution of 4-(2-{3,3-difluoro-2-[4-(5-fluoropyridin-2-yl)phenyl]-2-hydroxypropyl}-1-trityl-1H-imidazol-4-yl)-3,3-dimethylbutane-1,2-diol (300 mg, 0.43 mmol) in tetrahydrofuran/water (2:1) (10 mL) at 0° C. After stirring at ambient temperature until complete (by LCMS), the reaction mixture was quenched with saturated aqueous sodium bicarbonate and extracted with methylene chloride. The combined organic extracts were dried (magnesium sulfate) and concentrated in vacuo. Chromatography over silica eluting with 0-40% ethyl acetate/hexane afforded 3-(2-{3,3-difluoro-2-[4-(5-fluoropyridin-2-yl)phenyl]-2-hydroxypropyl}-1-trityl-1H-imidazol-4-yl)-2,2-dimethylpropanal.

Step C: Sodium borohydride (8 mg, 0.2 mmol) was added to a solution of 3-(2-{3,3-difluoro-2-[4-(5-fluoropyridin-2-yl)phenyl]-2-hydroxypropyl}-1-trityl-1H-imidazol-4-yl)-2,2-dimethylpropanal (70 mg, 0.1 mmol) in methanol (3 mL). After stirring at ambient temperature until the reaction was complete (LCMS), the reaction mixture was quenched with water and extracted with methylene chloride. The combined organic extracts were dried (magnesium sulfate) and concentrated in vacuo to afford 3-(2-{3,3-difluoro-2-[4-(5-fluoropyridin-2-yl)phenyl]-2-hydroxypropyl}-1-trityl-1H-imidazol-4-yl)-2,2-dimethylpropan-1-ol which was used without further purification.

Step B: 4M Hydrogen chloride in dioxane (1 mL, 0.25 mmol) was added to a solution of 3-(2-{3,3-difluoro-2-[4-(5-fluoropyridin-2-yl)phenyl]-2-hydroxypropyl}-1-trityl-1H-imidazol-4-yl)-2,2-dimethylpropan-1-ol (from previous step) in methanol (1 mL). After stirring at 70° C. for 1 h, volatiles were removed. The residue was basified with saturated aqueous sodium bicarbonate and extracted with ethyl acetate. Combined extracts were dried (magnesium sulfate) and concentrated Chromatography over silica eluting with 0-100% acetone/methylene chloride afforded the title compound. LCMS: 420 (M+H) found.

EXAMPLE 175

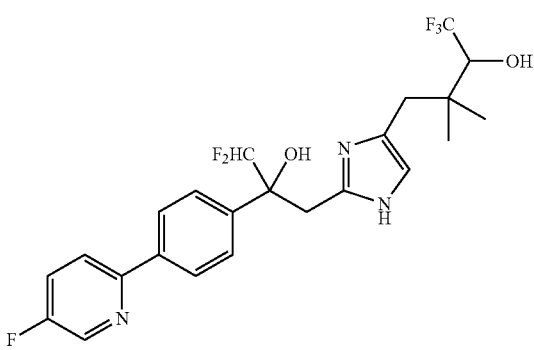

4-(2-{3,3-difluoro-2-[4-(5-fluoropyridin-2-yl)phenyl]-2-hydroxypropyl}-1H-imidazol-4-yl)-1,1,1-trifluoro-3,3-dimethylbutan-2-ol Step A: (Trifluoromethyl)trimethylsilane (33 µL, 0.2 mmol) followed by TBAF (1 M in tetrahydrofuran) (10 µL, 0.01 mmol) were added to a solution of 3-(2-{3,3-difluoro-2-[4-(5-fluoropyridin-2-yl)phenyl]-2-hydroxypropyl}-1-trityl-1H-imidazol-4-yl)-2,2-dimethylpropanal (70 mg, 0.1 mmol) at 0° C. After stirring at ambient temperature for 1 h, the reaction mixture was quenched with water and extracted with methylene chloride. The combined organic extracts were dried (magnesium sulfate) and concentrated in vacuo. Chromatography over silica eluting with 0-40% ethyl acetate/hexane afforded a mixture of 4-(2-{3,3-difluoro-2-[4-(5-fluoropyridin-2-yl)phenyl]-2-hydroxypropyl}-1-trityl-1H-imidazol-4-yl)-1,1,1-trifluoro-3,3-dimethylbutan-2-ol and 1,1-difluoro-2-[4-(5-fluoropyridin-2-yl)phenyl]-3-(4-{4,4,4-trifluoro-2,2-dimethyl-3-[(trimethylsilyl)oxy]butyl}-1-trityl-1H-imidazol-2-yl)propan-2-ol which was used in the next stage without further purification.

Step B: 4M Hydrogen chloride in dioxane (1 mL, 0.25 mmol) was added to a solution of 4-(2-{3,3-difluoro-2-[4-(5-fluoropyridin-2-yl)phenyl]-2-hydroxypropyl}-1-trityl-1H-imidazol-4-yl)-1,1,1-trifluoro-3,3-dimethylbutan-2-ol and 1,1-difluoro-2-[4-(5-fluoropyridin-2-yl)phenyl]-3-(4-{4,4,4-trifluoro-2,2-dimethyl-3-[(trimethylsilyl)oxy]butyl}-1-trityl-1H-imidazol-2-yl)propan-2-ol (from previous step) in methanol (2 mL). After stirring at 70° C. for 1 h, volatiles were removed. The residue was basified with saturated aqueous sodium bicarbonate and extracted with ethyl acetate. Combined extracts were dried (magnesium sulfate) and concentrated Chromatography over silica eluting with 0-60% acetone/methylene chloride afforded the title compound. LCMS: 488 (M+H).

EXAMPLE 176

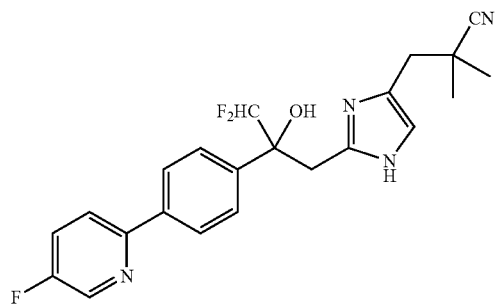

3-(2-{3,3-difluoro-2-[4-(5-fluoropyridin-2-yl)phenyl]-2-hydroxypropyl}-1H-imidazol-4-yl)-2,2-dimethylpropanenitrile Step A: To a dichloromethane (0.3 mL) solution of 3-(2-{3,3-difluoro-2-[4-(5-fluoropyridin-2-yl)phenyl]-2-hydroxypropyl}-1-trityl-1H-imidazol-4-yl)-2,2-dimethylpropanal (32 mg, 0.049 mmol) was added hydroxylamine hydrochloride (8.0 mg, 0.12 mmol). Formic acid (2 mL) was then added as solvent, and the reaction mixture was heated to 100° C. for 45 minutes. It was cooled to room temperature and added to saturated aqueous potassium carbonate. The reaction mixture was extracted with dichloromethane/ethyl acetate. The combined organic extracts were concentrated in vacuo and purified by reversed-phase high performance liquid chromatography to afford the title compound as the trifluoroacetate salt.
$^1$H NMR (500 MHz, CDCl$_3$) δ 8.61 (s, 1H), 7.97 (d, J=5.2 Hz, 2H), 7.73 (d, J=8.1 Hz, 2H), 7.66 (d, J=8.2 Hz, 2H), 6.99 (s, 1H), 5.90 (t, J=55.6 Hz, 1H), 3.80 (d, J=4.9 Hz, 1H), 3.60 (d, J=4.9 Hz, 1H), 2.81 (s, 2H), 1.30 (s, 3H), 1.25 (s, 3H).

EXAMPLE 177

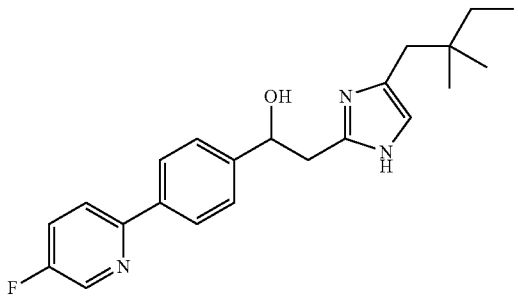

2-[4-(2,2-dimethylbutyl)-1H-imidazol-2-yl]-1-[4-(5-fluoropyridin-2-yl)phenyl]ethanol Step A: n-Butyllithium (2.5 M in hexanes) (0.53 mL, 1.32 mmol) was added to a solution of 4-(2,2-dimethylbutyl)-2-methyl-1-trityl-1H-imidazole (360 mg, 0.88 mmol) in tetrahydrofuran (15 mL) at −78° C. dropwise. After stirring at -78° C. for 40 min, 4-(5-fluoropyridin-2-yl)-N-methoxy-N-methylbenzamide (340 mg, 1.32 mmol) in tetrahydrofuran (5 mL) was added dropwise. After warming slowly to ambient temperature, the reaction mixture was quenched with saturated aqueous ammonium chloride. The reaction mixture was partitioned between water and ethyl acetate. The organic phase was dried (magnesium sulfate) and concentrated in vacuo. Chromatography over silica eluting with 0-20% ethyl acetate/hexane afforded 2-[4-(2,2-dimethylbutyl)-1-trityl-1H-imidazol-2-yl]-1-[4-(5-fluoropyridin-2-yl)phenyl]ethanone contaminated with an unidentified byproduct. This material was used in the next step without further purification.

Step B: Lithium borohydride (22 mg, 1 mmol) was added to a -78° C. solution of 2-[4-(2,2-dimethylbutyl)-1-trityl-1H-imidazol-2-yl]-1-[4-(5-fluoropyridin-2-yl)phenyl]ethanone (200 mg, 0.33 mmol) in methanol (20 mL). After stirring at ambient temperature for 1.5 h, the reaction mixture was quenched with acetone (1 mL) and concentrated in vacuo. Chromatography over silica eluting with 0-30% ethyl acetate/hexane afforded 2-[4-(2,2-dimethylbutyl)-1-trityl-1H-imidazol-2-yl]-1-[4-(5-fluoropyridin-2-yl)phenyl]ethanol.

Step C: Hydrogen chloride (4 M in dioxane) (1.5 mL, 0.67 mmol) was added to a solution of 2-[4-(2,2-dimethylbutyl)-1-trityl-1H-imidazol-2-yl]-1-[4-(5-fluoropyridin-2-yl)phenyl]ethanol (200 mg, 0.33 mmol) in methanol (6 mL). After stirring at ambient temperature for 3 h, volatiles were removed. The residue was partitioned between 1 N hydrochloric acid and diethyl ether. The aqueous phase was washed with diethyl ether, basified with saturated aqueous sodium carbonate and extracted with diethyl ether and ethyl acetate. Combined extracts were dried (magnesium sulfate) and concentrated in vacuo to afford the title compound. Purification by HPLC (Gilson; Chiralcel OJ column; 10 mL/min; 10% isopropanol/heptane). (M+H) found 368.

EXAMPLE 178

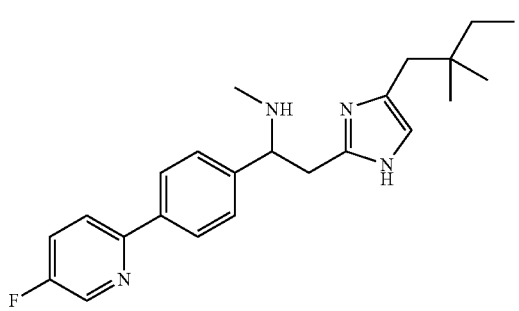

2-[4-(2,2-dimethylbutyl)-1H-imidazol-2-yl]-1-[4-(5-fluoropyridin-2-yl)phenyl]-N-methylethanamine Step A: Methylamine (2 M in tetrahydrofuran) (24 mL, 47.5 mmol) was added to an ambient temperature solution of p-nitrobenzenesulfonyl chloride (3.5 g, 15.8 mmol) in tetrahydrofuran (30 mL). After stirring at ambient temperature for 30 min, the reaction mixture was poured into water and extracted with ethyl aceate. The organic phase was dried (magnesium sulfate) and concentrated to afford N-methyl-4-nitrobenzenesulfonamide which was used without further purification.

Step B: DEAD (1.3 mL, 8.2 mmol) was added to an ambient temperature solution of 2-[4-(2,2-dimethylbutyl)-1-trityl-1H-imidazol-2-yl]-1-[4-(5-fluoropyridin-2-yl)phenyl]ethanol (2.5 g, 4.1 mmol), N-methyl-4-nitrobenzenesulfonamide (1.8 g, 8.2 mmol) and triphenylphosphine (2.7 g, 10.2 mmol) in tetrahydrofuran (20 mL). After stirring at ambient temperature overnight, the reaction mixture was concentrated. Chromatography over silica eluting with 0-60% ethyl acetate/hexane afforded N-{2-[4-(2,2-dimethylbutyl)-1-trityl-1H-imidazol-2-yl]-1-[4-(5-fluoropyridin-2-yl)phenyl]ethyl}-N-methyl-4-nitrobenzenesulfonamide.

Step C: Potassium carbonate (1.1 g, 7.7 mmol) was added to an ambient temperature solution of N-{2-[4-(2,2-dimethylbutyl)-1-trityl-1H-imidazol-2-yl]-1-[4-(5-fluoropyridin-2-yl)phenyl]ethyl}-N-methyl-4-nitrobenzenesulfonamide (2.5 g, 3.1 mmol) and benzenethiol (0.64 mL, 6.2 mmol) in N,N-dimethylformamide (20 mL). After stirring at 50° C. for 3 h, then at 70° C. for a further 3 h, the reaction mixture was cooled and partitioned between diethyl ether and saturated aqueous sodium bicarbonate. The organic phase was dried (magnesium sulfate) and concentrated. Chromatography over silica eluting with 0-100% ethyl acetate (containing 5% 2 M ammonia in methanol)/hexane afforded 2-[4-(2,2-dimethylbutyl)-1-trityl-1H-imidazol-2-yl]-1-[4-(5-fluoropyridin-2-yl)phenyl]-N-methylethanamine.

Step D: Hydrogen chloride (4 M in dioxane) (2.6 mL, 10.5 mmol) was added to a solution of 2-[4-(2,2-dimethylbutyl)-1-trityl-1H-imidazol-2-yl]-1-[4-(5-fluoropyridin-2-yl)phenyl]-N-methylethanamine (1.3 g, 2.1 mmol) in methanol (20 mL). After stirring at 60° C. for 1 h, volatiles were removed. The residue was partitioned between 1 N hydrochloric acid and hexane/diethyl:ether (3:1). The aqueous phase was washed with hexane/diethyl ether (3:1), basified with saturated aqueous sodium carbonate and extracted with ethyl acetate. Combined extracts were dried (magnesium sulfate) and concentrated in vacuo to afford the title compound. Purification by HPLC (Gilson; Chiralcel AD column; 50% isopropanol/heptane) afforded the pure enantiomers. (M+H) found 381.

EXAMPLE 179

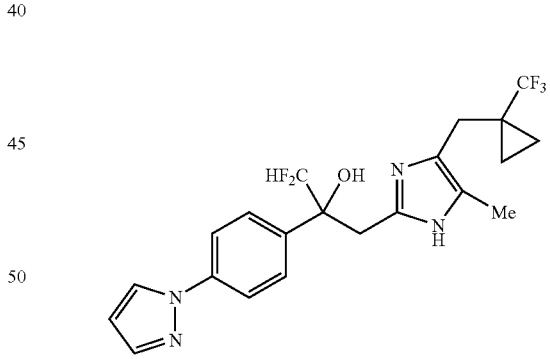

1,1-difluoro-3-(5-methyl-4-{[1-(trifluoromethyl)cyclopropyl]methyl}-1H-imidazol-2-yl)-2-[4-(1H-pyrazol-1-yl)phenyl]propan-2-ol Step A: N-Bromosuccinimide (95 mg, 0.53 mmol) was added to a solution of 1,1-difluoro-2-[4-(1H-pyrazol-1-yl)phenyl]-3-(4-{[1-(trifluoromethyl)cyclopropyl]methyl}-1H-imidazol-2-yl)propan-2-ol (200 mg, 0.53 mmol) in acetonitrile (5 mL) at ambient temperature. After stirring for 1 hr, the reaction mixture was concentrated in vacuo. Chromatography over silica eluting with 0-100% ethyl acetate/hexane afforded 3-(5-bromo-4-{[1-(trifluoromethyl)cyclopropyl]

methyl}-1H-imidazol-2-yl)-1,1-difluoro-2-[4-(1H-pyrazol-1-yl)phenyl]propan-2-ol as an orange solid.

Step B: Bis(triphenylphosphine)palladium(II)dichloride (94 mg, 0.13 mmol) was added to a solution of 3-(5-bromo-4-{[1-(trifluoromethyl)cyclopropyl]methyl}-1H-imidazol-2-yl)-1,1-difluoro-2-[4-(1H-pyrazol-1-yl)phenyl]propan-2-ol (202 mg, 0.45 mmol), tetramethyltin (319 mg, 1.78 mmol), lithium chloride (151 mg, 3.57 mmol), and triphenylphosphine (47 mg, 0.18 mmol) in degassed N,N-dimethylformamide (10 mL) at ambient temperature. The solution was stirred at 120° C. for 2 hr. The solution was cooled to ambient temperature and saturated aqueous potassium fluoride (10 mL) was added. The mixture was stirred for 1 hr at ambient temperature. Diethyl ether and water was added and the layers were separated. The aqueous layer was extracted with diethyl ether. The combined organic layers were washed with brine, dried (MgSO$_4$), and concentrated in vacuo. Chromatography over C-18 silica eluting with 10-100% acetonitrile/water afforded the title compound as a white solid. $^1$H NMR (500 MHz, CD$_3$OD) δ 8.22 (d, J=2.5 Hz, 1H), 7.77-7.72 (m, 2H), 7.62-7.51 (m, 3H), 6.53 (t, J=2.0 Hz, 1H), 6.14 (t, J=55.2 Hz, 1H), 3.57-3.48 (m, 2H), 2.90 (dd, J=15.7, 60.7 Hz, 2H), 2.16 (s, 3H), 0.86 (dd, J=5.0, 5.0 Hz, 2H), 0.52 (dd, J=9.5, 33.0 Hz, 2H). Individual enantiomer (E1 or E2) was obtained by HPLC separation on a chiral column.

The compounds in Table 7 were prepared using the appropriate starting materials and reagents following procedures similar to those described above for Example 179:

TABLE 7

| Example | Name | Structure | Enantiomer | HPLC-mass spectrum m/e |
|---|---|---|---|---|
| 180 | 1,1,1-trifluoro-3-(5-methyl-4-{[1-(trifluoromethyl)cyclopropyl]methyl}-1H-imidazol-2-yl)-2-[4-(1H-pyrazol-1-yl)phenyl]propan-2-ol | 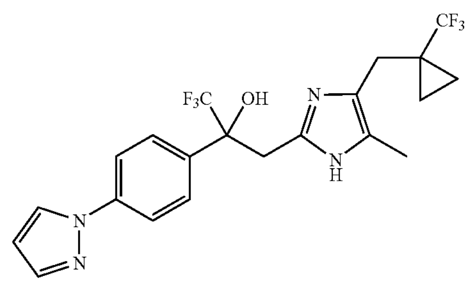 | E1 | 459 (M + H) |
| 181 | 1-(5-methyl-4-{[1-(trifluoromethyl)cyclopropyl]methyl}-1H-imidazol-2-yl)-2-[4-(1H-pyrazol-1-yl)phenyl]propan-2-ol | 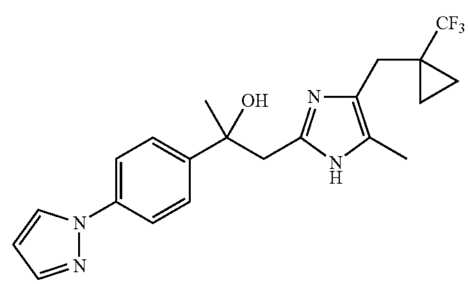 | E1 | 405 (M + H) |
| 182 | | 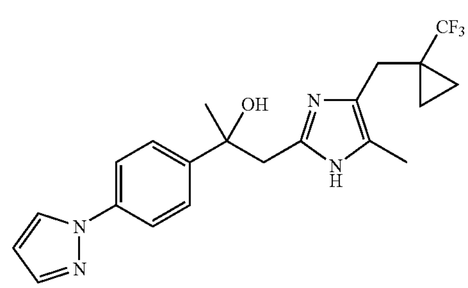 | E2 | 405 (M + H) |
| 183 | 1,1,1-trifluoro-3-{5-methyl-4-[(1-methylcyclopropyl)methyl]-1H-imidazol-2-yl}-2-[4-(1H-pyrazol-1-yl)phenyl]propan-2-ol | 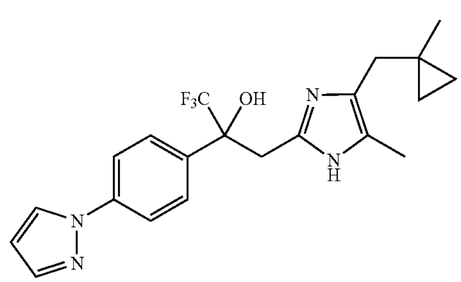 | E1 | 405 (M + H) |

TABLE 7-continued

| Example | Name | Structure | Enantiomer | HPLC-mass spectrum m/e |
|---|---|---|---|---|
| 184 | 1,1-difluoro-3-{5-methyl-4-[(1-methylcyclopropyl)methyl]-1H-imidazol-2-yl}-2-[4-(1H-pyrazol-1-yl)phenyl]propan-2-ol | 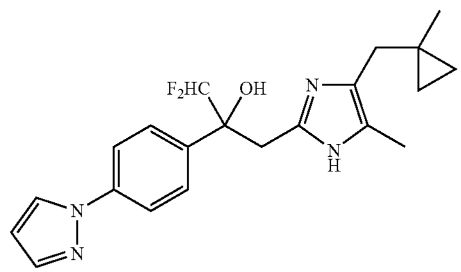 | E1 | 387 (M + H) |
| 185 | 3-[4-(2,2-dimethylpropyl)-5-methyl-1H-imidazol-2-yl]-1,1-difluoro-2-[4-(1H-pyrazol-1-yl)phenyl]propan-2-ol | 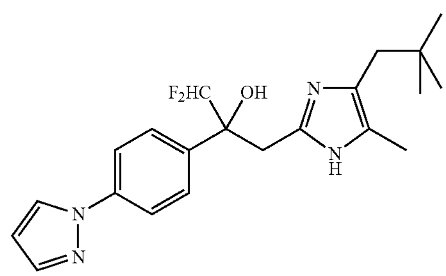 | E1 | 389 (M + H) |
| 186 | 1-[4-(2,2-dimethylpropyl)-5-methyl-1H-imidazol-2-yl]-2-[4-(1H-pyrazol-1-yl)phenyl]propan-2-ol | 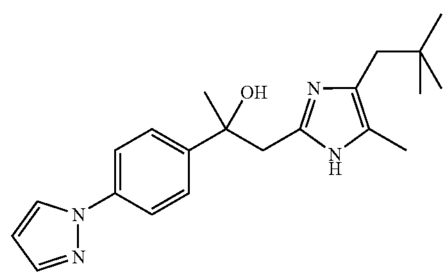 | E1 | 353 (M + H) |
| 187 | 3-[4-(2,2-dimethylpropyl)-5-vinyl-1H-imidazol-2-yl]-1,1,1-trifluoro-2-[4-(5-fluoropyridin-2-yl)phenyl]propan-2-ol | 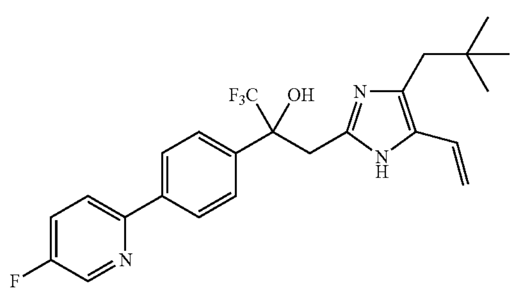 | E1 | 448 (M + H) |
| 188 | 3-[4-(2,2-dimethylpropyl)-5-methyl-1H-imidazol-2-yl]-1,1-difluoro-2-[4-(5-fluoropyridin-2-yl)phenyl]propan-2-ol | 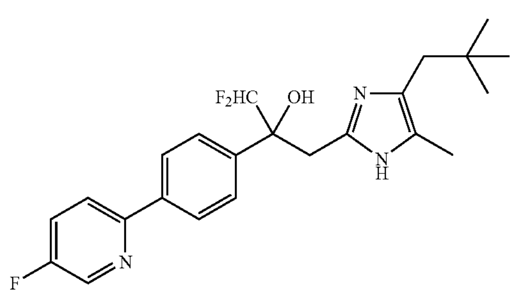 | E1 | 418 (M + H) |

TABLE 7-continued

| Example | Name | Structure | Enantiomer | HPLC-mass spectrum m/e |
|---|---|---|---|---|
| 189 | 3-[4-(2,2-dimethylpropyl)-5-methyl-1H-imidazol-2-yl]-1,1,1-trifluoro-2-[4-(5-fluoropyridin-2-yl)phenyl]propan-2-ol | 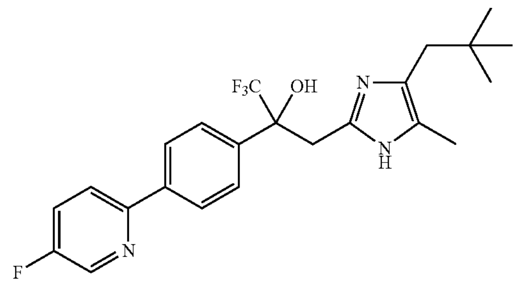 | E1 | 436 (M + H) |
| 190 | 2-[4-(5-fluoropyridin-2-yl)phenyl]-1-(5-methyl-4-{[1-(trifluoromethyl)cyclopropyl]methyl}-1H-imidazol-2-yl)propan-2-ol | 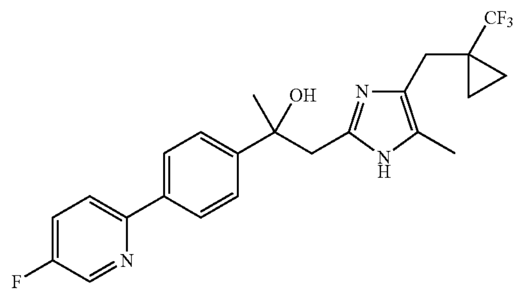 | E1 | 434 (M + H) |
| 191 | | 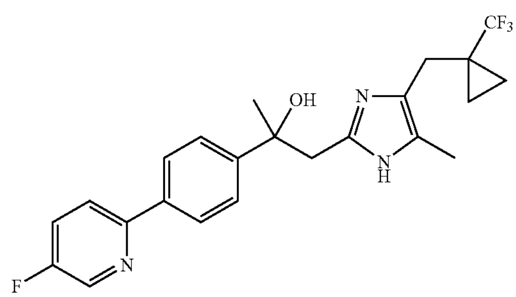 | E2 | 434 (M + H) |

*E1 is derived from the faster eluting enantiomer of the des-methyl precursor by HPLC on a chiralpak AD or AD-H column eluting with IPA/heptane and E2 is derived from the slower eluting enantiomer of the des-methyl precursor by HPLC on a chiralpak AD or AD-H column eluting with IPA/heptane.

EXAMPLE 192

3-[4-(2,2-dimethylpropyl)-5-ethyl-1H-imidazol-2-yl]-1,1,1-trifluoro-2-[4-(5-fluoropyridin-2-yl)phenyl]propan-2-ol

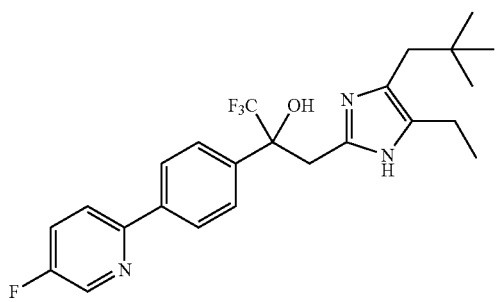

Pd (10 wt % on activated carbon) (ca. 1 mg, cat.) was added to a degassed solution of 3-[4-(2,2-dimethylpropyl)-5-vinyl-1H-imidazol-2-yl]-1,1,1-trifluoro-2-[4-(5-fluoropyridin-2-yl)phenyl]propan-2-ol (3 mg, 0.007 mmol) in methanol (1 mL). After stirring under an atmosphere of hydrogen for 1 h, the reaction mixture was filtered through celite rinsing with methanol. The filtrate was concentrated in vacuo to afford the title compound. $^1$H NMR (500 MHz, CD$_3$OD) δ 8.53 (d, J=3.0 Hz, 1H), 7.99 (d, J=8.4 Hz, 2H), 7.90 (dd, J=4.3, 8.8 Hz, 1H), 7.72-7.60 (m, 4H), 3.63 (bs, 2H), 2.52 (1, J=7.6 Hz, 2H), 2.38 (AB, J=14.9 Hz, 2H), 1.10 (t, J=7.6 Hz, 3H), 0.76 (s, 9H).

EXAMPLE 193

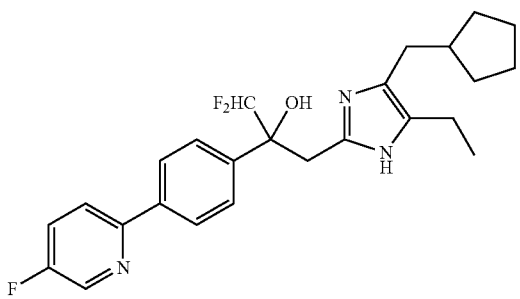

3-[4-(cyclopentylmethyl)-5-ethyl-1H-imidazol-2-yl]-1,1-difluoro-2-[4-(5-fluoropyridin-2-yl)phenyl]propan-2-ol The title compound was prepared using the procedure outlined in Example 192. LCMS: 444 (M+H).

EXAMPLE 194

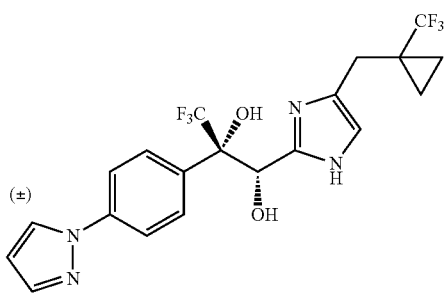

(1S*,2S*)-3,3,3-trifluoro-2-[4-(1H-pyrazol-1-yl)phenyl]-1-(4-{[1-(trifluoromethyl)-cyclopropyl]methyl}-1H-imidazol-2-yl)propane-1,2-diol Step A: A suspension of (2R)-1,1,1-trifluoro-2-[4-(1H-pyrazol-1-yl)phenyl]-3-(4-{[1-(trifluoromethyl)cyclopropyl]methyl}-1H-imidazol-2-yl)propan-2-ol in acetic acid (10 mL)/acetic anhydride (10 mL) was heated to reflux. The reaction mixture was poured into 1M sodium hydroxide solution until basic and extracted with diethyl ether. The crude product was dissolved in a mixture of methanol and acetonitrile and charged with 1M sodium hydroxide. It was heated to reflux overnight, and the reaction mixture was extracted with diethyl ether. The combined organic extracts were washed with brine, dried (potassium carbonate) and concentrated in vacuo to afford 1-{4-[(Z)-1-(trifluoromethyl)-2-(4-{[1-(trifluoromethyl)cyclopropyl]methyl}-1H-imidazol-2-yl)vinyl]phenyl}-1H-pyrazole, which was used without further purification.

Step B: In a 250-mL round-bottom flask, a mixture of 1-{4-[(Z)-1-(trifluoromethyl)-2-(4-{[1-(trifluoromethyl)cyclopropyl]methyl}-1H-imidazol-2-yl)vinyl}-1H-pyrazole (5.05 g, 11.8 mmol) and 60 wt % sodium hydride (0.89 g, 22 mmol) were mixed with tetrahydrofuran (80 mL). After bubbling ceased, dimethylsulfamoyl chloride (2.6 mL, 24.26 mmol) was added, and the reaction mixture was stirred overnight. The reaction mixture was quenched with water and extracted with diethyl ether. The combined organic extracts were washed with brine, dried (potassium carbonate), and concentrated in vacuo to afford an orange solid. Chromatography over silica eluting with 25-40% ethyl acetate/hexanes afforded N,N-dimethyl-4-{[1-(trifluoromethyl)cyclopropyl]methyl}-2-{(1Z)-3,3,3-trifluoro-2-[4-(1H-pyrazol-1-yl)phenyl]prop-1-en-1-yl}-1H-imidazole-1-sulfonamide, as a yellow solid.

Step C: To a 100-mL round-bottom flask containing a dichloromethane (10 mL) solution of N,N-dimethyl-4-{[1-(trifluoromethyl)cyclopropyl]methyl}-2-{(1Z)-3,3,3-trifluoro-2-[4-(1H-pyrazol-1-yl)phenyl]prop-1-en-1-yl}-1H-imidazole-1-sulfonamide (493 mg, 0.924 mmol) was added a solution of benzyltriethylammonium chloride (23.5 mg, 0.103 mmol) in 5 M sodium hydroxide (1 mL, 5.00 mmol). An aqueous solution of potassium permanganate (146 mg, 0.924 mmol) was added slowly to the reaction mixture via syringe pump over 2 hours. The reaction was left stirring at room temperature for another 60 hours. Chromatography over silica eluting with ethyl acetate/hexanes afforded N,N-dimethyl-2-{(1S*,2S*)-3,3,3-trifluoro-1,2-dihydroxy-2-[4-(1H-pyrazol-1-yl)phenyl]propyl}-4-{[1-(trifluoromethyl)cyclopropyl]methyl}-1H-imidazole-1-sulfonamide, as a white solid.

Step D: In a quartz tube, a methanol (4.0 mL) solution of N,N-dimethyl-2-{(1S*,2S*)-3,3,3-trifluoro-1,2-dihydroxy-2-[4-(1H-pyrazol-1-yl)phenyl]propyl}-4-{[1-(trifluoromethyl)cyclopropyl]methyl}-1H-imidazole-1-sulfonamide (132 mg, 0.233 mmol) was charged with concentrated hydrochloric acid (0.8 mL, 8.0 mmol). The reaction mixture was irradiated with microwave (120° C., 10 min). Purification of the reaction mixture by reversed-phase mass-directed high-performance liquid chromatography afforded the title compound as the trifluoroacetate salt. The purified fractions were basified with saturated potassium carbonate solution and extracted with ethyl acetate. The combined organic extracts were washed with brine, dried (potassium carbonate), and concentrated in vacuo to afford the title compound in the free base form. $^1$H NMR (500 MHz, CDCl$_3$) δ 7.88 (d, J=2.5 Hz, 1H), 7.71 (d, J=1.4 Hz, 1H), 7.57 (s, 4H), 6.51 (s, 1H), 6.48 (t, J=2.1 Hz, 1H), 5.43 (s, 1H), 2.76 (d, J=15.3 Hz, 1H), 2.67 (d, J=15.4 Hz, 1H), 0.68-0.76 (m, 2H), 0.24-0.34 (m, 2H).

EXAMPLE 195

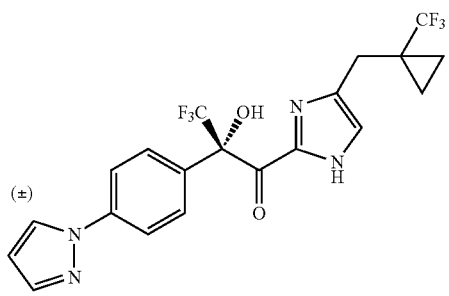

(±)-3,3,3-trifluoro-2-hydroxy-2-[4-(1H-pyrazol-1-yl)phenyl]-1-(4-{[1-(trifluoromethyl)cyclo-propyl]methyl}-1H-imidazol-2-yl)propan-1-one Step A: To a dichloromethane (5.0 mL) solution of oxalyl chloride (250 μL, 2.86 mmol) at −40° C. was added dimethyl sulfoxide (400 µL, 5.63 mmol). After 2 minutes, a dichloromethane (5.0 mL) solution of N,N-dimethyl-2-{(1S*,2S*)-3,3,3-trifluoro-1,2-dihydroxy-2-[4-(1H-pyrazol-1-yl)phenyl]propyl}-4-{[1-(trifluoromethyl)cyclopropyl]methyl}-1H-imidazole-1-sulfonamide (147 mg, 0.259 mmol) was slowly added. After 5 minutes, triethylamine (180 µL, 1.29 mmol) was added, and the reaction mixture was allowed to warm up to room temperature and stirred for 48 hours. The reaction mixture was quenched with water and extracted with diethyl ether. The reaction mixture was concentrated in vacuo to afford a crude solid. Chromatography over silica eluting with ethyl acetate/hexanes afforded, N,N-dimethyl-2-{3,3,3-trifluoro-2-hydroxy-2-[4-(1H-pyrazol-1-yl)phenyl]propanoyl}-4-{[1-(trifluoromethyl)-cyclopropyl]methyl}-1H-imidazole-1-sulfonamide, as an off-white solid.

Step B: A methanol (1.0 mL) solution of N,N-dimethyl-2-{3,3,3-trifluoro-2-hydroxy-2-[4-(1H-pyrazol-1-yl)phenyl]propanoyl}-4-{[1-(trifluoromethyl)cyclopropyl]methyl}-1H-imidazole-1-sulfonamide (11 mg, 0.019 mmol) was charged with concentrated hydrochloric acid (0.5 mL, 6.0 mmol) and heated to 80° C. for 1 hour. Purification of the reaction mixture by reversed-phase mass-directed high-performance liquid chromatography afforded the title compound as the trifluoroacetate salt. (M+H) found 459.

EXAMPLE 196

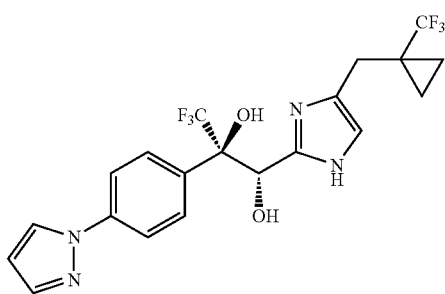

(1R*,2S*)-3,3,3-trifluoro-2-[4-(1H-pyrazol-1-yl)phenyl]-1-(4-{[1-(trifluoromethyl)cyclopropyl]methyl}-1H-imidazol-2-yl)propane-1,2-diol Step A: The racemic compound N,N-dimethyl-2-{3,3,3-trifluoro-2-hydroxy-2-[4-(1H-pyrazol-1-yl)phenyl]propanoyl}-4-{[1-(trifluoromethyl)cyclopropyl]methyl}-1H-imidazole-1-sulfonamide (199 mg, 0.352 mmol) was separated into the enantiomers by normal phase preparative chiral high-performance liquid chromatography (Chiralpak AD, 75/25 Heptane/Isopropanol, 18 mL/min, ~5 mg per injection). The faster eluting enantiomer was collected as E1, and the slower eluting enantiomer was collected as E2.

Step B: To an ethanol (5 mL) solution of E2 (56.5 mg, 0.100 mmol) was added sodium borohydride (3.8 mg, 0.10 mmol), and the resultant reaction mixture was stirred for ~15 min. It was quenched with water and extracted with ethyl acetate. The combined organic extracts were dried and concentrated in vacuo. Chromatography over silica eluting with 15-50% ethyl acetate/hexanes afforded N,N-dimethyl-2-{(1S,2R)-3,3,3-trifluoro-1,2-dihydroxy-2-[4-(1H-pyrazol-1-yl)phenyl]propyl}-4-{[1-(trifluoromethyl)cyclopropyl]methyl}-1H-imidazole-1-sulfonamide as the less polar product.

Step C: A methanol (2.0 mL) solution of N,N-dimethyl-2-{(1S,2R)-3,3,3-trifluoro-1,2-dihydroxy-2-[4-(1H-pyrazol-1-yl)phenyl]propyl}-4-{[1-(trifluoromethyl)cyclopropyl]methyl}-1H-imidazole-1-sulfonamide (20.2 mg, 0.036 mmol) was charged with concentrated hydrochloric acid (0.5 mL, 6.0 mmol) and heated to 70° C. After the starting material has been all consumed, the reaction mixture was quenched by sodium bicarbonate and extracted with dichloromethane/ethyl acetate. The combined organic extracts were concentrated in vacuo to afford the title compound. (M+H) found 461.

EXAMPLE 197

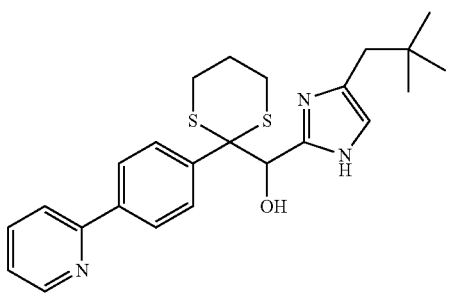

[4-(2,2-dimethylpropyl)-1H-imidazol-2-yl][2-(4-pyridin-2-ylphenyl)-1,3-dithian-2-yl]methanol Step A: Propanedithiol (0.72 mL, 7.1 mmol) followed by boron trifluoride diethyl etherate (0.7 mL, 7.1 mmol) were added to a 0° C. solution of 4-pyridin-2-ylbenzaldehyde (1 g, 5.5 mmol). After stirring at ambient temperature for a few minutes, the reaction was quenched with saturated aqueous sodium bicarbonate and extracted with methylene chloride and diethyl ether. The combined organic extracts were dried (magnesium sulfate) and concentrated in vacuo. Chromatography over silica eluting with 0-40% ethyl acetate/hexane afforded 2-[4-(1,3-dithian-2-yl)phenyl]pyridine.

Step B: n-Butyllithium (2.5 M in hexane) (0.14 mL, 0.17 mol) was added to a –78° C. solution of 2-[4-(1,3-dithian-2-yl)phenyl]pyridine (50 mg, 0.18 mmol) in tetrahydrofuran (3 mL). After stirring at 0° C. for 10 min, the reaction mixture was re-cooled to –78° C. and a solution of 4-(2,2-dimethylpropyl)-2-formyl-N,N-dimethyl-1H-imidazole-1-sulfonamide (100 mg, 0.37 mmol) in tetrahydrofuran (1 mL) was added. After stirring at –78° C. for 5 min then at ambient temperature for a further 10 min, the reaction mixture was quenched with water and extracted with methylene chloride. The combined organic extracts were dried (magnesium sulfate) and concentrated in vacuo. Preparatory plate chromatography eluting with 50% ethyl acetate/hexane afforded 4-(2,2-dimethylpropyl)-2-{hydroxy[2-(4-pyridin-2-ylphenyl)-1,3-dithian-2-yl]methyl}-N,N-dimethyl-1H-imidazole-1-sulfonamide. LCMS: 547 (M+H).

Step C, 1.5 N Hydrochloric acid (1 mL) was added to a solution of 4-(2,2-dimethylpropyl)-2-{hydroxy[2-(4-pyridin-2-ylphenyl)-1,3-dithian-2-yl]methyl}-N,N-dimethyl-1H-imidazole-1-sulfonamide in tetrahydrofuran (1 mL). After heating in a sealed tube at 70° C. for a few minutes until no further reaction (LCMS), the reaction mixture was cooled to 0° C., quenched with 10% aqueous sodium hydroxide and extracted with ethyl acetate. The combined organic extracts were dried (magnesium sulfate) and concentrated in vacuo.

Preparatory plate chromatography eluting with 10% methanol/ethyl aceate afforded the title compound. LCMS: 440 (M+H).

EXAMPLE 198

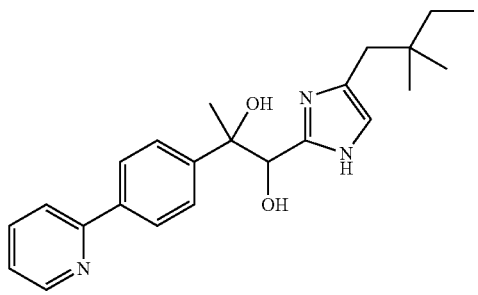

1-[4-(2,2-dimethylbutyl)-1H-imidazol-2-yl]-2-(4-pyridin-2-ylphenyl)propane-1,2-diol Step A: 4-(2,2-Dimethylbutyl)-2-{hydroxy[2-(4-pyridin-2-ylphenyl)-1,3-dithian-2-yl]methyl}-N,N-dimethyl-1H-imidazole-1-sulfonamide was prepared using the procedure outlined in Step A of Example 196. LCMS: 561 (M+H).

Step B: [Bis(trifluoroacetoxy)iodo]benzene (184 mg, 0.48 mmol) was added to a 0° C. solution of 4-(2,2-dimethylbutyl)-2-{hydroxy[2-(4-pyridin-2-ylphenyl)-1,3-dithian-2-yl]methyl}-N,N-dimethyl-1H-imidazole-1-sulfonamide (110 mg, 0.20 mmol) in acetonitrile/water (3:1) (4 mL). After stirring at 0° C. until no further reaction (LCMS), the reaction mixture was quenched with saturated aqueous sodium thiosulfate/saturated aqueous sodium bicarbonate (1:1) and extracted with methylene chloride. The combined organic extracts were dried (magnesium sulfate) and concentrated in vacuo to afford 4-(2,2-dimethylbutyl)-2-[1-hydroxy-2-oxo-2-(4-pyridin-2-ylphenyl)ethyl]-N,N-dimethyl-1H-imidazole-1-sulfonamide which was used in the next step without further purification.

Step C: Methylmagnesium bromide (3 M in diethyl ether) (28 μL, 0.09 mmol) was added to a 0° C. solution of 4-(2,2-dimethylbutyl)-2-[1-hydroxy-2-oxo-2-(4-pyridin-2-ylphenyl)ethyl]-N,N-dimethyl-1H-imidazole-1-sulfonamide (20 mg, 0.04 mmol) in tetrahydrofuran (2 mL). After stirring at 0° C. until no further reaction (LCMS), the reaction mixture was quenched with saturated aqueous ammonium chloride and extracted with methylene chloride. The combined organic extracts were dried (magnesium sulfate) and concentrated in vacuo. Chromatography over silica eluting with 0-100% ethyl acetate/hexane afforded 2-[1,2-dihydroxy-2-(4-pyridin-2-ylphenyl)propyl]-4-(2,2-dimethylbutyl)-N,N-dimethyl-1H-imidazole-1-sulfonamide.

Step D: 1.5 N Hydrochloric acid (1 mL) was added to a solution of 4-(2,2-dimethylpropyl)-2-[1-hydroxy-2-(4-pyridin-2-ylphenyl)ethyl]-N,N-dimethyl-1H-imidazole-1-sulfonamide (7 mg, 0.02 mmol) in tetrahydrofuran (1 mL). After heating in a sealed tube at 70° C. for 2 h, the reaction mixture was cooled to 0° C., quenched with 10% aqueous sodium hydroxide and extracted with ethyl acetate. The combined organic extracts were dried (magnesium sulfate) and concentrated in vacuo. Preparatory plate chromatography eluting with 10% methanol/ethyl acetate afforded the title compound. LCMS: 380 (M+H).

EXAMPLE 199

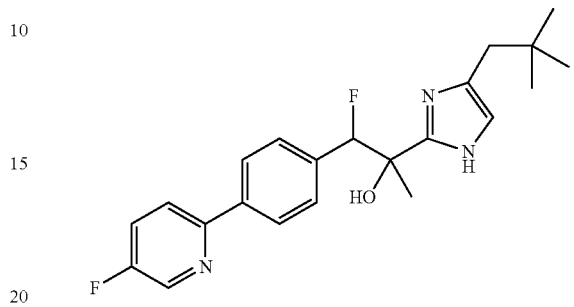

2-[4-(2,2-dimethylpropyl)-1H-imidazol-2-yl]-1-fluoro-1-[4-(5-fluoropyridin-2-yl)phenyl]propan-2-ol Step A: Lithium hexamethyldisilazide (1 M in tetrahydrofuran) (92 mL, 0.09 mmol) was added to a −78° C. solution of 4-(2,2-dimethylbutyl)-2-{[4-(5-fluoropyridin-2-yl)phenyl]acetyl}-N,N-dimethyl-1H-imidazole-1-sulfonamide (35 mg, 0.08 mmol) in tetrahydrofuran (2 mL). After stirring at −78° C. for 10 min, a solution of N-fluorobenzenesulfonimide (36 mg, 0.11 mmol) in tetrahydrofuran (1 mL) was added. The reaction was allowed to warm to ambient temperature, quenched with water and extracted with methylene chloride and ethyl acetate. The combined organic extracts were dried (magnesium sulfate) and concentrated in vacuo. Chromatography over silica eluting with 0-50% ethyl acetate/hexane afforded 4-(2,2-dimethylpropyl)-2-{fluoro[4-(5-fluoropyridin-2-yl)phenyl]acetyl}-N,N-dimethyl-1H-imidazole-1-sulfonamide.

Step B: Methylmagnesium bromide (3 M in diethyl ether) (ca. 15 μL, 0.04 mmol) was added to a 0° C. solution of 4-(2,2-dimethylpropyl)-2-{fluoro[4-(5-fluoropyridin-2-yl)phenyl]acetyl}-N,N-dimethyl-1H-imidazole-1-sulfonamide (10 mg, 0.02 mmol) in tetrahydrofuran (3 mL). After warming slowly to ambient temperature, the reaction was quenched with a few drops of water and concentrated in vacuo. Chromatography over silica eluting with 0-50% ethyl acetate/hexane afforded 4-(2,2-dimethylpropyl)-2-{2-fluoro-2-[4-(5-fluoropyridin-2-yl)phenyl]-1-hydroxy-1-methylethyl}-N,N-dimethyl-1H-imidazole-1-sulfonamide.

Step C: Hydrogen chloride (4 M in 1,4-dioxane) (1 mL, 4 mmol) was added to an ambient temperature solution of 4-(2,2-dimethylpropyl)-2-{2-fluoro-2-[4-(5-fluoropyridin-2-yl)phenyl]-1-hydroxy-1-methylethyl}-N,N-dimethyl-1H-imidazole-1-sulfonamide (ca. 10 mg, 0.02 mmol) in methanol (2 mL). After stirring at 70° C. for 1 h, volatiles were removed. The residue was partitioned between methanol/ethyl acetate and 10% aqueous sodium hydroxide. The aqueous phase was extracted with ethyl acetate. The combined organic extracts were dried (magnesium sulfate) and concentrated in vacuo. Chromatography over silica eluting with 0-100% acetone/ methylene chloride then with 0-100% ethyl acetate/hexane afforded the title compound. LCMS: 386 (M+H).

EXAMPLE 200

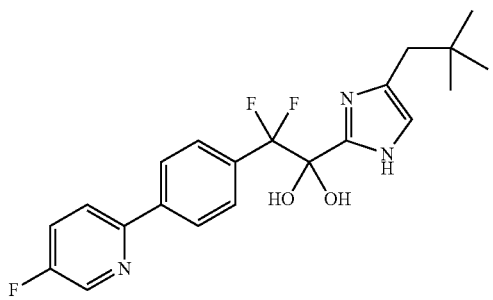

1-[4-(2,2-dimethylpropyl)-1H-imidazol-2-yl]-2,2-difluoro-2-[4-(5-fluoropyridin-2-yl)phenyl]ethane-1,1-diol Step A: Hydrogen chloride (4 M in 1,4-dioxane) (3 mL, 18 mmol) was added to an ambient temperature solution of 4-bromomandelic acid (5 g, 21.6 mmol) in methanol (50 mL). After stirring at ambient temperature overnight, the reaction mixture was concentrated in vacuo to afford methyl (4-bromophenyl)(hydroxy)acetate which was used in the subsequent step without further purification.

Step B: Dess-Martin periodinane (7.6 g, 17.96 mmol) was added to an ambient temperature solution of methyl (4-bromophenyl)(hydroxy)acetate (4 g, 16.33 mmol) in methylene chloride (100 mL). After stirring at ambient temperature for 2 h, the reaction mixture was quenched with saturated aqueous sodium thiosulfate/saturated aqueous sodium bicarbonate (1:1) and extracted with methylene chloride. The combined organic extracts were dried (magnesium sulfate) and concentrated in vacuo. Chromatography over silica eluting with 0-50% ethyl acetate/hexane afforded methyl (4-bromophenyl)(oxo)acetate.

Step C: Diethylaminosulfur trifluoride (3.12 g, 19.33 mmol) was added neat methyl (4-bromophenyl)(oxo)acetate (3.82 g, 15.72 mmol) at 0° C. After stirring at ambient temperature overnight, the reaction mixture was carefully quenched with saturated aqueous sodium bicarbonate and extracted with methylene chloride. The combined organic extracts were dried (magnesium sulfate) and concentrated in vacuo. Chromatography over silica eluting with 0-50% ethyl acetate/hexane afforded methyl (4-bromophenyl)(difluoro)acetate.

Step D: Lithium hydroxide (3.22 g, 31.4 mmol) was added to an ambient temperature solution of methyl (4-bromophenyl)(difluoro)acetate (4.13 g, 15.7 mmol) in tetrahydrofuran/water (10:1) (20 mL). After stirring at ambient temperature for 1 h, the reaction mixture was diluted with water and extracted with ethyl acetate. The aqueous phase was acidified with 1.5 N hydrochloric acid and extracted with ethyl acetate. The combined organic extracts were dried (magnesium sulfate) and concentrated in vacuo.

Sodium bicarbonate (13.21 g, 15.7 mmol) was added to an ambient temperature solution of the crude residue, N,O-dimethylhydroxylamine hydrochloride (3.07 g, 31.4 mmol), 1-[3-(dimethylamino) propyl]-3-ethylcarbodiimide hydrochloride (6.03 g, 31.4 mmol) and 1-hydroxybenzotriazole (4.25 g, 31.4 mmol) in methylene chloride (60 mL). After stirring at ambient temperature overnight, the reaction was quenched with water and extracted with methylene chloride. The combined organic extracts were dried (magnesium sulfate) and concentrated in vacuo. Chromatography over silica eluting with 0-100% ethyl acetate/hexane afforded 2-(4-bromophenyl)-2,2-difluoro-N-methoxy-N-methylacetamide.

Step E: Palladium tetrakis(triphenylphosphine) (236 mg, 0.20 mmol) was added to a degassed, ambient temperature solution of 2-(4-bromophenyl)-2,2-difluoro-N-methoxy-N-methylacetamide (600 mg, 2.05 mmol), 2-bromo-5-fluoropyridine (360 mg, 2.05 mmol) and hexamethylditin (670 mg, 2.05 mmol) in 1,4-dioxane (20 mL). After stirring at reflux overnight, the reaction mixture was diluted with water and extracted with methylene chloride and ethyl acetate. The combined organic extracts were dried (magnesium sulfate) and concentrated in vacuo. Chromatography over silica eluting with 0-60% ethyl acetate/hexane afforded 2,2-difluoro-2-[4-(5-fluoropyridin-2-yl)phenyl]-N-methoxy-N-methylacetamide.

Step F: n-Butyllithium (1.6 M in hexane) (0.60 mL, 0.96 mmol) was added to a −78° C. solution of 4-(2,2-dimethylpropyl)-N,N-dimethyl-1H-imidazole-1-sulfonamide (234 mg, 0.96 mmol) in tetrahydrofuran (10 mL). After stirring at −78° C. for 10 min, 2,2-difluoro-2-[4-(5-fluoropyridin-2-yl)phenyl]-N-methoxy-N-methylacetamide (296 mg, 0.96 mmol) was added and the reaction allowed to warm to ambient temperature, quenched with water and extracted with methylene chloride and ethyl acetate. The combined organic extracts were dried (magnesium sulfate) and concentrated in vacuo. Chromatography over silica eluting with 0-50% ethyl acetate/hexane afforded 2-{difluoro[4-(5-fluoropyridin-2-yl)phenyl]acetyl}-4-(2,2-dimethylpropyl)-N,N-dimethyl-1H-imidazole-1-sulfonamide.

Step G: Hydrogen chloride (4 M in 1,4-dioxane) (1 mL, 4 mmol) was added to an ambient temperature solution of 2-{difluoro[4-(5-fluoropyridin-2-yl)phenyl]acetyl}-4-(2,2-dimethylpropyl)-N,N-dimethyl-1H-imidazole-1-sulfonamide (20 mg, 0.04 mmol) in methanol (2 mL). After stirring at 70° C. for 1 h, volatiles were removed. The residue was partitioned between ethyl acetate and 10% aqueous sodium hydroxide. The aqueous phase was extracted with ethyl acetate. The combined organic extracts were dried (magnesium sulfate) and concentrated in vacuo. Chromatography over silica eluting with 0-50% ethyl acetate/hexane afforded the title compound. LCMS: 406 (M+H).

EXAMPLE 201

1-[5-(cyclopentylthio)-1-methyl-1H-imidazol-2-yl]-2-[4-(1H-pyrazol-1-yl)phenyl]propan-2-ol

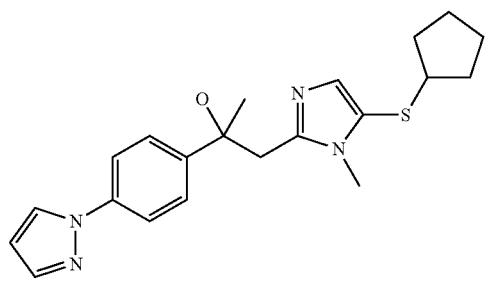

The title compound was prepared using the procedure outlined in Example 30. (M+H) found: 383.

Biological Assays

A. Bombesin Receptor Subtype 3 (BRS3) Binding Assays

Human embryonic kidney (HEK 293) cells expressing human BRS-3 were cultured to confluence and harvested by aspirating the culture medium and rinsing twice with 1×PBS without Mg$^{++}$ and Ca$^{++}$. Cellstriper Solution (Cellgrow #25-056-Cl, 3 mL) was added to each T-175 flask until all cells dissociated and then an additional 15 mL 1×PBS without Mg$^{++}$ and Ca$^{++}$ were added to each flask. Dissociated cells were collected by centrifuging at 1000 rpm for 10 minutes. Cell pellets were resuspended and homogenized at 4° C. using a Polytron homogenizer (setting 40, 20 stokes) in approximately 10 mL membrane preparation buffer (10 mM Tris pH 7.4, 0.01 mM Pefabloc, 10 µM phosphoramidon and 40 µg/mL Bacitracin) per T175 flask. After centrifugation at 2200 rpm (1000×g) for 10 minutes at 4° C., the supernatant was transferred to a clean centrifuge tube and spun at 18,000 rpm (38,742×g) for 15 minutes. at 4° C. Membranes were resuspended in the above membrane preparation buffer (1 mL/T-175 flask), homogenized, aliquoted, quickly frozen in liquid nitrogen and stored at −80° C.

For the [$^{125}$I]-[D-Tyr$^6$,β-Ala$^{11}$,Phe$^{13}$,Nle$^{14}$]-Bombesin(6-14), "[$^{125}$I]-dY-peptide", radioligand assay the specific binding of [$^{125}$I]-dY-peptide to human BRS3 was measured by filtration assay in 96-well plate format. The receptor membrane (2 µg/well) in binding buffer (50 mM Tris pH 7.4, 5 mM MgCl$_2$, 0.1% BSA and protease inhibitor cocktail) was mixed with compound in DMSO (1% final concentration) and 30 pM [$^{125}$I]-dY-peptide. After incubation for 1-2 hours at room temperature, membrane-bound [$^{125}$I]-dY-peptide was separated from free [$^{125}$I]-dY-peptide by filtering through GF/C filters presoaked in 1% PEI solution. The filters were washed five times with ice-cold washing buffer (1×PBS without Mg$^{++}$ and Ca$^{++}$). The radioactivity was determined by adding 30 µl of microscintillant/well after each plate was dried at room temperature overnight or placed at 50° C. for 1 hr.

The radioligand, [$^3$H]-1-{4-[(4,5-difluoro-2-hydroxycarbonylphenyl)phenyl]}-2-(4-cyclohexylmethyl-1H-imidazol-2-yl)ethane, was used for binding to receptor membranes generated with BRS3 from other species and was also utilized for the human receptor. Cell membranes (5 to 20 µg/well) were added to binding buffer (25 mM Tris pH 7.4, 10 mM MgCl$_2$, 2 mM EDTA and protease I cocktail) containing compound in DMSO (1% final concentration) and 660 µM [$^3$H]-biphenyl. After incubation for 1-2 hours at room temperature, membrane bound [$^3$H]-biphenyl was separated from free radiologand by filtering through GF/C filters presoaked in 1% PEI solution. The filters were washed five times with ice-cold washing buffer (50 mM Tris pH 7.4, 10 mM MgCl$_2$, 2.5 mM EDTA and 0.02% Triton X-100). The radioactivity was determined by adding 30 µl of microscintillant/well after each plate was dried at room temperature overnight or placed at 50° C. for 1 hr.

A Packard Top Count was used to read the filter plates. The data in % inhibition of binding was plotted vs. the log molar concentration of receptor ligand (compound). The IC$_{50}$ was reported as the inflection point of the resulting sigmoidal curve. The maximum inhibition observed at the highest compound concentration tested was reported for compounds which did not generate a curve.

The binding assays for the rat and mouse Bombesin Receptor Subtype 3 (BRS3) were performed in a similar fashion.

B. Cell Culture of Human, Rat and Mouse BRS3 Expressing Cell Lines

An NFATCHO cell line stably expressing human BRS3 cDNA was generated using standard cell biology techniques and used to prepare receptor membranes for the human "[$^{125}$I]-dY-peptide binding assay. The cell line was cultured in T175 flasks in Iscove's Modified Dulbecco's Medium with L-glutamine and 25 mM HEPES buffer (Gibco #12440-046) supplemented with 10% FBS (cat# SH30070.03, Hyclone, Logan, Utah), 1×HT Supplement (0.1 mM Sodium Hypoxanthine and 16 µM Thymidine Gibco #11067-030), 2 mM L-glutamine (Gibco #25030-081), 100 units/mL Penicillin-G and 100 µg/mL Streptomycin (Gibco #15140-122) and 1 mg/mL Geneticin (Gibco #10131-027).

HEK293/AEQ cell lines stably expressing either human, rat or mouse BRS3 cDNA were generated using standard cell biology techniques and were used for all functional assays and to prepare membranes for the rat BRS3 binding assay. The cell lines were routinely cultured in T75 or T175 flasks in Dulbecco's Modified Eagle Medium (Gibco #11965-084) supplemented with 10% FBS, 25 mM HEPES buffer solution (Gibco #15630-080), 0.5 mg/mL Geneticin and 50 µg/mL Hygromycin B (Boehringer Mannheim #14937400).

Transient transfection of mouse BRS3 cDNA, as well as BRS3 cDNA from other species, in the HEK293AEQ cell line was achieved using the Lipofectamine transfection method following the recommended protocol (Invitrogen Lipofectamine 2000 #11668-027). The transfected cells were used to prepare membranes for the [$^3$H]-biphenyl binding assay and for the functional assays. The cells were maintained in culture under the same conditions used for the human and rat stable BRS3 HEK293AEQ cell lines.

All cells were grown as attached monolayers to approximately 90% confluency in tissue culture flasks under the appropriate media in an incubator at 37° C. with 5% CO$_2$. Cells were passed 1:3 to 1:5 twice a week depending on the rate of growth.

C. BRS3 Functional Assays

1) Aequorin Bioluminescent assay to measure intracellular Ca$^{++}$

The apoaequorin containing HEK293AEQ cell lines expressing BRS3 were first charged with coelenterazine (Molecular Probes #C-14260) by rinsing confluent T75 flasks with 12 mL Hams F-12 media (Gibco #11765-054) containing 300 mM glutathione and 0.1% FBS. The same media (8 mL) containing 20 µM coelenterzine was added to the cells and incubated at 37° C. for 1 hr. The media was aspirated and the flasks rinsed with 6 mL ECB buffer (140 mM NaCl, 20 mM KCl, 20 mM HEPES, 5 mM glucose, 1 mM MgCl, 1 mM CaCl, 0.1 mg/mL BSA, pH 7.4). The cells were dissociated with a rubber-tipped scraper in 6 mL of fresh ECB buffer and collected by centrifugation at 2500 rpm for 5 minutes. The cell pellets were resuspended in ECB buffer to a concentration of 200,000 cells/mL and were either used right away or quickly frozen in liquid nitrogen for storage at −80° C. for up to six weeks.

The Aequorin assay itself was performed in 96-well format using a Wallac Microbeta luminometer equipped with microinjector module. Compounds in DMSO (0.5% final concentration) were titrated in the plates at 2× concentration in a volume of 0.1 mL ECB buffer. The cells (20,000 per well) were then injected in 0.1 mL ECB buffer and the bioluminescence monitored for 30 seconds. Alternatively, total bioluminescence was determined over 10 minutes. The bioluminescent readings were plotted vs. the log molar concentration of receptor ligand (compound). The $EC_{50}$ for activation was reported as the inflection point of the resulting sigmoidal curve.

2) Inositol Phosphate SPA Assay (IP) to Measure IP3 Accumulation

The IP functional assay was performed in 96-well format. The BRS3 expressing HEK293AEQ cells were plated on poly-D-lysine plates (~25,000 cells/0.15 mL) and kept in culture for 24 hours. The media from each well was aspirated and the cells were washed with PBS without $Mg^{++}$ and $Ca^{++}$. Inositol labeling media consisting of Inositol-free DMEM media (ICN #1642954) supplemented with 10% FBS, 1×HT Supplement, 2 mM glutamine, 70 mM HEPES buffer solution and 0.02% BSA to which $^3H$-myo-inositol (NEN #NET114A 1 mCi/mL, 25 Ci/mmol) was added so that there was 1 µCi $^3H$-myo-inositol in 150 µL media per well. After 18 hours of labeling, 5 µl 300 mM LiCl was added to each well, mixed, and incubated for 20 minutes at 37° C. Compound (1.5 µl of 100× compound in DMSO) was added and incubated for an additional 60 minutes at 37° C. The labeled media was aspirated, and the reaction terminated by lysing the cells with the addition of 60 µl 10 mM formic acid for 60 minutes at room temperature. A 20 µl aliquot of the lysate was transferred from each well to a clear-bottom Opti-plate which contained 70 µL RNA binding YSi SPA-beads (Amersham RPNQ0013) that had been suspended in 10% glycerol at 1 mg beads/70 µl of solution. After mixing, the plates were left at room temperature for 2 hours and were then counted using a Wallac Microbeta luminometer. The data in cpm (counts per minute) as plotted vs. the log molar concentration of receptor ligand (compound). The $EC_{50}$ for activation was reported as the inflection point of the resulting sigmoidal curve.

D. In-Vivo Overnight Food Intake and Body Weight in C57 Obese Male Mice

Methods: Male C57 mice were made obese by maintenance on a high fat diet (45-60% kcal from fat), such as Research Diets RD12492, starting at 6 weeks of age. Obese mice, approximately 20-52 weeks old and weighing approximately 45-62 g, were individually housed and acclimated for several days prior to testing. On the day of study, mice were orally dosed (n=6-8/group) with either vehicle only (10% Tween-water) or BRS-3 agonists (various doses). A known CB1R inverse agonist, AM251 (3 mg/kg), was used as the positive control for inter- and intra-experimental control. BRS-3 agonists were dosed approximately 60 minutes prior to the onset of the dark cycle. Overnight food intake and body weight were measured and analyzed. All data are presented as mean±SEM. Statistical significance was calculated using Student's t-test with differences considered significant when 2-tailed p<0.05.

Compounds useful in the present invention decrease overnight food intake by at least 10% and/or decrease body weight overnight by at least 1% relative to placebo.

E. In-Vivo Chronic Administration on Body Weight in C57 Obese Male Mice

Methods: Male C57 mice were made obese by maintenance on a high fat diet (45-60% kcal from fat), such as Research Diets RD12492, starting at 6 weeks of age. Obese mice, approximately 20-52 weeks old and weighing approximately 45-62 g, were individually housed and acclimated for several days prior to testing. During the study, mice were orally dosed (n=7-9/group) with either vehicle only (10% Tween-water) or BRS-3 agonists (various doses). A known anorectic agent, dexfenfluramine (10-15 mg/kg) was used as the positive control for inter- and intra-experimental control. Two doses (PO) of BRS-3 agonist were administered each day for 14 days. The first dose was given approximately 60 minutes prior to the onset of the dark cycle and the second, 5 hours after the first dose. A single dose of dexfenfluramine was given approximately 60 minutes prior to the onset of the dark cycle and vehicle was dosed for the second dose, 5 hours after the first dose. Daily food intake and body weight were measured and analyzed. All data are presented as mean±SEM. Statistical significance was calculated using Student's t-test with differences considered significant when 2-tailed p<0.05.

Compounds useful in the present invention, by day 14, decrease cumulative food intake by at least 10% and/or decrease body weight by at least 2% relative to placebo.

The racemates and chiral HPLC separated enantiomers of the present invention, including the racemates and chiral HPLC separated enantiomers in Examples 1-201, were tested and found to bind to the bombesin subtype 3 receptor with $IC_{50}$ values less than 10 µM, and to agonize the bombesin subtype 3 receptor with $EC_{50}$ values less than 10 µM. Preferred racemates and chiral HPLC separated enantiomers of the present invention, including the racemates and chiral HPLC separated enantiomers in Examples 1-201, were tested and found to bind to the bombesin subtype 3 receptor with $IC_{50}$ values less than 1 µM, and to agonize the bombesin subtype 3 receptor with $EC_{50}$ values less than 1 µM.

| BRS-3 Receptor Binding Activity for Selected Compounds | |
|---|---|
| Example No. | BRS-3 binding $IC_{50}$ (nM) |
| 4 | 19 |
| 40 | 15 |
| 1 | 18 |
| 49 | 54 |
| 45 | 71 |
| 55 | 56 |
| 52 | 19 |
| 72 | 12 |
| 31a | 36 |
| 60 | 23 |
| 75 | 11 |
| 78 | 17 |

Examples of Pharmaceutical Compositions

As a specific embodiment of an oral composition of a composition of the present invention, 5 mg of Example 1 is formulated with sufficient finely divided lactose to provide a total amount of 580 to 590 mg to fill a size 0 hard gelatin capsule.

As another specific embodiment of an oral composition of a compound of the present invention, 2.5 mg of Example 1 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the practices of the present invention. It is intended, therefore, that the invention be limited only by the scope of the claims which follow and that such claims be interpreted as broadly as is reasonable.

What is claimed is:

1. A compound of formula I:

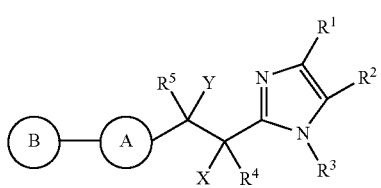

or a pharmaceutically acceptable salt thereof; wherein

A is aryl, wherein aryl is unsubstituted or substituted with 0 to 4 substituents selected from $R^6$;

B is a mono- or bicyclic ring selected from the group consisting of:
(1) —$C_{3-8}$cycloalkyl,
(2) —$C_{3-8}$cycloalkenyl,
(3) —$C_{2-8}$heterocycloalkyl,
(4) —$C_{2-8}$heterocycloalkenyl,
(5) -aryl, and
(6) -heteroaryl,
wherein cycloalkyl, cycloalkenyl, heterocycloalkyl, heterocycloalkenyl, aryl, and heteroaryl are unsubstituted or substituted with 0 to 4 substituents selected from $R^7$;

X is independently selected from the group consisting of:
(1) hydrogen,
(2) —$C_{1-6}$alkyl,
(3) —$C_{2-8}$alkenyl,
(4) —$C_{2-8}$alkynyl,
(5) —$(CH_2)_n C_{3-7}$cycloalkyl,
(6) —$(CH_2)_n C_{2-7}$heterocycloalkyl,
(7) —$(CH_2)_n$aryl,
(8) —$(CH_2)_n$heteroaryl,
(9) —$CF_3$,
(10) halogen,
(11) —$OR^{11}$,
(12) —$OCF_3$,
(13) —$COR^9$,
(14) —$CO_2R^{11}$,
(15) —$CON(R^9)_2$,
(16) —$N(R^{11})_2$,
(17) —$N(R^9)C(O)C_{1-6}$alkyl,
(18) —$N(R^9)CO_2R^{11}$,
(19) —$N(R^9)SO_2C_{1-6}$alkyl,
(20) —$N(R^9)SO_2N(R^9)_2$,
(21) —SH,
(22) —$S(O)_{0-2}C_{1-6}$alkyl, and
(23) —$SO_2N(R^{11})_2$,
wherein alkyl, alkenyl, alkynyl, cycloalkyl, heterocycloalkyl, aryl, heteroaryl and —$(CH_2)_n$ are unsubstituted or substituted with one to five substituents selected from $R^8$, and wherein X and $R^4$ together with the atoms to which they are attached may form a 3-6 membered cycloalkyl ring containing 0-3 heteroatoms independently selected from oxygen, sulfur, and $NR^9$, and wherein the 3-6 membered cycloalkyl ring is unsubstituted or substituted with 1 to 4 substituents selected from $R^8$, provided that at least one of X, Y, $R^4$ and $R^5$ is not hydrogen;

Y is independently selected from the group consisting of:
(1) halogen,
(2) —$OR^{11}$,
(3) —$OCF_3$,
(4) —$COR^9$,
(5) —$CO_2R^9$,
(6) —$CON(R^9)_2$,
(7) —CN,
(8) —$N(R^{11})_2$,
(9) —$N(R^9)C(O)C_{1-6}$alkyl,
(10) —$N(R^9)CO_2R^{11}$,
(11) —$N(R^9)SO_2C_{1-6}$alkyl,
(12) —$N(R^9)SO_2N(R^9)_2$,
(13) —SH,
(14) —$S(O)_{0-2}C_{1-6}$ alkyl, and
(15) —$SO_{0-2}N(R^{11})_2$,
wherein alkyl is unsubstituted or substituted with one to five substituents selected from $R^8$, and wherein Y and $R^6$ or Y and $R^5$ together with the atoms to which they are attached may form a 3-6 membered cycloalkyl ring containing 0-3 heteroatoms independently selected from oxygen, sulfur, and $NR^9$, and wherein the 3-6 membered cycloalkyl ring is unsubstituted or substituted with 1 to 4 substituents selected from $R^8$;

$R^1$ and $R^2$ are each independently selected from the group consisting of:
(1) hydrogen,
(2) —$(CH_2)_n$halogen,
(3) —$(CH_2)_n OR^{11}$,
(4) —$(CH_2)_n$CN,
(5) —$(CH_2)_n CF_3$,
(6) —$(CH_2)_n CHF_2$,
(7) —$(CH_2)_n CH_2F$,
(8) —$(CH_2)_n CCl_3$,
(9) —$C_{1-8}$alkyl,
(10) —$(CH_2)_n C_{2-8}$alkenyl,
(11) —$(CH_2)_n C_{2-8}$alkynyl,
(12) —$(CH_2)_n C_{3-10}$cycloalkyl,
(13) —$(CH_2)_n C_{3-10}$cycloalkenyl,
(14) —$(CH_2)_n C_{2-12}$heterocycloalkyl,
(15) —$SC_{1-8}$alkyl,
(16) —$SC_{3-8}$cycloalkyl,
(17) —$(CH_2)_n$aryl,
(18) —$(CH_2)_n$heteroaryl,
(19) —$(CH_2)_n CO_2R^9$, and
(20) —$(CH_2)_n COC_{1-8}$alkyl,
provided that $R^1$ and $R^2$ are not both hydrogen, wherein alkyl, alkenyl, alkynyl, cycloalkyl, cycloalkenyl, heterocycloalkyl, aryl, heteroaryl, and $(CH_2)_n$ are unsubstituted or substituted with 1 to 5 substituents selected from $R^{10}$, and wherein two $R^{10}$ substituents together with the atom to which they are attached may form a 3-6 membered cycloalkyl or cycloalkenyl ring containing 0 to 3 heteroatoms independently selected from oxygen, sulfur, and $NR^9$, and wherein the 3-6 membered cycloalkyl or cycloalkenyl ring is unsubstituted or substituted with 1 to 4 substituents selected from $R^{10}$;

$R^3$ is selected from the group consisting of:
(1) hydrogen,
(2) —$C_{1-6}$alkyl, and
(3) —$COC_{1-6}$alkyl;

$R^4$ and $R^5$ are each independently selected from the group consisting of:
(1) hydrogen,
(2) halogen,
(3) —$C_{1-6}$alkyl,
(4) —$(CH_2)_nC_{3-8}$cycloalkyl,
(5) —$(CH_2)_nC_{2-8}$heterocycloalkyl,
(6) —$C_{1-6}$alkoxy,
(7) —OH,
(8) —$CH_2F$,
(9) —$CHF_2$,
(10) —$CF_3$,
(11) —CN,
(12) —$SR^{11}$,
(13) aryl, and
(14) heteroaryl,
wherein alkyl, alkoxy, cycloalkyl, heterocycloalkyl, aryl, heteroaryl, and $(CH_2)_n$ are unsubstituted or substituted with one to five substituents selected from $R^8$;
$R^6$ is selected from the group consisting of:
(1) —$C_{1-6}$alkyl,
(2) —$(CH_2)_n$halogen,
(3) —$(CH_2)_nOR^{11}$,
(4) —$(CH_2)_n$CN,
(5) —$(CH_2)_nCF_3$,
(6) —$(CH_2)_nCO_2R^9$,
(7) —$(CH_2)_nN(R^{11})_2$,
(8) —$(CH_2)_nNO_2$,
(9) —$(CH_2)_nNR^9COC_{1-6}$alkyl,
(10) —$(CH_2)_nNR^9CO_2C_{1-6}$alkyl,
(11) —$(CH_2)_nNR^9SO_2C_{1-6}$alkyl, and
(12) —$(CH_2)_nSO_{0-2}C_{1-6}$alkyl,
wherein alkyl is substituted with 1 to 3 halogens;
$R^7$ is selected from the group consisting of:
(1) —$(CH_2)_n$halogen,
(2) —$C_{1-6}$alkyl,
(3) —$C_{2-6}$alkenyl,
(4) —$(CH_2)_nC_{3-8}$cycloalkyl,
(5) —$(CH_2)_n$heterocycloalkyl,
(6) oxo,
(7) —$(CH_2)_nOR^{11}$,
(8) —$(CH_2)_n$CN,
(9) —$(CH_2)_nCOR^9$,
(10) —$(CH_2)_nCO_2R^{11}$,
(11) —$(CH_2)_nCONR^9N(R^9)_2$,
(12) —$(CH_2)_nO(CH_2)_nCO_2R^9$,
(13) —$(CH_2)_nNO_2$,
(14) —$(CH_2)_nCON(R^9)_2$,
(15) —$(CH_2)_nN(R^{11})_2$,
(16) —$(CH_2)_nNR^9(CH_2)_nCO_2R^9$,
(17) —$(CH_2)_nNR^9COC_{1-6}$alkyl,
(18) —$(CH_2)_nSO_2N(R^9)_2$,
(19) —$(CH_2)_nNR^9SO_2C_{1-6}$alkyl,
(20) —$(CH_2)_nSO_{0-2}R^{11}$,
(21) —$(CH_2)_nOP(O)_2OH$,
(22) —CH=N—OH,
(23) —$(CH_2)_n$aryl,
(24) —$(CH_2)_n$heteroaryl, and
(25) —$(CH_2)_nO(CH_2)_n$heteroaryl,
wherein alkyl, alkenyl, cycloalkyl, heterocycloalkyl, aryl, heteroaryl, and —$(CH_2)_n$ are unsubstituted or substituted with 1 to 3 halogens;
$R^8$ is selected from the group consisting of:
(1) oxo,
(2) —OH,
(3) halogen,
(4) —CN,
(5) —$CF_3$,
(6) —$CHF_2$,
(7) —$CH_2F$,
(8) —$C_{1-8}$alkyl,
(9) —$C_{1-8}$alkoxy,
(10) —$COC_{1-8}$alkyl,
(11) —$CO_2C_{1-8}$alkyl, and
(12) —$CO_2H$,
wherein each alkyl and alkoxy carbon is unsubstituted or substituted with 1 to 3 halogen substituents;
$R^9$ is selected from the group consisting of:
(1) hydrogen, and
(2) —$C_{1-6}$alkyl,
wherein alkyl is unsubstituted or substituted with 1 to 3 substituents selected from halogen and —OH;
$R^{10}$ is independently selected from the group consisting of:
(1) halogen,
(2) —OH,
(3) oxo,
(4) —CN,
(5) —$CCl_3$,
(6) —$CF_3$,
(7) —$CHF_2$,
(8) —$CH_2F$,
(9) —$SO_2C_{1-6}$alkyl,
(10) —$COC_{1-8}$alkyl,
(11) —$CO_2C_{1-8}$alkyl,
(12) —$CO_2H$
(13) —$C_{1-8}$alkyl, and
(14) —$C_{1-8}$alkoxy,
wherein alkyl and alkoxy are unsubstituted or substituted with 1 to 4 substituents selected from —$C_{1-6}$alkyl and halogen, and wherein the —$C_{1-6}$alkyl substituent is unsubstituted or substituted with 1 to 3 halogens;
$R^{11}$ is selected from the group consisting of:
(1) hydrogen,
(2) —$C_{1-6}$alkyl,
(3) —$C_{3-8}$cycloalkyl,
(4) —$C_{2-7}$heterocycloalkyl,
(5) —$(CH_2)_m$phenyl, and
(6) —$(CH_2)_m$heteroaryl,
wherein alkyl, cycloalkyl, and heterocycloalkyl are unsubstituted or substituted with 1 to 3 halogens or —OH, and wherein phenyl and heteroaryl are unsubstituted or substituted with 1 to 3 halogens;
each n is independently 0, 1, 2, 3 or 4; and
each m is independently 1, 2, 3 or 4.

2. The compound of claim 1 wherein A is phenyl, wherein A is unsubstituted or substituted with 0 to 4 substituents selected from $R^6$; or a pharmaceutically acceptable salt thereof.

3. The compound of claim 1 wherein B is a ring selected from the group consisting of: cyclopentyl, phenyl, pyridine, pyrazole, triazole, thiazole, isothiazole, thiadiazole, and (1,4,5,6)tetrahydro-7H-pyrazolo-{3,4-b}-pyridine-7yl, wherein B is unsubstituted or substituted with 0 to 4 substituents selected from $R^7$; or a pharmaceutically acceptable salt thereof.

4. The compound of claim 1 wherein $R^2$ is selected from the group consisting of: hydrogen, halogen, —$(CH_2)_nOH$, —$C_{1-8}$alkyl, —$(CH_2)_nC_{2-8}$alkenyl, —$(CH_2)_nC_{3-8}$cycloalkyl, —$SC_{1-8}$cycloalkyl, and —$(CH_2)_n$phenyl, wherein alkyl, alkenyl, cycloalkyl, phenyl, and $(CH_2)_n$ are unsubstituted or substituted with 1 to 4 substituents selected from $R^{10}$; or a pharmaceutically acceptable salt thereof.

5. The compound of claim 1 wherein $R^2$ and $R^3$ are hydrogen; or a pharmaceutically acceptable salt thereof.

6. The compound of claim 5 wherein $R^1$ is selected from the group consisting of: $-(CH_2)_nOH$, $-(CH_2)_nCN$, $-(CH_2)_nCF_3$, $-(CH_2)_nCHF_2$, $-(CH_2)_nCH_2F$, $-C_{1-8}$alkyl, $-(CH_2)_nC_{2-8}$alkenyl, and $-(CH_2)_nC_{3-8}$cycloalkyl, wherein alkyl, alkenyl, cycloalkyl, and $(CH_2)_n$ are unsubstituted or substituted with 1 to 4 substituents selected from $R^{10}$; or a pharmaceutically acceptable salt thereof.

7. The compound of claim 6 wherein X is selected from the group consisting of: hydrogen, halogen, and —OH, provided that at least one of X, Y, $R^4$ and $R^5$ is not hydrogen; or a pharmaceutically acceptable salt thereof.

8. The compound of claim 7 wherein Y is selected from the group consisting of: halogen, —OH, —$OC_{1-6}$alkyl, —$CO_2R^9$, —$CON(R^9)_2$, —$N(R^{11})_2$, —$N(R^9)C(O)C_{1-6}$alkyl, —$N(R^9)CO_2R^{11}$, and —$N(R^9)SO_2C_{1-6}$alkyl, and —$SC_{1-6}$alkyl, wherein alkyl is unsubstituted or substituted with one to five substituents selected from $R^8$, and wherein Y and $R^5$ together with the atoms to which they are attached may form a 3-6 membered cycloalkyl ring containing 0-3 heteroatoms independently selected from oxygen, sulfur, and $NR^9$, and wherein the 3-6 membered cycloalkyl ring is unsubstituted or substituted with 1 to 4 substituents selected from $R^8$; or a pharmaceutically acceptable salt thereof.

9. The compound of claim 1 of formula III:

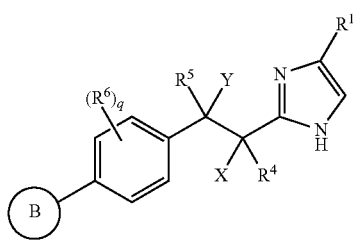

or a pharmaceutically acceptable salt thereof; wherein
B is a mono- or bicyclic ring selected from the group consisting of:
  (1) —$C_{3-8}$cycloalkyl,
  (2) -aryl, and
  (3) -heteroaryl,
wherein cycloalkyl, aryl, heteroaryl are unsubstituted or substituted with 0 to 4 substituents selected from $R^7$;
X is independently selected from the group consisting of:
  (1) hydrogen,
  (2) halogen, and
  (3) —OH,
provided that at least one of X, Y, $R^4$ and $R^5$ is not hydrogen;
Y is independently selected from the group consisting of:
  (1) halogen,
  (2) —OH,
  (3) —$OC_{1-6}$alkyl,
  (4) —$N(R^{11})_2$,
  (5) —$N(R^9)C(O)C_{1-6}$alkyl,
  (6) —$N(R^9)CO_2R^{11}$,
  (7) —$N(R^9)SO_2C_{1-6}$alkyl,
  (8) —SH, and
  (9) —$SC_{1-6}$alkyl,
wherein alkyl is unsubstituted or substituted with one to five substituents selected from $R^8$;
$R^1$ is independently selected from the group consisting of:
  (1) —$(CH_2)_nOH$,
  (2) —$(CH_2)_nCN$,
  (3) —$(CH_2)_nCF_3$,
  (4) —$(CH_2)_nCHF_2$,
  (5) —$(CH_2)_nCH_2F$,
  (6) —$C_{1-8}$alkyl,
  (7) —$(CH_2)_nC_{2-8}$alkenyl, and
  (8) —$(CH_2)_nC_{3-8}$cycloalkyl,
wherein alkyl, alkenyl, cycloalkyl, and $(CH_2)_n$ are unsubstituted or substituted with 1 to 4 substituents selected from $R^{10}$;
$R^4$ and $R^5$ are each independently selected from the group consisting of:
  (1) hydrogen,
  (2) halogen,
  (3) —$C_{1-6}$alkyl,
  (4) —$(CH_2)_nC_{3-8}$cycloalkyl,
  (5) —OH,
  (6) —$CHF_2$, and
  (7) —$CF_3$,
wherein alkyl, cycloalkyl, and $(CH_2)_n$ are unsubstituted or substituted with one to five substituents selected from $R^8$;
$R^6$ is selected from the group consisting of:
  (1) —$C_{1-6}$alkyl, and
  (2) halogen;
$R^7$ is selected from the group consisting of:
  (1) halogen,
  (2) —$C_{1-6}$alkyl,
  (3) —$COC_{1-6}$alkyl,
  (4) —$CO_2R^9$,
  (5) —$CON(R^9)_2$,
  (6) —$NH_2$,
  (7) —$NHCO_2C_{1-6}$alkyl, and
  (8) —$SOC_{1-6}$alkyl,
wherein alkyl is unsubstituted or substituted with 1 to 3 halogens;
$R^8$ is selected from the group consisting of:
  (1) oxo,
  (2) —OH,
  (3) halogen,
  (4) —CN,
  (5) —$CF_3$,
  (6) —$CHF_2$,
  (7) —$CH_2F$, and
  (8) —$C_{1-8}$alkyl,
wherein each alkyl carbon is unsubstituted or substituted with 1 to 3 halogen substituents;
$R^9$ is selected from the group consisting of:
  (1) hydrogen, and
  (2) —$C_{1-6}$alkyl,
wherein alkyl is unsubstituted or substituted with 1 to 3 substituents selected from halogen and —OH;
$R^{10}$ is selected from the group consisting of:
  (1) —OH,
  (2) oxo, and
  (3) —$CF_3$;
$R^{11}$ is selected from the group consisting of:
  (1) hydrogen, and
  (2) —$C_{1-6}$alkyl,
wherein each alkyl carbon is unsubstituted or substituted with 1 to 3 halogens;
each n is independently 0, 1, 2, 3 or 4; and
each q is independently 0, 1, 2, 3 and 4.

10. The compound of claim 9 wherein:
B is heteroaryl, wherein heteroaryl is unsubstituted or substituted with 0 to 4 substituents selected from $R^7$;
X, $R^4$, and $R^6$ are hydrogen;
Y is —OH;

$R^1$ is independently selected from the group consisting of:
(1) —$C_{1-8}$alkyl, and
(2) —$(CH_2)_nC_{3-8}$cycloalkyl,
wherein alkyl, cycloalkyl, and $(CH_2)_n$ are unsubstituted or substituted with 1 to 4 substituents selected from $R^{10}$;

$R^5$ is each independently selected from the group consisting of:
(1) hydrogen,
(2) —$C_{1-6}$alkyl,
(3) —$CHF_2$, and
(4) —$CF_3$,
wherein alkyl is unsubstituted or substituted with one to five substituents selected from $R^8$; and $R^7$ is halogen;
or a pharmaceutically acceptable salt thereof.

11. The compound of claim 1 selected from the group consisting of:

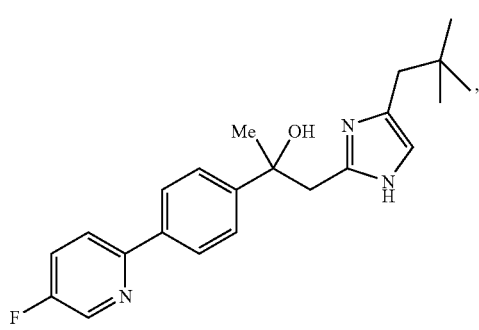,

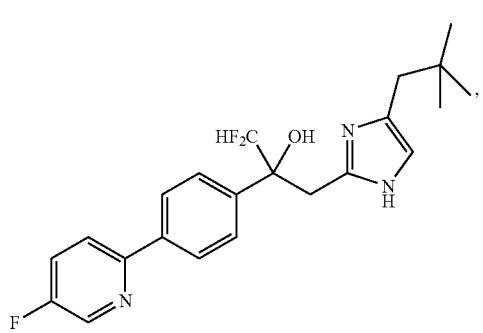,

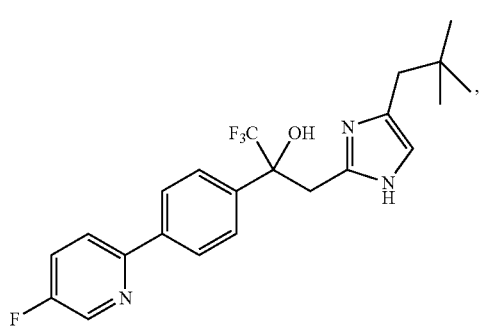,

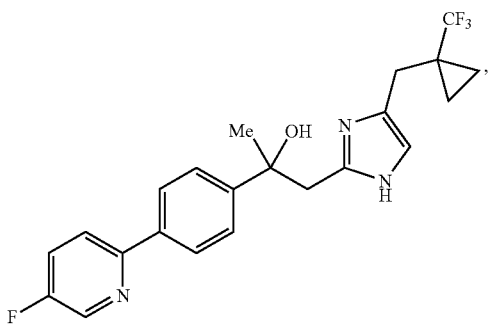,

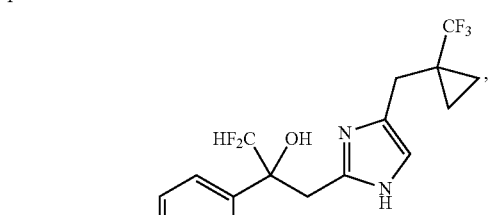,

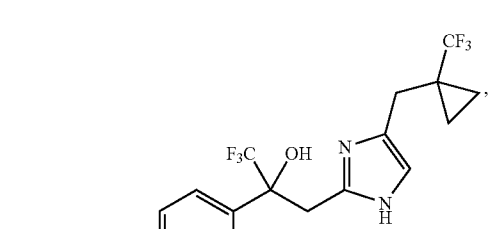,

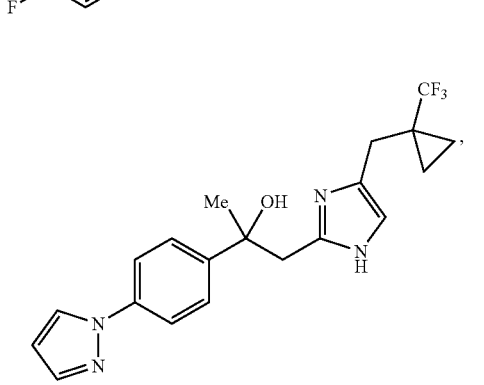,

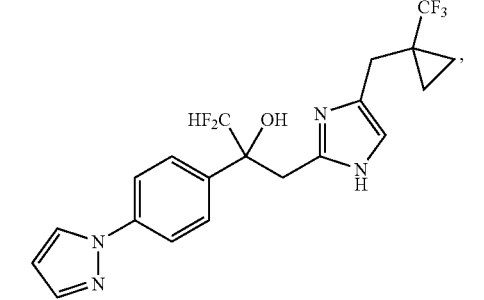,

-continued

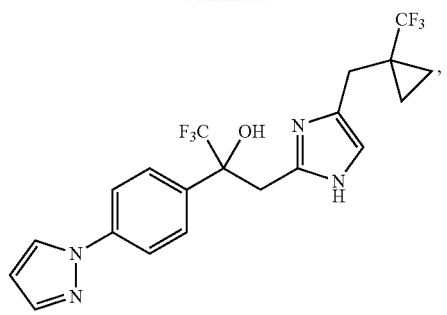

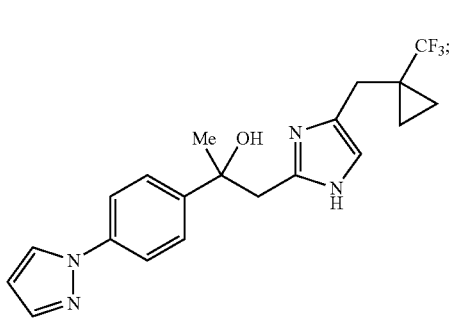

or a pharmaceutically acceptable salt thereof.

12. The compound of claim 11 which is:

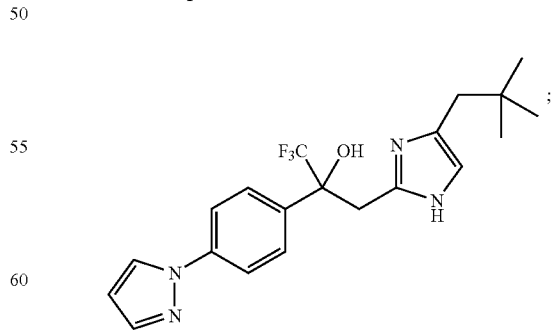

or a pharmaceutically acceptable salt thereof.

13. The compound of claim 11 which is:

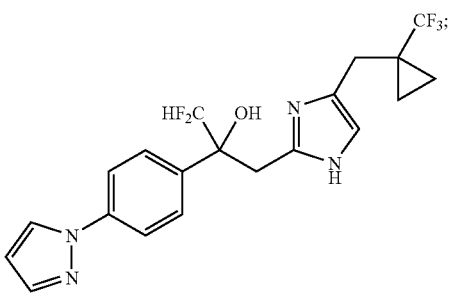

or a pharmaceutically acceptable salt thereof.

14. The compound of claim 11 which is:

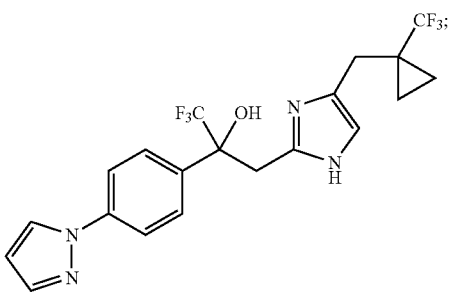

or a pharmaceutically acceptable salt thereof.

15. The compound of claim 11 which is:

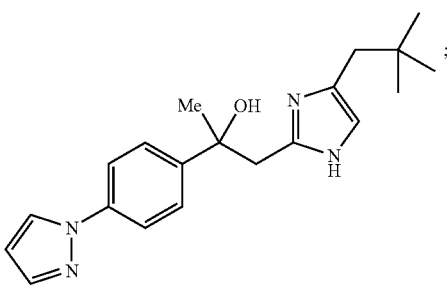

or a pharmaceutically acceptable salt thereof.

16. The compound of claim 11 which is:

or a pharmaceutically acceptable salt thereof.

17. A composition which comprises a compound of claim 1, or a pharmaceutically acceptable salt thereof, and a pharmaceutically acceptable carrier.

18. The compound of claim 1 which is:
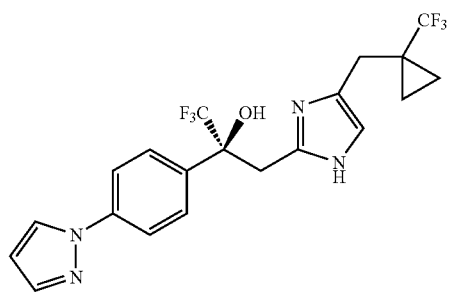
or a pharmaceutically acceptable salt thereof.
19. The compound of claim 1 which is:
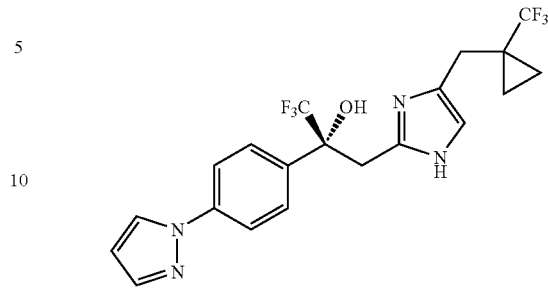
or a pharmaceutically acceptable salt thereof.
* * * * *